US006916635B2

(12) United States Patent
(10) Patent No.: US 6,916,635 B2
(45) Date of Patent: Jul. 12, 2005

Hearing et al.

(54) HYBRID ADENOVIRUS/ADENO-ASSOCIATED VIRUS VECTORS AND METHODS OF USE THEREOF

(75) Inventors: Patrick Hearing, St. James, NY (US); Wadie F. Bahou, Setauket, NY (US); Ziv Sandalon, Port Jefferson Station, NY (US); Dmitri V. Gnatenko, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 214 days.

(21) Appl. No.: 09/782,378

(22) Filed: Feb. 12, 2001

(65) Prior Publication Data

US 2002/0102731 A1 Aug. 1, 2002

Related U.S. Application Data

(60) Provisional application No. 60/237,747, filed on Oct. 2, 2000.

(51) Int. Cl.[7] ........................ C12N 15/64; C12N 15/09; C12N 15/00; C12N 15/63; C07H 21/04

(52) U.S. Cl. ............................ 435/91.4; 435/6; 435/29; 435/320.1; 435/235.1; 435/325; 435/455; 536/23.1

(58) Field of Search ........................... 435/320.1, 235.1, 435/6, 29, 455, 325, 91.4; 536/23.1

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,589,377 | A | 12/1996 | Lebkowski et al. |
| 5,691,176 | A | 11/1997 | Lebkowski et al. |
| 5,789,390 | A | 8/1998 | Descamps et al. |
| 5,837,484 | A | 11/1998 | Trempe |
| 5,872,005 | A | 2/1999 | Wang et al. |
| 5,877,011 | A | 3/1999 | Armentano et al. |
| 5,891,690 | A | 4/1999 | Massie |
| 6,040,174 | A | 3/2000 | Imler et al. |

FOREIGN PATENT DOCUMENTS

| | | |
|---|---|---|
| EP | 185 573 | 5/1992 |
| WO | WO 88/10311 | 12/1988 |
| WO | WO 90/09441 | 8/1990 |
| WO | WO 91/11525 | 8/1991 |
| WO | WO 91/18088 | 11/1991 |
| WO | WO 99/53085 | 10/1999 |

OTHER PUBLICATIONS

Gnatenko, et al. Blood, Nov. 15, 1999, vol. 94, No. 10 SUPPL. Part 1, p. 181a. Meeting Info: Forty–first Annual Meeting of the American Society of Hematology. New Orleans, Lousiana, USA, Dec. 3–7, 1999.*

Benihoud et al. (1999) "Adenovirus vectors for gene delivery," Curr. Opin. Biotechnol. 10:440–7.

Brenner (1999) "Gene Transfer by Adenovectors," Blood 94:3965–7.

Kochanek (1999) "High–Capacity Adenoviral Vectors for Gene Transfer and Somatic Gene Therapy," Hum. Gene. Ther. 10:2451–9.

Wold (1999) "Immune responses to adenoviruses: viral evasion mechanisms and their implications for the clinic," Human Press, Totowa, NJ.

(Continued)

*Primary Examiner*—Gerry Leffers

(74) *Attorney, Agent, or Firm*—Medlen & Carroll, LLP

(57) ABSTRACT

The invention provides recombinant vectors including adenovirus/adeno-associated virus (Ad/AAV) vectors and mini-adenovirus (mAd) vectors. Further, the invention provides cells containing these vectors, and methods for making and using the vectors and cells. The compositions and methods of the invention are useful in transferring nucleotide sequences of interest into a cell, including, but not limited to, in gene therapy applications.

7 Claims, 7 Drawing Sheets

OTHER PUBLICATIONS

Tripathy et al. (1996) "Immune responses to transgene–encoded proteins limit the stability of gene expression after injection of replication–defective adenovirus vectors," Nat. Med. 2:545–50.

Yang et al. (1996) "Role of Viral Antigens in Destructive Cellular Immune Responses to Adenovirus Vector–Transduced Cells in Mouse Lung," J. Virol. 70:7209–12.

Thrasher et al. (1995) "Generation of recombinant adeno–associated virus (rAAV) from an adenoviral vector and functional reconstitution of the NADPH–oxidase," Gene Ther. 2:481–485.

Fisher et al. (1996) "A Novel Adenovirus–Adeno–Associated Virus Hybrid Vector That Displays Efficient Rescue and Delivery of the AAV Genome," Human Gene Ther. 7:2079–2087.

Lieber et al. (1999) "Integrating Adenovirus–Adeno–Associated Virus Vectors Devoid of All Viral Genes," J. Virol. 73:9314–9324.

Liu et al. (1999) "Production of recombinant adeno–associated virus vectors using a packaging cell line and a hybrid recombinant adenovirus,"Gene Ther. 6:293–299.

Berns et al. (1995) "Adenovirus and Adeno–Associated Virus as Vectors for Gene Therapy," Ann. NY Acad. Sci. 772:95–104.

Muzyczka (1992) "Use of Adeno–Associated Virus as a General Transduction Vector for Mammalian Cells," Curr. Top. Microbiol. Immunol. 158:97–129.

Rolling and Samulski (1995) Mol. Biotechnol. 3:9–15.

Bett et al. (1993) "Packaging Capacity and Stability of Human Adenovirus Type 5 Vectors," J. Virol. 67:5911–21.

Parks and Graham (1997) "A Helper–Dependent System for Adenovirus Vector Production Helps Define a Lower Limit for Efficient DNA Packaging," J. Virol. 71:3293–8.

Akli et al. (1993) "Transfer of a foreign gene into the brain using adenovirus vectors," Nature Genetics 3:224.

Stratford–Perricaudet et al. (1990) "Evaluation of the Transfer and Expression in Mice of an Enzyme–Encoding Gene Using a Human Adenovirus Vector," Human Gene Ther. 1:241.

Levrero et al. (1991) "Defective and nondefective adenovirus vectors for expressing foreign genes in vitro and in vivo," Gene 101:195.

Le Gal la Salle et al. (1993) "An Adenovirus Vector for Gene Transfer into Neurons and Glia in the Brain," Science 259:988.

Roemer and Friedmann (1992) "Concepts and strategies for human gene therapy," Eur. J. Biochem. 208:211.

Dobson et al. (1990) "A Latent, Nonpathogenic HSV–1–Derived Vector Stably Expresses β–Galactosidase in Mouse Neurons," Neuron 5:353.

Chiocca et al. (1990) "Transfer and Expression of the *lacZ* Gene in Rat Brain Neurons Mediated by Herpes Simplex Virus Mutants," New Biol. 2:739.

Miyanohara et al. (1992) "Direct Gene Transfer to the Liver with Herpes Simplex Virus Type 1 Vectors," Transient Production of Physiologically Relevant Levels of Circulating Factor IX, New Biol. 4:238.

Xiao et al. (1997) "A Novel 165–Base–Pair Terminal Repeat Sequence Is the Sole *cis* Requirement for the Adeno–Associated Virus Life Cycle," J. Virol. 71:941–948.

Ryan et al. (1996) "Sequence Requirements for Binding of Rep68 to the Adeno–Associated Virus Terminal Repeats," J. Virol. 70:1542–1553.

Imler et al. (1996) "Novel complementation cell lines derived from human lung carcinoma A549 cells support the growth of E–1 deleted adenovirus vectors," Gene Ther. 3:75–84.

Fallaux et al. (1998) "New Helper Cells and Matched Early Region 1–Deleted Adenovirus Vectors Prevent Generation of Replication–Competent Adenoviruses," Human Gene Ther. 9:1909–1917.

Fallaux et al. (1996) "Characterization of 911: A New Helper Cell Line for the Titration and Propagation of Early Region 1–Deleted Adenoviral Vectors," Human Gene Ther. 7:215–222.

Weinberg et al. (1983) "A cell line that supports the growth of a defective early region 4 deletion mutant of human adenovirus type 2," Proc. Natl. Acad. Sci. USA 80:5383–5386.

Brough et al. (1996) "A Gene Transfer Vector–Cell Line System for Complete Functional Complementation of Adenovirus Early Regions E1 and E4," J. Virol. 70:6497–501.

Hearing et al. (1987) "Identification of a Repeated Sequence Element Required for Efficient Encapsidation of the Adenovirus Type 5 Chromosome," J. Virol. 61:2555–8.

Zolotukhin et al. (1996) "A Humanized Green Fluorescent Protein cDNA Adapted for High–Level Expression in Mammalian Cells," J. Virol. 70:4646–54.

Stow (1981) "Cloning of a DNA Fragment from the Left––Hand Terminus of the Adenovirus Type 2 Genome and Its Use in Site–Directed Mutagenesis," J. Virol. 37:171–180.

Graham et al. (1977) "Characteristics of a Human Cell Line Transformed by DNA from Human Adenovirus Type 5," J. Gen. Virol. 36:59–74.

Thimmappaya et al. (1982) "Adenovirus VAI RNA Is Required for Efficient Translation of Viral mRNAs at Late Times after Infection," Cell, Dec. 31 (3 Pt 2): 543–551.

Tollefson et al. (1996) "The Adenovirus Death Protein (E3–11.6K) Is Required at Very Late Stages of Infection for Efficient Cell Lysis and Release of Adenovirus from Infected Cells," J. Virol. 70(4):2296–2306.

Steinwaerder et al. (1999) "Generation of Adenovirus Vectors Devoid of All Viral Genes by Recombination between Inverted Repeats," J. Virol. 73:9303–13.

Clark et al. (1996) "A stable cell line carrying adenovirus–inducible rep and cap genes allows for infectivity titration of adeno–associated virus vectors," Gene Ther. 3:1124–32.

Hirt (1967) "Selective Extraction of Polyoma DNA from Infected Mouse Cell Cultures," J. Mol. Biol. 26:365–9.

Nevins (1981) "Mechanism of Activation of Early Viral Transcription by the Adenovirus E1A Gene Product," Cell 26:213–20.

Sandalon et al. (1997) "*In Vitro* Assembly of SV40 Virions and Pseudovirions: Vector Development for Gene Therapy," Hum. Gene Ther. 8:843–9.

Gnatenko et al. (1999) "An Adenovirus/Adeno–associated Hybrid Virus Generates a Mini–Adenovirus Devoid of all Viral Genes," Blood (supplement) 94:181a, Abstract No. 788.

Molin et al. (1998) "Two Novel Adenovirus Vector Systems Permitting Regulated Protein Expression in Gene Transfer Experiments," J. Virol. 72:8358–8361.

Recchia et al. (1999) "Site–specific integration mediated by a hybrid adenovirus/adeno–associated virus vector," Proc. Natl. Acad. Sci. USA 96:2615–2620.

Sandalon et al. (2000) "AAV Rep Protein Enhances the Generation of a Recombinant Mini–Adenovirus Utilizing an Ad/AAV Hybrid Virus," J. Virol. 74:10381–9.

* cited by examiner

HYBRID ADENOVIRUS/ADENO-ASSOCIATED VIRUS VECTORS AND METHODS OF USE THEREOF

This application claims priority to pending application Ser. No. 60/237,747, filed Oct. 2, 2000.

FIELD OF THE INVENTION

The invention relates to recombinant vectors including adenovirus/adeno-associated virus (Ad/AAV) vectors and mini-adenovirus (mAd) vectors. Further, the invention relates to cells containing these vectors, and methods for making and using the vectors and cells. The compositions and methods of the invention are useful in transferring nucleotide sequences of interest into a cell, e.g., in in vitro gene expression and in gene therapy applications.

BACKGROUND OF THE INVENTION

The human adenovirus (Ad) has been exploited as a vector for gene delivery [Benihoud et al. (1999) Curr Opin Biotechnol 10:440–7; Brenner (1999) Blood 94:3965–7; Kochanek (1999) Hum. Gene. Ther. 10:2451–9]. Adenovirus is a common DNA virus that naturally infects the airway epithelia as well as other tissues in the body. The advantages of using adenovirus in gene delivery include the facts that its life cycle has been well characterized, its genome may be easily manipulated in the laboratory, and recombinant viruses are readily grown to high titers. In addition, adenovirus has a wide host cell range that includes non-dividing cells in vitro and in vivo. It is possible to achieve efficient gene expression in quiescent and differentiated cells. Finally, adenovirus is a relatively benign human virus that is associated with mild disease, and importantly is not associated with the development of any human malignancy.

However, several disadvantages exist for the use of adenovirus as a vector for long term gene transfer. First, it is evident from animal studies that adenovirus elicits an inflammatory response shortly after infection, and a subsequent cytotoxic T cell response directed against virus-infected cells [reviewed in Wold (1999) Human Press, Totowa, N.J.]. The result is immune clearance of virus-infected cells and extinction of expression of any foreign gene introduced by the recombinant viral vector. In the context of gene therapy in which repeated application of adenovirus-derived vectors may be required for continued treatment of certain diseases, the rapid immune response to adenovirus infection severely compromises the use of this system for long term gene therapy. It appears likely that the expression of adenovirus encoded proteins leads to immune recognition [Tripathy et al. (1996) Nat. Med. 2:545–50; Yang et al. (1996) J. Virol. 70:7209–12]. A second disadvantage is that the Ad has no direct means to persist in infected cells [Benihoud et al. (1999) Curr Opin Biotechnol 10:440–7; Brenner (1999) Blood 94:3965–7; Kochanek (1999) Hum. Gene. Ther. 10:2451–9], thus further limiting its use for long term gene therapy.

To avoid some of the problems associated with using adenovirus in gene transfer, one approach of the prior art has been to generate "gutted" adenoviruses which lack all adenovirus coding regions. While gutted adenoviruses have the advantage of allowing efficient gene transfer as well as minimizing an adverse immune response, they nonetheless require serial passage, and stuffer fragments to maintain a certain genome size which allows for efficient propagation. Additionally, gutted adenoviruses are not stably integrated into the cell genome, thus limiting their use for long term gene transfer applications.

An alternative approach by the prior art to circumvent some of the limitations of adenovirus-based vectors has been to use adenovirus "hybrid" viruses which incorporate desirable features from adenovirus as well as from other types of viruses as a means of generating unique vectors with highly specialized properties. For example, viral vector chimeras were generated between adenovirus and adeno-associated virus (AAV) [Thrasher et al. (1995) Gene Ther. 2:481–485; Fisher et al. (1996) Hum. Gene Ther. 7:2079–2087; Lieber et al. (1999) J. Virol. 73:9314–9324; Liu et al. (1999) Gene Ther. 6:293–299]. However, generation of the adenovirus/adeno-associated virus vectors of the prior art is inefficient.

Thus, what is needed are compositions and methods for efficient generation of vectors that may be used in gene transfer applications which are exemplified by, but not limited to, gene therapy applications. Preferably, these compositions and methods should also be non-immunogenic and non-toxic, and should permit stable integration into cells.

SUMMARY OF THE INVENTION

The invention provides recombinant compositions and rapid and efficient methods for generating mini-adenovirus (mAd) vectors which are capable of introducing any nucleotide sequence of interest into a cell, including, but not limited to, in the applications of gene therapy. The invention provides recombinant vectors including adenovirus/adeno-associated virus (Ad/AAV) vectors and mAd vectors, as well as cells containing these vectors. The unique configuration of the invention's parental Ad/AAV hybrid vectors overcomes the inefficiency of the prior's methods of generating mAd vectors. Furthermore, the methods of the invention provide an improvement to the methods of generating mAd vectors which are capable of stably packaging and transducing nucleotide sequences of interest.

In one embodiment, the invention provides a recombinant vector, comprising in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence. In a preferred embodiment, the vector further comprises an adeno-associated virus terminal repeat D sequence operably linked to the adeno-associated virus terminal repeat sequence to form adeno-associated virus terminal repeat-DD sequence. In another preferred embodiment, the vector further comprises an adeno-associated virus terminal repeat D sequence operably linked to the 5' end of the nucleotide sequence of interest. In yet another preferred embodiment, the packaging sequence is linked to the 5' end or the 3' end of the nucleotide sequence of interest. In yet another preferred embodiment, the nucleotide sequence of interest comprises adeno-associated virus rep gene region. While not limiting the invention to a particular type of nucleotide sequence, in another preferred embodiment, the nucleotide sequence of interest comprises a reporter gene. Without intending to limit the invention to a particular reporter gene, in a more preferred embodiment, the reporter gene is selected from green fluorescent protein gene, *E. coli* .beta.-galactosidase gene, human placental alkaline phosphatase gene, and chloramphemcol acetyltransferase gene. In an alternative preferred embodiment, the vector lacks one or more adenovirus genes. In a more preferred embodiment, the vector is a gutted adenovirus vector. In another alternative preferred embodiment, the vector lacks one or more adenovirus early gene region selected from E1, E2, E3, and E4 gene regions. In a more preferred embodiment, the vector lacks the E1 gene region. In yet a more preferred embodiment, the vector lacks the E1 gene region and further lacks the E3 gene region. In an alternative preferred embodiment, the vector lacks the E3 gene region. In another alternative preferred embodiment, the vector lacks the E4 gene region. In an alternative preferred embodiment, the vector lacks the E2 gene region.

The invention also provides a recombinant adenovirus comprising a recombinant vector, wherein the recombinant vector comprises in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence.

The invention additionally provides a cell comprising a recombinant vector, wherein the recombinant vector comprises in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence. Without intending to limit the cell to any particular type or source, in one embodiment, the cell is a cell line. In a preferred embodiment, the cell line is selected from a HeLa-derived cell line, A549-derived cell line, 293-derived cell line, HepG2-derived cell line, COS1-derived cell line, HMEC-derived cell line, KB-derived cell line, JW-22-derived cell line, Neo6-derived cell line, and C12-derived cell line. In an alternative embodiment, the cell is a primary cell. In a preferred embodiment, the primary cell is a human endothelial cell. In another alternative embodiment, the cell is contained in a mammal. In a more preferred embodiment, the mammal is selected from mouse and human. In an alternative embodiment the vector lacks adenovirus E1 gene region, and the cell is capable of expressing adenovirus E1 gene region. In a preferred embodiment, the cell is a 293-derived cell. In another alternative embodiment, the vector lacks adenovirus E1 gene region and further lacks adenovirus E3 gene region. In a preferred embodiment, the cell is a 293-derived cell. In yet another alternative embodiment, the vector lacks adenovirus E3 gene region. In a further alternative embodiment, the vector lacks adenovirus E4 gene region, and the cell is capable of expressing adenovirus E4 gene region. In a preferred embodiment, the cell is a W162-derived cell. In another embodiment, the vector lacks adenovirus E2 early gene region, and the cell is capable of expressing adenovirus E2 early gene region.

Also provided by the invention is a recombinant vector, comprising in operable combination: a) adeno-associated virus terminal repeat DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats. In one embodiment, the vector further comprises first and second inverted adeno-associated virus terminal repeat D sequences flanking the first and second inverted copies of the nucleotide sequence of interest, wherein the first and second inverted adeno-associated virus terminal repeat D sequences are flanked by the left and right inverted terminal repeats of adenovirus. In another embodiment, the vector further comprises a second adenovirus packaging sequence linked to one of the inverted terminal repeats. In yet another embodiment, the vector further comprises (e) first and second inverted adeno-associated virus terminal repeat D sequences flanking the first and second inverted copies of the nucleotide sequence of interest, wherein the first and second inverted adeno-associated virus terminal repeat D sequences are flanked by the left and right inverted terminal repeats of adenovirus, and (f) a second adenovirus packaging sequence linked to one of the inverted terminal repeats.

The invention also provides a recombinant adenovirus comprising a vector, wherein the vector comprises in operable combination: a) adeno-associated virus terminal repeat DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats.

Further provided herein is a cell comprising a vector, wherein the vector comprises in operable combination: a) adeno-associated virus terminal repeat DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats.

The invention additionally provides a first method comprising: a) providing: i) a first recombinant vector as described above [i.e., a recombinant vector, comprising in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence], wherein the first vector lacks one or more adenovirus early gene regions selected from E1, E2, E3, and E4 gene regions; and ii) a cell capable of expressing the one or more adenovirus early gene regions which are lacking from the first vector; b) introducing the first vector into the cell to produce a transformed cell; and c) culturing the transformed cell under conditions such that a second vector is produced, the second vector selected from the recombinant vector described above [i.e., a recombinant vector, comprising in operable combination: a) adeno-associated virus terminal repeat-DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats] and a recombinant vector comprising in operable combination: i) a nucleotide sequence of interest having a 5' end and a 3' end; ii) left and right inverted terminal repeats of adenovirus flanking the nucleotide sequence of interest; and iii) adenovirus packaging sequence linked to one of the inverted terminal repeats. In one embodiment, the recombinant vector further comprises first and second inverted copies of adeno-associated virus terminal repeat-DD sequence flanking the nucleotide sequence of interest, and optionally further comprises a second adenovirus packaging sequence linked to one of the inverted terminal repeats. In another preferred embodiment, invention provides a second method in which the cell is capable of expressing one or more Rep proteins, and the culturing results in expression of the one or more Rep proteins. In yet another preferred embodiment, the second vector is encapsidated. In a more preferred embodiment, the method further comprises d) recovering the encapsidated second vector. In yet a more preferred embodiment, the method further comprises e) purifying the recovered encapsidated second vector. In an alternative more preferred embodiment, the method further comprises e) administering the purified encapsidated second vector to a host cell. In a more preferred embodiment, the administering is under conditions such that the nucleotide sequence of interest in the encapsidated second vector is expressed. In an alternative more preferred embodiment, the host cell is a cultured cell. In another alternative more preferred embodiment, the host cell is comprised in a mammal. In a yet more preferred embodiment, the mammal is selected from mouse and human. In another preferred embodiment, expression of one or more Rep proteins are inducible.

Also provided herein is a third method, comprising: a) providing: i) a first recombinant vector as described above [i.e., a recombinant vector, comprising in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence], wherein the first vector lacks one or more adenovirus early gene regions selected from E1, E2, and E4 gene regions; ii) a cell capable of expressing one or more Rep proteins; and iii) helper adenovirus; b) introducing the first vector and genome of the helper adenovirus into the cell to produce a transformed cell; and c) culturing the transformed cell under conditions such that the transformed cell expresses the one or more Rep proteins, and a second vector is produced, the second vector selected from the recombinant vector described above [i.e., a recombinant vector, comprising in operable combination: a) adeno-associated virus terminal repeat-DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats] and a recombinant vector comprising in operable combination: i) a nucleotide sequence of interest having a 5' end and a 3' end; ii) left and right inverted terminal repeats of adenovirus flanking the nucleotide sequence of interest; and iii) adenovirus packaging sequence linked to one of the inverted terminal repeats. In a preferred embodiment, the recombinant vector further comprises first and second inverted copies of adeno-associated virus terminal repeat D sequence flanking the nucleotide sequence of interest, and optionally further comprises a second adenovirus packaging sequence linked to one of the inverted terminal repeats. In a more preferred embodiment, the cell lacks expression of the one or more adenovirus early gene regions which are lacking from the first vector.

The invention provides yet a fourth method, comprising: a) providing: i) a first recombinant vector of as described above [i.e., a recombinant vector, comprising in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence], wherein the first vector lacks one or more adenovirus early gene regions selected from E1, E2, and E4 gene regions; ii) a cell capable of expressing the one or more adenovirus early gene regions which are lacking from the first vector; and iii) adeno-associated virus; b) introducing the first vector and genome of the adeno-associated virus into the cell to produce a transformed cell; and c) culturing the transformed cell under conditions such that a second vector is produced, the second vector selected from the recombinant vector described supra [i.e., a recombinant vector, comprising in operable combination: a) adeno-associated virus terminal repeat-DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats] and a recombinant vector comprising in operable combination: i) a nucleotide sequence of interest having a 5' end and a 3' end; ii) left and right inverted terminal repeats of adenovirus flanking the nucleotide sequence of interest; and iii) adenovirus packaging sequence linked to one of the inverted terminal repeats. In one preferred embodiment, the recombinant vector further comprises first and second inverted copies of adeno-associated virus terminal repeat D sequence flanking the nucleotide sequence of interest, and optionally further comprises a second adenovirus packaging sequence linked to one of the inverted terminal repeats.

Also provided by the invention is a fifth method comprising: a) providing: i) a first recombinant vector as described above [i.e., a recombinant vector, comprising in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence], wherein the first vector lacks adenovirus E3 early gene region; and ii) a cell; b) introducing the first vector into the cell to produce a transformed cell; and c) culturing the transformed cell under conditions such that a second vector is produced, the second vector selected from the recombinant vector described supra [i.e., a recombinant vector, comprising in operable combination: a) adeno-associated virus terminal repeat DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats] and a recombinant vector comprising in operable combination: i) a nucleotide sequence of interest having a 5' end and a 3' end; ii) left and right inverted terminal repeats of adenovirus flanking the nucleotide sequence of interest; and iii) adenovirus packaging sequence linked to one of the inverted terminal repeats. In one preferred embodiment, the recombinant vector further comprises first and second inverted copies of adeno-associated virus terminal repeat D sequence flanking the nucleotide sequence of interest, and optionally further comprises a second adenovirus packaging sequence linked to one of the inverted terminal repeats. In one preferred embodiment, the invention provides a sixth method wherein the cell is capable of expressing one or more Rep proteins, and the culturing results in expression of the one or more Rep proteins.

The invention provides a seventh method comprising: a) providing: i) a first recombinant vector as described above [i.e., a recombinant vector, comprising in operable combination: a) a nucleotide sequence of interest having a 5' end and a 3' end; b) left and right inverted terminal repeats of adenovirus flanking the nucleotide sequence of interest; c) adenovirus packaging sequence linked to one of the inverted terminal repeats; and d) a first adeno-associated virus terminal repeat sequence operably linked to the 3' end of the nucleotide sequence of interest, wherein the vector lacks a second adeno-associated virus terminal repeat sequence], wherein the nucleotide sequence of interest in the first vector comprises adeno-associated virus rep gene region; and ii) a cell; b) introducing the first vector into the cell to produce a transformed cell; and c) culturing the transformed cell under conditions such that the transformed cell expresses one or more Rep proteins, and a second vector is produced, the second vector selected from the recombinant vector described above [i.e., a recombinant vector, comprising in operable combination: a) adeno-associated virus terminal repeat-DD sequence; b) first and second inverted copies of a nucleotide sequence of interest flanking the adeno-associated virus terminal repeat-DD sequence; c) left and right inverted terminal repeats of adenovirus flanking the first and second inverted copies of the nucleotide sequence of interest; and d) first adenovirus packaging sequence linked to one of the inverted terminal repeats] and a recombinant vector comprising in operable combination: i) a nucleotide sequence of interest having a 5' end and a 3' end; ii) left and right inverted terminal repeats of adenovirus flanking the nucleotide sequence of interest; and iii) adenovirus packaging sequence linked to one of the inverted terminal repeats. In one preferred embodiment, the recombinant vector further comprises first and second inverted copies of adeno-associated virus terminal repeat D sequence flanking the nucleotide sequence of interest, and optionally further comprises a second adenovirus packaging sequence linked to one of the inverted terminal repeats. In a more preferred embodiment, the first vector lacks one or more adenovirus early gene regions selected from E1, E2, and E4 gene regions, and the cell is capable of expressing the adenovirus early gene region which is lacking from the first vector. In an alternative more preferred embodiment, the first vector lacks adenovirus E3 gene region.

DEFINITIONS

Figure 1:
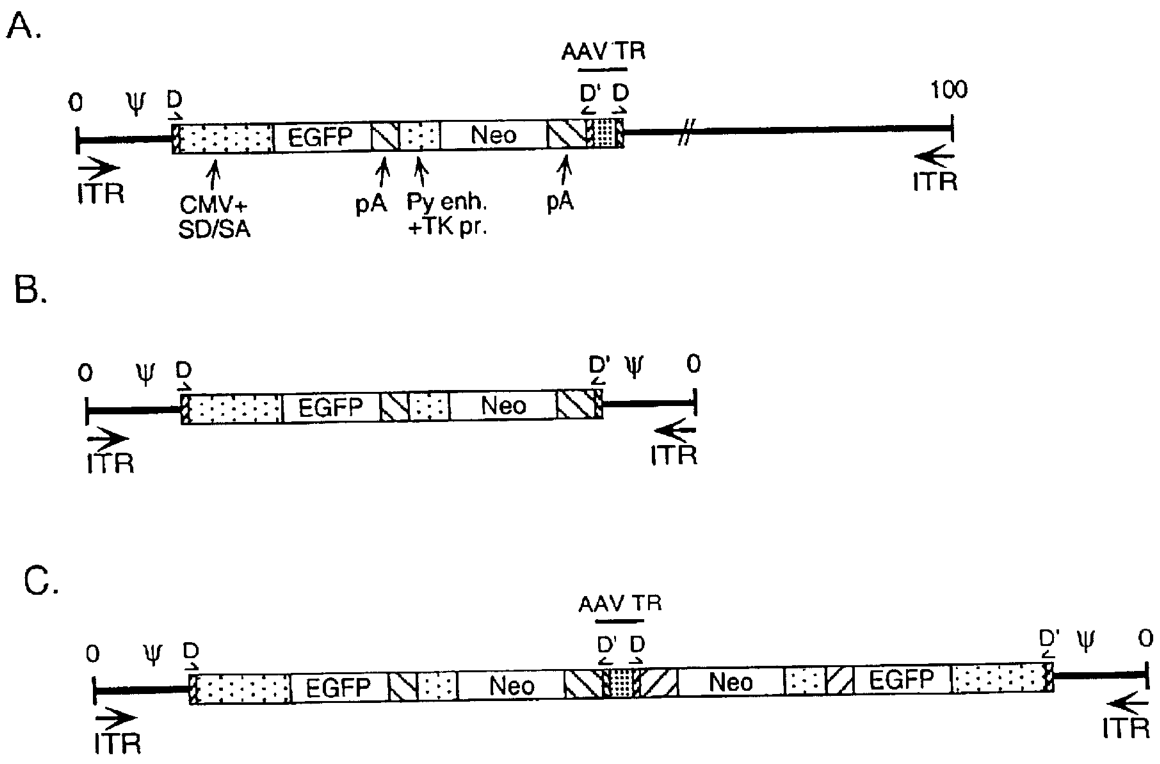
FIG. 1 shows viral genomic maps of exemplary (A) Ad/AAV hybrid virus, (B) monomeric mini-adenovirus (mAd), and (C) dimeric mAd.

To facilitate understanding of the invention, a number of terms are defined below.

The term "recombinant vector" as used herein refers to a nucleic acid molecule which is capable of transferring nucleic acid sequences contained therein into a cell, and which is produced by means of molecular biological techniques. Recombinant vectors are exemplified by linear DNA, plasmid DNA, viruses, etc.

The terms "operably linked," "in operable combination," and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest into mRNA and/or the synthesis of a polypeptide encoded by the nucleotide sequence of interest. Similarly, operably linking adenovirus terminal repeats (TRs) to a nucleotide sequence of interest means that the sequences are linked in such a way such that the adenovirus TRs are capable of directing replication of the nucleotide sequence of interest. Also, operably linking an adenovirus packaging sequence to a nucleotide sequence of interest refers to linkage of these sequences such that the adenovirus packaging sequence is capable of directing packaging of the nucleotide sequence of interest into an encapsidated adenovirus virion.

The term "inverted" when made in reference to two nucleotide sequences means that the two sequences are linked (in the presence or absence of intervening nucleotides) such that the first sequence is in a 5' to 3' orientation relative to the second sequence which is in a 3' to 5' orientation, where the 3' ends of the first and second sequences are arranged in proximity to one another, while the 5' ends of the first and second sequences are separated by the 3' ends of the first and second sequences. Thus, the term "inverted terminal repeats" refers to a first and second terminal repeats whose 3' ends are linked (in the presence or absence of intervening nucleotides) together.

The term "oligonucleotide" as used herein is defined as a molecule containing from two (2) to one hundred (100), preferably from ten (10) to fifty (50), and more preferably from twenty (20) to thirty (30) deoxyribonucleotides or ribonucleotides. Oligonucleotides may be generated by several methods known in the art including, but not limited to, chemical synthesis, DNA replication, reverse transcription, restriction digestion, polymerase chain reaction, and the like.

The term "gene" refers to a DNA sequence that comprises regulatory and coding sequences necessary for the production of RNA or a polypeptide. The term "gene" encompasses both cDNA and genomic forms of a given nucleotide sequence. For example, the term "gene" includes, but is not limited to the coding region of a structural gene as well as sequences located adjacent to the coding region on both the 5' and 3' ends for a distance of at least several kilobases on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. A genomic form or clone of a gene contains coding sequences, termed "exons," alternating with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

As used herein, the term "purified" refers to molecules, either nucleic or amino acid sequences, that are removed from their natural environment, isolated or separated. "Substantially purified" molecules are at least 60% free, preferably at least 75% free, and more preferably at least 90% free from other components with which they are naturally associated. The terms "purify" and "purifying" denote carrying out one or more steps to generate a purified molecule.

The terms "flanking," and "flank" when made in reference to a first and second nucleotide sequences in relation to a third nucleotide sequence mean that the first nucleotide sequence is linked to the 5' end of the third sequence, and the second nucleotide sequence is linked to the 3' end of the third sequence. For example, the configuration of left and right inverted terminal repeats of adenovirus flanking a nucleotide sequence of interest means that the left inverted terminal repeat is linked to the 5' end of the nucleotide sequence of interest, and the right inverted terminal repeat is linked to the 3' end of the nucleotide sequence of interest.

The terms "lack" and "lacking" a nucleotide sequence when made in reference to a vector means that the vector contains at least one deletion (i.e., absence of one or more nucleotides) in the nucleotide sequence. Deletions may be continuous (i.e., uninterrupted) or discontinuous (i.e., interrupted). Deletions may lie in a coding sequence or a regulatory sequence. A deletion can be a partial deletion (i.e., involving removal of a portion ranging in size from one (1) nucleotide residue to the entire nucleic acid sequence minus one nucleic acid residue) or a total deletion of the nucleotide sequence. Deletions are preferred which prevent the production of at least one expression product encoded by the nucleotide sequence. For example, a vector which lacks an adenovirus E1 gene region refers to a vector which contains at least one deletion in the E1 gene region. Preferably, though not necessarily, the deletion prevents the production of at least one of the multiple proteins encoded by the E1 gene region.

The term "virus" refers to obligate, ultramicroscopic, intracellular parasites incapable of autonomous replication (i.e., replication requires the use of the host cell's machinery).

The terms "replication defective virus," "replication-incompetent virus," and "defective virus" refer to a virus which is substantially incapable of autonomous replication, but is nevertheless capable of being replicated and encapsidated in a "complementation cell," i.e., a cell which provides the virus in trans with the product(s) for which it is defective so as to generate a virus particle. Preferably the defective virus is "infectious," i.e., capable of delivering a nucleotide sequence contained therein into the cell.

A "helper virus" refers to a virus which is replication-competent in a particular host cell (e.g., the host may provide Ad gene products such as E1 proteins for a helper adenovirus). This replication-competent virus is used to supply in trans functions (e.g., proteins) which are lacking in a second replication-incompetent virus; the first replication-competent virus is said to "help" the second replication-incompetent virus thereby permitting the propagation of the second viral genome in the cell containing the helper and second viruses. The helper virus is preferably an adenovirus of avian, bovine, ovine, murine, porcine, canine, simian, and human origin. In a preferred embodiment, the helper virus is a human adenovirus (e.g., Example 4).

The term "free of contamination with helper virus" when in reference to a sample that is suspected of containing helper virus and adenovirus, means that the number of infectious particles of helper virus in the sample is from zero % to 1%, more preferably from zero % to 0.5%, and most preferably from zero % to 0.05%, when compared to the number of infectious particles of adenovirus in the same sample.

The term "adeno-associated virus rep gene region" refers to a nucleotide sequence which is derived from an adeno-associated virus, and which encodes one or more of Rep78 and Rep68 polypeptides that are required in trans for AAV replication, and for efficient AAV replication and excision from the host genome [Berns et al. (1995) Ann N Y Acad Sci 772:95–104; Muzyczka (1992) Curr. Top. Microbiol. Immunol. 158:97–129; Rolling and Samulski (1995) Mol. Biotechnol. 3:9–15]. In a preferred embodiment, the adeno-associated virus rep gene region is derived from AAV2 strain.

The term "Rep-mediated excision" means excision of a fragment of a nucleotide sequence which is mediated by one or more Rep proteins.

The term "derived cell" when in relation to a parent cell refers to a cell which is obtained from the parent cell in the absence or presence of modifications to the parent cell, including, but not limited to, infection with virus, transfection with DNA sequences, mutagenesis (e.g., using chemicals, radiation, etc.), and selection of the parent cells.

The term "capable of expressing a protein" when made with reference to a cell means that the cell expresses the protein when all the elements necessary for the protein's expression are present. For example, where a cell contains a gene encoding the Rep protein under control of an inducible promoter, the cell is referred to as being capable of expressing Rep protein since the cell will express Rep protein when the promoter inducing agent is supplied to the cell.

DESCRIPTION OF THE INVENTION

The invention provides recombinant vectors including adenovirus/adeno-associated virus (Ad/AAV) vectors and mini-adenovirus (mAd) vectors, as well as cells containing these vectors. Further, the invention provides rapid and efficient methods for generating mAd vectors which are capable of introducing any nucleotide sequence of interest into a cell, including, but not limited to, in the applications of gene therapy. The unique configuration of the invention's parental Ad/AAV hybrid vectors overcomes the inefficiency of the prior's methods of generating mAd vectors by exploiting the unique genetic characteristics of AAV TRs when used in combination with Rep-mediated excision to substantially improve the levels of excision of the hybrid vectors from adenovirus genomes, thereby yielding mAd vectors which are preferably devoid of all coding viral sequences. The methods of the invention provide an improvement to the methods of generating mAd vectors which are capable of stably packaging and transducing nucleotide sequences of interest.

The vectors provided herein are easily manufactured, and combine the advantages of adenovirus (high titer, high infectivity, large capacity, lack of association with human malignancy) with the integration capability of AAV, making them particularly suitable for stable gene transfer which is useful in, for example, gene therapy approaches.

A further advantage of the invention's vectors is that, by virtue of containing AAV TR and D sequences that flank the gene of interest, they are expected by the inventors to integrate into cellular chromosomal DNA. Integration is important for stable gene transfer into cells. Thus, the invention's vectors are preferred over the prior art's first generation adenovirus vectors where adenovirus, as an episomal vector, would otherwise be lost after several cell divisions.

Another advantage of the vectors provided herein is that they are packaged efficiently into stable virus particles even when using relatively small DNA molecules. In contrast, in several previous attempts to generate adenoviruses containing smaller than unit length viral genomes, the packaging process was found to be inefficient when DNA molecules were below 75% of the Ad genome size [Bett et al. (1993) J. Virol 67:5911–21; Parks and Graham (1997) J. Virol. 71:3293–8].

Yet another advantage of the vectors provided herein is that they are less cytotoxic than first generation adenovirus vectors since no adenovirus genes are expressed within transduced cells. In other words, like "gutted" adenoviruses, the invention's vectors are devoid of all adenovirus genes whose expression may cause immunological or toxic side effects.

The mAd vectors of the invention provide distinct advantages over the new generation "gutted" adenoviruses. First, the invention's mAd generation does not require stuffer fragments to maintain a certain genome size and does not require serial passage in cell lines. Second, the invention's mAd genomes retain all or part of the AAV TRs, thereby providing the potential for stable integration and long term gene expression. Third, the invention's mAd vectors may be used to obtain efficient packaging of mAd with a small genome size.

The vectors (e.g., plasmids and viruses) of the present invention are distinguished from those of the prior art [Thrasher et al. (1995) Gene Ther. 2:481–485; Fisher et al. (1996) Hum. Gene Ther. 7:2079–2087; Lieber et al. (1999) J. Virol. 73:9314–9324; Liu et al. (1999) Gene Ther. 6:293–299] in that the prior art's vectors were designed to generate recombinant AAV vectors using vectors with two complete (i.e., full-length) AAV TRs flanking the nucleotide sequence of interest. In contrast, the instant invention's parental Ad/AAV hybrid vectors require only one AAV TR sequence, at either the 5' or 3' ends of the nucleotide sequence of interest. Furthermore, the prior art did not employ a AAV TR DD sequence to generate their recombinant AAV, vectors but rather used AAV TR sequences that contain a single D sequence.

The invention is further described under (A) Adenovirus/Adeno-Associated Virus (Ad/AAV) Hybrid Vectors, (B) Mini-Adenovirus (mAd) Vectors, and (C) Gene Transfer Using Recombinant Vectors.

A. Adenovirus/Adeno-associated Virus (Ad/AAV) Hybrid Vectors

The recombinant Ad/AAV hybrid vectors of the invention contain nucleotide sequences derived from each of adenovirus and adeno-associated virus genome. In particular, the vectors of the invention exploit the unique features of the AAV terminal repeat (TR) within the context of an Ad/AAV as a strategy for rapid and efficient generation of mAd. Data provided herein demonstrates that excision and generation of mAd from the parental Ad/AAV hybrid vector was achieved in the exemplary 293 cells through recombination, but without selection for mAd production. Analysis of mAd isolated from 293 cells indicated that mAd DNA exists as monomer and dimer forms within the recombinant viral capsid. In a preferred embodiment, formation of recombinant mAd may be made more rapid and more efficient by using Rep-mediated excision utilizing the AAV terminal repeat sequences present in the Ad/AAV hybrid virus genome. Data presented herein demonstrates that mAd generated using the invention's methods were infectious and capable of transferring functional genes to recipient cells.

The parental Ad/AAV hybrid vectors are depicted by the exemplary vector of FIGS. 1A, 7A and are characterized by containing a nucleotide sequence of interest flanked by left and right inverted terminal repeats (ITRs) of adenovirus, an adenovirus packaging sequence, and an adeno-associated virus terminal repeat (AAV TR) sequence which is preferably, though not necessarily, linked to the 3' end of the nucleotide sequence of interest. The invention's parental Ad/AAV hybrid vectors which contain the AAV TR sequences in a unique configuration are particularly useful for generating mAd vectors (described infra). In particular, the configuration of the invention's parental Ad/AAV hybrid vectors exploits the genetic characteristics of the AAV TRs when employed in the context of Rep-excision.

1. Adenovirus Sequences

The invention's parental Ad/AAV vectors (and mAd vectors) are contemplated to contain adenovirus sequences which may be derived from any adenovirus. The term "adenovirus" refers to a double-stranded DNA adenovirus of animal origin, preferably of avian, bovine, ovine, murine, porcine, canine, simian, and human origin. Avian adenoviruses are exemplified by serotypes 1 to 10 which are available from the ATCC, such as, for example, the Phelps (ATCC VR-432), Fontes (ATCC VR-280), P7-A (ATCC VR-827), IBH-2A (ATCC VR-828), J2-A (ATCC VR-829), T8-A (ATCC VR-830), and K-11 (ATCC VR-921) strains, or else the strains designated as ATCC VR-831 to 835. Bovine adenoviruses are illustrated by those available from the ATCC (types 1 to 8) under reference numbers ATCC VR-313, 314, 639–642, 768 and 769. Ovine adenoviruses include the type 5 (ATCC VR-1343) or type 6 (ATCC VR-1340). Murine adenoviruses are exemplified by FL (ATCC VR-550) and E20308 (ATCC VR-528). Porcine adenovirus (5359) may also be used. Adenoviruses of canine origin include all the strains of the CAVI and CAV2 adenoviruses [for example, Manhattan strain or A26/61 (ATCC VR-800) strain]. Simian adenoviruses are also contemplated, and they include the adenoviruses with the ATCC reference numbers VR-591–594, 941–943, and 195–203. Human adenoviruses, of which there greater than fifty (50) serotypes are known in the art, are also contemplated, including the Ad2, Ad3, Ad4, Ad5, Ad7, Ad9, Ad12, Ad17, and Ad40 adenoviruses. In a preferred embodiment, the adenovirus is human. In a more preferred embodiment, the human adenovirus is selected from Ad2 and Ad5. In a yet more preferred embodiment the human adenovirus is Ad5.

Adenoviruses of animal origin can be obtained, for example, from strains deposited in collections, then amplified in competent cell lines and modified as required. Techniques for producing, isolating and modifying adenoviruses have been described in the literature and may be used within the scope of the present invention [Akli et al., Nature Genetics 3 (1993) 224; Stratford-Perricaudet et al., Human Gene Therapy 1 (1990) 241; patent EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO 91/18088, WO 90/09441, WO 88/10311, WO 91/11525]. These different viruses can then be modified, for example, by deletion, substitution, addition, etc. The complete genome sequences have been determined for human adenovirus type 2 (GenBank Accession No. J01917; SEQ ID NO:3), human adenovirus type 5 (GenBank Accession No. M73260, SEQ ID NO:4; and GenBank Accession No. NC_001406, SEQ ID NO:5), human adenovirus type 12 (GenBank Accession No. NC_001460, X73487; SEQ ID NO:25); human adenovirus type 17 (GenBank Accession No. NC_002067, AF108105; SEQ ID NO:26), and human adenovirus type 40 (GenBank Accession No. L19443; SEQ ID NO:27).

The term adenovirus "left and right inverted terminal repeats" refers to two copies of an adenovirus sequence which are required for replication of a nucleotide sequence of interest disposed therebetween. The left and right inverted terminal repeats (ITRs) are short elements located at the 5' and 3' termini of the linear Ad genome, respectively, and are required for replication of the viral DNA. Referring to the exemplary human Ad5 genome sequence of GenBank Accession No. M73260 (SEQ ID NO:4), the left ITR is located between 1–103 bp in the Ad genome (also referred to as 0–0.3 mu). The right ITR is located from ~36,000 bp to the end of the genome (also referred to as 99.7–100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR (LITR) as an arrow extending from the 5' end of the genome, the head of the 5' or left ITR is located at mu 0 and the tail of the left ITR is located at 0.3 mu (further, the head of the left ITR is referred to as the 5' end of the left ITR and the tail of the left ITR is referred to as teh 3' of the left ITR. The tail of the right or 3' ITR is located at mu 100 and the head of the right ITR is located at ~mu 99.5; the head of the right ITR is referred to as the 5' end of the right ITR and the tail of the right ITR is referred to as the 3' end of the right ITR (RITR). In the linear Ad genome, the ITRs face each other with the head of each ITR pointing inward toward the bulk of the genome. When arranged in a "tail to tail orientation" the tails of each ITR (which comprise the 3' end of the LITR and the 5' end of the RITR) are located in proximity to one another while the heads of each ITR are separated and face outward.

The terms "adenovirus packaging sequence" and "adenovirus Ψ sequence" refer to a sequence which is required for encapsidation of the mature linear adenovirus genome into adenovrius particles. The adenovirus packaging sequence comprises five or more (AI–AVII) packaging signals and is required for encapsidation of the mature linear genome; referring to the exemplary human Ad5 genome sequence of GenBank Accession No. M73260 (SEQ ID NO:4), the packaging signals are located from ~194 to 358 bp (about 0.5–1.0 mu). Preferably, the adenovirus packaging sequence is placed in proximity to either the LITR or RITR. Furthermore, the adenovirus packaging sequence may be linked to either the 5' end (FIGS. 1A, 7A) or the 3' end of the nucleotide sequence of interest.

2. Adeno-Associated Virus Sequences

The parental Ad/AAV hybrid vectors (and mAd vectors) provided herein are contemplated to contain adeno-associated virus sequences. The terms "adeno-associated virus" and "AAV" refer to an adeno-associated virus of any serotype including AAV1, AAV2, AAV3 and AAV4 strain. In a preferred embodiment, the adeno-associated virus is of AAV2 strain.

The genome of the AAVs has been cloned, sequenced and characterized. For example, the genomic sequences of AAV2 are provided in GenBank accession No. J01901 (SEQ ID NO:1) and GenBank No. NC_001401 (SEQ ID NO:2). In general, the AAV genome comprises about 4,700 bases and contains, at each end, an inverted repeat region (ITR) of approximately 145 bases, serving as the origin of replication of the virus. The remainder of the genome is divided into 2 essential regions: the left-hand part of the genome, containing the rep gene involved in replication of the virus and expression of the viral genes and; the right-hand part of the genome, containing the cap gene encoding the capsid proteins of the virus.

In particular, the invention's parental Ad/AAV hybrid vectors are characterized by, among other things, containing an adeno-associated virus terminal repeat sequence. The terms "adeno-associated virus terminal repeat," "AAV TR," "intact AAV TR," and "full-length AAV TR" are used interchangeably to refer to a nucleotide sequence which is derived from an AAV and which, in the presence of either Rep 68 or Rep 78, is sufficient for site-specific viral DNA integration. Alternatively, the AAV TR refers to a nucleotide sequence which is derived from an AAV and which is involved in AAV DNA replication, AAV DNA excision, or AAV DNA packaging into virus. In a preferred embodiment, the AAV TR is derived from AAV2 strain and is exemplified by the 145-bp sequence [5'-ttggccactc cctctctgcg cgctcgctcg ctcactgagg ccgggcgacc aaaggtcgcc cgacgcccgg gctttgcccg ggcggcctca gtgagcgagc gagcgcgcag agagggagtg gccaactcca tcactagggg ttcct-3' (SEQ ID NO:6)] from nucleotide 1 to nucleotide 145 of the AAV2 genomic sequence of GenBank No. J01901 (SEQ ID NO:1).

In one preferred embodiment, the parental Ad/AAV hybrid vectors of the invention further contain an adeno-associated virus terminal repeat D sequence operably linked to the AAV TR sequence to form adeno-associated virus terminal repeat DD (AAV TR-DD) sequence [Xiao et al. (1997) J. Virol. 71:941–948 and Ryan et al. (1996) J. Virol. 70:1542–1553].

The terms "adeno-associated virus terminal repeat D sequence," "AAV TR-D sequence," and "D sequence" are equivalent and refer to a nucleotide sequence which is located at the 3' end of either the flip configuration [A/C/C'/B/B'/A'/D] of the palindromic AAV TR sequence or the flop configuration [A/B/B'/C/C'/A'/D] of the palindromic AAV TR sequence; the "flip" and "flop" configurations differ in the location of the B and B' sequences relative to each other. In a preferred embodiment, the adeno-associated virus terminal repeat D sequence is derived from the AAV2 strain and is exemplified by the 20-bp sequence [5'-ctcca tcactagggg ttcct-3' (SEQ ID NO:7)] from nucleotide 126 to nucleotide 145 of AAV2 genomic sequence of GenBank No. J01901 (SEQ ID NO:1).

The terms "adeno-associated virus terminal repeat DD sequence" and "AAV TR-DD" interchangeably refer to an AAV sequence which functions as a cis-acting element in AAV when Rep proteins and adenovirus helper functions are supplied in trans as described in Xiao et al. (1997) supra and Ryan et al. (1996) supra. The AAV TR DD comprises (a) the AAV TR sequence that contains a D sequence at its 3' end, and (b) an inverted D sequence operably linked to the 5' end of the AAV TR sequence. Thus, the AAV TR-DD contains two inverted D sequences flanking either the flip configuration [A/C/C'/B/B'/A'/D] of the palindromic sequence or the flop configuration [A/B/B'/C/C'/A'/D] of the palindromic sequence. Thus, the AAV TR-DD may have the sequence D'/A/B/B'/C/C'/A'/D or D'/A/B'/B/C/C'/A'/D. In a preferred embodiment, the AAV TR-DD is derived from AAV2 strain and is exemplified by the 165-bp sequence [5'-aggaa cccctagtga tggag ttggccactc cctctctgcg cgctcgctcg ctcactgagg ccgggcgacc aaaggtcgcc cgacgcccgg gctttgcccg ggcggcctca gtgagcgagc gagcgcgcag agagggagtg gccaactcca tcactagggg ttcct-3' (SEQ ID NO:8)] of the AAV2 genomic sequence of GenBank No. J01901 (SEQ ID NO:1).

In a more preferred embodiment, the parental Ad/AAV hybrid vectors of the invention further contain an adeno-associated virus terminal repeat D sequence operably linked to the 5' end of the nucleotide sequence of interest. The presence of this additional D sequence is preferred where, for example, the parental Ad/AAV hybrid vector is used to generate mAd vectors in via recombination with a first D sequence that is located at the 3' end of the nucleotide sequence of interest in the absence of Rep-mediated excision of the parental vector.

3. Nucleotide Sequences of Interest

The parental Ad/AAV hybrid vectors (and mAd vectors) of the invention are contemplated to contain a nucleotide sequence of interest. The term "nucleotide sequence of interest" and "polypeptide of interest" refer to any nucleotide sequence and polypeptide sequence, respectively, the manipulation of which may be deemed desirable for any reason by one of ordinary skill in the art.

Nucleotide sequences of interest may be "endogenous" (i.e., "wild-type") or "heterologous" (i.e., "foreign"). The terms "endogenous" and "wild-type" nucleotide sequence and polypeptide sequence refer to a nucleotide and polypeptide sequences, respectively, which have the characteristics of that nucleotide and polypeptide sequence when isolated from a naturally occurring source. For example, a wild-type gene is that which is most frequently observed in a population and is thus arbitrarily designated the "normal" or "wild-type" form of the gene.

In contrast, the term "heterologous" nucleotide and polypeptide sequences refers to sequences which are not endogenous to the cell into which they are introduced. For example, heterologous DNA includes a nucleotide sequence which is ligated to, or is manipulated to become ligated to, a nucleic acid sequence to which it is not ligated in nature, or to which it is ligated at a different location in nature. Heterologous nucleic acid and polypeptide sequences also include a "modified" or "mutant" form of an endogenous nucleotide and polypeptide sequence, respectively. The term "modified" and "mutant" when made in reference to nucleotide and polypeptide sequences refers to a nucleotide sequence or polypeptide sequence which displays modifications in sequence and/or functional properties (i.e., altered characteristics) when compared to the wild-type nucleotide or polypeptide sequences, respectively. It is noted that naturally-occurring mutants can be isolated; these are identified by the fact that they have altered characteristics when compared to the wild-type nucleotide or polypeptide sequence. Generally, although not necessarily, heterologous DNA encodes RNA and proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc. Yet another example of a heterologous DNA includes a nucleotide sequence which encodes a ribozyme which is produced in the cell into which it is introduced, and which is ligated to a promoter sequence to which it is not naturally ligated in that cell.

In one preferred embodiment, the heterologous nucleotide sequence of interest contains an adeno-associated virus rep gene region. In a more preferred embodiment, the AAV rep gene region encodes one or more of the Rep 68 and Rep78 proteins. As further described below, parental Ad/AAV vectors of the invention which contain the AAV rep gene region are useful in more efficiently generating mAd vectors (as compared to vectors which lack expression of rep gene region) by facilitating excision of the mAd sequences from the adenovirus genome.

It is desirable, though not necessary, to include a reporter gene in the parental Ad/AAV hybrid vectors (and mAd vectors) of the invention in order to facilitate detection of the presence and/or expression of the vector sequences. The term "reporter gene" refers to a gene which encodes a reporter molecule (e.g., RNA, polypeptide, etc.) which is detectable in any detection system, including, but not limited to enzyme (e.g., ELISA, as well as enzyme-based histochemical assays), fluorescent, radioactive, and luminescent systems. Exemplary reporter genes include, for example, green fluorescent protein gene, *E. coli* β-galactosidase gene, human placental alkaline phosphatase gene, and chloramphenicol acetyltransferase gene. It is not intended that the present invention be limited to any particular detection system or label. However, in a preferred embodiment, the reporter gene is the green fluorescent protein gene used in plasmid pAd/AAV-EGFP-Neo (Example 2, infra).

The nucleotide sequence of interest may also include a sequence encoding a selectable marker. The terms "selectable marker" or "selectable gene product" as used herein refer to the use of a gene which encodes an enzymatic activity that confers resistance to an antibiotic or drug upon the cell in which the selectable marker is expressed. Selectable markers may be "positive"; i.e., genes which encode an enzymatic activity which can be detected in any mammalian cell or cell line. Examples of dominant selectable markers include, but are not limited to, (1) the bacterial aminoglycoside 3' phosphotransferase gene (also referred to as the neo gene) which confers resistance to the drug G418 in mammalian cells, (2) the bacterial hygromycin G phosphotransferase (hyg) gene which confers resistance to the antibiotic hygromycin, and (3) the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Selectable markers may be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin. In one preferred embodiment, the selectable marker gene is the neo gene in plasmid pAd/AAV-EGFP-Neo (Example 2, infra).

The invention contemplates nucleotide sequences of interest which include, but are not limited to, coding and regulatory sequences. The term "coding sequence" refers to a DNA sequence which encodes mRNA and/or a polypeptide. Examples of coding sequences of interest which encode a polypeptide include sequences encoding cytokines such as interferon alpha, interferon gamma, and interleukins; sequences encoding membrane receptors such as the receptors recognized by pathogenic organisms (viruses such as HIV, bacteria or parasites); sequences encoding coagulation factors such as factor VIII and factor IX; sequences encoding dystrophin; sequences encoding insulin; sequences encoding proteins which participate directly or indirectly in cellular ion channels, such as the cystic fibrosis transmembrane conductance regulator (CFTR) protein; sequences encoding a protein which is capable of inhibiting the activity of another protein, wherein the other protein is encoded by a pathogenic gene that is present in the genome of a pathogenic organism, or wherein the other protein is encoded by a cellular gene (e.g., oncogene) whose expression is deregulated; sequences encoding a protein that inhibits enzyme activity, such as $\alpha_1$-antitrypsin or a viral protease inhibitor; sequences encoding variants of pathogenic proteins which have been mutated so as to impair their biological function, such as, for example, trans-dominant variants of the TAT protein of the HIV virus which are capable of competing with the natural protein for binding to the target sequence, thereby preventing the activation of HIV; sequences encoding antigenic epitopes in order to increase the host cell's immunity; sequences encoding major histocompatibility complex (MHC) classes I and II proteins, as well as sequences encoding the proteins which are inducers of these MHC genes; sequences encoding cellular enzymes produced by pathogenic organisms; sequences encoding suicide genes which are exemplified by the TK-HSV-1 suicide gene and the cytosine deaminase gene.

In another alternative embodiment the nucleotide sequence of interest is a regulatory sequence. The term "regulatory sequence" refers to a nucleotide sequence which controls some aspect of the expression of nucleic acid sequences and which does not encode mRNA and/or a polypeptide. For example, a promoter is a regulatory element which facilitates the initiation of transcription of an operably linked coding region. Other regulatory elements are splicing signals, polyadenylation signals, termination signals, enhancer elements, etc. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types. Viral promoter which are particularly useful include those from the genes E1A, and MLP. Additionally, the SV40 early gene enhancer is very active in a wide variety of cell types from many mammalian species and has been widely used for the expression of proteins in mammalian cells. Other examples of promoter/enhancer elements active in a broad range of mammalian cell types are those from the human elongation factor 1$\alpha$ gene; the long terminal repeats of the Rous sarcoma virus (LTR-RSV): the regulatory sequences of the metallothionein gene; the immunoglobulin gene control region which is active in lymphoid cells; mouse mammary tumor virus control region which is active in testicular, breast, lymphoid and mast cells; the human beta actin promoter; tRNA promoter; 5S rRNA promoters; histone gene promoters; CMV promoter (located between positions +1 to +596 in vector plasmid pCR3 from Invitrogen); RSV promoter (can be isolated from vector plasmid pRc/RSV from Invitrogen); SV40 promoter (located between positions +3530 to +3192 in vector plasmid pCR3 from Invitrogen); PEPCK promoter; MT promoter, SR$\alpha$ promoter; P450 family promoters; GAL7 promoter; $T_7$ promoter having the 23-bp sequence (SEQ ID NO:9) 5'-TAATACGACTCACTATAGGGCGA-3'); $T_3$ promoter having the 24-bp sequence (SEQ ID NO:10) 5'-TTATTAACCCTCACTAAAGGGAAG-3'; SP6 promoter having the 23-bp sequence (SEQ ID NO:11) 5'-ATTTAGGTGACACTATAGAATAC-3'; and K11 promoter. The $T_7$ promoter, $T_3$ promoter, SP6 promoter and K11 promoter have been described in U.S. Pat. No. 5,591,601, the entire contents of which are incorporated by reference. In one preferred embodiment, the promoter is the CMV enhancer/promoter which was used to express EGFP in plasmid pAd/AAV-EGFP-Neo. In an alternative preferred embodiment, the promoter is the polyoma enhancer/TK promoter which was used to express Neo in plasmid pAd/AAV-EGFP-Neo. In yet another preferred embodiment, the promoter is the human small RNA H1 promoter which was used to express human factor VIII in plasmid pAd/AAV-FVIII (Example 2, infra).

Also included among regulatory sequences are signal sequences which direct a synthesized polypeptide sequence into the secretory pathways of the target cell. Signal sequences may be endogenous or heterologous with respect to the cell into which they are introduced.

In a preferred embodiment, the nucleotide sequence of interest (whether coding or regulatory) is therapeutic. The term "therapeutic nucleotide sequence" refers to a nucleic acid sequence which, or whose encoded mRNA and/or polypeptide product, reduces, delays, or eliminates undesirable pathologic effects in a cell, tissue, organ, or animal. The therapeutic nucleotide sequence may be homologous or heterologous with respect to the sequences of the target cell.

Homologous therapeutic nucleotide sequences are useful for expressing wild-type proteins where it is desirable to, for example, compensate for either insufficient expression of a wild-type protein product in the cell or to bring about expression of a mutant protein product whose biological activity is reduced relative to the wild-type protein.

Heterologous therapeutic nucleotide sequences are useful in, for example, expressing a mutant protein which is less active, more active, and/or more stable, than the wild-type protein. Alternatively, heterologous therapeutic nucleotide sequences may be used to express a heterologous protein which is derived from a species that is different from the target cell species, such that the expressed heterologous protein complements or supplies a deficient activity in the target cell, thus allowing the latter to resist a pathological process, or else stimulate an immune response.

Another use of heterologous therapeutic nucleotide sequences is in the generation of vaccines against microorganisms (e.g., viruses, bacteria, etc.) or against cancer cells. This may be achieved, for example, where the nucleotide sequence of interest encodes an antigenic peptide which is capable of generating an immune response in a host animal or human, or which encodes variable regions from specific antibodies and immunomodulator genes. For example, the encoded antigenic polypeptides may be derived from the Epstein Barr virus, the HIV virus, the hepatitis B virus (such as those described in patent EP 185 573), or the pseudorabies virus. Alternatively, the antigenic polypeptides may be specific for tumors (such as those described in patent EP 259 212).

Illustrative therapeutic nucleotide sequences include, but are not limited to, sequences which encode enzymes; lymphokines (e.g., interleukins, interferons, TNF, etc.); growth factors (e.g., erythropoietin, G-CSF, M-CSF, GM-CSF, etc.); neurotransmitters or their precursors or enzymes responsible for synthesizing them; trophic factors (e.g., BDNF, CNTF, NGF, IGF, GMF, aFGF, bFGF, NT3, NT5, HARP/pleiotrophin, etc.); apolipoproteins (e.g., ApoAI, ApoAIV, ApoE. etc.); lipoprotein lipase (LPL); the tumor-suppressing genes (e.g., p53, Rb, Rap1A, DCC k-rev, etc.); factors involved in blood coagulation (e.g., Factor VII, Factor VIII, Factor IX, etc.); DNA repair enzymes; suicide genes (thymidine kinase or cytosine deaminase); blood products; hormones; etc.

In one preferred embodiment, the therapeutic nucleotide sequence encodes a wild-type gene for which a mutant has been associated with a human disease. Such wild-type genes are exemplified, but not limited to, the adenosine deaminase (ADA) gene (GenBank Accession No. M13792; SEQ ID NO:12) associated with adenosine deaminase deficiency with severe combined immune deficiency; alpha-1-antitrypsin gene (GenBank Accession No. M11465; SEQ ID NO:13) associated with alpha1-antitrypsin deficiency; beta chain of hemoglobin gene (GenBank Accession No. NM_000518; SEQ ID NO:14) associated with beta thalassemia and Sickle cell disease; receptor for low density lipoprotein gene (GenBank Accession No. D16494; SEQ ID NO:15) associated with familial hypercholesterolemia; lysosomal glucocerebrosidase gene (GenBank Accession No. K02920; SEQ ID NO:16) associated with Gaucher disease; hypoxanthine-guanine phosphoribosyltransferase (HPRT) gene (GenBank Accession No. M26434, J00205, M27558, M27559, M27560, M27561, M29753, M29754, M29755, M29756, M29757; SEQ ID NO:17) associated with Lesch-Nyhan syndrome; lysosomal arylsulfatase A (ARSA) gene (GenBank Accession No. NM_000487; SEQ ID NO:18) associated with metachromatic leukodystrophy; ornithine transcarbamylase (OTC) gene (GenBank Accession No. NM_000531; SEQ ID NO:19) associated with omithine transcarbamylase deficiency; phenylalanine hydroxylase (PAH) gene (GenBank Accession No. NM_000277; SEQ ID NO:20) associated with phenylketonuria; purine nucleoside phosphorylase (NP) gene (GenBank Accession No. NM_000270; SEQ ID NO:21) associated with purine nucleoside phosphorylase deficiency; the dystrophin gene (GenBank Accession Nos. M18533, M17154, and M18026; SEQ ID NO:22) associated with muscular dystrophy; the utrophin (also called the dystrophin related protein) gene (GenBank Accession No. NM_007124; SEQ ID NO:23) whose protein product has been reported to be capable of functionally substituting for the dystrophin gene; and the human cystic fibrosis transmembrane conductance regulator (CFTR) gene (GenBank Accession No.M28668; SEQ ID NO:24) associated with cystic fibrosis. In a preferred embodiment, the therapeutic gene is human Factor VIII (Example 2, infra).

In an alternative embodiment the nucleotide sequence of interest is an antisense DNA sequence. The term "antisense DNA sequence" as used herein refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Sense mRNA generally is ultimately translated into a polypeptide. Thus an "antisense DNA sequence" is a sequence which has the same sequence as the non-coding strand in a DNA duplex, and which encodes an "antisense RNA," i.e., a ribonucleotide sequence whose sequence is complementary to a "sense mRNA" sequence. Antisense RNA may be produced by any method, including synthesis by splicing an antisense DNA sequence to a promoter which permits the synthesis of antisense RNA. The transcribed antisense RNA strand combines with natural mRNA produced by the cell to form duplexes. These duplexes then block either the further transcription of the mRNA or its translation, or promote its degradation. Thus, antisense DNA sequences are useful in, for example, inhibiting the activity of a protein which is produced by a pathogenic gene or which is present in the genome of a pathogenic organism. Alternatively, antisense DNA sequences may be used to inhibit a cellular gene whose expression is deregulated (e.g., an oncogene). Methods of generating and using antisense DNA sequences are known in the art (see for example, patent EP 140 308).

In yet another embodiment, the nucleotide sequences of interest encode a ribozyme. The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." The nucleotide sequence of the ribozyme binding regions may be completely complementary or partially complementary to the substrate RNA sequence with which the ribozyme binding regions hybridize. Complete complementarity is preferred in order to increase the specificity, as well as the turnover rate (i.e., the rate of release of the ribozyme from the cleaved RNA product), of the ribozyme. Partial complementarity, while less preferred, may be used to design a ribozyme binding region containing more than about 10 nucleotides. While contemplated to be within the scope of the claimed invention, partial complementarity is generally less preferred than complete complementarity since a binding region having partial complementarity to a substrate RNA exhibits reduced specificity and turnover rate of the ribozyme when compared to the specificity and turnover rate of a ribozyme which contains a binding region having complete complementarity to the substrate RNA. A ribozyme may hybridize to a partially or completely complementary DNA sequence but cannot cleave the hybridized DNA sequence since ribozyme cleavage requires a 2'-OH on the target molecule, which is not available on DNA sequences. Nucleotide sequences of interest which encode a ribozyme are useful where selective inactivation of target RNAs is desirable. Methods for making and using ribozymes are within the ordinary skill in the art (see, e.g., patent EP 321 201).

4. Generating Parental Ad/AAV Hybrid Vectors

One advantage of the invention's parental Ad/AAV hybrid vectors and mAd vectors is that they may be used to replace adenovirus genes in the vector with a sequence of interest. Thus, in a preferred embodiment, the invention's vectors lack one or more adenovirus genes. In a more preferred embodiment, the vectors of the instant invention are "gutted." The term "gutted vector" when referring to a vector that is derived from a virus refers to a recombinant vector (e.g., plasmid, virus, naked DNA) which lacks all the coding sequences which are otherwise present in the wild-type virus from which the vector is derived. Gutted vectors may contain non-coding viral sequences, e.g., terminal repeat sequences, and packaging sequences. For example, a gutted adenovirus vector lacks all adenovirus coding sequences and optionally contains adenovirus terminal repeat sequences and/or packaging sequences (e.g., FIGS. 1A and 7A). Gutted vectors are particularly preferred since they do not express viral vector proteins and hence do not induce an adverse immune or toxic response in a cell.

While gutted vectors are preferred, it is expressly contemplated that the invention also encompasses vectors which do not lack one or more adenovirus genes. These vectors may be used to generate gutted mini-adenoviruses.

In a particularly preferred embodiment, a recombinant vector according to the invention is derived from the genome of a wild-type adenovirus by deletion of all or part of the adenovirus early gene regions. The term "adenovirus early gene regions" refers to nucleotide sequences which are derived from adenovirus and which are transcribed prior to replication of the adenovirus genome. The early gene regions comprise E1a, E1b, E2a, E2b, E3 and E4. The E1a gene products are involved in transcriptional regulation; the E1b gene products are involved in the shut-off of host cell functions, mRNA transport, regulation of apoptosis induction, and inhibition of p53 tumor suppressor. E2a encodes a DNA-binding protein (DBP); E2b encodes the viral DNA polymerase and preterminal protein (pTP). The E3 gene products are not essential for viral growth in cell culture. The E4 regions encode regulatory proteins involved in transcriptional and post-transcriptional regulation of viral gene expression; a subset of the E4 proteins are essential for viral growth. In contrast to the adenovirus early gene regions, the "adenovirus late gene regions" refers to adenovirus nucleotide sequences which are transcribed after replication. The products of the late genes (e.g., L1–5) are predominantly components of the virion as well as proteins involved in the assembly of virions. The VA genes produce VA RNAs which block the host cell from shutting down viral protein synthesis. The early and late gene regions of adenovirus have been characterized (e.g., in Ad2 genomic sequence; GenBank No. J01917; SEQ ID NO:3).

Particularly preferred gutted parental Ad/AAV hybrid vectors of the invention are exemplified by, but not restricted to, plasmid pAd/AAV-EGFP-Neo in which the EGFP-Neo expression cassette replaces E1a and E1b early gene regions, and by plasmid pAd/AAV-FVIII in which the FVIII expression cassette replaces E1a, E1b, and E3 early gene regions.

Linear DNA, plasmids, and viruses which contain gutted viruses that lack adenovirus early gene region(s) may be made using standard molecular biological techniques, and as disclosed herein. For example, replication defective recombinant Ad/AAV hybrid viruses which contain a deletion in an early gene region (e.g., E1a and E1b) may be generated as disclosed herein by propagation in a packaging cell line (e.g., 293 cell line) which supplies the deleted early gene region proteins in trans. Recombinant adenoviruses are created by making use of intracellular recombination between a much larger plasmid encoding most of the viral genome and the invention's parental Ad/AAV hybrid plasmids which contain the gene of interest flanked by regions of homology with the viral integration site. Standard methods may be used to construct the recombinant adenoviruses, e.g., by transfecting the plasmid into sub-confluent monolayers of a complementation cell using calcium phosphate precipitation and a glycerol shock, or by using an infectious plasmid clone. Parental recombinant Ad/AAV hybrid viral stocks are preferably titered on monolayers of complementing cells, and isolated single plaques are obtained and tested for expression of the gene of interest (e.g., using ELISA). Viral stocks are amplified and titered on complementing cells, and stored in aliquots at −70° C.; if necessary, stocks are concentrated by centrifugation on density gradients.

B. Mini-Adenovirus (mAd) Vectors

The invention further provides dimeric and monomeric mAd vectors. The invention's monomeric mAd vectors are depicted by the exemplary vectors of FIGS. 1B and 7F and contain a nucleotide sequence of interest flanked by left and right inverted terminal repeats (ITRs) of adenovirus and an adenovirus packaging sequence linked to one of said ITRs. The packaging sequence may be linked either to the 3' or the 5' ends of the nucleotide sequence of interest. In a preferred embodiment, the monomeric mAd vector contains two packaging sequences which flank the nucleotide sequence of interest, and which are each flanked by the left and right adenovirus ITRs. In a more preferred embodiment, the monomeric mAd vector further contains an AAV TR D sequence operably linked to the 5' end or to the 3' end of the nucleotide sequence of interest. In a yet more preferred embodiment, the monomeric mAd contains two D sequences which flank the nucleotide sequence of interest, wherein the D sequences are flanked by the adenovirus left and right ITRs (FIGS. 1B, 7F).

The invention also provides dimeric mAd vectors which are exemplified by those in FIGS. 1C and 7E and which contain an adeno-associated virus terminal repeat DD (AAV TR-DD) sequence, first and second inverted copies of a nucleotide sequence of interest flanking the AAV TR-DD sequence, left and right inverted terminal repeats (ITRs) of adenovirus flanking the first and second inverted copies of the nucleotide sequence of interest, and a first adenovirus packaging sequence. Optionally, in a more preferred embodiment, the dimeric mAd vector may additionally contain a second adenovirus packaging sequence such that the first and second packaging sequences flank the nucleotide sequence of interest, as shown by the exemplary vector of FIG. 1C. In one embodiment, the dimeric mAd vectors further contains first and second inverted AAV TR-D sequences flanking the first and second inverted copies of the nucleotide sequence of interest, wherein the first and second inverted AAV TR-D sequences are flanked by the left and right inverted terminal repeats (ITRs) of adenovirus. In a particularly preferred embodiment, the dimeric mAd vectors further contain first and second inverted adeno-associated virus terminal repeat D sequences flanking the first and second inverted copies of the nucleotide sequence of interest, wherein the first and second inverted adeno-associated virus terminal repeat D sequences are flanked by the left and right inverted terminal repeats (ITRs) of adenovirus, and also contain a second adenovirus packaging sequence (FIGS. 1C and 7E).

The dimeric and monomeric mAd vectors of the invention may be generated using conventional recombinant molecular biological techniques in combination with the teachings herein. Alternatively, the invention's dimeric and monomeric mAd vectors may be generated using the invention's parental Ad/AAV hybrid vectors. In a preferred embodiment, the dimeric and monomeric mAd vectors are produced using the invention's parental Ad/AAV hybrid vectors in one of the following methods.

Figure 2:
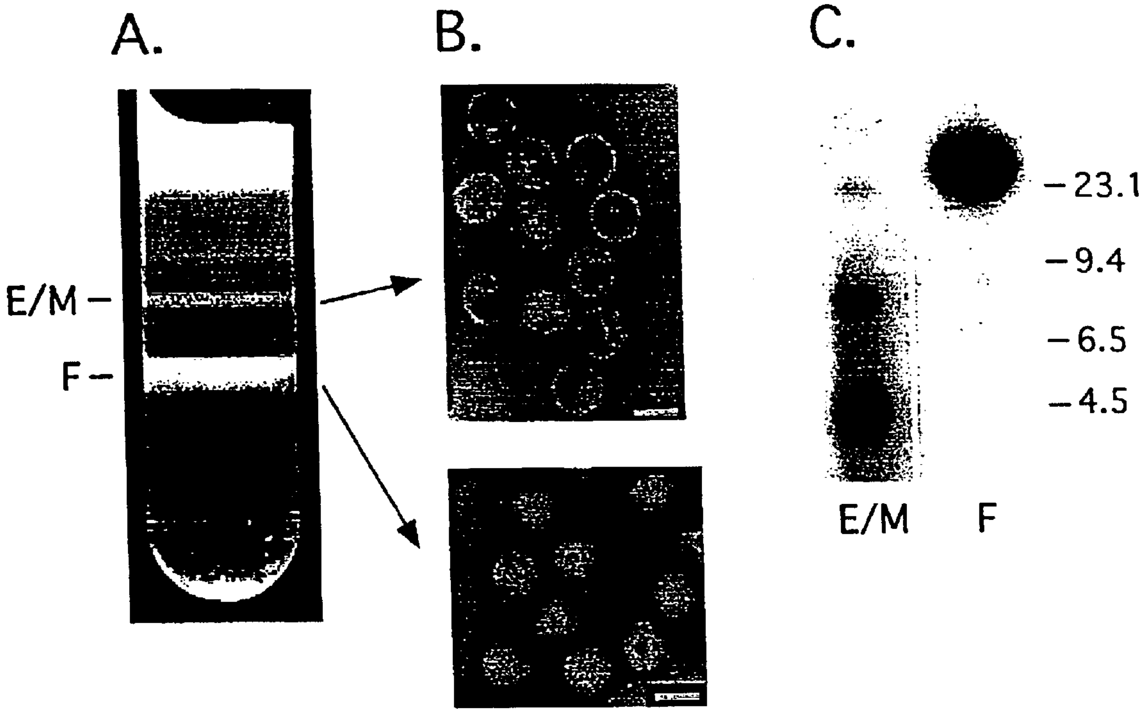
FIG. 2 shows production and characterization of mad produced in 293 cells. Viruses were separated on a $CsCl_2$ step gradient (A), analyzed by electron microscopy (B), and by Southern blot using an EGFP/Neo probe (C).

In a first method, a first parental Ad/AAV hybrid vector which lacks one or more adenovirus early gene region selected from E1, E2, and E4 gene regions is introduced into a complementing cell which is capable of expressing the adenovirus early gene(s) that are lacking from the first parental Ad/AAV hybrid vector to generate a transformed cell. The transformed cell is cultured so that it produces a monomeric and/or dimeric mAd vector. This method is exemplified herein by infecting 293 cells (which are engineered to express E1) with parental plasmid pAd/AAV-EGFP-Neo which lacks the E1 gene region (Example 3). In particular, data presented herein demonstrates mAd production in this method using 293 cells (Example 3, FIG. 2). An advantage of this method is that the generated mAd is free of contamination with helper virus, thus eliminating adverse immunologic or toxic responses by the recipient cell.

However, data disclosed herein shows that this first method is inefficient in generating the mAd vectors; using 293 cells, it was found that efficient generation of mAd was observed only after 3–4 serial virus amplification cycles. When $CsCl_2$-purified parental Ad/AAV hybrid virus was used for 293 cell infections, inefficient excision of the mAd DNA from the parental Ad/AAV virus was observed, resulting in inefficient mAd production. However, these problems were overcome when using Rep-mediated excision, as further described below in, for example, the invention's second method.

Complementing cells which are suitable for use in the first method (and other methods described below), and which express one or more adenovirus early gene region sequences are known in the art. For example, E1-complementing cell lines include the cell line designated BMAdE1-220-8 (ATCC #CRL-12407) which is disclosed and claimed in U.S. Pat. No. 5,891,690 the contents of which are incorporated by reference; the 293 cell line (ATCC #CRL-1573) which was established by stable transfection of a human embryonic kidney cells with human Ad5 DNA containing the full length E1 region; human lung A549 cells which were stably transformed with E1 sequences containing the E1A, E1B and pIX regions, and which express high levels of E1 RNA and proteins [Imler et al., 1996 Gene Ther. 3:75–84]. Other E1-complememting cell lines are the PER.C6 cell line [Fallaux et al. (1998) Hum. Gene Ther. 9:1909–1917] and the 911 cell line [Fallaux et al. (1996) Hum. Gene Ther. 7:215–222].

E-4 complementing cell lines are also available in the prior art, such as the W162 cell line [Weinberg et al. (1983) Proc. Natl. Acad. Sci. USA 80:5383–5386] and the cell line described by Brough et al. (1996) J. Virol. 70:6497–501].

Complementation cell lines which express the adenovirus E1 early gene region in addition to one or more of the adenovirus E2 and E4 early gene regions have been described and claimed in, for example, U.S. Pat. Nos. 6,040,174 and 5,872,005, whose entire contents are incorporated by reference. These cells are exemplified by cells which are derived from a cell line selected from Vero, BHK, A549, MRC5, and WI 38 and which are claimed in U.S. Pat. No. 6,040,174.

The inefficiency of the invention's first method is overcome by a second method which is identical to the first method described above, with the exception that in the second method, the complementing cell is also capable of expressing one or more AAV Rep proteins (preferably Rep 68 and/or Rep 78) in addition to the one or more adenovirus early genes.

It was the inventors' hypothesis that the unique configuration of the parental Ad/AAV hybrid vectors (in which the AAV TR sequence is introduced into the Ad genome flanking a heterologous DNA insert), coupled with expression of the AAV Rep protein, would allow for the excision of the AAV TR/insert from the recombinant Ad genome and packaging into recombinant virions. The second method is particularly preferred since it is rapid and permits efficient excision and generation of mAd from the parental Ad/AAV hybrid vectors.

Cell lines which are useful in the second method (and other methods described below) and which express AAV Rep proteins as well as one or more adenovirus early gene region products have been previously described. For example, U.S. Pat. No. 5,872,005 describes and claims cells which express adenovirus E2A and E4 (and optionally either E1 or E3) early gene regions as well as the AAV rep gene.

Yet other examples of cells which express AAV Rep proteins include cells described and claimed in U.S. Pat. Nos. 5,837,484; 5,589,377; 5,789,390; and 5,691,176, the entire contents of each of which is hereby incorporated by reference. Such cells may be derived from, for example, 293, HeLa, KB and JW-22 cells (U.S. Pat. No. 5,589,377). In one embodiment, the cell which expresses AAV Rep proteins is the Neo6 cell which is derived from 293 cells (U.S. Pat. No. 5,837,484).

While recent evidence suggests that expression of Rep proteins may not be detrimental to cell viability in some human cell lines, it is preferred that the rep gene region be placed under control of an inducible promoter. Inducible promoters are known in the art, such as the $Cd^{2+}$-inducible metallothionein promoter, alpha inhibin promoter, and steroid hormone-inducible MMTV promoter or growth hormone promoter. In a preferred embodiment, the inducible promoter is the $Cd^{2+}$-inducible metallothionein promoter which is used to drive expression of the AAV rep gene region in Neo6 cells (U.S. Pat. No. 5,837,484).

In a third method of the invention, the parental Ad/AAV hybrid vector which lacks one or more adenovirus early gene regions selected from E1, E2, and E4 gene region is introduced together with a helper adenovirus into a cell that is capable of expressing Rep protein. In this method, expression of the Rep proteins facilitates excision of the mAd from the cell genome to yield one or both monomeric and dimeric mAd vectors. This method provides improved generation of mAd vectors as compared to the first method since it exploits Rep-mediated excision. One limitation of this approach, however, is the use of helper adenovirus to complement the deleted early region genes which are needed for efficient replication of the Ad/AAV hybrid virus. While data presented herein shows that contamination of the purified mAd preparation with helper virus was low (less than 0.01%), this level of contamination may not be desirable for some applications, e.g., gene therapy. On the other hand, contamination of the purified mAd preparation with helper virus may be of no moment in some applications, such as using the mAd to transfer a gene in vitro to a cell for the purpose of producing a recombinant protein of interest.

In an alternative embodiment of the third method, the parental Ad/AAV hybrid vector which lacks adenovirus early gene E1 regions is introduced together with a helper SV40 virus into a cell that is capable of expressing Rep protein.

Figure 3:
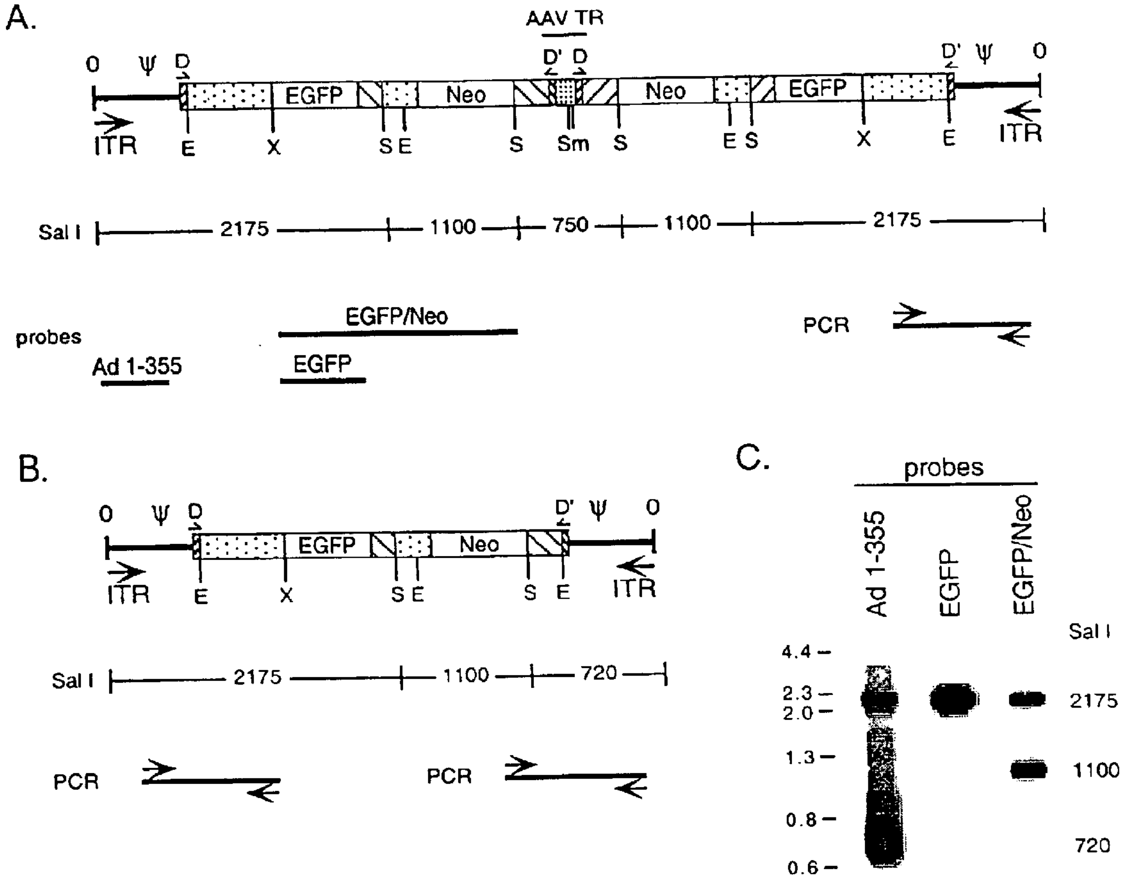
FIG. 3 shows viral genomic maps of the mAd dimeric genome (A) and monomeric mAd genome (B) as determined using restriction endonuclease digestion, Southern blot, PCR using specific primer pairs, and nucleotide sequence analysis of the PCR products. A southern blot of SalI digested DNA is shown in panel C.

The invention's third method is exemplified by infection of C12 cells which express AAV Rep proteins with Ad/AAV EGFP/Neo virus (Example 4) and the generation of two distinct mAd forms (FIG. 3) during replication of the hybrid Ad/AAV vector: a monomeric form that contains a single transgene copy (FIG. 1B) and a dimeric form that carries duplicated copies of the transgene cassette (FIG. 1C). Both forms were found in approximately equimolar ratios within the virion mixture (FIG. 3, fraction E/M). Importantly, data presented herein demonstrates that both monomeric and dimeric forms are biologically active in vitro and in vivo in that they were demonstrated successfully to transfer functional genes into target cells.

Figure 7:
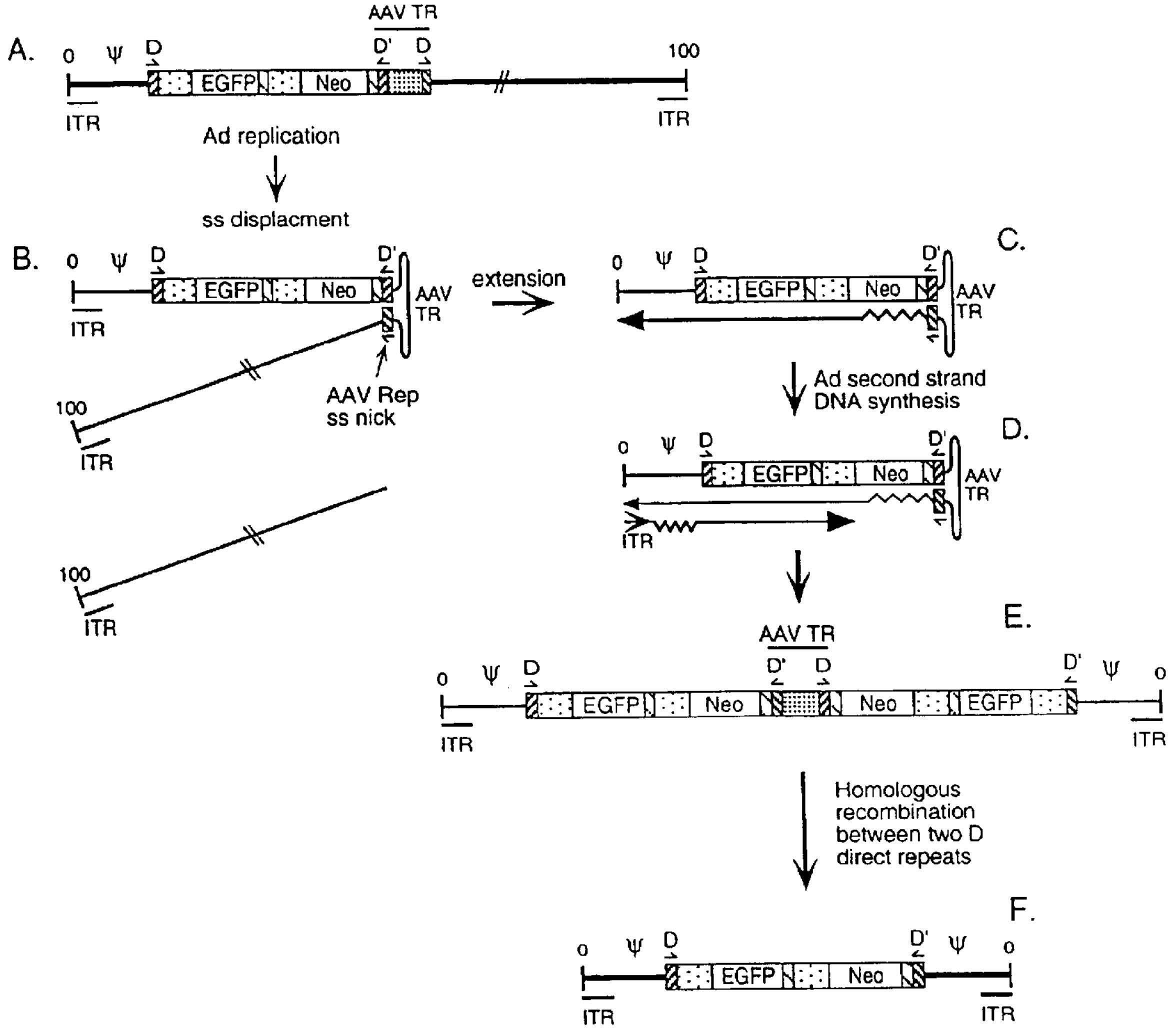
FIG. 7 shows a model for mAd formation The parental Ad/AAV hybrid virus is depicted in (A), the AAV secondary structure in (B), synthesis of the Ad second strand (D), the dimer mAd genome structure (E), and the monomeric mAd genome structure (F).

While it is not necessary to understand any particular mechanism in order to practice the invention, and without intending to limit the invention to any particular mechanism, the inventors hypothesize that the mAd genomes were formed via the mechanism depicted in FIG. 7. Adenovirus replicates by a strand displacement mechanism thereby releasing a single strand of viral DNA during each replication initiation event [Van der Vliet (1995) Curr. Top. Microbiol. Immunol. 199:1–30]. The inventors thus hypothesized that the AAV TR-DD in the displaced single strand DNA molecule would form an AAV TR secondary structure (FIG. 7B). The AAV TR-DD sequence may facilitate this product. The TR D sequence contains the site that the AAV Rep protein targets for endonucleolytic cleavage [Berns et al (1995) Ann. NY Acad. Sci. 772:95–104; Muzyczka (1992) Curr. Top. Microbiol. Immunol. 158:97–129; Rolling and Samulski (1995) Mol. Biotechnol. 3:9–15]. Production of Rep in C12 cells following adenovirus infection was conceived by the inventors to induce such a cleavage resulting in release of the right end of the hybrid virus genome (FIG. 7B). The inventors speculate that the apparent ~2 kbp single-stranded, monomeric mAd genome (FIG. 3, arrow) corresponds to this cleaved product. This cleavage would yield a 3' end within the cleaved D segment that could be extended by the Ad DNA polymerase or cellular DNA polymerase to generate a fully double-stranded molecule covalently linked at the right end (FIG. 7C). The molecule would contain an intact double-stranded left Ad ITR that could serve as a template for the Ad replication initiation complex (FIG. 7D) for second strand DNA synthesis to generate a fully duplicated mAd genome (FIG. 7E). The inventors' proposed model is fully consistent with their analysis of the structure of the dimeric mAd genome produced in C12 cells including the observation that the internal AAV TR sequence is intact.

In a fourth method provided herein, a parental Ad/AAV hybrid vector which lacks one or more adenovirus early gene region selected from E1, E2, and E4 gene region is introduced together with adeno-associated virus into a complementing cell which is capable of expressing the adenovirus early gene regions that are lacking from the vector. This is a particularly advantageous method since infection with AAV is used to provide the Rep excision functions, thus improving the efficiency of generating the mAd vectors. Additionally, mAd viruses may be purified from contaminating AAV particles by $CsCl_2$ equilibrium centrifugation.

The fifth method provided by the invention is contemplated to involve introducing a parental Ad/AAV hybrid vector which lacks adenovirus E3 early gene region into a cell to produce the monomeric and dimeric mAd vectors. An advantage of this method is that the recipient cell need not (although it may) be engineered to express adenovirus early gene regions since E3 early gene region products are not essential for viral growth in cell culture. A further advantage of this method is that the generated mAd are devoid of contamination with helper virus.

While a disadvantage of the fifth method is its low efficiency in generating mAd vectors, this is overcome in the invention's sixth method which is identical to the fifth method with the exception that it employs a Rep-expressing recipient cell for introduction of the parental Ad/AAV hybrid vector. It is contemplated that expression of Rep products in the cell would enhance excision of the mAd vectors from the cell's genome.

A seventh method of the invention is contemplated to involve introducing into a cell a parental Ad/AAV hybrid vector which contains the AAV rep gene region in addition to a nucleotide sequence of interest. This method contemplates that expression of Rep proteins by the vector would enhance the excision efficiency, thus improving the yield of the mAd vectors in the absence of contamination with helper adenovirus or AAV. The packaged mAd particles may be separated from virions with full-length genomes based on their lighter buoyant density in $CsCl_2$ gradients.

The second, third, fourth, sixth, and seventh methods are preferred since they allow efficient mAd generation by exploiting Rep-mediated excision. The second, fourth, sixth, and seventh methods are particularly preferred since they also do not employ helper adenovirus, thus avoiding contamination of the mAd vectors with helper adenovirus.

In a preferred embodiment, the mAd vectors which are generated in accordance with any one of the above-described seven methods are encapsidated. The term "encapsidated" when made in reference to a nucleotide sequence refers to a nucleotide sequence which has been packaged or encapsidated into a viral particle. Data presented herein demonstrates that mAd genomes were packaged efficiently into stable virus particles.

Encapsidated vectors of the invention may be recovered following transfection or infection of target cells using methods known in the art. When used herein, "recovering" encapsidated vectors refers to the collection of the vectors by, for example, lysis of the cell (e.g., freeze-thawing) and removing the cell debris by pelleting (Example 1). "Purifying" the encapsidated vectors refers to the isolation of the recovered encapsidated vectors in a more concentrated form (relative to the cell lysate), e.g., using $CsCl_2$ density gradients as described in Example 1; purification of recovered encapsidated vectors permits their physical separation from parental virus and any helper virus (if present) (see FIGS. 2A, 5A).

C. Gene Transfer Using Recombinant Vectors

The invention's recombinant vectors (i.e., Ad/AAV hybrid vectors and mAd vectors) are useful in introducing a nucleotide sequence of interest into a target cell for gene transfer applications in vitro, ex vivo, and in vivo.

In vitro, the vectors may be used, for example, to transfer a gene to a cell for the purpose of producing a recombinant protein of interest. Ex vivo, the vectors can be used for transferring a gene to a population of cells which has been removed from an organism, and, where appropriate, selected and amplified, with the aim of conferring desired properties an these cells with a view to re-administering the cells to an organism. In vivo, the vectors can be used for transferring genes by directly administering a solution which is purified and, where appropriate, combined with one or more pharmaceutical excipients. In this latter case, the recombinant vectors can be formulated for the purpose of administering them by the topical, cutaneous, oral, rectal, vaginal, parenteral, intranasal, intravenous, intramuscular, subcutaneous, intraocular, transdermal, intrathecal, etc., route. Preferably, the vectors are combined with a pharmaceutical excipient which is acceptable for an injectable formulation, especially for injection directly into the desired organ. These formulations can, in particular, be sterile or isotonic solutions, or dry, especially lyophilized, compositions which allow the constitution of injectable solutions by the addition of, as the case may be, sterilized water or physiological serum. The doses of vectors used for the injection, as well as the number of administrations, can be empirically adapted according to different parameters, especially according to the mode of administration used, the pathology concerned, the gene to be expressed, or else the sought-after duration of the treatment.

The invention's vectors thus provide a particularly advantageous tool for delivering therapeutic sequences into a cell or tissue in need of the therapeutic sequence. More particularly, the invention's vectors find application in methods which are applicable to diseases that result from a deficiency in a nucleotide or polypeptide sequence, by incorporating the deficient nucleotide sequence or a sequence encoding the deficient polypeptide into the invention's vectors.

The vectors of the invention may be introduced into cells using techniques well known in the art. The term "introducing" a nucleic acid sequence into a cell refers to the introduction of the nucleic acid sequence into a target cell to produce a transformed cell. Methods of introducing nucleic acid sequences into cells are well known in the art. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus. In a preferred embodiment, the vectors of the invention are encapsidated into viral particles and used to infect cells to bring about cell transformation.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA) which detects the presence of a polypeptide encoded by one or more of the nucleotide sequences of interest. Alternatively, transient transformation may be detected by detecting the activity of the protein (e.g., β-glucuronidase) encoded by the nucleotide sequence of interest. The term "transient transformant" refer to a cell which has transiently incorporated one or more nucleotide sequences of interest. Transient transformation with the invention's vectors may be desirable in, for example, cell biology or cell cycle investigations which require efficient gene transfer.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more nucleotide sequences of interest, genomic DNA from the transient transformant does not contain the nucleotide sequence of interest. Stable transformation of a cell may be detected by Southern blot hybridization of genomic DNA of the cell with nucleic acid sequences which are capable of binding to one or more of the nucleotide sequences of interest. Alternatively, stable transformation of a cell may also be detected by the polymerase chain reaction of genomic DNA of the cell to amplify the nucleotide sequence of interest. In a preferred embodiment, transformation is stable, as demonstrated by data herein (Example 4).

The term "amplification" is defined as the production of additional copies of a nucleic acid sequence and is generally carried out using polymerase chain reaction technologies well known in the art. As used herein, the term "polymerase chain reaction" ("PCR") refers to the method of K. B. Mullis, U.S. Pat. Nos. 4,683,195 and 4,683,202, hereby incorporated by reference. PCR methods are well known in the art [Dieffenbach and Dveksler (1995) *PCR Primer, a Laboratory Manual*, Cold Spring Harbor Press, Plainview, N.Y.]. With PCR, it is possible to amplify a single copy of a specific target nucleotide sequence to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment).

Any type of cell into which the invention's vectors may be introduced is expressly included within the scope of this invention. Such cells are exemplified by embryonic cells (e.g., oocytes, sperm cells, embryonic stem cells, 2-cell embryos, protocorm-like body cells, callus cells, etc.), adult cells (e.g., brain cells, fruit cells etc.), undifferentiated cells (e.g., fetal cells, tumor cells, etc.), differentiated cells (e.g., skin cells, liver cells, etc.), dividing cells, senescing cells, cultured cells, and the like.

The target cells into which the invention's vectors are introduced may be primary cells, cultured cells, or cell contained in an animal. A "primary cell" is a cell which is directly obtained from a tissue or organ of an animal in the absence of culture. Preferably, though not necessarily, a primary cell is capable of undergoing ten or fewer passages in in vitro culture before senescence and/or cessation of proliferation. In contrast, a "cultured cell" is a cell which has been maintained and/or propagated in vitro. Cultured cells include "cell lines", i.e., cells which are capable of a greater number of passages in vitro before cessation of proliferation and/or senescence as compared to primary cells from the same source. A cell line includes, but does not require, that the cells be capable of an infinite number of passages in culture.

The animals containing target cells are preferably mammalian. In a more preferred embodiment, the "mammal" is rodent, primate (including simian and human) ovine, bovine, ruminant, lagomorph, porcine, caprine, equine, canine, feline, ave, etc.

EXPERIMENTAL

The following examples serve to illustrate certain preferred embodiments and aspects of the present invention and are not to be construed as limiting the scope thereof.

Example 1

Cell Culture and Viruses

Unless otherwise mentioned, the exemplary cells and viruses described in the following Examples were manipulated as follows.

293 (ATCC #CRL-1573), Hela (ATCC #CCL-2) and A549 (ATCC #CCL-185) cells were maintained as monolayer cultures in Dulbecco Modified Eagle Medium (DMEM) containing 10% bovine calf serum (HyClone). C12 cells that carry the AAV Rep and Cap genes [Clark et al. (1996) Gene Ther. 3:1124–32] were propagated in DMEM containing 10% heat-inactivated fetal bovine serum (HyClone).

HepG2 (ATCC #HB-8065), COSI (ATCC #CRL-1650), HMEC [Ades et al. (1992) 99(6):683–690] cells, and primary human endothelial cells (HUVEC) were cultured using methods known in the art. Briefly, HepG2 cells were propagated in Eagle Minimal Essential Medium (EMEM) containing 10% fetal bovine serum. COS1 cells were propagated in DMEM containing 10% fetal bovine serum. HMEC cells were propagated in DMEM containing 10% bovine serum, 1 $\mu$g/ml hydrocortisone, and 10 ng/ml epidermal growth factor. HUVEC were propagated in DMEM containing 10% fetal bovine serum.

For viral infections, cells were grown to ~75% confluency and infected with viruses at low and high multiplicities of infection at the values described below for 1 hour at 37° C. For preparation of virions, infected cell lysates were prepared by suspension of cells in Tris-buffered saline solution following four freeze-thaw cycles. Cell lysates were cleared by centrifugation at 3000× g at 15° C. for 15 minutes, followed by incubation with 500 units/ml DNase I and 250 mg/ml RNAse A in the presence of 2 mM $MgCl_2$ and 2 mM $CaCl_2$ for 30 minutes at 37° C.

Purified virus particles were prepared by centrifugation over a $CsCl_2$ step gradient (1.4 g/cc-1.25 g/cc $CsCl_2$) and rebanded by equilibrium centrifugation (1.35 g/cc $CsCl_2$) [Wold (1999) Humana Press, Totowa, N.J.]. Virus particles were quantified by lysis of dilutions in buffer containing 0.1% SDS, and absorbance at 260 nm measured; 1 O.D. unit at 260 nm equals $10^{12}$ particles/ml. Helper virus contamination level was determined by plaque assay on 293 cells.

Example 2

Construction of Exemplary Adenovirus/Adeno-Associated Virus Hybrid Plasmid and Virus This Example discloses generation of Ad/AAV hybrid plasmids and viruses containing either the green fluorescent protein (EGFP) reporter gene and the neomycin selectable marker (Neo) gene, or the human Factor VIII gene.

The adenovirus/adeno-associated virus hybrid plasmid pAd/AAV-EGFP-Neo was generated through multiple cloning manipulations beginning with plasmid pBS-TR-3D (Drs. Sergei Zolotukhin and Nick Muzyczka, University of Florida Gene Therapy Center). pBS-TR-3D is based in plasmid BlueScript (pBS) and contains within the pBS polylinker region of the left AAV terminal repeat sequence (145 bp, A/B/B'/C/C'/A'/D=flop configuration) [Muzyczka (1992) Curr. Top. Microbiol. Immunol. 158:97–129], a 1300 bp fragment of stuffer DNA, and the right AAV terminal repeat with a double-D (DD) sequence (165 bp, D'/A/B/B'/C/C'/A'/D=flop configuration) [Xiao et al (1997) J. Virol. 71:941–8]. The Ad5 left end 420 bp containing the inverted terminal repeat (ITR) and packaging domain [Hearing et al. (1987) J. Virol. 61:2555–8] was inserted next to the left AAV TR. Ad5 DNA sequences from nt. 3330–3940 of the adenovirus 5 genome sequence (SEQ ID NO:4) were inserted next to the AAV right TR. Finally, the 1300 bp stuffer DNA was replaced with the EGFP-Neo expression cassettes from plasmid pTR-UF2 [Zolotukhin et al. (1996) J. Virol. 70:4646–54]. Sequence analysis of this plasmid showed that the intact left AAV TR was lost and only the AAV TR D sequence remained. The plasmid was linearized using a restriction site outside the Ad5 ITR and used for recombination into Ad5 d1309 (containing a deletion of from nucleotide 423 to 3329 of Ad5 genome of GenBank accession No. M73260; SEQ ID NO:4) according to the method of Stowe [Stow (1981) J. Virol. 37:171–180]. Virus plaques were isolated on 293 cells [Graham et al. (1977) J. Gen. Virol. 36:59–74] (used to complement the deletion of the Ad5 E1 region). Virus stocks were amplified in 293 cells and confirmed by restriction endonuclease digestion and nucleotide sequence analysis of viral DNA's.

The inventor's results demonstrated generation of a recombinant Ad/AAV hybrid virus that carries the green fluorescent protein (EGFP) reporter gene and the neomycin selectable marker (Neo) gene flanked by the AAV terminal repeat D-sequence on the left side and a complete AAV terminal repeat on the right side containing an additional D-sequence (TR-DD) [Xiao et al. (1997) J. Virol. 71:941–8] (FIG. 1A). In particular, the virus genome depicted in FIG. 1A carries from left to right: the left end of Ad5 containing the ITR and packaging domain, the AAV TR D sequence, an EGFP/Neo expression cassette from the plasmid pTRUF2 [Zolotukhin et al. (1996) J Virol 70: 4646–54] (The EGFP gene is driven from the CMV promoter and the Neo gene is under the control of the polyoma enhancer and TK promoter. Both genes ended with the SV40 poly adenylation signal), an intact AAV terminal repeat with a double D sequence (TR-DD), and the remainder of the Ad genome. Ad5 sequences between nt 421 and 3330 are missing from this virus backbone (E1 deletion).

The adenovirus/adeno-associated virus hybrid plasmid pAd/AAV-FVIII was generated essentially as described above for pAd/AAV-EGFP-Neo, except that instead of inserting the EGFP-Neo cassette into E1a/E1b-deleted (d1309) Ad5 genome, plasmid pAd/AAV-FVIII was engineered to contain B-domain deleted factor VIII lacking amino acids 761–1639, which was generated by PCR mutagenesis using the full-length human factor VIII cDNA as starting material, and which was inserted into E1a/E1b/E3-deleted (d1327) Ad5 genomes [Thimmappaya et al. (1982) Cell Dec. 31 (3 Pt 2): 543–551; Tollefson et al. (1996) J. Virol. 70(4):2296–2306]. The pAd/AAV-FVIII vector was constructed using standard molecular biology techniques.

Example 3

Generation of Exemplary Monomeric and Dimeric Mini-adenoviruses in Exemplary 293 Cells This Example demonstrates generation of monomeric and dimeric min-adenoviruses using the parental Ad/AAV hybrid viruses of Example 2.

A. Mini-adenoviruses Using Ad/AAV EGFP/Neo Virus

For generation of mini-adenoviruses using the parental Ad/AAV EGFP/Neo virus, 293 cells which complement the E1 deletion in the hybrid virus to allow virus replication were infected with a cellular lysate containing the parental Ad/AAV hybrid virus which carries the EGFP-Neo cassette as described in Example 2 (from a third passage virus stock) using an MOI of 10 PFU/cell. Two days after infection, cleared cellular lysates were prepared and treated with 500 U/ml DNase I and 250 mg/ml RNase A. Ad/AAV and mAd viruses were separated on a $CsCl_2$ step gradient. The lower band (F) represent full virus particles. The upper band (E/M) represents lighter particles that includes empty particles, light intermediate particles, mini-adenoviruses and protein aggregates.

The viral particles were also examined by transmission electron microscopy. $CsCl_2$-purified viruses were adsorbed onto formvar-carbon-coated copper grids and stained with saturated solution of uranyl acetate. Electron microscopy demonstrated that the viral particles in the E/M (empty/mini) fraction have the same morphology as mature wild type adenovirus (F, full fraction). Negative staining showed that viral particles found in the F fraction are homogeneously electron dense (FIG. 2B). The lighter band contained a mixture of two populations: empty and DNA-containing particles with the same size and shape as wild type adenovirus (FIG. 2B). The DNA in these particles was DNase I resistant, confirming that it is packaged within the virions.

DNA analysis was also carried out on the viral particles. During normal replication of wild type AAV with an Ad helper virus, both monomer length as well as dimer length AAV genome products are observed as part of the replication pathway [Berns et al. (1995) Ann N Y Acad. Sci. 772:95–104; Muzyczka (1992) Curr. Top. Microbiol. Immunol. 158:97–129; Rolling and Samulski (1995) Mol. Biotechnol. 3:9–15]. Thus, Southern blot analysis using an EGFP/Neo probe was used to determine whether monomer and/or dimer lengths of the parental Ad/AAV hybrid DNA molecule were generated.

For the analysis of viral DNA in purified virions, 1/10 volume (50 $\mu$l) aliquots from each virus preparation were incubated in 50 mM Tris pH 8.0, 1 mM EDTA, 0.5% SDS and 1 mg/ml proteinase K for 1 hr at 50° C. Samples were then separated on 0.8% agarose gel and transferred to a nylon membrane (Hybond $N^+$; Amersham). The blots were hybridized to an Ad5 left end DNA fragment (nt. 1–355) or to a 3.1 kbp Bgl II fragment (EGFP/Neo cassette) obtained from the plasmid pTRUF2 [Zolotukhin et al. (1996) J. Virol. 70:4646–54].

DNA analysis from each virus population shown in FIG. 2A demonstrated that full virus particles contained the parental Ad/AAV hybrid virus genome as a single DNA molecule about 36 kbp in size (FIG. 2C). The E/M virus particles contained two small genomes at ~4 kbp and ~8 kbp in length.

Extensive characterization of these molecules by PCR, restriction enzyme digestion and nucleotide sequence analysis demonstrated that they correspond to monomer (FIG. 1B) and dimer (FIG. 1C) forms of mini-adenovirus. The approaches used to analyze the mini-adenovirus genomes are depicted in FIGS. 3A and 3B and a representative Southern blot is shown (FIG. 3C).

FIG. 3 shows that digestion with SalI yields distinct fragments that were identified by hybridization with probes corresponding to Ad5 nt 1–355, EGFP, and EGFP/Neo. The SalI restriction sites are indicated by (S), and the predicted SalI cleavage pattern is shown under the schematics of the mAd genomes in (A) and (B). Cleavage with other restriction enzymes was evaluated similarly using EcoRI (E), XbaI (X) and SmaI (Sm). Specific PCR products that were generated are indicated by arrows (primers) and solid lines (products).

FIG. 3 also shows that restriction endonuclease digestion of monomeric and dimeric mini-adenovirus genomes resulted in the release of DNA fragments of specific length whose origin was determined by hybridization with specific probes. For example, digestion with SalI generated two fragments (~700 bp and ~2.2 kbp) that were recognized by a probe corresponding to the Ad5 left end (nt. 1–355; FIGS. 3B and 3C). An ~2.2 kbp fragment was observed using an EGFP-specific probe, and this fragment as well as an ~1.1 kbp fragment was detected using an EGFP/Neo probe (FIGS. 3A, 3B and 3C). The inventors' model for mAd structure was further supported by comparable analyses using EcoRI, XbaI and SmaI digestion. EcoRI and XbaI digestion confirmed the mini-adenovirus genome structure indicated by SalI digestion. The AAV terminal repeat contains two SmaI restriction sites. Digestion of the dimeric mini-adenovirus genome with SmaI confirmed the integrity of the AAV terminal repeat structure. Specific nucleotide primers were used within the Ad left end and the EGFP and Neo genes to amplify DNA fragments that were predicted from the restriction mapping, and all PCR products were of the predicted size (data not shown). Finally, the precise junctions of Ad5 DNA with the EGFP/Neo expression cassette were determined by nucleotide sequence analysis of the PCR products.

Collectively, the above-described analyses confirm the structures of monomeric and dimeric mini-adenovirus genomes depicted in FIGS. 1 and 3. In particular, the monomer form (FIG. 1B) contained the EGFP/Neo expression cassette flanked on both sides by an identical fragment of Ad5 DNA (nt. 1–420) containing the Ad5 ITR and packaging domain, as well as the AAV TR D sequence. The remainder of the AAV terminal repeat was missing from this mAd genome. Without intending to limit the invention to any particular mechanism or theory, the inventors believe that this molecule could arise by simple homologous recombination between the AAV TR D sequences present in the parental virus genome as proposed by Steinwaerder et al. [Steinwaerder et al. (1999) J. Virol. 73:9303–13] or by homologous recombination between the two AAV D direct repeats present in the dimer form (FIG. 1C).

The dimeric form (FIG. 1C) contained a duplicated monomer genome where the left end of Ad5 (nt. 1–420), AAV TR D sequence and the EGFP-Neo expression cassette were duplicated in an inverted manner. An intact AAV TR was present at the junction of the duplication. While not intending to limit the invention to any particular theory or mechanism, it is the inventor's consideration that this molecule could have arisen from a recombination event between two internal D sequences present in the parent Ad/AAV hybrid virus, or through single strand displacement as shown in FIG. 7. No selection was imposed to generate the monomeric or the dimeric mini-adenovirus genomes.

Thus, this Example demonstrates generation in 293 cells of monomeric and dimeric mini-adenoviruses which contain the genomes depicted in FIGS. 1 and 3.

B. Mini-Adenoviruses Using pAd/AAV-FVIII Plasmid

Mini-adenoviruses were generated using the parental pAd/AAV-FVIII plasmid essentially as described above for generating mini-adenoviruses using the parental pAd/AAV-EGFP-Neo plasmid. Southern blot analysis using a FVIII probe was used to determine whether monomer and/or dimer lengths of the parental Ad/AAV hybrid DNA molecule were generated. DNA analysis of $CsCl_2$-purified virus population demonstrated that full virus particles contained the parental Ad/AAV hybrid virus genome as a single DNA molecule about 36 kbp in size and min-adenoviruses at ~5.5 kbp and ~11 kbp in length.

Mini-adenovirus-Factor VIII was also produced using the C12 cell sytem which is further described infra (Example 4).

These results further confirmed generation in 293 cells of monomeric and dimeric mini-adenoviruses.

Example 4

Efficient Excision and Replication of Exemplary Mini-Adenoviruses in Exemplary C12 Cells in the Presence of Helper Adenovirus The inventors hypothesized that the presence of the Rep 78/68 proteins during the replication cycle may improve the efficiency of mAd genome excision through the AAV TR. To test this hypothesis, the replication efficiency of mini-adenovirus in HeLa versus C12 cells was first compared. C12 cells are a HeLa cell derivative that inducibly expresses AAV Rep and Cap proteins in response to adenovirus infection [Clark et al. (1996) Gene Ther. 3:1124–32].

C12 cells were co-infected with the Ad/AAV hybrid virus at a low multiplicity of infection (10 PFU/cell) with wild type adenovirus helper (10 PFU/cell) to initiate Rep expression and replication. For viral replication assays, infected cell monolayers were washed three times with Tris-buffered saline solution at 24 hr after infection and low molecular weight DNA was isolated by the method of Hirt [Hirt (1967) J. Mol. Biol. 26:365–9]. Replicating DNA was analyzed by Southern blot 24 hr after infection using the left end of the Ad5 genome (FIG. 4A) and EGFP/Neo DNA (FIG. 4B) as probes. HeLa and C12 cells were infected with $CsCl_2$-purified Ad/AAV recombinant virus at a multiplicity of 10 PFU/cell with (+) or without (−) wild type Ad5 helper virus.

Figure 4:
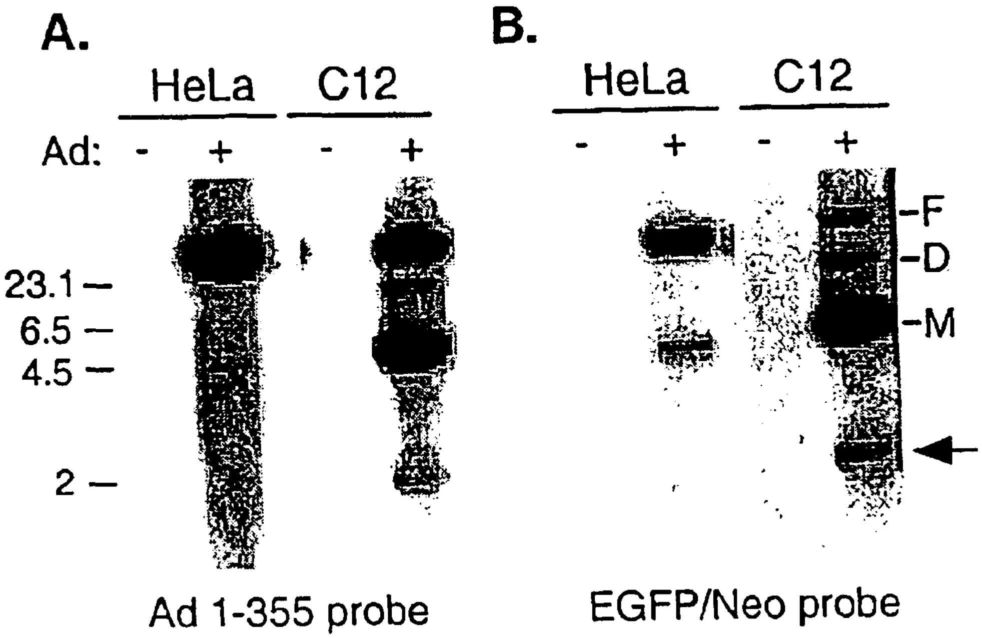
FIG. 4 shows Southern blots of DNA isolated from HeLa and C12 cells which were infected with $CsCl_2$-purified Ad/AAV recombinant virus using Ad5 nt 1–355 (A) and EGFP/Neo (B) as DNA probes.

FIG. 4 shows that the majority of the replicated DNA in HeLa cells was full length Ad/AAV DNA (F). In C12 cells a large proportion of the replicated DNA represents monomer (M) and dimer (D) forms of mAd genome. The arrow indicates a sub-monomer band that was found only in C12 cells.

The Ad5 left end probe detected both the wild type Ad helper virus and the Ad/AAV hybrid virus and excised products, while the EGFP/Neo probe was specific for Ad/AAV hybrid virus genomes. As shown in FIG. 4, mAd genomes were produced efficiently in C12 cells in comparison to HeLa cells suggesting mini-genome formation via AAV Rep-mediated excision. Replication of the parental Ad/AAV hybrid virus genome and production of the mini-adenovirus genome required coinfection with wild type Ad helper virus, consistent with the requirement for E1 expression for productive viral infection with E1-replacement adenoviruses. In addition, the inventors noted the production of a small (~2 kbp) Ad/AAV hybrid virus-specific DNA species with infections of C12 cells (arrow in FIG. 4). The size of this DNA is consistent with that expected by the inventors for a single-stranded, monomeric mAd genome (FIG. 7B). A dimeric, single-stranded mAd genome was expected by the inventors to comigrate with the ~4 kbp double-stranded, monomeric mini-adenovirus genome. The production of EGFP-Neo-containing DNA molecules that lack the left terminus of the Ad5 genome was not detected indicating that the presence of a single AAV D sequence at the left side of the EGFP/Neo expression cassette in conjunction with an intact AAV terminal repeat on the right side was not sufficient to give rise to AAV genomes under these experimental conditions.

Figure 5:
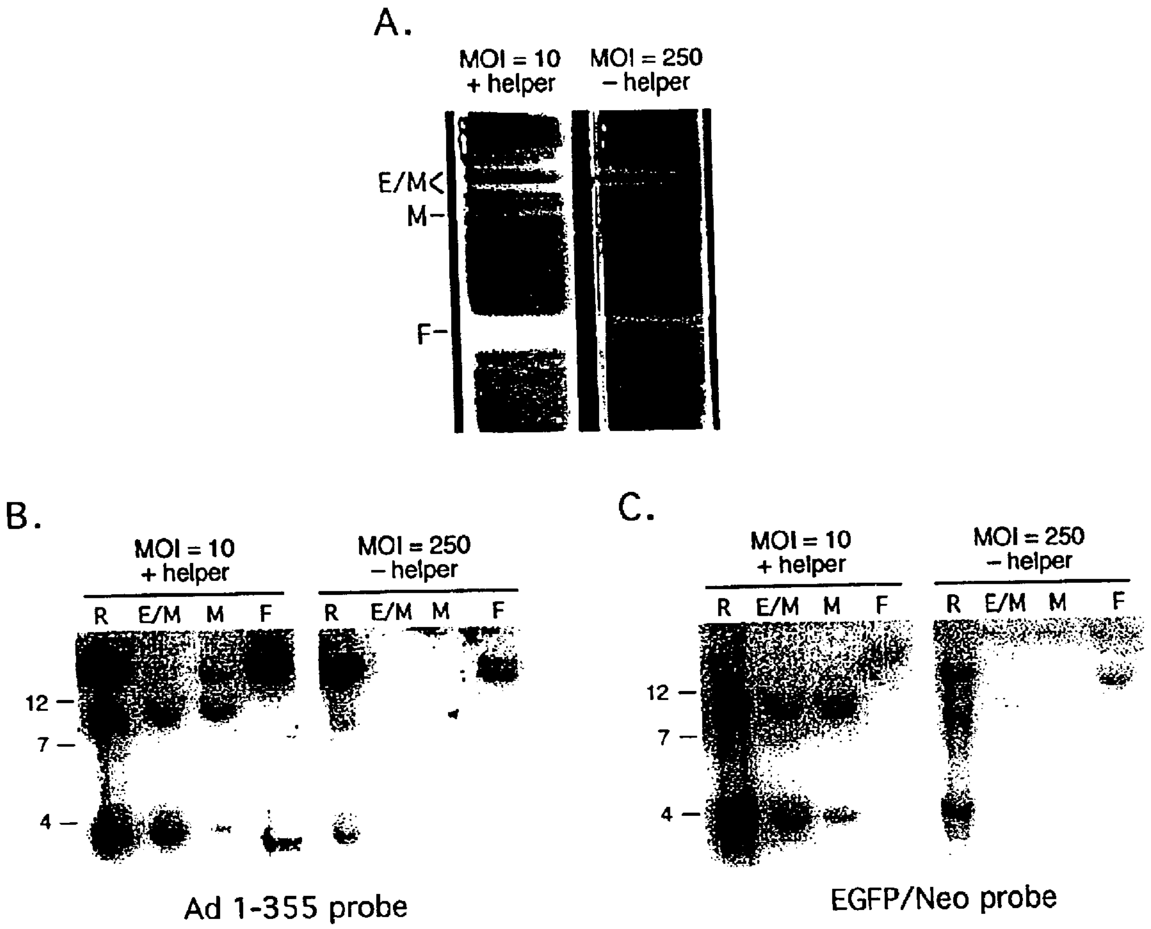
FIG. 5 shows molecular characterization of mAd from C12 cells infected with $CsCl_2$-purified parental Ad/AAV hybrid virus and wild type helper virus followed by $CsCl_2$ equilibrium ultracentrifugation (A) and Southern blot analysis of viruses produced in the C12 cells using either an Ad 1–355 bp probe (B) or an EGFP/Neo cassette from the parental Ad/AAV hybrid (C).

On the basis of these results, the inventors decided to further investigate the formation of mAd in C12 cells. Cells were co-infected with the parental Ad/AAV hybrid virus of Example 2 and wild type adenovirus helper at low multiplicity of infection (10 PFU/cell) or with the Ad/AAV hybrid virus at a high multiplicity of infection (250 PFU/cell) without helper virus. At low MOI, Ad E1 mutants are defective so a helper virus is required to ensure virus replication. At high MOI, Ad E1 mutants are "leaky" so viral replication may occur without helper virus (Nevins (1981) Cell 26:213–20). Viral particles were separated by a step gradient (1.4–1.25 g/cc $CsCl_2$) followed by equilibrium centrifugation (1.35 g/cc $CsCl_2$) as shown in FIG. 5A. FIG. 5A shows that four major bands were visualized. The densest band (F) represents intact, parental Ad/AAV hybrid virus particles and helper virus. The two light bands (E/M) were collected and analyzed together. The middle fraction (M) was novel to C12 cells co-infected with helper adenovirus (FIG. 5A, MOI=10 PFU/cell with helper virus compared to MOI=250 PFU/cell without helper virus), in comparison to the results described above in Example 3 with 293 cells and was analyzed separately. Electron microscopy showed a mixture of empty and DNA-containing particles in both light fractions (E/M, M). These particles showed the same morphology as mature wild type virus.

Southern blot analyses were performed to identify the DNA content of each viral population and to analyze the replicated pool of DNA in the infected cells (FIG. 5B, C). Replicated DNA was isolated 24 hr after infection and analyzed by Southern blot (lane R). Viral DNA was prepared from each fraction from the $CsCl_2$ equilibrium gradient and analyzed by Southern blot (lanes E/M, M, F). Membranes were hybridized either to a left end Ad nt 1–355 bp probe or to the EGFP/Neo cassette from the parent Ad/AAV. Markers are indicated in kbp on the left. When the pool of intracellular, replicated viral DNA was analyzed (lane R), the results showed that the newly formed mAd was produced far more efficiently in the presence of helper virus at low MOI, than found without helper virus at high MOI even though the parental hybrid virus was capable of efficient replication alone at high MOI. Three genomic forms were generated during the replication process: ~4 kbp corresponding to monomers, ~8 kbp corresponding to dimers, and the high molecular weight form corresponding to full length parental Ad/AAV hybrid viral DNA (lane R).

Quantification of the replicated and packaged products by phosphoimager analysis showed that 10% of the replicated mini-adenovirus DNA molecules found in the pool of intracellular DNA were packaged into particles in comparison to 12% of the helper virus genomes that were found to be packaged into virus particles. The mAd genomes were protected from DNase I digestion and thus were completely packaged genomes.

When the DNA content of the separated virus particles was analyzed, the lighter particles (E/M) were found to contain monomers and dimers of mAd DNA (FIG. 5B, E/M fraction). Hybridization with the EGFP/Neo transgene cassette revealed that these particles were free of parental hybrid virus (FIG. 5C, E/M fraction), although some helper virus was evident in this fraction (compare E/M fraction from FIGS. 5B and 5C). The mini-adenoviruses were formed efficiently only in the presence of wild type helper virus (FIGS. 5B and 4C, E/M fraction, MOI=10 PFU/cell versus MOI=250 PFU/cell). At high MOI without helper virus no mAd virus particles were detected on $CsCl_2$ equilibrium gradients (FIG. 5A) and in the regions of the gradients corresponding to the E/M and M fraction when analyzed by Southern blot (FIGS. 5B and 5C). Phosphoimager analysis indicated that 3% of the DNA molecules found in fraction E/M correspond to wild type Ad (FIG. 5B, line E/M).

To measure the level of infectious particles within that fraction, plaque assay on 293 cells was performed. The results demonstrated that the E/M fraction contained less than 0.01% contamination with infectious helper virus.

In addition, mAd containing FVIII were also produced when using the pAd/AAV-FVIII plasmid of Example 3 by infecting C12 cell in the presence of helper adenovirus. These results demonstrate the universality of the generation of mAd using this approach, regardless of the nature and source of the gene of interest.

Example 5

Exemplary Monomeric and Dimeric Mini-adenovirus Vectors Infect Cells in Vitro and in Vivo and Transduce Exemplary EGFP and FVIII Transgene Expression This Example demonstrates that mini-adenovirus vectors infect cells both in vitro and in vivo, and transduce gene expression of each of EGFP and FVIII.

A. Infection and Transduction in Vitro

Figure 6:
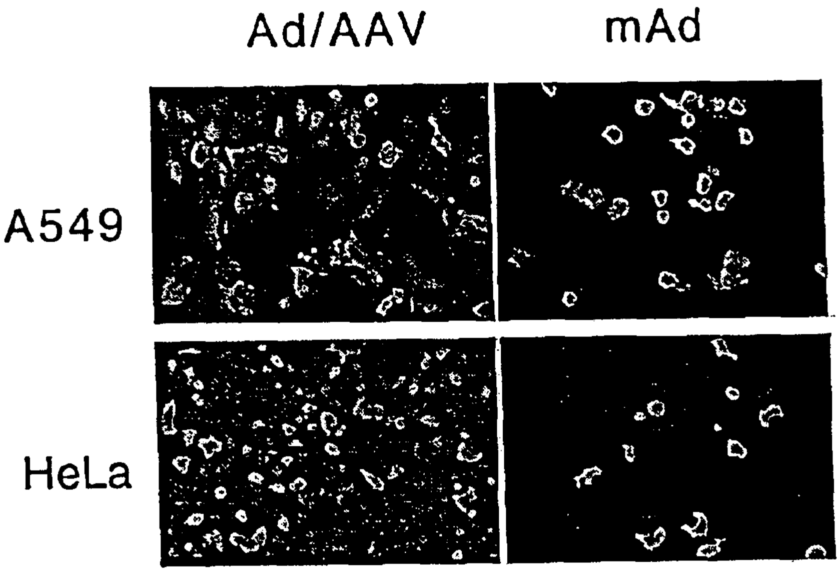
FIG. 6 shows GFP fluorescence in A549 or HeLa cells infected with parental Ad/AAV hybrid virus or mAd 48 hours after infection.

HeLa cells were infected with mAd from fraction E/M (FIG. 5A) in comparison to the parental Ad/AAV hybrid virus. In these experiments, the amount of viruses used for infections were standardized by quantifying virus particles by optical density at 260 nm. A549 and Hela cells were infected at a multiplicity of infection of 200 particles/cell or with the parental Ad/AAV-EGFP-Neo parental virus at the same multiplicity. At different times after infection[24 hr (data not shown) and 48 hr after infection (FIG. 6)], GFP fluorescence was observed using a fluorescein filter on an Axiovert 135 (Zeiss) microscope. FIG. 6 shows that transgene expression was visualized in ~15% of the mAd infected cells and in nearly all of the cells infected with the parental Ad/AAV hybrid virus at the same MOI. These results indicated that the mini-adenoviruses were infectious (albeit less infectious than a comparable amount of the parental Ad/AAV hybrid virus) of A549 and HeLa cells and that they were capable of transducing expression of the EGFP transgene. Similar results were obtained when infecting HepG2, COS-1, and HMEC cells, and primary HUVEC cells and when infecting COS1 cells with Ad/AAV-FVIII (detection of FVIII expression was accomplished by ELISA using a commercially available kit).

To directly test the infectivity of the mini-adenoviruses compared to the parental hybrid virus, an infectious center assay was used. Mini-adenoviruses were assayed for infectious units (IU) using 293 cells infected with wild type adenovirus as helper virus (10 PFU/cell) coinfected with logarithmic dilutions of DNAse I-treated mini-adenoviruses purified by $CsCl_2$ equilibrium centrifugation. Infectious centers were scored by in situ hybridization, as described [Sandalon et al. (1997) Hum. Gene Ther. 8:843–9], using EGFP/Neo as a probe. The number of infectious centers observed multiplied by the dilution factor was used in computing the titer of infectious units/ml. This value was compared to the number of physical virus particles/ml determined spectrophotometrically, and the physical particle to infectious particle ratio calculated. For wild type Ad5, the particle to PFU ratio is 20–25. This analysis demonstrated that the mini-adenoviruses were less infectious than the parental Ad/AAV hybrid virus.

The above results collectively demonstrate that the mini-adenoviruses were infectious of 293, A549, HeLa, HepG2, COS-1, HMEC cells, and and primary HUVEC cells, and also capable of transducing expression of each of the EGFP and FVIII transgenes in vitro in these cells.

B. Infection and Transduction in vivo

The tail vein of mice was used for injection of $CsCl_2$-purified mini-adenovirus vector which was derived from the parental Ad/AAV-EGFP-Neo hybrid virus and which was diluted in phosphate buffer saline (PBS) solution, or of control PBS solution. Treated mice were sacrificed 3 days to 1 week after injection, and liver sections were stained for EGFP fluorescence. Fluorescence imaging showed expression of EGFP in the liver of injected mice, demonstrating both the ability of the mini-adenoviruses to infect cells in vivo, and to transduce expression of the transgene which they carry.

From the above it is clear that the invention provides recombinant vectors including adenovirus/adeno-associated virus (Ad/AAV) vectors and mini-adenovirus (mAd) vectors, and cells containing these vectors. Further, it is also clear that the invention provides rapid, efficient, and improved methods for generating mAd vectors which are capable of introducing any nucleotide sequence of interest into a cell.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method for producing a recombinant vector comprising:

a) providing:

i) a first recombinant vector, comprising in operable combination:

1) a nucleotide sequence of interest having a 5' end and a 3' end;

2) left and right inverted terminal repeats of adenovirus flanking said nucleotide sequence of interest;

3) adenovirus packaging sequence linked to one of said inverted terminal repeats; and 4) a first adeno-associated virus terminal repeat sequence operably linked to said 3' end of said nucleotide sequence of interest, wherein said first vector lacks a second adeno-associated virus terminal repeat sequence, and lacks one or more adenovirsus early gene regions selected from E1, E2, E3, and E4 gene regions;

ii) a cell capable of expressing one or more Rep proteins; and iii) helper adenovirus;

b) introducing said first vector and genome of said helper adenovirus into said cell to produce a transformed cell; and c) culturing said transformed cell under conditions such that said transformed cell expresses said one or more Rep proteins, and a second vector is produced, said second vector selected from:

i) a vector, comprising in operable combination:

1) adeno-associated virus terminal repeat-DD sequence;

2) first and second inverted copies of a nucicotide sequence of interest flanking said adeno-associated virus terminal repeat-DD sequence;

3) left and right inverted terminal repeats of adenovirus flanking said first and second inverted copies of said nucleotide sequence of interest; and 4) an adenovirus packaging sequence linked to one of said inverted terminal repeats, and ii) a vector, comprising in operable combination:

1) a nucleotide sequence of interest having a 5' end and a 3' end;

2) left and right inverted terminal repeats of adenovirus flanking said nucleotide sequence of interest; and 3) an adenovirus packaging sequence linked to one of said inverted terminal repeats.

2. The method for producing the recombinant vector of claim 1, wherein expression of one or more Rep proteins is inducible.

3. The method for producing the recombinant vector of claim 1, wherein said cell lacks expression of said one or more adenovirus early gene regions which are lacking from said first vector.

4. The method of claim 1, wherein said cell comprises a primary cell.

5. The method of claim 4, wherein said primary cell is selected from the group consisting of mouse cells and human cells.

6. The method of claim 1, wherein said cell comprises a cell line.

7. The method of claim 6, whrein said cell line is selected from the group consisting of a HeLa cell line, an A549-derived cell line, a 293-derived cell line, a HepG2-derived cell line, a COS1 -derived cell line, an HMEC-derivcd cell line, a KB-derived cell line, a JW-22-derived cell line, a Neo6-derived cell line and a C12-derived cell line.

* * * * *

UNITED STATES PATENT AND TRADEMARK OFFICE

CERTIFICATE OF CORRECTION

PATENT NO. : 6,916,635 B2 
DATED : July 12, 2005
INVENTOR(S) : Patrick Hearing et al.

It is certified that error appears in the above-identified patent and that said Letters Patent is hereby corrected as shown below:

Column 1,
Line 6, insert -- This invention was made with government support under NIH Grant Nos. HL53665 and A141636. The government has certain rights in the invention. --.

Signed and Sealed this

Twentieth Day of September, 2005

JON W. DUDAS
*Director of the United States Patent and Trademark Office*

SEQUENCE LISTING

<160> NUMBER OF SEQ ID NOS: 27

<210> SEQ ID NO 1
<211> LENGTH: 4675
<212> TYPE: DNA
<213> ORGANISM: Human adeno-associated virus 2

<400> SEQUENCE: 1
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctggagg ggtggagtcg tgacgtgaat tacgtcatag 180
ggttagggag gtcctgtatt agaggtcacg tgagtgtttt gcgacatttt gcgacaccat 240
gtggtcacgc tgggtattta agcccgagtg agcacgcagg gtctccattt tgaagcggga 300
ggtttgaacg cgcagccgcc atgccggggt tttacgagat tgtgattaag gtccccagcg 360
accttgacgg gcatctgccc ggcatttctg acagctttgt gaactgggtg gccgagaagg 420
aatgggagtt gccgccagat tctgacatgg atctgaatct gattgagcag gcacccctga 480
ccgtggccga gaagctgcag cgcgactttc tgacggaatg gcgccgtgtg agtaaggccc 540
cggaggccct tttctttgtg caatttgaga agggagagag ctacttccac atgcacgtgc 600
tcgtggaaac caccggggtg aaatccatgg ttttgggacg tttcctgagt cagattcgcg 660
aaaaactgat tcagagaatt taccgcggga tcgagccgac tttgccaaac tggttcgcgg 720
tcacaaagac cagaaatggc gccggaggcg ggaacaaggt ggtggatgag tgctacatcc 780
ccaattactt gctccccaaa acccagcctg agctccagtg ggcgtggact aatatggaac 840
agtatttaag cgcctgtttg aatctcacgg agcgtaaacg gttggtggcg cagcatctga 900
cgcacgtgtc gcagacgcag gagcagaaca aagagaatca gaatcccaat tctgatgcgc 960
cggtgatcag atcaaaaact tcagccaggt acatggagct ggtcgggtgg ctcgtggaca 1020
aggggattac ctcggagaag cagtggatcc aggaggacca ggcctcatac atctccttca 1080
atgcggcctc caactcgcgg tcccaaatca aggctgcctt ggacaatgcg ggaaagatta 1140
tgagcctgac taaaaccgcc cccgactacc tggtgggcca gcagcccgtg gaggacattt 1200
ccagcaatcg gatttataaa attttggaac taaacgggta cgatccccaa tatgcggctt 1260
ccgtctttct gggatgggcc acgaaaaagt tcggcaagag gaacaccatc tggctgtttg 1320
ggcctgcaac taccgggaag accaacatcg cggaggccat agcccacact gtgcccttct 1380
acgggtgcgt aaactggacc aatgagaact ttcccttcaa cgactgtgtc gacaagatgg 1440
tgatctggtg ggaggagggg aagatgaccg ccaaggtcgt ggagtcggcc aaagccattc 1500
tcggaggaag caaggtgcgc gtggaccaga aatgcaagtc ctcggcccag atagacccga 1560
ctcccgtgat cgtcacctcc aacaccaaca tgtgcgccgt gattgacggg aactcaacga 1620
ccttcgaaca ccagcagccg ttgcaagacc ggatgttcaa atttgaactc acccgccgtc 1680
tggatcatga ctttgggaag gtcaccaagc aggaagtcaa agactttttc cggtgggcaa 1740
aggatcacgt ggttgaggtg gagcatgaat tctacgtcaa aaagggtgga gccaagaaaa 1800
gacccgcccc cagtgacgca gatataagtg agcccaaacg ggtgcgcgag tcagttgcgc 1860
agccatcgac gtcagacgcg gaagcttcga tcaactacgc agacaggtac caaaacaaat 1920
gttctcgtca cgtgggcatg aatctgatgc tgtttccctg cagacaatgc gagagaatga 1980
atcagaattc aaatatctgc ttcactcacg gacagaaaga ctgtttagag tgctttcccg 2040

-continued

```
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag ggtcttgtg    2340
cttcctgggt acaagtacct cggacccttc aacggactcg acaagggaga gccggtcaac   2400
gaggcagacg ccgcggccct cgagcacgta caaagcctac gaccggcagc tcgacagcgg   2460
agacaacccg tacctcaagt acaaccacgc cgacgcggag tttcaggagc gccttaaaga   2520
agatacgtct tttgggggca acctcggacg agcagtcttc caggcgaaaa agagggttct   2580
tgaacctctg ggcctggttg aggaacctgt taagacggct ccgggaaaaa agaggccggt   2640
agagcactct cctgtggagc cagactcctc ctcgggaacc ggaaaggcgg gccagcagcc   2700
tgcaagaaaa agattgaatt ttggtcagac tggagacgca gactcagtac ctgaccccca   2760
gcctctcgga cagccaccag cagccccctc tggtctggga actaatacga tggctacagg   2820
cagtggcgca ccaatggcag acaataacga gggcgccgac ggagtgggta attcctccgg   2880
aaattggcat tgcgattcca catggatggg cgacagagtc atcaccacca gcacccgaac   2940
ctgggccctg cccacctaca acaaccacct ctacaaacaa atttccagcc aatcaggagc   3000
ctcgaacgac aatcactact ttggctacag caccccttgg gggtattttg acttcaacag   3060
attccactgc cacttttcac cacgtgactg gcaaagactc atcaacaaca actggggatt   3120
ccgacccaag agactcaact tcaagctctt taacattcaa gtcaaagagg tcacgcagaa   3180
tgacggtacg acgacgattg ccaataacct taccagcacg gttcaggtgt ttactgactc   3240
ggagtaccag ctcccgtacg tcctcggctc ggcgcatcaa ggatgcctcc cgccgttccc   3300
agcagacgtc ttcatggtgc cacagtatgg atacctcacc ctgaacaacg ggagtcaggc   3360
agtaggacgc tcttcatttt actgcctgga gtactttcct tctcagatgc tgcgtaccgg   3420
aaacaacttt accttcagct acacttttga ggacgttcct ttccacagca gctacgctca   3480
cagccagagt ctggaccgtc tcatgaatcc tctcatcgac cagtacctgt attacttgag   3540
cagaacaaac actccaagtg gaaccaccac gcagtcaagg cttcagtttt ctcaggccgg   3600
agcgagtgac attcgggacc agtctaggaa ctggcttcct ggaccctgtt accgccagca   3660
gcgagtatca aagacatctg cggataacaa caacagtgaa tactcgtgga ctggagctac   3720
caagtaccac ctcaatggca gagactctct ggtgaatccg gccatggcaa gccacaagga   3780
cgatgaagaa aagtttttc ctcagagcgg ggttctcatc tttgggaagc aaggctcaga    3840
gaaaacaaat gtgaacattg aaaaggtcat gattacagac gaagaggaaa tcggaacaac   3900
caatcccgtg gctacggagc agtatggttc tgtatctacc aacctccaga gaggcaacag   3960
acaagcagct accgcagatg tcaacacaca aggcgttctt ccaggcatgg tctggcagga   4020
cagagatgtg taccttcagg ggcccatctg ggcaaagatt ccacacacgg acggacattt   4080
tcacccctct cccctcatgg gtggattcgg acttaaacac cctcctccac agattctcat   4140
caagaacacc ccggtacctg cgaatccttc gaccaccttc agtgcggcaa agtttgcttc   4200
cttcatcaca cagtactcca cgggacacgg tcagcgtgga gatcgagtgg gagctgcaga   4260
aggaaaacag caaacgctgg aatcccgaaa ttcagtacac ttccaactac aacaagtctg   4320
ttaatcgtgg acttaccgtg gatactaatg gcgtgtattc agagcctcgc cccattggca   4380
```

-continued

```
ccagatacct gactcgtaat ctgtaattgc ttgttaatca ataaaccgtt taattcgttt   4440

cagttgaact ttggtctctg cgtatttctt tcttatctag tttccatggc tacgtagata   4500

agtagcatgg cgggttaatc attaactaca aggaacccct agtgatggag ttggccactc   4560

cctctctgcg cgctcgctcg ctcactgagg ccgggcgacc aaaggtcgcc cgacgcccgg   4620

gctttgcccg ggcggcctca gtgagcgagc gagcgcgcag agagggagtg gccaa        4675
```

<210> SEQ ID NO 2
<211> LENGTH: 4675
<212> TYPE: DNA
<213> ORGANISM: Human adeno-associated virus 2

<400> SEQUENCE: 2

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgtgaat tacgtcatag    180

ggttagggag gtcctgtatt agaggtcacg tgagtgtttt gcgacatttt gcgacaccat    240

gtggtcacgc tgggtattta agcccgagtg agcacgcagg gtctccattt tgaagcggga    300

ggtttgaacg cgcagccgcc atgccggggt tttacgagat tgtgattaag gtccccagcg    360

accttgacgg gcatctgccc ggcatttctg acagctttgt gaactgggtg gccgagaagg    420

aatgggagtt gccgccagat tctgacatgg atctgaatct gattgagcag gcacccctga    480

ccgtggccga gaagctgcag cgcgactttc tgacggaatg gcgccgtgtg agtaaggccc    540

cggaggccct tttctttgtg caatttgaga agggagagag ctacttccac atgcacgtgc    600

tcgtggaaac caccggggtg aaatccatgg ttttgggacg tttcctgagt cagattcgcg    660

aaaaactgat tcagagaatt taccgcggga tcgagccgac tttgccaaac tggttcgcgg    720

tcacaaagac cagaaatggc gccggaggcg ggaacaaggt ggtggatgag tgctacatcc    780

ccaattactt gctccccaaa acccagcctg agctccagtg ggcgtggact aatatggaac    840

agtatttaag cgcctgtttg aatctcacgg agcgtaaacg gttggtggcg cagcatctga    900

cgcacgtgtc gcagacgcag gagcagaaca aagagaatca gaatcccaat tctgatgcgc    960

cggtgatcag atcaaaaact tcagccaggt acatggagct ggtcgggtgg ctcgtggaca   1020

aggggattac ctcggagaag cagtggatcc aggaggacca ggcctcatac atctccttca   1080

atgcggcctc caactcgcgg tcccaaatca aggctgcctt ggacaatgcg ggaaagatta   1140

tgagcctgac taaaaccgcc cccgactacc tggtgggcca gcagcccgtg gaggacattt   1200

ccagcaatcg gatttataaa attttggaac taaacgggta cgatccccaa tatgcggctt   1260

ccgtctttct gggatgggcc acgaaaaagt tcggcaagag gaacaccatc tggctgtttg   1320

ggcctgcaac taccgggaag accaacatcg cggaggccat agcccacact gtgcccttct   1380

acgggtgcgt aaactggacc aatgagaact ttcccttcaa cgactgtgtc gacaagatgg   1440

tgatctggtg ggaggagggg aagatgaccg ccaaggtcgt ggagtcggcc aaagccattc   1500

tcggaggaag caaggtgcgc gtggaccaga aatgcaagtc ctcggcccag atagacccga   1560

ctcccgtgat cgtcacctcc aacaccaaca tgtgcgccgt gattgacggg aactcaacga   1620

ccttcgaaca ccagcagccg ttgcaagacc ggatgttcaa atttgaactc acccgccgtc   1680

tggatcatga ctttgggaag gtcaccaagc aggaagtcaa agactttttc cggtgggcaa   1740

aggatcacgt ggttgaggtg gagcatgaat tctacgtcaa aaagggtgga gccaagaaaa   1800

gacccgcccc cagtgacgca gatataagtg agcccaaacg ggtgcgcgag tcagttgcgc   1860
```

-continued

```
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgta caaagcctac gaccggcagc tcgacagcgg   2460
agacaacccg tacctcaagt acaaccacgc cgacgcggag tttcaggagc gccttaaaga   2520
agatacgtct tttgggggca acctcggacg agcagtcttc caggcgaaaa agagggttct   2580
tgaacctctg ggcctggttg aggaacctgt taagacggct ccgggaaaaa agaggccggt   2640
agagcactct cctgtggagc cagactcctc ctcgggaacc ggaaaggcgg gccagcagcc   2700
tgcaagaaaa agattgaatt ttggtcagac tggagacgca gactcagtac ctgaccccca   2760
gcctctcgga cagccaccag cagccccctc tggtctggga actaatacga tggctacagg   2820
cagtggcgca ccaatggcag acaataacga gggcgccgac ggagtgggta attcctccgg   2880
aaattggcat tgcgattcca catggatggg cgacagagtc atcaccacca gcacccgaac   2940
ctgggccctg cccacctaca acaaccacct ctacaaacaa atttccagcc aatcaggagc   3000
ctcgaacgac aatcactact ttggctacag caccccttgg gggtattttg acttcaacag   3060
attccactgc cacttttcac cacgtgactg gcaaagactc atcaacaaca actggggatt   3120
ccgacccaag agactcaact tcaagctctt taacattcaa gtcaaagagg tcacgcagaa   3180
tgacggtacg acgacgattg ccaataacct taccagcacg gttcaggtgt ttactgactc   3240
ggagtaccag ctcccgtacg tcctcggctc ggcgcatcaa ggatgcctcc cgccgttccc   3300
agcagacgtc ttcatggtgc cacagtatgg atacctcacc ctgaacaacg ggagtcaggc   3360
agtaggacgc tcttcatttt actgcctgga gtactttcct tctcagatgc tgcgtaccgg   3420
aaacaacttt accttcagct acacttttga ggacgttcct ttccacagca gctacgctca   3480
cagccagagt ctggaccgtc tcatgaatcc tctcatcgac cagtacctgt attacttgag   3540
cagaacaaac actccaagtg gaaccaccac gcagtcaagg cttcagtttt ctcaggccgg   3600
agcgagtgac attcgggacc agtctaggaa ctggcttcct ggaccctgtt accgccagca   3660
gcgagtatca aagacatctg cggataacaa caacagtgaa tactcgtgga ctggagctac   3720
caagtaccac ctcaatggca gagactctct ggtgaatccg gccatggcaa gccacaagga   3780
cgatgaagaa aagtttttc ctcagagcgg ggttctcatc tttgggaagc aaggctcaga   3840
gaaaacaaat gtgaacattg aaaaggtcat gattacagac gaagaggaaa tcggaacaac   3900
caatcccgtg gctacggagc agtatggttc tgtatctacc aacctccaga gaggcaacag   3960
acaagcagct accgcagatg tcaacacaca aggcgttctt ccaggcatgg tctggcagga   4020
cagagatgtg taccttcagg ggcccatctg ggcaaagatt ccacacacgg acggacattt   4080
tcacccctct cccctcatgg gtggattcgg acttaaacac cctcctccac agattctcat   4140
caagaacacc ccggtacctg cgaatccttc gaccaccttc agtgcggcaa agtttgcttc   4200
```

-continued

```
cttcatcaca cagtactcca cgggacacgg tcagcgtgga gatcgagtgg gagctgcaga   4260

aggaaaacag caaacgctgg aatcccgaaa ttcagtacac ttccaactac aacaagtctg   4320

ttaatcgtgg acttaccgtg gatactaatg gcgtgtattc agagcctcgc cccattggca   4380

ccagatacct gactcgtaat ctgtaattgc ttgttaatca ataaaccgtt taattcgttt   4440

cagttgaact ttggtctctg cgtatttctt tcttatctag tttccatggc tacgtagata   4500

agtagcatgg cgggttaatc attaactaca aggaacccct agtgatggag ttggccactc   4560

cctctctgcg cgctcgctcg ctcactgagg ccgggcgacc aaaggtcgcc cgacgcccgg   4620

gctttgcccg ggcggcctca gtgagcgagc gagcgcgcag agagggagtg gccaa        4675
```

<210> SEQ ID NO 3
<211> LENGTH: 35937
<212> TYPE: DNA
<213> ORGANISM: Human adeno-associated virus 2

<400> SEQUENCE: 3

```
catcatcata atatacctta ttttggattg aagccaatat gataatgagg gggtggagtt     60

tgtgacgtgg cgcggggcgt gggaacgggg cgggtgacgt agtagtgtgg cggaagtgtg    120

atgttgcaag tgtggcggaa cacatgtaag cgccggatgt ggtaaaagtg acgtttttgg    180

tgtgcgccgg tgtatacggg aagtgacaat tttcgcgcgg ttttaggcgg atgttgtagt    240

aaatttgggc gtaaccaagt aatgtttggc cattttcgcg ggaaaactga ataagaggaa    300

gtgaaatctg aataattctg tgttactcat agcgcgtaat atttgtctag ggccgcgggg    360

actttgaccg tttacgtgga gactcgccca ggtgtttttc tcaggtgttt tccgcgttcc    420

gggtcaaagt tggcgtttta ttattatagt cagctgacgc gcagtgtatt tatacccggt    480

gagttcctca agaggccact cttgagtgcc agcgagtaga gttttctcct ccgagccgct    540

ccgacaccgg gactgaaaat gagacatatt atctgccacg gaggtgttat taccgaagaa    600

atggccgcca gtcttttgga ccagctgatc gaagaggtac tggctgataa tcttccacct    660

cctagccatt ttgaaccacc taccttcac gaactgtatg atttagacgt gacggccccc     720

gaagatccca acgaggaggc ggtttcgcag atttttcccg agtctgtaat gttggcggtg    780

caggaaggga ttgacttatt cacttttccg ccggcgcccg gttctccgga gccgcctcac    840

ctttcccggc agcccgagca gccggagcag agagccttgg gtccggtttc tatgccaaac    900

cttgtgccgg aggtgatcga tcttacctgc cacgaggctg gctttccacc cagtgacgac    960

gaggatgaag agggtgagga gtttgtgtta gattatgtgg agcaccccgg gcacggttgc   1020

aggtcttgtc attatcaccg gaggaatacg gggacccag atattatgtg ttcgctttgc    1080

tatatgagga cctgtggcat gtttgtctac agtaagtgaa aattatgggc agtcggtgat   1140

agagtggtgg gtttggtgtg gtaatttttt tttaattttt acagttttgt ggtttaaaga   1200

atttgtatt gtgatttttt aaaaggtcct gtgtctgaac ctgagcctga gcccgagcca    1260

gaaccggagc ctgcaagacc tacccggcgt cctaaattgg tgcctgctat cctgagacgc   1320

ccgacatcac ctgtgtctag agaatgcaat agtagtacgg atagctgtga ctccggtcct   1380

tctaacacac ctcctgagat acacccggtg gtcccgctgt gccccattaa accagttgcc   1440

gtgagagttg gtgggcgtcg ccaggctgtg gaatgtatcg aggacttgct taacgagtct   1500

gggcaacctt tggacttgag ctgtaaacgc cccaggccat aaggtgtaaa cctgtgattg   1560

cgtgtgtggt taacgccttt gtttgctgaa tgagttgatg taagtttaat aaagggtgag   1620

ataatgttta acttgcatgg cgtgttaaat ggggcggggc ttaaagggta tataatgcgc   1680
```

-continued

```
cgtgggctaa tcttggttac atctgacctc atggaggctt gggagtgttt ggaagatttt   1740
tctgctgtgc gtaacttgct ggaacagagc tctaacagta cctcttggtt ttggaggttt   1800
ctgtggggct cctcccaggc aaagttagtc tgcagaatta aggaggatta caagtgggaa   1860
tttgaagagc ttttgaaatc ctgtggtgag ctgtttgatt ctttgaatct gggtcaccag   1920
gcgcttttcc aagagaaggt catcaagact ttggattttt ccacaccggg gcgcgctgcg   1980
gctgctgttg ctttttttgag ttttataaag gataaatgga gcgaagaaac ccatctgagc   2040
ggggggtacc tgctggattt tctggccatg catctgtgga gagcggtggt gagacacaag   2100
aatcgcctgc tactgttgtc ttccgtccgc ccggcaataa taccgacgga ggagcaacag   2160
caggaggaag ccaggcggcg gcggcggcag gagcagagcc catggaaccc gagagccggc   2220
ctggaccctc gggaatgaat gttgtacagg tggctgaact gtttccagaa ctgagacgca   2280
ttttaaccat taacgaggat gggcaggggc taaagggggt aaagagggag cggggggctt   2340
ctgaggctac agaggaggct aggaatctaa cttttagctt aatgaccaga caccgtcctg   2400
agtgtgttac ttttcagcag attaaggata attgcgctaa tgagcttgat ctgctggcgc   2460
agaagtattc catagagcag ctgaccactt actggctgca gccaggggat gattttgagg   2520
aggctattag ggtatatgca aaggtggcac ttaggccaga ttgcaagtac aagattagca   2580
aacttgtaaa tatcaggaat tgttgctaca tttctgggaa cggggccgag gtggagatag   2640
atacggagga tagggtggcc tttagatgta gcatgataaa tatgtggccg gggggtgcttg   2700
gcatggacgg ggtggttatt atgaatgtga ggtttactgg tcccaatttt agcggtacgg   2760
ttttcctggc caataccaat cttatcctac acggtgtaag cttctatggg tttaacaata   2820
cctgtgtgga agcctggacc gatgtaaggg ttcggggctg tgccttttac tgctgctgga   2880
agggggtggt gtgtcgcccc aaaagcaggg cttcaattaa gaaatgcctg tttgaaaggt   2940
gtaccttggg tatcctgtct gagggtaact ccagggtgcg ccacaatgtg gcctccgact   3000
gtggttgctt catgctagtg aaaagcgtgg ctgtgattaa gcataacatg gtgtgtggca   3060
actgcgagga cagggcctct cagatgctga cctgctcgga cggcaactgt cacttgctga   3120
agaccattca cgtagccagc cactctcgca aggcctggcc agtgtttgag cacaacatac   3180
tgacccgctg ttccttgcat ttgggtaaca ggaggggggt gttcctacct taccaatgca   3240
atttgagtca cactaagata ttgcttgagc ccgagagcat gtccaaggtg aacctgaacg   3300
gggtgtttga catgaccatg aagatctgga aggtgctgag gtacgatgag acccgcacca   3360
ggtgcagacc ctgcgagtgt ggcggtaaac atattaggaa ccagcctgtg atgctggatg   3420
tgaccgagga gctgaggccc gatcacttgg tgctggcctg cacccgcgct gagtttggct   3480
ctagcgatga agatacagat tgaggtactg aaatgtgtgg gcgtggctta agggtgggaa   3540
agaatatata aggtgggggt ctcatgtagt tttgtatctg ttttgcagca gccgccgcca   3600
tgagcgccaa ctcgtttgat ggaagcattg tgagctcata tttgacaacg cgcatgcccc   3660
catgggccgg ggtgcgtcag aatgtgatgg gctccagcat tgatggtcgc cccgtcctgc   3720
ccgcaaactc tactaccttg acctacgaga ccgtgtctgg aacgccgttg gagactgcag   3780
cctccgccgc cgcttcagcc gctgcagcca ccgcccgcgg gattgtgact gactttgctt   3840
tcctgagccc gcttgcaagc agtgcagctt cccgttcatc cgcccgcgat gacaagttga   3900
cggctctttt ggcacaattg gattctttga cccgggaact taatgtcgtt tctcagcagc   3960
tgttggatct gcgccagcag gtttctgccc tgaaggcttc ctcccctccc aatgcggttt   4020
```

-continued

```
aaaacataaa taaaaaccag actctgtttg gattttgatc aagcaagtgt cttgctgtct   4080
ttatttaggg gttttgcgcg cgcggtaggc ccgggaccag cggtctcggt cgttgagggt   4140
cctgtgtatt ttttccagga cgtggtaaag gtgactctgg atgttcagat acatgggcat   4200
aagcccgtct ctggggtgga ggtagcacca ctgcagagct tcatgctgcg gggtggtgtt   4260
gtagatgatc cagtcgtagc aggagcgctg ggcgtggtgc ctaaaaatgt ctttcagtag   4320
caagctgatt gccaggggca ggcccttggt gtaagtgttt acaaagcggt taagctggga   4380
tgggtgcata cgtggggata tgagatgcat cttggactgt atttttaggt tggctatgtt   4440
cccagccata tccctccggg gattcatgtt gtgcagaacc accagcacag tgtatccggt   4500
gcacttggga aatttgtcat gtagcttaga aggaaatgcg tggaagaact tggagacgcc   4560
cttgtgacct ccgagatttt ccatgcattc gtccataatg atggcaatgg gcccacgggc   4620
ggcggcctgg gcgaagatat ttctgggatc actaacgtca tagttgtgtt ccaggatgag   4680
atcgtcatag gccattttta caaagcgcgg gcggagggtg ccagactgcg gtataatggt   4740
tccatccggc ccaggggcgt agttaccctc acagatttgc atttcccacg ctttgagttc   4800
agatgggggg atcatgtcta cctgcggggc gatgaagaaa accgtttccg ggtaggggga   4860
gatcagctgg gaagaaagca ggttcctgag cagctgcgac ttaccgcagc cggtgggccc   4920
gtaaatcaca cctattaccg gctgcaactg gtagttaaga gagctgcagc tgccgtcatc   4980
cctgagcagg ggggccactt cgttaagcat gtccctgact tgcatgtttt ccctgaccaa   5040
atgcgccaga aggcgctcgc cgcccagcga tagcagttct tgcaaggaag caaagttttt   5100
caacggtttg aggccgtccg ccgtaggcat gcttttgagc gtttgaccaa gcagttccag   5160
gcggtcccac agctcggtca cgtgctctac ggcatctcga tccagcatat ctcctcgttt   5220
cgcgggttgg ggcggctttc gctgtacggc agtagtcggt gctcgtccag acgggccagg   5280
gtcatgtctt tccacgggcg cagggtcctc gtcagcgtag tctgggtcac ggtgaagggg   5340
tgcgctccgg gctgcgcgct ggccagggtg cgcttgaggc tggtcctgct ggtgctgaag   5400
cgctgccggt cttcgccctg cgcgtcggcc aggtagcatt tgaccatggt gtcatagtcc   5460
agcccctccg cggcgtggcc cttggcgcgc agcttgccct tggaggaggc gccgcacgag   5520
gggcagtgca gacttttaag ggcgtagagc ttgggcgcga gaaataccga ttccggggag   5580
taggcatccg cgccgcaggc cccgcagacg gtctcgcatt ccacgagcca ggtgagctct   5640
ggccgttcgg ggtcaaaaac caggtttccc ccatgctttt tgatgcgttt cttacctctg   5700
gtttccatga gccggtgtcc acgctcggtg acgaaaaggc tgtccgtgtc cccgtataca   5760
gacttgagag gcctgtcctc gagcggtgtt ccgcggtcct cctcgtatag aaactcggac   5820
cactctgaga cgaaggctcg cgtccaggcc agcacgaagg aggctaagtg ggaggggtag   5880
cggtcgttgt ccactagggg gtccactcgc tccagggtgt gaagacacat gtcgccctct   5940
tcggcatcaa ggaaggtgat tggtttatag gtgtaggcca cgtgaccggg tgttcctgaa   6000
ggggggctat aaaagggggt gggggcgcgt tcgtcctcac tctcttccgc atcgctgtct   6060
gcgagggcca gctgttgggg tgagtactcc ctctcaaaag cgggcatgac ttctgcgcta   6120
agattgtcag tttccaaaaa cgaggaggat ttgatattca cctggcccgc ggtgatgcct   6180
ttgagggtgg ccgcgtccat ctggtcagaa aagacaatct ttttgttgtc aagcttggtg   6240
gcaaacgacc cgtagagggc gttggacagc aacttggcga tggagcgcag ggtttggttt   6300
ttgtcgcgat cggcgcgctc cttggccgcg atgtttagct gcacgtattc gcgcgcaacg   6360
caccgccatt cgggaaagac ggtggtgcgc tcgtcgggca ccaggtgcac gcgccaaccg   6420
```

-continued

```
cggttgtgca gggtgacaag gtcaacgctg gtggctacct ctccgcgtag gcgctcgttg   6480
gtccagcaga ggcggccgcc cttgcgcgaa cagaatggcg gtagtgggtc tagctgcgtc   6540
tcgtccgggg ggtctgcgtc cacggtaaag accccgggca gcaggcgcgc gtcgaagtag   6600
tctatcttgc atccttgcaa gtctagcgcc tgctgccatg cgcgggcggc aagcgcgcgc   6660
tcgtatgggt tgagtggggg accccatggc atggggtggg tgagcgcgga ggcgtacatg   6720
ccgcaaatgt cgtaaacgta gaggggctct ctgagtattc caagatatgt agggtagcat   6780
cttccaccgc ggatgctggc gcgcacgtaa tcgtatagtt cgtgcgaggg agcgaggagg   6840
tcgggaccga ggttgctacg ggcgggctgc tctgctcgga agactatctg cctgaagatg   6900
gcatgtgagt tggatgatat ggttggacgc tggaagacgt tgaagctggc gtctgtgaga   6960
cctaccgcgt cacgcacgaa ggaggcgtag gagtcgcgca gcttgttgac cagctcggcg   7020
gtgacctgca cgtctagggc gcagtagtcc agggtttcct tgatgatgtc atacttatcc   7080
tgtccctttt ttttccacag ctcgcggttg aggacaaact cttcgcggtc tttccagtac   7140
tcttggatcg gaaacccgtc ggcctccgaa cggtaagagc ctagcatgta gaactggttg   7200
acggcctggt aggcgcagca tccctttttct acgggtagcg cgtatgcctg cgcggccttc   7260
cggagcgagg tgtgggtgag cgcaaaggtg tccctaacca tgactttgag gtactggtat   7320
ttgaagtcag tgtcgtcgca tccgccctgc tcccagagca aaaagtccgt gcgctttttg   7380
gaacgcgggt ttggcagggc gaaggtgaca tcgttgaaaa gtatctttcc cgcgcgaggc   7440
ataaagttgc gtgtgatgcg gaagggtccc ggcacctcgg aacggttgtt aattacctgg   7500
gcggcgagca cgatctcgtc gaagccgttg atgttgtggc ccacgatgta aagttccaag   7560
aagcgcgggg tgcccttgat ggagggcaat tttttaagtt cctcgtaggt gagctcctca   7620
ggggagctga gcccgtgttc tgacagggcc cagtctgcaa gatgagggtt ggaagcgacg   7680
aatgagctcc acaggtcacg ggccattagc atttgcaggt ggtcgcgaaa ggtcctaaac   7740
tggcgaccta tggccatttt ttctggggtg atgcagtaga aggtaagcgg gtcttgttcc   7800
cagcggtccc atccaaggtc cacggctagg tctcgcgcgg cggtcaccag aggctcatct   7860
ccgccgaact tcataaccag catgaagggc acgagctgct tcccaaaggc ccccatccaa   7920
gtataggtct ctacatcgta ggtgacaaag agacgctcgg tgcgaggatg cgagccgatc   7980
gggaagaact ggatctcccg ccaccagttg gaggagtggc tgttgatgtg gtgaaagtag   8040
aagtccctgc gacgggccga acactcgtgc tggcttttgt aaaaacgtgc gcagtactgg   8100
cagcggtgca cgggctgtac atcctgcacg aggttgacct gacgaccgcg cacaaggaag   8160
cagagtggga atttgagccc ctcgcctggc gggtttggct ggtggtcttc tacttcggct   8220
gcttgtcctt gaccgtctgg ctgctcgagg ggagttatgg tggatcggac caccacgccg   8280
cgcgagccca aagtccagat gtccgcgcgc ggcggtcgga gcttgatgac aacatcgcgc   8340
agatgggagc tgtccatggt ctggagctcc cgcggcgaca ggtcaggcgg gagctcctgc   8400
aggtttacct cgcatagccg ggtcagggcg cgggctaggt ccaggtgata cctgatttcc   8460
aggggctggt tggtggcggc gtcgatgact tgcaagaggc cgcatccccg cggcgcgact   8520
acggtaccgc gcggcgggcg gtgggccgcg ggggtgtcct tggatgatgc atctaaaagc   8580
ggtgacgcgg gcgggccccc ggaggtaggg ggggctcggg acccgccggg agaggggggca   8640
ggggcacgtc ggcgccgcgc gcgggcagga gctggtgctg cgcgcggagg ttgctggcga   8700
acgcgacgac gcggcggttg atctcctgaa tctggcgcct ctgcgtgaag acgacgggcc   8760
```

-continued

```
cggtgagctt gaacctgaaa gagagttcga cagaatcaat ttcggtgtcg ttgacggcgg   8820
cctggcgcaa aatctcctgc acgtctcctg agttgtcttg ataggcgatt tcggccatga   8880
actgctcgat ctcttcctcc tggagatctc cgcgtccggc tcgctccacg gtggcggcga   8940
ggtcgttgga gatgcgggcc atgagctgcg agaaggcgtt gaggcctccc tcgttccaga   9000
cgcggctgta gaccacgccc ccttcggcat cgcgggcgcg catgaccacc tgcgcgagat   9060
tgagctccac gtgccgggcg aagacggcgt agtttcgcag gcgctgaaag aggtagttga   9120
gggtggtggc ggtgtgttct gccacgaaga agtacataac ccagcgtcgc aacgtggatt   9180
cgttgatatc ccccaaggcc tcaaggcgct ccatggcctc gtagaagtcc acggcgaagt   9240
tgaaaaactg ggagttgcgc gccgacacgg ttaactcctc ctccagaaga cggatgagct   9300
cggcgacagt gtcgcgcacc tcgcgctcaa aggctacagg ggcctcttct tcttcaatct   9360
cctcttccat aagggcctcc ccttcttctt cttcttctgg cggcggtggg ggaggggga    9420
cacggcggcg acgacggcgc accgggaggc ggtcgacaaa gcgctcgatc atctccccgc   9480
ggcgacggcg catggtctcg gtgacggcgc ggccgttctc gcgggggcgc agttggaaga   9540
cgccgcccgt catgtcccgg ttatgggttg gcgggggct gccgtgcggc agggatacgg     9600
cgctaacgat gcatctcaac aattgttgtg taggtactcc gccaccgagg gacctgagcg   9660
agtccgcatc gaccggatcg gaaaacctct cgagaaaggc gtctaaccag tcacagtcgc   9720
aaggtaggct gagcaccgtg gcgggcggca gcgggtggcg gtcggggttg tttctggcgg   9780
aggtgctgct gatgatgtaa ttaaagtagg cggtcttgag acggcggatg gtcgacagaa   9840
gcaccatgtc cttgggtccg gcctgctgaa tgcgcaggcg gtcggccatg ccccaggctt   9900
cgttttgaca tcggcgcagg tctttgtagt agtcttgcat gagcctttct accggcactt   9960
cttcttctcc ttcctcttgt cctgcatctc ttgcatctat cgctacggcg gcggcggagt  10020
ttggccgtag gtggcgccct cttcctccca tgcgtgtgac cccgaagccc ctcatcggct  10080
gaagcagggc caggtcggcg acaacgcgct cggctaatat ggcctgctgc acctgcgtga  10140
gggtagactg gaagtcatcc atgtccacaa agcggtggta tgcgcccgtg ttgatggtgt  10200
aagtgcagtt ggccataacg gaccagttaa cggtctggtg acccggctgc gagagctcgg  10260
tgtacctgag acgcgagtaa gcccttgagt caaagacgta gtcgttgcaa gtccgcacca  10320
ggtactgata tcccaccaaa aagtgcggcg gcggctggcg gtagaggggc cagcgtaggg  10380
tggccggggc tccgggggcg aggtcttcca acataaggcg atgatatccg tagatgtacc  10440
tggacatcca ggtgatgccg gcggcggtgg tggaggcgcg cggaaagtcg cggacgcggt  10500
tccagatgtt gcgcagcggc aaaaagtgct ccatggtcgg gacgctctgg ccggtgaggc  10560
gtgcgcagtc gttgacgctc tagaccgtgc aaaaggagag cctgtaagcg ggcactcttc  10620
cgtggtctgg tggataaatt cgcaagggta tcatggcgga cgaccggggt tcgaaccccg  10680
gatccggccg tccgccgtga tccatgcggt taccgcccgc gtgtcgaacc caggtgtgcg  10740
acgtcagaca acgggggagc gctccttttg gcttccttcc aggcgcggcg gctgctgcgc  10800
tagctttttt ggccactggc cgcgcgcggc gtaagcggtt aggctggaaa gcgaaagcat  10860
taagtggctc gctccctgta gccggagggt tattttccaa gggttgagtc gcaggacccc  10920
cggttcgagt ctcgggccgg ccggactgcg gcgaacgggg gtttgcctcc ccgtcatgca  10980
agaccccgct tgcaaattcc tccggaaaca gggacgagcc cctttttgc ttttcccaga   11040
tgcatccggt gctgcggcag atgcgccccc ctcctcagca gcggcaagag caagagcagc  11100
ggcagacatg cagggcaccc tcccttctc ctaccgcgtc aggaggggca acatccgcgg   11160
```

-continued ctgacgcggc ggcagatggt gattacgaac ccccgcggcg ccgggcccgg cactacctgg 11220
acttggagga gggcgagggc ctggcgcggc taggagcgcc ctctcctgag cgacacccaa 11280
gggtgcagct gaagcgtgac acgcgcgagg cgtacgtgcc gcggcagaac ctgtttcgcg 11340
accgcgaggg agaggagccc gaggagatgc gggatcgaaa gttccacgca gggcgcgagt 11400
tgcggcatgg cctgaaccgc gagcggttgc tgcgcgagga ggactttgag cccgacgcgc 11460
ggaccgggat tagtcccgcg cgcgcacacg tggcggccgc cgacctggta accgcgtacg 11520
agcagacggt gaaccaggag attaactttc aaaaaagctt taacaaccac gtgcgcacgc 11580
ttgtggcgcg cgaggaggtg gctataggac tgatgcatct gtgggacttt gtaagcgcgc 11640
tggagcaaaa cccaaatagc aagccgctca tggcgcagct gttccttata gtgcagcaca 11700
gcagggacaa cgaggcattc agggatgcgc tgctaaacat agtagagccc gagggccgct 11760
ggctgctcga tttgataaac attctgcaga gcatagtggt gcaggagcgc agcttgagcc 11820
tggctgacaa ggtggccgcc attaactatt ccatgctcag tctgggcaag ttttacgccc 11880
gcaagatata ccatacccct tacgttccca tagacaagga ggtaaagatc gaggggttct 11940
acatgcgcat ggcgttgaag gtgcttacct tgagcgacga cctgggcgtt tatcgcaacg 12000
agcgcatcca caaggccgtg agcgtgagcc ggcggcgcga gctcagcgac cgcgagctga 12060
tgcacagcct gcaaagggcc ctggctggca cgggcagcgg cgatagagag gccgagtcct 12120
actttgacgc gggcgctgac ctgcgctggg ccccaagccg acgcgccctg gaggcagctg 12180
gggccggacc tgggctggcg gtggcacccg cgcgcgctgg caacgtcggc ggcgtggagg 12240
aatatgacga ggacgatgag tacgagccag aggacggcga gtactaagcg gtgatgtttc 12300
tgatcagatg atgcaagacg caacggaccc ggcggtgcgg gcggcgctgc agagccagcc 12360
gtccggcctt aactccacgg acgactggcg ccaggtcatg gaccgcatca tgtcgctgac 12420
tgcgcgtaac cctgacgcgt tccggcagca gccgcaggcc aaccggctct ccgcaattct 12480
ggaagcggtg gtcccggcgc gcgcaaaccc cacgcacgag aaggtgctgg cgatcgtaaa 12540
cgcgctggcc gaaaacaggg ccatccggcc cgatgaggcc ggcctggtct acgacgcgct 12600
gcttcagcgc gtggctcgtt acaacagcgg caacgtgcag accaacctgg accggctggt 12660
gggggatgtg cgcgaggccg tggcgcagcg tgagcgcgcg cagcagcagg gcaacctggg 12720
ctccatggtt gcactaaacg ccttcctgag tacacagccc gccaacgtgc cgcggggaca 12780
ggaggactac accaactttg tgagcgcact gcggctaatg gtgactgaga caccgcaaag 12840
tgaggtgtac cagtccgggc cagactattt tttccagacc agtagacaag gcctgcagac 12900
cgtaaacctg agccaggctt tcaagaactt gcaggggctg tggggggtgc gggctcccac 12960
aggcgaccgc gcgaccgtgt ctagcttgct gacgcccaac tcgcgcctgt tgctgctgct 13020
aatagcgccc ttcacggaca gtggcagcgt gtcccgggac acatacctag gtcacttgct 13080
gacactgtac cgcgaggcca taggtcaggc gcatgtggac gagcatactt tccaggagat 13140
tacaagtgtc agccgcgcgc tggggcagga ggacacgggc agcctggagg caaccctgaa 13200
ctacctgctg accaaccggc ggcagaagat cccctcgttg cacagtttaa acagcgagga 13260
ggagcgcatc ttgcgctatg tgcagcagag cgtgagcctt aacctgatgc gcgacggggt 13320
aacgcccagc gtggcgctgg acatgaccgc gcgcaacatg gaaccgggca tgtatgcctc 13380
aaaccggccg tttatcaatc gcctaatgga ctacttgcat cgcgcggccg ccgtgaaccc 13440
cgagtatttc accaatgcca tcttgaaccc gcactggcta ccgcccccctg gtttctacac 13500

-continued

```
cgggggattt gaggtgcccg agggtaacga tggattcctc tgggacgaca tagacgacag  13560
cgtgttttcc ccgcaaccgc agaccctgct agagttgcaa cagcgcgagc aggcagaggc  13620
ggcgctgcga aaggaaagct tccgcaggcc aagcagcttg tccgatctag gcgctgcggc  13680
cccgcggtca gatgcgagta gcccatttcc aagcttgata gggtctttta ccagcactcg  13740
caccacccgc ccgcgcctgc tgggcgagga ggagtaccta aacaactcgc tgctgcagcc  13800
gcagcgcgaa aagaacctgc ctccggcatt tcccaacaac gggatagaga gcctagtgga  13860
caagatgagt agatggaaga cgtatgcgca ggagcacagg gatgtgcccg gcccgcgccc  13920
gcccacccgt cgtcaaaggc acgaccgtca gcggggtctg gtgtgggagg acgatgactc  13980
ggcagacgac agcagcgtcc tggatttggg agggagtggc aacccgtttg cgcaccttcg  14040
ccccaggctg gggagaatgt tttaaaaaaa aaaaaaaaaa gcatgatgca aaataaaaaa  14100
ctcaccaagg ccatggcacc gagcgttggt tttcttgtat tccccttagt atgcagcgcg  14160
cggcgatgta tgaggaaggt cctcctccct cctacgagag cgtggtgagc gcggcgccag  14220
tggcggcggc gctgggttcc cccttcgatg ctcccctgga cccgccgttt gtgcctccgc  14280
ggtacctgcg gcctaccggg gggagaaaca gcatccgtta ctctgagttg gcacccctat  14340
tcgacaccac ccgtgtgtac cttgtggaca acaagtcaac ggatgtggca tccctgaact  14400
accagaacga ccacagcaac tttctaacca cggtcattca aaacaatgac tacagcccgg  14460
gggaggcaag cacacagacc atcaatcttg acgaccgttc gcactggggc ggcgacctga  14520
aaaccatcct gcataccaac atgccaaatg tgaacgagtt catgtttacc aataagttta  14580
aggcgcgggt gatggtgtcg cgctcgctta ctaaggacaa acaggtggag ctgaaatatg  14640
agtgggtgga gttcacgctg cccgagggca actactccga gaccatgacc atagacctta  14700
tgaacaacgc gatcgtggag cactacttga aagtgggcag gcagaacggg gttctggaaa  14760
gcgacatcgg ggtaaagttt gacacccgca acttcagact ggggtttgac ccagtcactg  14820
gtcttgtcat gcctggggta tatacaaacg aagccttcca tccagacatc attttgctgc  14880
caggatgcgg ggtggacttc acccacagcc gcctgagcaa cttgttgggc atccgcaagc  14940
ggcaaccctt ccaggagggc tttaggatca cctacgatga cctggagggt ggtaacattc  15000
ccgcactgtt ggatgtggac gcctaccagg caagcttaaa agatgacacc gaacagggcg  15060
gggatggcgc aggcggcggc aacaacagtg gcagcggcgc ggaagagaac tccaacgcgg  15120
cagccgcggc aatgcagccg gtggaggaca tgaacgatca tgccattcgc ggcgacacct  15180
ttgccacacg ggcggaggag aagcgcgctg aggccgaggc agcggcagaa gctgccgccc  15240
ccgctgcgca acccgaggtc gagaagcctc agaagaaacc ggtgatcaaa cccctgacag  15300
aggacagcaa gaaacgcagt tacaacctaa taagcaatga cagcaccttc acccagtacc  15360
gcagctggta ccttgcatac aactacggcg accctcagac cgggatccgc tcatggaccc  15420
tcctttgcac tcctgacgta acctgcggct cggagcaggt ctactggtcg ttgccagaca  15480
tgatgcaaga ccccgtgacc ttccgctcca cgagccagat cagcaacttt ccggtggtgg  15540
gcgccgagct gttgcccgtg cactccaaga gcttctacaa cgaccaggcc gtctactccc  15600
agctcatccg ccagtttacc tctctgaccc acgtgttcaa tcgctttccc gagaaccaga  15660
ttttggcgcg cccgccagcc cccaccatca ccaccgtcag tgaaaacgtt cctgctctca  15720
cagatcacgg gacgctaccg ctgcgcaaca gcatcggagg agtccagcga gtgaccatta  15780
ctgacgccag acgccgcacc tgcccctacg tttacaaggc cctgggcata gtctcgccgc  15840
gcgtcctatc gagccgcact ttttgagcaa acatgtccat ccttatatcg cccagcaata  15900
```

-continued

```
acacaggctg gggcctgcgc ttcccaagca agatgtttgg cggggcaaag aagcgctccg  15960
accaacaccc agtgcgcgtg cgcgggcact accgcgcgcc ctggggcgcg cacaaacgcg  16020
gccgcactgg gcgcaccacc gtcgatgacg ccattgacgc ggtggtggag gaggcgcgca  16080
actacacgcc cacgccgcca ccagtgtcca cagtggacgc ggccattcag accgtggtgc  16140
gcggagcccg gcgttatgct aaaatgaaga gacggcggag gcgcgtagca cgtcgccacc  16200
gccgccgacc cggcactgcc gcccaacgcg cggcggcggc cctgcttaac cgcgcacgtc  16260
gcaccggccg acgggcggcc atgcgggccg ctcgaaggct ggccgcgggt attgtcactg  16320
tgccccccag gtccaggcga cgagcggccg ccgcagcagc cgcggccatt agtgctatga  16380
ctcagggtcg caggggcaac gtgtactggg tgcgcgactc ggttagcggc ctgcgcgtgc  16440
ccgtgcgcac ccgccccccg cgcaactaga ttgcaagaaa aaactactta gactcgtact  16500
gttgtatgta tccagcggcg gcggcgcgca acgaagctat gtccaagcgc aaaatcaaag  16560
aagagatgct ccaggtcatc gcgccggaga tctatggccc cccgaagaag gaagagcagg  16620
attacaagcc ccgaaagcta aagcgggtca aaaagaaaaa gaaagatgat gatgatgatg  16680
aacttgacga cgaggtggaa ctgctgcacg caaccgcgcc caggcggcgg gtacagtgga  16740
aaggtcgacg cgtaagacgt gttttgcgac ccggcaccac cgtagttttt acgcccggtg  16800
agcgctccac ccgcacctac aagcgcgtgt atgatgaggt gtacggcgac gaggacctgc  16860
ttgagcaggc caacgagcgc ctcggggagt ttgcctacgg aaagcggcat aaggacatgt  16920
tggcgttgcc gctggacgag ggcaacccaa cacctagcct aaagcccgtg acactgcagc  16980
aggtgctgcc cacgcttgca ccgtccgaag aaaagcgcgg cctaaagcgc gagtctggtg  17040
acttggcacc caccgtgcag ctgatggtac ccaagcgcca gcgactggaa gatgtcttgg  17100
aaaaaatgac cgtggagcct gggctggagc ccgaggtccg cgtgcggcca atcaagcagg  17160
tggcaccggg actgggcgtg cagaccgtgg acgttcagat acccaccacc agtagcacta  17220
gtattgccac tgccacagag ggcatggaga cacaaacgtc cccggttgcc tcggcggtgg  17280
cagatgccgc ggtgcaggcg gccgctgcgg ccgcgtccaa aacctctacg gaggtgcaaa  17340
cggacccgtg gatgtttcgc gtttcagccc cccggcgccc gcgccgttcc aggaagtacg  17400
gcaccgccag cgcactactg cccgaatatg ccctacatcc ttccatcgcg cctacccccg  17460
gctatcgtgg ctacacctac cgccccagaa gacgagcgac tacccgacgc cgaaccacca  17520
ctggaacccg ccgccgccgt cgccgtcgcc agcccgtgct ggccccgatt tccgtgcgca  17580
gggtggctcg cgaaggaggc aggaccctgg tgctgccaac agcgcgctac caccccagca  17640
tcgtttaaaa gccggtcttt gtggttcttg cagatatggc cctcacctgc cgcctccgtt  17700
tcccggtgcc gggattccga ggaagaatgc accgtaggag gggcatggcc ggccacggcc  17760
tgacgggcgg catgcgtcgt gcgcaccacc ggcggcggcg cgcgtcgcac cgtcgcatgc  17820
gcggcggtat cctgcccctc cttattccac tgatcgccgc ggcgattggc gccgtgcccg  17880
gaattgcatc cgtggccttg caggcgcaga gacactgatt aaaaacaagt tgcatgtgga  17940
aaaatcaaaa taaaaagtct ggagtctcac gctcgcttgg tcctgtaact attttgtaga  18000
atggaagaca tcaactttgc gtctctggcc ccgcgacacg gctcgcgccc gttcatggga  18060
aactggcaag atatcggcac cagcaatatg agcggtggcg ccttcagctg gggctcgctg  18120
tggagcggca ttaaaaattt cggttccacc attaagaact atggcagcaa ggcctggaac  18180
agcagcacag gccagatgct gagggacaag ttgaaagagc aaaatttcca acaaaaggtg  18240
```

-continued gtagatggcc tggcctctgg cattagcggg gtggtggacc tggccaacca ggcagtgcaa 18300
aataagatta acagtaagct tgatccccgc cctcccgtag aggagcctcc accggccgtg 18360
gagacagtgt ctccagaggg gcgtggcgaa aagcgtccgc ggcccgacag ggaagaaact 18420
ctggtgacgc aaatagatga gcctccctcg tacgaggagg cactaaagca aggcctgccc 18480
accacccgtc ccatcgcgcc catggctacc ggagtgctgg gccagcacac acctgtaacg 18540
ctggacctgc ctcccccgc tgacacccag cagaaacctg tgctgccagg gccgtccgcc 18600
gttgttgtaa cccgccctag ccgcgcgtcc ctgcgccgtg ccgccagcgg tccgcgatcg 18660
atgcggcccg tagccagtgg caactggcaa agcacactga acagcatcgt gggtctgggg 18720
gtgcaatccc tgaagcgccg acgatgcttc taaatagcta acgtgtcgta tgtgtcatgt 18780
atgcgtccat gtcgccgcca gaggagctgc tgagccgccg tgcgcccgct ttccaagatg 18840
gctacccctt cgatgatgcc gcagtggtct tacatgcaca tctcgggcca ggacgcctcg 18900
gagtacctga gccccgggct ggtgcagttt gcccgcgcca ccgagacgta cttcagcctg 18960
aataacaagt ttagaaaccc cacggtggca cctacgcacg acgtaaccac agaccggtcc 19020
cagcgtttga cgctgcggtt catccctgtg gaccgcgagg ataccgcgta ctcgtacaaa 19080
gcgcggttca ccctggctgt gggtgacaac cgtgtgcttg atatggcttc cacgtacttt 19140
gacatccgcg gcgtgctgga caggggggcct acttttaagc cctactccgg cactgcctac 19200
aacgctctag ctcccaaggg cgctcctaac tcctgtgagt gggaacaaac cgaagatagc 19260
ggccgggcag ttgccgagga tgaagaagag gaagatgaag atgaagaaga ggaagaagaa 19320
gagcaaaacg ctcgagatca ggctactaag aaaacacatg tctatgccca ggctcctttg 19380
tctggagaaa caattacaaa aagcgggcta caaataggat cagacaatgc agaaacacaa 19440
gctaaacctg tatacgcaga tccttcctat caaccagaac ctcaaattgg cgaatctcag 19500
tggaacgaag ctgatgctaa tgcggcagga gggagagtgc ttaaaaaaac aactcccatg 19560
aaaccatgct atggatctta tgccaggcct acaaatcctt ttggtggtca atccgttctg 19620
gttccggatg aaaaaggggt gcctcttcca aaggttgact tgcaattctt ctcaaatact 19680
acctctttga acgaccggca aggcaatgct actaaaccaa aagtggtttt gtacagtgaa 19740
gatgtaaata tggaaacccc agacacacat ctgtcttaca aacctggaaa aggtgatgaa 19800
aattctaaag ctatgttggg tcaacaatct atgccaaaca gacccaatta cattgctttc 19860
agggacaatt ttattggcct aatgtattat aacagcactg gcaacatggg tgttcttgct 19920
ggtcaggcat cgcagctaaa tgccgtggta gatttgcaag acagaaacac agagctgtcc 19980
tatcaactct tgcttgattc cataggtgat agaaccagat atttttctat gtggaatcag 20040
gctgtagaca gctatgatcc agatgttaga atcattgaaa accatggaac tgaggatgaa 20100
ttgccaaatt attgttttcc tcttggggggt attggggtaa ctgacaccta tcaagctatt 20160
aaggctaatg gcaatggctc aggcgataat ggagatacta catggacaaa agatgaaact 20220
tttgcaacac gtaatgaaat aggagtgggt aacaactttg ccatggaaat taacctaaat 20280
gccaacctat ggagaaattt cctttactcc aatattgcgc tgtacctgcc agacaagcta 20340
aaatacaacc ccaccaatgt ggaaatatct gacaacccca acacctacga ctacatgaac 20400
aagcgagtgg tggctcccgg gcttgtagac tgctacatta accttggggc gcgctggtct 20460
ctggactaca tggacaacgt taatcccttt aaccaccacc gcaatgcggg cctccgttat 20520
cgctccatgt tgttgggaaa cggccgctac gtgccctttc acattcaggt gccccaaaag 20580
ttttttgcca ttaaaaacct cctcctcctg ccaggctcat atacatatga atggaacttc 20640

-continued

```
aggaaggatg ttaacatggt tctgcagagc tctctgggaa acgatcttag agttgacggg  20700
gctagcatta agtttgacag catttgtctt tacgccacct tcttccccat ggcccacaac  20760
acggcctcca cgctggaagc catgctcaga aatgacacca acgaccagtc ctttaatgac  20820
tacctttccg ccgccaacat gctatacccc atacccgcca acgccaccaa cgtgcccatc  20880
tccatcccat cgcgcaactg ggcagcattt cgcggttggg ccttcacacg cttgaagaca  20940
aaggaaaccc cttccctggg atcaggctac gacccttact acacctactc tggctccata  21000
ccatacctt gacggaacctt ctatcttaat cacaccttta agaaggtggc cattaccttt  21060
gactcttctg ttagctggcc gggcaacgac cgcctgctta ctcccaatga gtttgagatt  21120
aaacgctcag ttgacgggga gggctacaac gtagctcagt gcaacatgac caaggactgg  21180
ttcctggtgc agatgttggc caactacaat attggctacc agggcttcta cattccagaa  21240
agctacaagg accgcatgta ctcgttcttc agaaacttcc agcccatgag ccggcaagtg  21300
gttgacgata ctaaatacaa ggagtatcag caggttggaa ttcttcacca gcataacaac  21360
tcaggattcg taggctacct cgctcccacc atgcgcgagg gacaggctta ccccgccaac  21420
gtgccctacc cactaatagg caaaaccgcg gttgacagta ttacccagaa aaagtttctt  21480
tgcgatcgca ccctttggcg catcccattc tccagtaact ttatgtccat gggcgcactc  21540
acagacctgg gccaaaacct tctctacgcc aactccgccc acgcgctaga catgactttt  21600
gaggtggatc ccatggacga gcccaccctt ctttatgttt tgtttgaagt ctttgacgtg  21660
gtccgtgtgc accagccgca ccgcggcgtc atcgagaccg tgtacctgcg cacgcccttc  21720
tcggccggca acgccacaac ataaaagaag caagcaacat caacaacagc tgccgccatg  21780
ggctccagtg agcaggaact gaaagccatt gtcaaagatc ttggttgtgg gccatatttt  21840
ttgggcacct atgacaagcg ctttccaggc tttgtttctc cacacaagct cgcctgcgcc  21900
atagtcaata cggccggtcg cgagactggg ggcgtacact ggatggcctt tgcctggaac  21960
ccgcgctcaa aaacatgcta cctctttgag ccctttggct tttctgacca acgactcaag  22020
caggtttacc agtttgagta cgagtcactc ctgcgccgta gcgccattgc ttcttccccc  22080
gaccgctgta taacgctgga aaagtccacc caaagcgtgc aggggcccaa ctcggccgcc  22140
tgtggactat tctgctgcat gtttctccac gcctttgcca actggcccca aactcccatg  22200
gatcacaacc ccaccatgaa ccttattacc ggggtaccca actccatgct taacagtccc  22260
caggtacagc ccaccctgcg tcgcaaccag gaacagctct acagcttcct ggagcgccac  22320
tcgccctact tccgcagcca cagtgcgcag attaggagcg ccacttcttt ttgtcacttg  22380
aaaaacatgt aaaaataatg tactaggaga cactttcaat aaaggcaaat gtttttattt  22440
gtacactctc gggtgattat ttaccccccca cccttgccgt ctgcgccgtt taaaaatcaa  22500
aggggttctg ccgcgcatcg ctatgcgcca ctggcaggga cacgttgcga tactggtgtt  22560
tagtgctcca cttaaactca ggcacaacca tccgcggcag ctcggtgaag ttttcactcc  22620
acaggctgcg caccatcacc aacgcgttta gcaggtcggg cgccgatatc ttgaagtcgc  22680
agttggggcc tccgccctgc gcgcgcgagt tgcgatacac agggttgcag cactggaaca  22740
ctatcagcgc cgggtggtgc acgctggcca gcacgctctt gtcggagatc agatccgcgt  22800
ccaggtcctc cgcgttgctc agggcgaacg gagtcaactt tggtagctgc cttcccaaaa  22860
agggtgcatg cccaggcttt gagttgcact cgcaccgtag tggcatcaga aggtgaccgt  22920
gcccggtctg ggcgttagga tacagcgcct gcatgaaagc cttgatctgc ttaaaagcca  22980
```

-continued

```
cctgagcctt tgcgccttca gagaagaaca tgccgcaaga cttgccggaa aactgattgg  23040
ccggacaggc cgcgtcatgc acgcagcacc ttgcgtcggt gttggagatc tgcaccacat  23100
ttcggcccca ccggttcttc acgatcttgg ccttgctaga ctgctccttc agcgcgcgct  23160
gcccgttttc gctcgtcaca tccatttcaa tcacgtgctc cttatttatc ataatgctcc  23220
cgtgtagaca cttaagctcg ccttcgatct cagcgcagcg gtgcagccac aacgcgcagc  23280
ccgtgggctc gtggtgcttg taggttacct ctgcaaacga ctgcaggtac gcctgcagga  23340
atcgccccat catcgtcaca aaggtcttgt tgctggtgaa ggtcagctgc aacccgcggt  23400
gctcctcgtt tagccaggtc ttgcatacgg ccgccagagc ttccacttgg tcaggcagta  23460
gcttgaagtt tgcctttaga tcgttatcca cgtggtactt gtccatcaac gcgcgcgcag  23520
cctccatgcc cttctcccac gcagacacga tcggcaggct cagcgggttt atcaccgtgc  23580
tttcactttc cgcttcactg gactcttcct tttcctcttg cgtccgcata ccccgcgcca  23640
ctgggtcgtc ttcattcagc cgccgcaccg tgcgcttacc tcccttgccg tgcttgatta  23700
gcaccggtgg gttgctgaaa cccaccattt gtagcgccac atcttctctt tcttcctcgc  23760
tgtccacgat cacctctggg gatggcgggc gctcgggctt gggagagggg cgcttctttt  23820
tctttttgga cgcaatggcc aaatccgccg tcgaggtcga tggccgcggg ctgggtgtgc  23880
gcggcaccag cgcatcttgt gacgagtctt cttcgtcctc ggactcgaga cgccgcctca  23940
gccgcttttt tgggggcgcg cggggaggcg gcggcgacgg cgacggggac gacacgtcct  24000
ccatggttgg tggacgtcgc gccgcaccgc gtccgcgctc gggggtggtt tcgcgctgct  24060
cctcttcccg actggccatt tccttctcct ataggcagaa aaagatcatg gagtcagtcg  24120
agaaggagga cagcctaacc gccccctttg agttcgccac caccgcctcc accgatgccg  24180
ccaacgcgcc taccaccttc cccgtcgagg cacccccgct tgaggaggag gaagtgatta  24240
tcgagcagga cccaggtttt gtaagcgaag acgacgagga tcgctcagta ccaacagagg  24300
ataaaaagca agaccaggac gacgcagagg caaacgagga acaagtcggg cgggggggacc  24360
aaaggcatgg cgactaccta gatgtgggag acgacgtgct gttgaagcat ctgcagcgcc  24420
agtgcgccat tatctgcgac gcgttgcaag agcgcagcga tgtgcccctc gccatagcgg  24480
atgtcagcct tgcctacgaa cgccacctgt tctcaccgcg cgtacccccc aaacgccaag  24540
aaaacggcac atgcgagccc aacccgcgcc tcaacttcta ccccgtattt gccgtgccag  24600
aggtgcttgc cacctatcac atctttttcc aaaactgcaa gataccccta tcctgccgtg  24660
ccaaccgcag ccgagcggac aagcagctgg ccttgcggca gggcgctgtc atacctgata  24720
tcgcctcgct cgacgaagtg ccaaaaatct ttgagggtct tggacgcgac gagaaacgcg  24780
cggcaaacgc tctgcaacaa gaaaacagcg aaaatgaaag tcactgtgga gtgctggtgg  24840
aacttgaggg tgacaacgcg cgcctagccg tgctgaaacg cagcatcgag gtcacccact  24900
ttgcctaccc ggcacttaac ctacccccca aggttatgag cacagtcatg agcgagctga  24960
tcgtgcgccg tgcacgaccc ctggagaggg atgcaaactt gcaagaacaa accgaggagg  25020
gcctacccgc agttggcgat gagcagctgg cgcgctggct tgagacgcgc gagcctgccg  25080
acttggagga gcgacgcaag ctaatgatgg ccgcagtgct tgttaccgtg gagcttgagt  25140
gcatgcagcg gttctttgct gacccggaga tgcagcgcaa gctagaggaa acgttgcact  25200
acacctttcg ccagggctac gtgcgccagg cctgcaaaat ttccaacgtg gagctctgca  25260
acctggtctc ctaccttgga attttgcacg aaaaccgcct cgggcaaaac gtgcttcatt  25320
ccacgctcaa gggcgaggcg cgccgcgact acgtccgcga ctgcgtttac ttatttctgt  25380
```

-continued gctacacctg gcaaacggcc atgggcgtgt ggcagcaatg cctggaggag cgcaacctaa 25440
aggagctgca gaagctgcta aagcaaaact tgaaggacct atggacggcc ttcaacgagc 25500
gctccgtggc cgcgcacctg gcggacatta tcttccccga acgcctgctt aaaaccctgc 25560
aacagggtct gccagacttc accagtcaaa gcatgttgca aaactttagg aactttatcc 25620
tagagcgttc aggaattctg cccgccacct gctgtgcgct tcctagcgac tttgtgccca 25680
ttaagtaccg tgaatgccct ccgccgcttt ggggtcactg ctaccttctg cagctagcca 25740
actaccttgc ctaccactcc gacatcatgg aagacgtgag cggtgacggc ctactggagt 25800
gtcactgtcg ctgcaaccta tgcaccccgc accgctccct ggtctgcaat tcgcaactgc 25860
ttagcgaaag tcaaattatc ggtacctttg agctgcaggg tccctcgcct gacgaaaagt 25920
ccgcggctcc ggggttgaaa ctcactccgg ggctgtggac gtcggcttac cttcgcaaat 25980
ttgtacctga ggactaccac gcccacgaga ttaggttcta cgaagaccaa tcccgcccgc 26040
caaatgcgga gcttaccgcc tgcgtcatta cccagggcca catccttggc caattgcaag 26100
ccatcaacaa agcccgccaa gagtttctgc tacgaaaggg acgggggtt tacctggacc 26160
cccagtccgg cgaggagctc aacccaatcc ccccgccgcc gcagccctat cagcagccgc 26220
gggcccttgc ttcccaggat ggcacccaaa aagaagctgc agctgccgcc gccgccaccc 26280
acggacgagg aggaatactg ggacagtcag gcagaggagg ttttggacga ggaggaggag 26340
atgatggaag actgggacag cctagacgaa gcttccgagg ccgaagaggt gtcagacgaa 26400
acaccgtcac cctcggtcgc attcccctcg ccggcgcccc agaaattggc aaccgttccc 26460
agcatcgcta caacctccgc tcctcaggcg ccgccggcac tgcctgttcg ccgacccaac 26520
cgtagatggg acaccactgg aaccagggcc ggtaagtcta agcagccgcc gccgttagcc 26580
caagagcaac aacagcgcca aggctaccgc tcgtggcgcg ggcacaagaa cgccatagtt 26640
gcttgcttgc aagactgtgg gggcaacatc tccttcgccc gccgctttct tctctaccat 26700
cacggcgtgg ccttcccccg taacatcctg cattactacc gtcatctcta cagcccctac 26760
tgcaccggcg gcagcggcag cggcagcaac agcagcggtc acacagaagc aaaggcgacc 26820
ggatagcaag actctgacaa agcccaagaa atccacagcg gcggcagcag caggaggagg 26880
agcgctgcgt ctggcgccca acgaacccgt atcgacccgc gagcttagaa ataggatttt 26940
tcccactctg tatgctatat ttcaacaaag caggggccaa gaacaagagc tgaaaataaa 27000
aaacaggtct ctgcgctccc tcacccgcag ctgcctgtat cacaaaagcg aagatcagct 27060
tcggcgcacg ctggaagacg cggaggctct cttcagcaaa tactgcgcgc tgactcttaa 27120
ggactagttt cgcgcccttt ctcaaattta agcgcgaaaa ctacgtcatc tccagcggcc 27180
acacccggcg ccagcacctg tcgtcagcgc cattatgagc aaggaaattc ccacgcccta 27240
catgtggagt taccagccac aaatgggact tgcggctgga gctgcccaag actactcaac 27300
ccgaataaac tacatgagcg cgggacccca catgatatcc cgggtcaacg gaatccgcgc 27360
ccaccgaaac cgaattctcc tcgaacaggc ggctattacc accacacctc gtaataacct 27420
taatccccgt agttggcccg ctgccctggt gtaccaggaa agtcccgctc ccaccactgt 27480
ggtacttccc agagacgccc aggccgaagt tcagatgact aactcagggg cgcagcttgc 27540
gggcggcttt cgtcacaggg tgcggtcgcc cgggcagggt ataactcacc tgaaaatcag 27600
agggcgaggt attcagctca acgacgagtc ggtgagctcc tctcttggtc tccgtccgga 27660
cgggacattt cagatcggcg gcgctggccg ctcttcattt acgccccgtc aggcgatcct 27720

-continued

```
aactctgcag acctcgtcct cggagccgcg ctccggaggc attggaactc tacaatttat  27780
tgaggagttc gtgccttcgg tttacttcaa cccctttttct ggacctcccg gccactaccc  27840
ggaccagttt attcccaact ttgacgcggt gaaagactcg gcggacggct acgactgaat  27900
gaccagtgga gaggcagagc gactgcgcct gacacacctc gaccactgcc gccgccacaa  27960
gtgctttgcc cgcggctccg gtgagttttg ttactttgaa ttgcccgaag agcatatcga  28020
gggcccggcg cacggcgtcc ggctcaccac ccaggtagag cttacacgta gcctgattcg  28080
ggagtttacc aagcgccccc tgctagtgga gcgggagcgg ggtccctgtg ttctgaccgt  28140
ggtttgcaac tgtcctaacc ctggattaca tcaagatctt tgttgtcatc tctgtgctga  28200
gtataataaa tacagaaatt agaatctact ggggctcctg tcgccatcct gtgaacgcca  28260
ccgtttttac ccacccaaag cagaccaaag caaacctcac ctccggtttg cacaagcggg  28320
ccaataagta ccttacctgg tactttaacg gctcttcatt tgtaatttac aacagtttcc  28380
agcgagacga agtaagtttg ccacacaacc ttctcggctt caactacacc gtcaagaaaa  28440
acaccaccac caccaccctc ctcacctgcc gggaacgtac gagtgcgtca ccggttgctg  28500
cgcccacacc tacagcctga gcgtaaccag acattactcc catttttcca aaacaggagg  28560
tgagctcaac tcccggaact caggtcaaaa aagcattttg cggggtgctg ggattttta  28620
attaagtata tgagcaattc aagtaactct acaagcttgt ctaatttttc tggaattggg  28680
gtcggggtta tccttactct tgtaattctg tttattctta tactagcact tctgtgcctt  28740
agggttgccg cctgctgcac gcacgtttgt acctattgtc agctttttaa acgctggggg  28800
caacatccaa gatgaggtac atgattttag gcttgctcgc ccttgcggca gtctgcagcg  28860
ctgccaaaaa ggttgagttt aaggaaccag cttgcaatgt tacatttaaa tcagaagcta  28920
atgaatgcac tactcttata aaatgcacca cagaacatga aaagcttatt attcgccaca  28980
aagacaaaat tggcaagtat gctgtatatg ctatttggca gccaggtgac actaacgact  29040
ataatgtcac agtcttccaa ggtgaaaatc gtaaaacttt tatgtataaa tttccatttt  29100
atgaaatgtg cgatattacc atgtacatga gcaaacagta caagttgtgg cccccacaaa  29160
agtgtttaga gaacactggc accttttgtt ccaccgctct gcttattaca gcgcttgctt  29220
tggtatgtac cttactttat ctcaaataca aaagcagacg cagttttatt gatgaaaaga  29280
aaatgccttg attttccgct tgcttgtatt cccctggaca atttactcta tgtgggatat  29340
gctccaggcg ggcaagatta tacccacaac cttcaaatca aactttcctg gacgttagcg  29400
cctgatttct gccagcgcct gcactgcaaa tttgatcaaa cccagcttca gcttgcctgc  29460
tccagagatg accggctcaa ccatcgcgcc cacaacggac tatcgcaaca ccactgctac  29520
cggactaaca tctgccctaa atttacccca agttcatgcc tttgtcaatg actgggcgag  29580
cttggacatg tggtggtttt ccatagcgct tatgtttgtt tgccttatta ttatgtggct  29640
tatttgttgc ctaaagcgca gacgcgccag accccccatc tataggccta tcattgtgct  29700
caacccacac aatgaaaaaa ttcatagatt ggacggtctg aaaccatgtt ctcttctttt  29760
acagtatgat taaatgagac atgattcctc gagttcttat attattgacc cttgttgcgc  29820
ttttctgtgc gtgctctaca ttggccgcgg tcgctcacat cgaagtagat tgcatcccac  29880
ctttcacagt ttacctgctt tacggatttg tcacccttat cctcatctgc agcctcgtca  29940
ctgtagtcat cgccttcatt cagttcattg actgggtttg tgtgcgcatt gcgtacctca  30000
ggcaccatcc gcaatacaga gacaggacta tagctgatct tctcagaatt ctttaattat  30060
gaaacggagt gtcatttttg ttttgctgat tttttgcgcc ctacctgtgc tttgctccca  30120
```

-continued

```
aacctcagcg cctcccaaaa gacatatttc ctgcagattc actcaaatat ggaacattcc  30180
cagctgctac aacaaacaga gcgatttgtc agaagcctgg ttatacgcca tcatctctgt  30240
catggttttt tgcagtacca tttttgccct agccatatat ccataccttg acattggctg  30300
gaatgccata gatgccatga accaccctac tttcccagtg cccgctgtca taccactgca  30360
acaggttatt gccccaatca atcagcctcg cccccccttct cccaccccca ctgagattag  30420
ctactttaat ttgacaggtg gagatgactg aatctctaga tctagaattg gatggaatta  30480
acaccgaaca gcgcctacta gaaaggcgca aggcggcgtc cgagcgagaa cgcctaaaac  30540
aagaagttga agacatggtt aacctacacc agtgtaaaag aggtatcttt tgtgtggtca  30600
agcaggccaa acttacctac gaaaaaacca ctaccggcaa ccgcctcagc tacaagctac  30660
ccacccagcg ccaaaaactg gtgcttatgg tgggagaaaa acctatcacc gtcacccagc  30720
actcggcaga aacagagggc tgcctgcact tcccctatca gggtccagag gacctctgca  30780
ctcttattaa aaccatgtgt ggtattagag atcttattcc attcaactaa cataaacaca  30840
caataaatta cttacttaaa atcagtcagc aaatctttgt ccagcttatt cagcatcacc  30900
tcctttcctt cctcccaact ctggtatctc agccgccttt tagctgcaaa ctttctccaa  30960
agtttaaatg ggatgtcaaa ttcctcatgt tcttgtccct ccgcacccac tatcttcata  31020
ttgttgcaga tgaaacgcgc cagaccgtct gaagacacct tcaaccccgt gtatccatat  31080
gacacagaaa ccgggcctcc aactgtgccc tttcttaccc ctccatttgt ttcacccaat  31140
ggtttccaag aaagtccccc tggagttctc tctctacgcg tctccgaacc tttggacacc  31200
tcccacggca tgcttgcgct taaaatgggc agcggtctta ccctagacaa ggccggaaac  31260
ctcacctccc aaaatgtaac cactgttact cagccactta aaaaaacaaa gtcaaacata  31320
agtttggaca cctccgcacc acttacaatt acctcaggcg ccctaacagt ggcaaccacc  31380
gctcctctga tagttactag cggcgctctt agcgtacagt cacaagcccc actgaccgtg  31440
caagactcca aactaagcat tgctactaaa gggcccatta cagtgtcaga tggaaagcta  31500
gccctgcaaa catcagcccc cctctctggc agtgacagcg acacccttac tgtaactgca  31560
tcacccccgc taactactgc cacgggtagc ttgggcatta acatggaaga tcctatttat  31620
gtaaataatg gaaaaatagg aattaaaata agcggtcctt tgcaagtagc acaaaactcc  31680
gatacactaa cagtagttac tggaccaggt gtcaccgttg aacaaaactc ccttagaacc  31740
aaagttgcag gagctattgg ttatgattca tcaaacaaca tggaaattaa aacgggcggt  31800
ggcatgcgta taaataacaa cttgttaatt ctagatgtgg attacccatt tgatgctcaa  31860
acaaaactac gtcttaaact ggggcaggga cccctgtata ttaatgcatc tcataacttg  31920
gacataaact ataacagagg cctatacctt tttaatgcat caaacaatac taaaaaactg  31980
gaagttagca taaaaaaatc cagtggacta aactttgata atactgccat agctataaat  32040
gcaggaaagg gtctggagtt tgatacaaac acatctgagt ctccagatat caacccaata  32100
aaaactaaaa ttggctctgg cattgattac aatgaaaacg gtgccatgat tactaaactt  32160
ggagcgggtt taagctttga caactcaggg gccattacaa taggaaacaa aaatgatgac  32220
aaacttaccc tgtggacaac cccagaccca tctcctaact gcagaattca ttcagataat  32280
gactgcaaat ttactttggt tcttacaaaa tgtgggagtc aagtactagc tactgtagct  32340
gctttggctg tatctggaga tctttcatcc atgacaggca ccgttgcaag tgttagtata  32400
ttccttagat ttgaccaaaa cggtgttcta atggagaact cctcacttaa aaaacattac  32460
```

-continued

```
tggaacttta gaaatgggaa ctcaactaat gcaaatccat acacaaatgc agttggattt  32520
atgcctaacc ttctagccta tccaaaaacc caaagtcaaa ctgctaaaaa taacattgtc  32580
agtcaagttt acttgcatgg tgataaaact aaacctatga tacttaccat tacacttaat  32640
ggcactagtg aatccacaga aactagcgag gtaagcactt actctatgtc ttttacatgg  32700
tcctgggaaa gtggaaaata caccactgaa acttttgcta ccaactctta caccttctcc  32760
tacattgccc aggaataaag aatcgtgaac ctgttgcatg ttatgtttca acgtgtttat  32820
ttttcaattg cagaaaattt caagtcattt ttcattcagt agtatagccc caccaccaca  32880
tagcttatat tgatcaccgt accttaatca aactcacaga accctagtat tcaacctgcc  32940
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcgcttaagt tcatgtcgct  33120
gtccagctgc tgagccacag gctgctgtcc aacttgcggt tgctcaacgg gcggcgaagg  33180
ggaagtccac gcctacatgg gggtagagtc ataatcgtgc atcaggatag ggcggtggtg  33240
ctgcagcagc gcgcgaataa actgctgccg ccgccgctcc gtcctgcagg aatacaacat  33300
ggcagtggtc tcctcagcga tgattcgcac cgcccgcagc atgagacgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatgcact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gtcagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtc tctgtctcaa aaggaggtag gcgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgtcgct  34140
tagctcgctc tgtgtagtag ttgtagtata tccactctct caaagcatcc aggcgccccc  34200
tggcttcggg ttctatgtaa actccttcat gcgccgctgc cctgataaca tccaccaccg  34260
cagaataagc cacacccagc caacctacac attcgttctg cgagtcacac acgggaggag  34320
cgggaagagc tggaagaacc atgttttttt tttttttatt ccaaaagatt atccaaaacc  34380
tcaaaatgaa gatctattaa gtgaacgcgc tcccctccgg tggcgtggtc aaactctaca  34440
gccaaagaac agataatggc atttgtaaga tgttgcacaa tggcttccaa aaggcaaact  34500
gccctcacgt ccaagtggac gtaaaggcta aacccttcag ggtgaatctc ctctataaac  34560
attccagcac cttcaaccat gcccaaataa ttttcatctc gccaccttat caatatgtct  34620
ctaagcaaat cccgaatatt aagtccggcc attgtaaaaa tctgctccag agcgccctcc  34680
accttcagcc tcaagcagcg aatcatgatt gcaaaaattc aggttcctca cagacctgta  34740
taagattcaa aagcggaaca ttaacaaaaa taccgcgatc ccgtaggtcc cttcgcaggg  34800
ccagctgaac ataatcgtgc aggtctgcac ggaccagcgc ggccacttcc ccgccaggaa  34860
```

-continued ccatgacaaa agaacccaca ctgattatga cacgcatact cggagctatg ctaaccagcg 34920
tagcccctat gtaagcttgt tgcatgggcg gcgatataaa atgcaaggtg ctgctcaaaa 34980
aatcaggcaa agcctcgcgc aaaaaagcaa gcacatcgta gtcatgctca tgcagataaa 35040
ggcaggtaag ttccggaacc accacagaaa aagacaccat ttttctctca aacatgtctg 35100
cgggttcctg cattaaacac aaaataaaat aacaaaaaaa aacatttaaa cattagaagc 35160
ctgtcttaca acaggaaaaa caacccttat aagcataaga cggactacgg ccatgccggc 35220
gtgaccgtaa aaaaactggt caccgtgatt aaaaagcacc accgacagtt cctcggtcat 35280
gtccggagtc ataatgtaag actcggtaaa cacatcaggt tggttaacat cggtcagtgc 35340
taaaaagcga ccgaaatagc ccgggggaat acatacccgc aggcgtagag acaacattac 35400
agcccccata ggaggtataa caaaattaat aggagagaaa aacacataaa cacctgaaaa 35460
accctcctgc ctaggcaaaa tagcaccctc ccgctccaga acaacataca gcgcttccac 35520
agcggcagcc ataacagtca gccttaccag taaaaaaacc tattaaaaaa caccactcga 35580
cacggcacca gctcaatcag tcacagtgta aaaagggcca agtacagagc gagtatatat 35640
aggactaaaa aatgacgtaa cggttaaagt ccacaaaaaa cacccagaaa accgcacgcg 35700
aacctacgcc cagaaacgaa agccaaaaaa cccacaactt cctcaaatct tcacttccgt 35760
tttcccacga tacgtcactt cccattttaa aaaaactaca attcccaata catgcaagtt 35820
actccgccct aaaacctacg tcacccgccc cgttcccacg ccccgcgcca cgtcacaaac 35880 tccacccccct cattatcata ttggcttcaa tccaaaataa ggtatattat gatgatg 35937

<210> SEQ ID NO 4
<211> LENGTH: 35935
<212> TYPE: DNA
<213> ORGANISM: Human adenovirus type 5

<400> SEQUENCE: 4
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagctgacg tgtagtgtat ttatacccgg 480
tgagttcctc aagaggccac tcttgagtgc cagcgagtag agttttctcc tccgagccgc 540
tccgacaccg ggactgaaaa tgagacatat tatctgccac ggaggtgtta ttaccgaaga 600
aatggccgcc agtcttttgg accagctgat cgaagaggta ctggctgata atcttccacc 660
tcctagccat tttgaaccac ctacccttca cgaactgtat gatttagacg tgacggcccc 720
cgaagatccc aacgaggagg cggtttcgca gatttttccc gactctgtaa tgttggcggt 780
gcaggaaggg attgacttac tcacttttcc gccggcgccc ggttctccgg agccgcctca 840
cctttcccgg cagcccgagc agccggagca gagagccttg ggtccggttt ctatgccaaa 900
ccttgtaccg gaggtgatcg atcttacctg ccacgaggct ggctttccac ccagtgacga 960
cgaggatgaa gagggtgagg agtttgtgtt agattatgtg gagcaccccg ggcacggttg 1020

-continued

```
caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaattttt tttttaattt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040
agcgggggt acctgctgga ttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg gggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
```

-continued

```
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtgggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
ggtaggggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag ggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
```

-continued

```
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtagggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atggggtggg tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtccctttt ttttccacag ctcgcggttg aggacaaact cttcgcggtc   7140
tttccagtac tcttggatcg gaaacccgtc ggcctccgaa cggtaagagc ctagcatgta   7200
gaactggttg acggcctggt aggcgcagca tccctttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgctttttg gaacgcggat ttggcagggc gaaggtgaca tcgttgaaga gtatctttcc   7440
cgcgcgaggc ataaagttgc gtgtgatgcg gaagggtccc ggcacctcgg aacggttgtt   7500
aattacctgg gcggcgagca cgatctcgtc aaagccgttg atgttgtggc ccacaatgta   7560
aagttccaag aagcgcggga tgcccttgat ggaaggcaat tttttaagtt cctcgtaggt   7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
```

-continued

```
cacaaggaag cagagtggga atttgagccc ctcgcctggc gggtttggct ggtggtcttc   8220
tacttcggct gcttgtcctt gaccgtctgg ctgctcgagg ggagttacgg tggatcggac   8280
caccacgccg cgcgagccca aagtccagat gtccgcgcgc ggcggtcgga gcttgatgac   8340
aacatcgcgc agatgggagc tgtccatggt ctggagctcc cgcggcgtca ggtcaggcgg   8400
gagctcctgc aggtttacct cgcatagacg ggtcagggcg cgggctagat ccaggtgata   8460
cctaatttcc aggggctggt tggtggcggc gtcgatggct tgcaagaggc cgcatccccg   8520
cggcgcgact acggtaccgc gcggcgggcg gtgggccgcg ggggtgtcct tggatgatgc   8580
atctaaaagc ggtgacgcgg gcgagccccc ggaggtaggg ggggctccgg acccgccggg   8640
agagggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccgggcg aagacggcgt agtttcgcag gcgctgaaag   9120
aggtagttga gggtggtggc ggtgtgttct gccacgaaga agtacataac ccagcgtcgc   9180
aacgtggatt cgttgatatc cccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataagggcc tccccttctt cttcttctgg cggcggtggg   9420
ggaggggga cacggcggcg acgacggcgc accgggaggc ggtcgacaaa gcgctcgatc   9480
atctccccgc ggcgacggcg catggtctcg gtgacggcgc ggccgttctc gcgggggcgc   9540
agttggaaga cgccgcccgt catgtcccgg ttatgggttg gcggggggct gccatgcggc   9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
ccccaggctt cgttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccgggggcg agatcttcca acataaggcg atgatatccg  10440
tagatgtacc tggacatcca ggtgatgccg gcggcggtgg tggaggcgcg cggaaagtcg  10500
```

-continued

```
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgcccgc gtgtcgaacc  10740
caggtgtgcg acgtcagaca acgggggagt gctccttttg gcttccttcc aggcgcggcg  10800
gctgctgcgc tagctttttt ggccactggc cgcgcgcagc gtaagcggtt aggctggaaa  10860
gcgaaagcat taagtggctc gctccctgta gccggagggt tattttccaa gggttgagtc  10920
gcgggacccc cggttcgagt ctcggaccgg ccggactgcg gcgaacgggg gtttgcctcc  10980
ccgtcatgca agaccccgct tgcaaattcc tccggaaaca gggacgagcc cctttttttgc  11040
ttttcccaga tgcatccggt gctgcggcag atgcgccccc ctcctcagca gcggcaagag  11100
caagagcagc ggcagacatg cagggcaccc tcccctcctc ctaccgcgtc aggaggggcg  11160
acatccgcgg ttgacgcggc agcagatggt gattacgaac cccgcggcg ccgggcccgg  11220
cactacctgg acttggagga gggcgagggc ctggcgcggc taggagcgcc ctctcctgag  11280
cggtacccaa gggtgcagct gaagcgtgat acgcgtgagg cgtacgtgcc gcggcagaac  11340
ctgtttcgcg accgcgaggg agaggagccc gaggagatgc gggatcgaaa gttccacgca  11400
gggcgcgagc tgcggcatgg cctgaatcgc gagcggttgc tgcgcgagga ggactttgag  11460
cccgacgcgc gaaccgggat tagtcccgcg cgcgcacacg tggcggccgc cgacctggta  11520
accgcatacg agcagacggt gaaccaggag attaactttc aaaaaagctt taacaaccac  11580
gtgcgtacgc ttgtggcgcg cgaggaggtg gctataggac tgatgcatct gtgggacttt  11640
gtaagcgcgc tggagcaaaa cccaaatagc aagccgctca tggcgcagct gttccttata  11700
gtgcagcaca gcagggacaa cgaggcattc agggatgcgc tgctaaacat agtagagccc  11760
gagggccgct ggctgctcga tttgataaac atcctgcaga gcatagtggt gcaggagcgc  11820
agcttgagcc tggctgacaa ggtggccgcc atcaactatt ccatgcttag cctgggcaag  11880
ttttacgccc gcaagatata ccatacccct tacgttccca tagacaagga ggtaaagatc  11940
gaggggttct acatgcgcat ggcgctgaag gtgcttacct tgagcgacga cctgggcgtt  12000
tatcgcaacg agcgcatcca caaggccgtg agcgtgagcc ggcggcgcga gctcagcgac  12060
cgcgagctga tgcacagcct gcaaagggcc ctggctggca cgggcagcgg cgatagagag  12120
gccgagtcct actttgacgc gggcgctgac ctgcgctggg ccccaagccg acgcgccctg  12180
gaggcagctg ggccggacc tgggctggcg gtggcacccg cgcgcgctgg caacgtcggc  12240
ggcgtggagg aatatgacga ggacgatgag tacgagccag aggacggcga gtactaagcg  12300
gtgatgtttc tgatcagatg atgcaagacg caacggaccc ggcggtgcgg gcggcgctgc  12360
agagccagcc gtccggcctt aactccacgg acgactggcg ccaggtcatg gaccgcatca  12420
tgtcgctgac tgcgcgcaat cctgacgcgt tccggcagca gccgcaggcc aaccggctct  12480
ccgcaattct ggaagcggtg gtcccggcgc gcgcaaaccc cacgcacgag aaggtgctgg  12540
cgatcgtaaa cgcgctggcc gaaaacaggg ccatccggcc cgacgaggcc ggcctggtct  12600
acgacgcgct gcttcagcgc gtggctcgtt acaacagcgg caacgtgcag accaacctgg  12660
accggctggt gggggatgtg cgcgaggccg tggcgcagcg tgagcgcgcg cagcagcagg  12720
gcaacctggg ctccatggtt gcactaaacg ccttcctgag tacacagccc gccaacgtgc  12780
cgcggggaca ggaggactac accaactttg tgagcgcact gcggctaatg gtgactgaga  12840
caccgcaaag tgaggtgtac cagtctgggc cagactattt tttccagacc agtagacaag  12900
```

-continued

```
gcctgcagac cgtaaacctg agccaggctt tcaaaaactt gcaggggctg tggggggtgc  12960
gggctcccac aggcgaccgc gcgaccgtgt ctagcttgct gacgcccaac tcgcgcctgt  13020
tgctgctgct aatagcgccc ttcacggaca gtggcagcgt gtcccgggac acatacctag  13080
gtcacttgct gacactgtac cgcgaggcca taggtcaggc gcatgtggac gagcatactt  13140
tccaggagat tacaagtgtc agccgcgcgc tggggcagga ggacacgggc agcctggagg  13200
caaccctaaa ctacctgctg accaaccggc ggcagaagat cccctcgttg cacagtttaa  13260
acagcgagga ggagcgcatt ttgcgctacg tgcagcagag cgtgagcctt aacctgatgc  13320
gcgacggggt aacgcccagc gtggcgctgg acatgaccgc gcgcaacatg gaaccgggca  13380
tgtatgcctc aaaccggccg tttatcaacc gcctaatgga ctacttgcat cgcgcggccg  13440
ccgtgaaccc cgagtatttc accaatgcca tcttgaaccc gcactggcta ccgccccctg  13500
gtttctacac cggggggattc gaggtgcccg agggtaacga tggattcctc tgggacgaca  13560
tagacgacag cgtgttttcc ccgcaaccgc agaccctgct agagttgcaa cagcgcgagc  13620
aggcagaggc ggcgctgcga aaggaaagct tccgcaggcc aagcagcttg tccgatctag  13680
gcgctgcggc cccgcggtca gatgctagta gcccatttcc aagcttgata gggtctctta  13740
ccagcactcg caccacccgc ccgcgcctgc tgggcgagga ggagtaccta aacaactcgc  13800
tgctgcagcc gcagcgcgaa aaaaacctgc ctccggcatt tcccaacaac gggatagaga  13860
gcctagtgga caagatgagt agatggaaga cgtacgcgca ggagcacagg gacgtgccag  13920
gcccgcgccc gcccacccgt cgtcaaaggc acgaccgtca gcggggtctg gtgtgggagg  13980
acgatgactc ggcagacgac agcagcgtcc tggatttggg agggagtggc aacccgtttg  14040
cgcaccttcg ccccaggctg gggagaatgt tttaaaaaaa aaaaagcatg atgcaaaata  14100
aaaaactcac caaggccatg gcaccgagcg ttggttttct tgtattcccc ttagtatgcg  14160
gcgcgcggcg atgtatgagg aaggtcctcc tccctcctac gagagtgtgg tgagcgcggc  14220
gccagtggcg gcggcgctgg gttctccctt cgatgctccc ctggacccgc cgtttgtgcc  14280
tccgcggtac ctgcggccta ccggggggag aaacagcatc cgttactctg agttggcacc  14340
cctattcgac accacccgtg tgtacctggt ggacaacaag tcaacggatg tggcatccct  14400
gaactaccag aacgaccaca gcaactttct gaccacggtc attcaaaaca atgactacag  14460
cccgggggag gcaagcacac agaccatcaa tcttgacgac cggtcgcact ggggcggcga  14520
cctgaaaacc atcctgcata ccaacatgcc aaatgtgaac gagttcatgt ttaccaataa  14580
gtttaaggcg cgggtgatgg tgtcgcgctt gcctactaag gacaatcagg tggagctgaa  14640
atacgagtgg gtggagttca cgctgcccga gggcaactac tccgagacca tgaccataga  14700
ccttatgaac aacgcgatcg tggagcacta cttgaaagtg ggcagacaga acggggttct  14760
ggaaagcgac atcggggtaa agtttgacac ccgcaacttc agactggggt ttgaccccgt  14820
cactggtctt gtcatgcctg gggtatatac aaacgaagcc ttccatccag acatcatttt  14880
gctgccagga tgcggggtgg acttcaccca cagccgcctg agcaacttgt tgggcatccg  14940
caagcggcaa cccttccagg agggctttag gatcacctac gatgatctgg agggtggtaa  15000
cattcccgca ctgttggatg tggacgccta ccaggcgagc ttgaaagatg acaccgaaca  15060
gggcgggggt ggcgcaggcg gcagcaacag cagtggcagc ggcgcggaag agaactccaa  15120
cgcggcagcc gcggcaatgc agccggtgga ggacatgaac gatcatgcca ttcgcggcga  15180
cacctttgcc acacgggctg aggagaagcg cgctgaggcc gaagcagcgg ccgaagctgc  15240
```

-continued cgccccgct gcgcaacccg aggtcgagaa gcctcagaag aaaccggtga tcaaacccct 15300
gacagaggac agcaagaaac gcagttacaa cctaataagc aatgacagca ccttcaccca 15360
gtaccgcagc tggtaccttg catacaacta cggcgaccct cagaccggaa tccgctcatg 15420
gaccctgctt tgcactcctg acgtaacctg cggctcggag caggtctact ggtcgttgcc 15480
agacatgatg caagaccccg tgaccttccg ctccacgcgc cagatcagca actttccggt 15540
ggtgggcgcc gagctgttgc ccgtgcactc caagagcttc tacaacgacc aggccgtcta 15600
ctcccaactc atccgccagt ttacctctct gacccacgtg ttcaatcgct ttcccgagaa 15660
ccagattttg gcgcgcccgc cagcccccac catcaccacc gtcagtgaaa acgttcctgc 15720
tctcacagat cacgggacgc taccgctgcg caacagcatc ggaggagtcc agcgagtgac 15780
cattactgac gccagacgcc gcacctgccc ctacgtttac aaggccctgg gcatagtctc 15840
gccgcgcgtc ctatcgagcc gcactttttg agcaagcatg tccatcctta tatcgcccag 15900
caataacaca ggctggggcc tgcgcttccc aagcaagatg tttggcgggg ccaagaagcg 15960
ctccgaccaa cacccagtgc gcgtgcgcgg gcactaccgc gcgccctggg gcgcgcacaa 16020
acgcggccgc actgggcgca ccaccgtcga tgacgccatc gacgcggtgg tggaggaggc 16080
gcgcaactac acgcccacgc cgccaccagt gtccacagtg gacgcggcca ttcagaccgt 16140
ggtgcgcgga gcccggcgct atgctaaaat gaagagacgg cggaggcgcg tagcacgtcg 16200
ccaccgccgc cgacccggca ctgccgccca acgcgcggcg gcggccctgc ttaaccgcgc 16260
acgtcgcacc ggccgacggg cggccatgcg ggccgctcga aggctggccg cgggtattgt 16320
cactgtgccc cccaggtcca ggcgacgagc ggccgccgca gcagccgcgg ccattagtgc 16380
tatgactcag ggtcgcaggg gcaacgtgta ttgggtgcgc gactcggtta gcggcctgcg 16440
cgtgcccgtg cgcacccgcc ccccgcgcaa ctagattgca agaaaaaact acttagactc 16500
gtactgttgt atgtatccag cggcggcggc gcgcaacgaa gctatgtcca agcgcaaaat 16560
caaagaagag atgctccagg tcatcgcgcc ggagatctat ggccccccga agaaggaaga 16620
gcaggattac aagccccgaa agctaaagcg ggtcaaaaag aaaaagaaag atgatgatga 16680
tgaacttgac gacgaggtgg aactgctgca cgctaccgcg cccaggcgac gggtacagtg 16740
gaaaggtcga cgcgtaaaac gtgttttgcg acccggcacc accgtagtct ttacgcccgg 16800
tgagcgctcc acccgcacct acaagcgcgt gtatgatgag gtgtacggcg acgaggacct 16860
gcttgagcag gccaacgagc gcctcgggga gtttgcctac ggaaagcggc ataaggacat 16920
gctggcgttg ccgctggacg agggcaaccc aacacctagc ctaaagcccg taacactgca 16980
gcaggtgctg cccgcgcttg caccgtccga agaaaagcgc ggcctaaagc gcgagtctgg 17040
tgacttggca cccaccgtgc agctgatggt acccaagcgc cagcgactgg aagatgtctt 17100
ggaaaaaatg accgtggaac ctgggctgga gcccgaggtc cgcgtgcggc caatcaagca 17160
ggtggcgccg ggactgggcg tgcagaccgt ggacgttcag atacccacta ccagtagcac 17220
cagtattgcc accgccacag agggcatgga gacacaaacg tccccggttg cctcagcggt 17280
ggcggatgcc gcggtgcagg cggtcgctgc ggccgcgtcc aagacctcta cggaggtgca 17340
aacggacccg tggatgtttc gcgtttcagc cccccggcgc ccgcgcggtt cgaggaagta 17400
cggcgccgcc agcgcgctac tgcccgaata tgccctacat ccttccattg cgcctacccc 17460
cggctatcgt ggctacacct accgccccag aagacgagca actacccgac gccgaaccac 17520
cactggaacc cgccgccgcc gtcgccgtcg ccagcccgtg ctggccccga tttccgtgcg 17580
cagggtggct cgcgaaggag gcaggaccct ggtgctgcca acagcgcgct accaccccag 17640

-continued

```
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag ggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
```

-continued

```
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aacctttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
acagctgccg ccatgggctc cagtgagcag gaactgaaag ccattgtcaa agatcttggt  21780
tgtgggccat attttttggg cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggcttttct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaacctta ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tctttttgtc acttgaaaaa catgtaaaaa taatgtacta gagacacttt caataaaggc  22380
```

-continued

```
aaatgctttt atttgtacac tctcgggtga ttatttaccc ccacccttgc cgtctgcgcc  22440
gtttaaaaat caaaggggtt ctgccgcgca tcgctatgcg ccactggcag ggacacgttg  22500
cgatactggt gtttagtgct ccacttaaac tcaggcacaa ccatccgcgg cagctcggtg  22560
aagttttcac tccacaggct gcgcaccatc accaacgcgt ttagcaggtc gggcgccgat  22620
atcttgaagt cgcagttggg gcctccgccc tgcgcgcgcg agttgcgata cacagggttg  22680
cagcactgga acactatcag cgccgggtgg tgcacgctgg ccagcacgct cttgtcggag  22740
atcagatccg cgtccaggtc ctccgcgttg ctcagggcga acggagtcaa ctttggtagc  22800
tgccttccca aaaagggcgc gtgcccaggc tttgagttgc actcgcaccg tagtggcatc  22860
aaaaggtgac cgtgcccggt ctgggcgtta ggatacagcg cctgcataaa agccttgatc  22920
tgcttaaaag ccacctgagc ctttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
gggcgcttct ttttcttctt gggcgcaatg gccaaatccg ccgccgaggt cgatggccgc  23820
gggctgggtg tgcgcggcac cagcgcgtct tgtgatgagt cttcctcgtc ctcggactcg  23880
atacgccgcc tcatccgctt ttttgggggc gcccggggag gcggcggcga cggggacggg  23940
gacgacacgt cctccatggt tgggggacgt cgcgccgcac cgcgtccgcg ctcgggggtg  24000
gtttcgcgct gctcctcttc ccgactggcc atttccttct cctataggca gaaaaagatc  24060
atggagtcag tcgagaagaa ggacagccta accgcccccct ctgagttcgc caccaccgcc  24120
tccaccgatg ccgccaacgc gcctaccacc ttccccgtcg aggcaccccc gcttgaggag  24180
gaggaagtga ttatcgagca ggacccaggt tttgtaagcg aagacgacga ggaccgctca  24240
gtaccaacag aggataaaaa gcaagaccag gacaacgcag aggcaaacga ggaacaagtc  24300
gggcgggggg acgaaaggca tggcgactac ctagatgtgg gagacgacgt gctgttgaag  24360
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccacctat cacatctttt tccaaaactg caagataccc  24600
ctatcctgcc gtgccaaccg cagccgagcg gacaagcagc tggccttgcg gcagggcgct  24660
gtcatacctg atatcgcctc gctcaacgaa gtgccaaaaa tctttgaggg tcttggacgc  24720
```

-continued

```
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc ccaaggtcat gagcacagtc  24900
atgagtgagc tgatcgtgcg ccgtgcgcag cccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
gtggagcttg agtgcatgca gcggttcttt gctgacccgg agatgcagcg caagctagag  25140
gaaacattgc actacacctt tcgacagggc tacgtacgcc aggcctgcaa gatctccaac  25200
gtggagctct gcaacctggt ctcctacctt ggaattttgc acgaaaaccg ccttgggcaa  25260
aacgtgcttc attccacgct caagggcgag gcgcgccgcg actacgtccg cgactgcgtt  25320
tacttatttc tatgctacac ctggcagacg gccatgggcg tttggcagca gtgcttggag  25380
gagtgcaacc tcaaggagct gcagaaactg ctaaagcaaa acttgaagga cctatggacg  25440
gccttcaacg agcgctccgt ggccgcgcac ctggcggaca tcattttccc cgaacgcctg  25500
cttaaaaccc tgcaacaggg tctgccagac ttcaccagtc aaagcatgtt gcagaacttt  25560
aggaacttta tcctagagcg ctcaggaatc ttgcccgcca cctgctgtgc acttcctagc  25620
gactttgtgc ccattaagta ccgcgaatgc cctccgccgc tttggggcca ctgctacctt  25680
ctgcagctag ccaactacct tgcctaccac tctgacataa tggaagacgt gagcggtgac  25740
ggtctactgg agtgtcactg tcgctgcaac ctatgcaccc cgcaccgctc cctggtttgc  25800
aattcgcagc tgcttaacga aagtcaaatt atcggtacct ttgagctgca gggtccctcg  25860
cctgacgaaa agtccgcggc tccggggttg aaactcactc cggggctgtg gacgtcggct  25920
taccttcgca aatttgtacc tgaggactac cacgcccacg agattaggtt ctacgaagac  25980
caatcccgcc cgccaaatgc ggagcttacc gcctgcgtca ttacccaggg ccacattctt  26040
ggccaattgc aagccatcaa caaagcccgc caagagtttc tgctacgaaa gggacggggg  26100
gtttacttgg acccccagtc cggcgaggag ctcaacccaa tccccccgcc gccgcagccc  26160
tatcagcagc agccgcgggc ccttgcttcc caggatggca cccaaaaaga agctgcagct  26220
gccgccgcca cccacggacg aggaggaata ctgggacagt caggcagagg aggttttgga  26280
cgaggaggag gaggacatga tggaagactg ggagagccta gacgaggaag cttccgaggt  26340
cgaagaggtg tcagacgaaa caccgtcacc ctcggtcgca ttcccctcgc cggcgcccca  26400
gaaatcggca accggttcca gcatggctac aacctccgct cctcaggcgc cgccggcact  26460
gcccgttcgc cgacccaacc gtagatggga caccactgga accagggccg gtaagtccaa  26520
gcagccgccg ccgttagccc aagagcaaca acagcgccaa ggctaccgct catggcgcgg  26580
gcacaagaac gccatagttg cttgcttgca agactgtggg ggcaacatct ccttcgcccg  26640
ccgctttctt ctctaccatc acggcgtggc cttcccccgt aacatcctgc attactaccg  26700
tcatctctac agcccatact gcaccggcgg cagcggcagc ggcagcaaca gcagcggcca  26760
cacagaagca aaggcgaccg gatagcaaga ctctgacaaa gcccaagaaa tccacagcgg  26820
cggcagcagc aggaggagga gcgctgcgtc tggcgcccaa cgaacccgta tcgacccgcg  26880
agcttagaaa caggattttt cccactctgt atgctatatt tcaacagagc aggggccaag  26940
aacaagagct gaaaataaaa aacaggtctc tgcgatccct cacccgcagc tgcctgtatc  27000
acaaaagcga agatcagctt cggcgcacgc tggaagacgc ggaggctctc ttcagtaaat  27060
actgcgcgct gactcttaag gactagtttc gcgccctttc tcaaatttaa gcgcgaaaac  27120
```

-continued

```
tacgtcatct ccagcggcca cacccggcgc cagcacctgt cgtcagcgcc attatgagca  27180
aggaaattcc cacgccctac atgtggagtt accagccaca aatgggactt gcggctggag  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataacctt aatccccgta gttggcccgc tgccctggtg taccaggaaa  27420
gtcccgctcc caccactgtg gtacttccca gagacgccca ggccgaagtt cagatgacta  27480
actcaggggc gcagcttgcg ggcggctttc gtcacagggt gcggtcgccc gggcagggta  27540
taactcacct gacaatcaga gggcgaggta ttcagctcaa cgacgagtcg gtgagctcct  27600
cgcttggtct ccgtccggac gggacatttc agatcggcgg cgccggccgt ccttcattca  27660
cgcctcgtca ggcaatccta actctgcaga cctcgtcctc tgagccgcgc tctggaggca  27720
ttggaactct gcaatttatt gaggagtttg tgccatcggt ctactttaac cccttctcgg  27780
gacctcccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acggcgtccg gcttaccgcc cagggagagc  28020
ttgcccgtag cctgattcgg gagtttaccc agcgcccccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggctcctat  28200
cgccatcctg taaacgccac cgtcttcacc cgcccaagca aaccaaggcg aaccttacct  28260
ggtactttta acatctctcc ctctgtgatt tacaacagtt tcaacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagactttt tccggacaga cctcaataac tctgtttacc agaacaggag gtgagcttag  28500
aaaaccctta gggtattagg ccaaaggcgc agctactgtg gggtttatga acaattcaag  28560
caactctacg ggctattcta attcaggttt ctctagaatc ggggttgggg ttattctctg  28620
tcttgtgatt ctctttattc ttatactaac gcttctctgc ctaaggctcg ccgcctgctg  28680
tgtgcacatt tgcatttatt gtcagctttt taaacgctgg ggtcgccacc caagatgatt  28740
aggtacataa tcctaggttt actcaccctt gcgtcagccc acggtaccac ccaaaaggtg  28800
gattttaagg agccagcctg taatgttaca ttcgcagctg aagctaatga gtgcaccact  28860
cttataaaat gcaccacaga acatgaaaag ctgcttattc gccacaaaaa caaaattggc  28920
aagtatgctg tttatgctat ttggcagcca ggtgacacta cagagtataa tgttacagtt  28980
ttccagggta aaagtcataa aactttttatg tatacttttc cattttatga aatgtgcgac  29040
attaccatgt acatgagcaa acagtataag ttgtggcccc cacaaaattg tgtggaaaac  29100
actggcactt tctgctgcac tgctatgcta attacagtgc tcgctttggt ctgtacccta  29160
ctctatatta aatacaaaag cagacgcagc tttattgagg aaaagaaaat gccttaattt  29220
actaagttac aaagctaatg tcaccactaa ctgctttact cgctgcttgc aaaacaaatt  29280
caaaaagtta gcattataat tagaatagga tttaaacccc ccggtcattt cctgctcaat  29340
accattcccc tgaacaattg actctatgtg ggatatgctc cagcgctaca accttgaagt  29400
caggcttcct ggatgtcagc atctgacttt ggccagcacc tgtcccgcgg atttgttcca  29460
```

-continued

```
gtccaactac agcgacccac cctaacagag atgaccaaca caaccaacgc ggccgccgct  29520
accggactta catctaccac aaatacaccc caagtttctg cctttgtcaa taactgggat  29580
aacttgggca tgtggtggtt ctccatagcg cttatgtttg tatgccttat tattatgtgg  29640
ctcatctgct gcctaaagcg caaacgcgcc cgaccaccca tctatagtcc catcattgtg  29700
ctacacccaa acaatgatgg aatccataga ttggacggac tgaaacacat gttcttttct  29760
cttacagtat gattaaatga gacatgattc ctcgagtttt tatattactg acccttgttg  29820
cgcttttttg tgcgtgctcc acattggctg cggtttctca catcgaagta gactgcattc  29880
cagccttcac agtctatttg ctttacggat ttgtcaccct cacgctcatc tgcagcctca  29940
tcactgtggt catcgccttt atccagtgca ttgactgggt ctgtgtgcgc tttgcatatc  30000
tcagacacca tccccagtac agggacagga ctatagctga gcttcttaga attctttaat  30060
tatgaaattt actgtgactt ttctgctgat tatttgcacc ctatctgcgt tttgttcccc  30120
gacctccaag cctcaaagac atatatcatg cagattcact cgtatatgga atattccaag  30180
ttgctacaat gaaaaaagcg atctttccga agcctggtta tatgcaatca tctctgttat  30240
ggtgttctgc agtaccatct tagccctagc tatatatccc taccttgaca ttggctggaa  30300
acgaatagat gccatgaacc acccaacttt ccccgcgccc gctatgcttc cactgcaaca  30360
agttgttgcc ggcggctttg tcccagccaa tcagcctcgc cccacttctc ccaccccac  30420
tgaaatcagc tactttaatc taacaggagg agatgactga caccctagat ctagaaatgg  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
aaaaaaaaat aataaagcat cacttactta aaatcagtta gcaaatttct gtccagttta  30900
ttcagcagca cctccttgcc ctcctcccag ctctggtatt gcagcttcct cctggctgca  30960
aactttctcc acaatctaaa tggaatgtca gtttcctcct gttcctgtcc atccgcaccc  31020
actatcttca tgttgttgca gatgaagcgc gcaagaccgt ctgaagatac cttcaacccc  31080
gtgtatccat atgacacgga aaccggtcct ccaactgtgc cttttcttac tcctcccttt  31140
gtatccccca atgggtttca agagagtccc cctggggtac tctctttgcg cctatccgaa  31200
cctctagtta cctccaatgg catgcttgcg ctcaaaatgg gcaacggcct ctctctggac  31260
gaggccggca accttacctc ccaaaatgta accactgtga gcccacctct caaaaaaacc  31320
aagtcaaaca taaacctgga aatatctgca cccctcacag ttacctcaga agccctaact  31380
gtggctgccg ccgcacctct aatggtcgcg ggcaacacac tcaccatgca atcacaggcc  31440
ccgctaaccg tgcacgactc caaacttagc attgccaccc aaggacccct cacagtgtca  31500
gaaggaaagc tagccctgca aacatcaggc cccctcacca ccaccgatag cagtaccctt  31560
actatcactg cctcaccccc tctaactact gccactggta gcttgggcat tgacttgaaa  31620
gagcccattt atacacaaaa tggaaaacta ggactaaagt acggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
```

-continued

```
tatccgtttg atgctcaaaa ccaactaaat ctaagactag gacagggccc tctttttata  31920
aactcagccc acaacttgga tattaactac aacaaaggcc tttacttgtt tacagcttca  31980
aacaattcca aaaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aattggccat ggcctagaat ttgattcaaa caaggctatg  32160
gttcctaaac taggaactgg ccttagtttt gacagcacag gtgccattac agtaggaaac  32220
aaaaataatg ataagctaac tttgtggacc acaccagctc catctcctaa ctgtagacta  32280
aatgcagaga aagatgctaa actcactttg gtcttaacaa aatgtggcag tcaaatactt  32340
gctacagttt cagttttggc tgttaaaggc agtttggctc caatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
ttttcatggg actggtctgg ccacaactac attaatgaaa tatttgccac atcctcttac  32760
actttttcat acattgccca agaataaaga atcgtttgtg ttatgtttca acgtgtttat  32820
ttttcaattg cagaaaattt caagtcattt ttcattcagt agtatagccc caccaccaca  32880
tagcttatac agatcaccgt accttaatca aactcacaga accctagtat tcaacctgcc  32940
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctacatgg gggtagagtc ataatcgtgc atcaggatag ggcggtggtg  33240
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtt tctgtctcaa aaggaggtag acgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgccgct  34140
tagatcgctc tgtgtagtag ttgtagtata tccactctct caaagcatcc aggcgccccc  34200
```

-continued

```
tggcttcggg ttctatgtaa actccttcat gcgccgctgc cctgataaca tccaccaccg  34260

cagaataagc cacacccagc caacctacac attcgttctg cgagtcacac acgggaggag  34320

cgggaagagc tggaagaacc atgttttttt ttttattcca aaagattatc caaaacctca  34380

aaatgaagat ctattaagtg aacgcgctcc cctccggtgg cgtggtcaaa ctctacagcc  34440

aaagaacaga taatggcatt tgtaagatgt tgcacaatgg cttccaaaag gcaaacggcc  34500

ctcacgtcca agtggacgta aaggctaaac ccttcagggt gaatctcctc tataaacatt  34560

ccagcacctt caaccatgcc caaataattc tcatctcgcc accttctcaa tatatctcta  34620

agcaaatccc gaatattaag tccggccatt gtaaaaatct gctccagagc gccctccacc  34680

ttcagcctca agcagcgaat catgattgca aaaattcagg ttcctcacag acctgtataa  34740

gattcaaaag cggaacatta acaaaaatac cgcgatcccg taggtccctt cgcagggcca  34800

gctgaacata atcgtgcagg tctgcacgga ccagcgcggc cacttccccg ccaggaacct  34860

tgacaaaaga acccacactg attatgacac gcatactcgg agctatgcta accagcgtag  34920

ccccgatgta agctttgttg catgggcggc gatataaaat gcaaggtgct gctcaaaaaa  34980

tcaggcaaag cctcgcgcaa aaaagaaagc acatcgtagt catgctcatg cagataaagg  35040

caggtaagct ccggaaccac cacagaaaaa gacaccattt ttctctcaaa catgtctgcg  35100

ggtttctgca taaacacaaa ataaaataac aaaaaaacat ttaaacatta gaagcctgtc  35160

ttacaacagg aaaaacaacc cttataagca taagacggac tacggccatg ccggcgtgac  35220

cgtaaaaaaa ctggtcaccg tgattaaaaa gcaccaccga cagctcctcg gtcatgtccg  35280

gagtcataat gtaagactcg gtaaacacat caggttgatt catcggtcag tgctaaaaag  35340

cgaccgaaat agcccggggg aatacatacc cgcaggcgta gagacaacat tacagccccc  35400

ataggaggta taacaaaatt aataggagag aaaaacacat aaacacctga aaaaccctcc  35460

tgcctaggca aaatagcacc ctcccgctcc agaacaacat acagcgcttc acagcggcag  35520

cctaacagtc agccttacca gtaaaaaaga aaacctatta aaaaaacacc actcgacacg  35580

gcaccagctc aatcagtcac agtgtaaaaa agggccaagt gcagagcgag tatatatagg  35640

actaaaaaat gacgtaacgg ttaaagtcca caaaaaacac ccagaaaacc gcacgcgaac  35700

ctacgcccag aaacgaaagc caaaaaaccc acaacttcct caaatcgtca cttccgtttt  35760

cccacgttac gtaacttccc attttaagaa aactacaatt cccaacacat acaagttact  35820

ccgccctaaa acctacgtca cccgccccgt tcccacgccc cgcgccacgt cacaaactcc  35880

acccccctcat tatcatattg gcttcaatcc aaaataaggt atattattga tgatg       35935
```

<210> SEQ ID NO 5
<211> LENGTH: 35935
<212> TYPE: DNA
<213> ORGANISM: Human adenovirus type 5

<400> SEQUENCE: 5

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420
```

-continued

```
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtcttttgg accagctgat cgaagaggta ctggctgata atcttccacc    660
tcctagccat tttgaaccac ctacccttca cgaactgtat gatttagacg tgacggcccc    720
cgaagatccc aacgaggagg cggtttcgca gatttttccc gactctgtaa tgttggcggt    780
gcaggaaggg attgacttac tcacttttcc gccggcgccc ggttctccgg agccgcctca    840
cctttcccgg cagcccgagc agccggagca gagagccttg ggtccggttt ctatgccaaa    900
ccttgtaccg gaggtgatcg atcttacctg ccacgaggct ggctttccac ccagtgacga    960
cgaggatgaa gagggtgagg agtttgtgtt agattatgtg gagcaccccg ggcacggttg   1020
caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaattttt tttttaattt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040
agcggggggt acctgctgga ttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
```

-continued

```
gtacggtttt cctggccaat accaacctta tcctacacgg tgtaagcttc tatgggttta   2820
acaatacctg tgtggaagcc tggaccgatg taagggttcg gggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
```

-continued

```
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag ggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtagggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atggggtggg tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtccctttt ttttccacag ctcgcggttg aggacaaact cttcgcggtc   7140
tttccagtac tcttggatcg gaaacccgtc ggcctccgaa cggtaagagc ctagcatgta   7200
gaactggttg acggcctggt aggcgcagca tccctttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgctttttg gaacgcggat ttggcagggc gaaggtgaca tcgttgaaga gtatctttcc   7440
cgcgcgaggc ataaagttgc gtgtgatgcg gaagggtccc ggcacctcgg aacggttgtt   7500
```

-continued

```
aattacctgg gcggcgagca cgatctcgtc aaagccgttg atgttgtggc ccacaatgta   7560
aagttccaag aagcgcggga tgcccttgat ggaaggcaat tttttaagtt cctcgtaggt   7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
cacaaggaag cagagtggga atttgagccc ctcgcctggc gggtttggct ggtggtcttc   8220
tacttcggct gcttgtcctt gaccgtctgg ctgctcgagg ggagttacgg tggatcggac   8280
caccacgccg cgcgagccca aagtccagat gtccgcgcgc ggcggtcgga gcttgatgac   8340
aacatcgcgc agatgggagc tgtccatggt ctggagctcc cgcggcgtca ggtcaggcgg   8400
gagctcctgc aggtttacct cgcatagacg ggtcagggcg cgggctagat ccaggtgata   8460
cctaatttcc aggggctggt tggtggcggc gtcgatggct tgcaagaggc cgcatccccg   8520
cggcgcgact acggtaccgc gcggcgggcg gtgggccgcg gggtgtcct tggatgatgc    8580
atctaaaagc ggtgacgcgg gcgagccccc ggaggtaggg ggggctccgg acccgccggg   8640
agaggggca ggggcacgtc ggcgccgcgc gcgggcagga gctggtgctg cgcgcgtagg    8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccgggcg aagacggcgt agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataagggcc tccccttctt cttcttctgg cggcggtggg   9420
ggaggggga cacggcggcg acgacggcgc accgggaggc ggtcgacaaa gcgctcgatc     9480
atctccccgc ggcgacggcg catggtctcg gtgacggcgc ggccgttctc gcgggggcgc   9540
agttggaaga cgccgcccgt catgtcccgg ttatgggttg gcgggggct gccatgcggc     9600
agggatacgg cgctaacgat gcatctcaac aattgttgtg taggtactcc gccgccgagg   9660
gacctgagcg agtccgcatc gaccggatcg gaaaacctct cgagaaaggc gtctaaccag   9720
tcacagtcgc aaggtaggct gagcaccgtg gcgggcggca gcgggcggcg gtcggggttg   9780
tttctggcgg aggtgctgct gatgatgtaa ttaaagtagg cggtcttgag acggcggatg   9840
gtcgacagaa gcaccatgtc cttgggtccg gcctgctgaa tgcgcaggcg gtcggccatg   9900
```

-continued

```
ccccaggctt cgttttgaca tcggcgcagg tctttgtagt agtcttgcat gagcctttct   9960
accggcactt cttcttctcc ttcctcttgt cctgcatctc ttgcatctat cgctgcggcg  10020
gcggcggagt ttggccgtag gtggcgccct cttcctccca tgcgtgtgac cccgaagccc  10080
ctcatcggct gaagcagggc taggtcggcg acaacgcgct cggctaatat ggcctgctgc  10140
acctgcgtga gggtagactg gaagtcatcc atgtccacaa agcggtggta tgcgcccgtg  10200
ttgatggtgt aagtgcagtt ggccataacg gaccagttaa cggtctggtg acccggctgc  10260
gagagctcgg tgtacctgag acgcgagtaa gccctcgagt caaatacgta gtcgttgcaa  10320
gtccgcacca ggtactggta tcccaccaaa aagtgcggcg gcggctggcg gtagaggggc  10380
cagcgtaggg tggccggggc tccgggggcg agatcttcca acataaggcg atgatatccg  10440
tagatgtacc tggacatcca ggtgatgccg gcggcggtgg tggaggcgcg cggaaagtcg  10500
cggacgcggt tccagatgtt gcgcagcggc aaaaagtgct ccatggtcgg gacgctctgg  10560
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgcccgc gtgtcgaacc  10740
caggtgtgcg acgtcagaca acgggggagt gctccttttg gcttccttcc aggcgcggcg  10800
gctgctgcgc tagctttttt ggccactggc cgcgcgcagc gtaagcggtt aggctggaaa  10860
gcgaaagcat taagtggctc gctccctgta gccggagggt tattttccaa gggttgagtc  10920
gcgggacccc cggttcgagt ctcggaccgg ccggactgcg gcgaacgggg gtttgcctcc  10980
ccgtcatgca agaccccgct tgcaaattcc tccggaaaca gggacgagcc cctttttttgc  11040
ttttcccaga tgcatccggt gctgcggcag atgcgccccc ctcctcagca gcggcaagag  11100
caagagcagc ggcagacatg cagggcaccc tcccctcctc ctaccgcgtc aggaggggcg  11160
acatccgcgg ttgacgcggc agcagatggt gattacgaac cccgcggcg ccgggcccgg  11220
cactacctgg acttggagga gggcgagggc ctggcgcggc taggagcgcc ctctcctgag  11280
cggtacccaa gggtgcagct gaagcgtgat acgcgtgagg cgtacgtgcc gcggcagaac  11340
ctgtttcgcg accgcgaggg agaggagccc gaggagatgc gggatcgaaa gttccacgca  11400
gggcgcgagc tgcggcatgg cctgaatcgc gagcggttgc tgcgcgagga ggactttgag  11460
cccgacgcgc gaaccgggat tagtcccgcg cgcgcacacg tggcggccgc cgacctggta  11520
accgcatacg agcagacggt gaaccaggag attaactttc aaaaaagctt taacaaccac  11580
gtgcgtacgc ttgtggcgcg cgaggaggtg gctataggac tgatgcatct gtgggacttt  11640
gtaagcgcgc tggagcaaaa cccaaatagc aagccgctca tggcgcagct gttccttata  11700
gtgcagcaca gcagggacaa cgaggcattc agggatgcgc tgctaaacat agtagagccc  11760
gagggccgct ggctgctcga tttgataaac atcctgcaga gcatagtggt gcaggagcgc  11820
agcttgagcc tggctgacaa ggtggccgcc atcaactatt ccatgcttag cctgggcaag  11880
ttttacgccc gcaagatata ccatacccct tacgttccca tagacaagga ggtaaagatc  11940
gaggggttct acatgcgcat ggcgctgaag gtgcttacct tgagcgacga cctgggcgtt  12000
tatcgcaacg agcgcatcca caaggccgtg agcgtgagcc ggcggcgcga gctcagcgac  12060
cgcgagctga tgcacagcct gcaaagggcc ctggctggca cgggcagcgg cgatagagag  12120
gccgagtcct actttgacgc gggcgctgac ctgcgctggg ccccaagccg acgcgccctg  12180
gaggcagctg ggccggacc tgggctggcg gtggcacccg cgcgcgctgg caacgtcggc  12240
```

-continued

```
ggcgtggagg aatatgacga ggacgatgag tacgagccag aggacggcga gtactaagcg  12300
gtgatgtttc tgatcagatg atgcaagacg caacggaccc ggcggtgcgg gcggcgctgc  12360
agagccagcc gtccggcctt aactccacgg acgactggcg ccaggtcatg gaccgcatca  12420
tgtcgctgac tgcgcgcaat cctgacgcgt tccggcagca gccgcaggcc aaccggctct  12480
ccgcaattct ggaagcggtg gtcccggcgc gcgcaaaccc cacgcacgag aaggtgctgg  12540
cgatcgtaaa cgcgctggcc gaaaacaggg ccatccggcc cgacgaggcc ggcctggtct  12600
acgacgcgct gcttcagcgc gtggctcgtt acaacagcgg caacgtgcag accaacctgg  12660
accggctggt gggggatgtg cgcgaggccg tggcgcagcg tgagcgcgcg cagcagcagg  12720
gcaacctggg ctccatggtt gcactaaacg ccttcctgag tacacagccc gccaacgtgc  12780
cgcggggaca ggaggactac accaactttg tgagcgcact gcggctaatg gtgactgaga  12840
caccgcaaag tgaggtgtac cagtctgggc cagactattt tttccagacc agtagacaag  12900
gcctgcagac cgtaaacctg agccaggctt tcaaaaactt gcaggggctg tggggggtgc  12960
gggctcccac aggcgaccgc gcgaccgtgt ctagcttgct gacgcccaac tcgcgcctgt  13020
tgctgctgct aatagcgccc ttcacggaca gtggcagcgt gtcccgggac acatacctag  13080
gtcacttgct gacactgtac cgcgaggcca taggtcaggc gcatgtggac gagcatactt  13140
tccaggagat tacaagtgtc agccgcgcgc tggggcagga ggacacgggc agcctggagg  13200
caaccctaaa ctacctgctg accaaccggc ggcagaagat cccctcgttg cacagtttaa  13260
acagcgagga ggagcgcatt ttgcgctacg tgcagcagag cgtgagcctt aacctgatgc  13320
gcgacggggt aacgcccagc gtggcgctgg acatgaccgc gcgcaacatg gaaccgggca  13380
tgtatgcctc aaaccggccg tttatcaacc gcctaatgga ctacttgcat cgcgcggccg  13440
ccgtgaaccc cgagtatttc accaatgcca tcttgaaccc gcactggcta ccgcccccctg  13500
gtttctacac cgggggattc gaggtgcccg agggtaacga tggattcctc tgggacgaca  13560
tagacgacag cgtgttttcc ccgcaaccgc agaccctgct agagttgcaa cagcgcgagc  13620
aggcagaggc ggcgctgcga aaggaaagct tccgcaggcc aagcagcttg tccgatctag  13680
gcgctgcggc cccgcggtca gatgctagta gcccatttcc aagcttgata gggtctctta  13740
ccagcactcg caccacccgc ccgcgcctgc tgggcgagga ggagtaccta aacaactcgc  13800
tgctgcagcc gcagcgcgaa aaaaacctgc ctccggcatt tcccaacaac gggatagaga  13860
gcctagtgga caagatgagt agatggaaga cgtacgcgca ggagcacagg gacgtgccag  13920
gcccgcgccc gcccacccgt cgtcaaaggc acgaccgtca gcggggtctg gtgtgggagg  13980
acgatgactc ggcagacgac agcagcgtcc tggatttggg agggagtggc aacccgtttg  14040
cgcaccttcg ccccaggctg gggagaatgt tttaaaaaaa aaaaagcatg atgcaaaata  14100
aaaaactcac caaggccatg gcaccgagcg ttggttttct tgtattcccc ttagtatgcg  14160
gcgcgcggcg atgtatgagg aaggtcctcc tccctcctac gagagtgtgg tgagcgcggc  14220
gccagtggcg gcggcgctgg gttctccctt cgatgctccc ctggacccgc cgtttgtgcc  14280
tccgcggtac ctgcggccta ccggggggag aaacagcatc cgttactctg agttggcacc  14340
cctattcgac accacccgtg tgtacctggt ggacaacaag tcaacggatg tggcatccct  14400
gaactaccag aacgaccaca gcaactttct gaccacggtc attcaaaaca atgactacag  14460
cccgggggag gcaagcacac agaccatcaa tcttgacgac cggtcgcact ggggcggcga  14520
cctgaaaacc atcctgcata ccaacatgcc aaatgtgaac gagttcatgt ttaccaataa  14580
gtttaaggcg cgggtgatgg tgtcgcgctt gcctactaag gacaatcagg tggagctgaa  14640
```

-continued atacgagtgg gtggagttca cgctgcccga gggcaactac tccgagacca tgaccataga 14700
ccttatgaac aacgcgatcg tggagcacta cttgaaagtg ggcagacaga acggggttct 14760
ggaaagcgac atcggggtaa agtttgacac ccgcaacttc agactggggt ttgaccccgt 14820
cactggtctt gtcatgcctg ggtatatac aaacgaagcc ttccatccag acatcatttt 14880
gctgccagga tgcggggtgg acttcaccca cagccgcctg agcaacttgt tgggcatccg 14940
caagcggcaa cccttccagg agggctttag gatcacctac gatgatctgg agggtggtaa 15000
cattcccgca ctgttggatg tggacgccta ccaggcgagc ttgaaagatg acaccgaaca 15060
gggcgggggt ggcgcaggcg gcagcaacag cagtggcagc ggcgcggaag agaactccaa 15120
cgcggcagcc gcggcaatgc agccggtgga ggacatgaac gatcatgcca ttcgcggcga 15180
cacctttgcc acacgggctg aggagaagcg cgctgaggcc gaagcagcgg ccgaagctgc 15240
cgcccccgct gcgcaacccg aggtcgagaa gcctcagaag aaaccggtga tcaaacccct 15300
gacagaggac agcaagaaac gcagttacaa cctaataagc aatgacagca ccttcaccca 15360
gtaccgcagc tggtaccttg catacaacta cggcgaccct cagaccggaa tccgctcatg 15420
gaccctgctt tgcactcctg acgtaacctg cggctcggag caggtctact ggtcgttgcc 15480
agacatgatg caagaccccg tgaccttccg ctccacgcgc cagatcagca actttccggt 15540
ggtgggcgcc gagctgttgc ccgtgcactc caagagcttc tacaacgacc aggccgtcta 15600
ctcccaactc atccgccagt ttacctctct gacccacgtg ttcaatcgct ttcccgagaa 15660
ccagattttg gcgcgcccgc cagcccccac catcaccacc gtcagtgaaa acgttcctgc 15720
tctcacagat cacgggacgc taccgctgcg caacagcatc ggaggagtcc agcgagtgac 15780
cattactgac gccagacgcc gcacctgccc ctacgtttac aaggccctgg gcatagtctc 15840
gccgcgcgtc ctatcgagcc gcactttttg agcaagcatg tccatcctta tatcgcccag 15900
caataacaca ggctggggcc tgcgcttccc aagcaagatg tttggcgggg ccaagaagcg 15960
ctccgaccaa cacccagtgc gcgtgcgcgg gcactaccgc gcgccctggg gcgcgcacaa 16020
acgcggccgc actgggcgca ccaccgtcga tgacgccatc gacgcggtgg tggaggaggc 16080
gcgcaactac acgcccacgc cgccaccagt gtccacagtg gacgcggcca ttcagaccgt 16140
ggtgcgcgga gcccggcgct atgctaaaat gaagagacgg cggaggcgcg tagcacgtcg 16200
ccaccgccgc cgacccggca ctgccgccca acgcgcggcg gcggccctgc ttaaccgcgc 16260
acgtcgcacc ggccgacggg cggccatgcg ggccgctcga aggctggccg cgggtattgt 16320
cactgtgccc cccaggtcca ggcgacgagc ggccgccgca gcagccgcgg ccattagtgc 16380
tatgactcag ggtcgcaggg gcaacgtgta ttgggtgcgc gactcggtta gcggcctgcg 16440
cgtgcccgtg cgcacccgcc ccccgcgcaa ctagattgca agaaaaaact acttagactc 16500
gtactgttgt atgtatccag cggcggcggc gcgcaacgaa gctatgtcca agcgcaaaat 16560
caaagaagag atgctccagg tcatcgcgcc ggagatctat ggccccccga agaaggaaga 16620
gcaggattac aagccccgaa agctaaagcg ggtcaaaaag aaaaagaaag atgatgatga 16680
tgaacttgac gacgaggtgg aactgctgca cgctaccgcg cccaggcgac gggtacagtg 16740
gaaaggtcga cgcgtaaaac gtgttttgcg acccggcacc accgtagtct ttacgcccgg 16800
tgagcgctcc acccgcacct acaagcgcgt gtatgatgag gtgtacggcg acgaggacct 16860
gcttgagcag gccaacgagc gcctcgggga gtttgcctac ggaaagcggc ataaggacat 16920
gctggcgttg ccgctggacg agggcaaccc aacacctagc ctaaagcccg taacactgca 16980

-continued

```
gcaggtgctg cccgcgcttg caccgtccga agaaaagcgc ggcctaaagc gcgagtctgg  17040
tgacttggca cccaccgtgc agctgatggt acccaagcgc cagcgactgg aagatgtctt  17100
ggaaaaaatg accgtggaac ctgggctgga gcccgaggtc cgcgtgcggc caatcaagca  17160
ggtggcgccg ggactgggcg tgcagaccgt ggacgttcag atacccacta ccagtagcac  17220
cagtattgcc accgccacag agggcatgga gacacaaacg tccccggttg cctcagcggt  17280
ggcggatgcc gcggtgcagg cggtcgctgc ggccgcgtcc aagacctcta cggaggtgca  17340
aacggacccg tggatgtttc gcgtttcagc cccccggcgc ccgcgcggtt cgaggaagta  17400
cggcgccgcc agcgcgctac tgcccgaata tgccctacat ccttccattg cgcctacccc  17460
cggctatcgt ggctacacct accgccccag aagacgagca actacccgac gccgaaccac  17520
cactggaacc cgccgccgcc gtcgccgtcg ccagcccgtg ctggccccga tttccgtgcg  17580
cagggtggct cgcgaaggag gcaggaccct ggtgctgcca acagcgcgct accaccccag  17640
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag ggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
```

-continued

```
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aacctttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
```

-continued acagctgccg ccatgggctc cagtgagcag gaactgaaag ccattgtcaa agatcttggt 21780
tgtgggccat attttttggg cacctatgac aagcgctttc caggctttgt ttctccacac 21840
aagctcgcct gcgccatagt caatacggcc ggtcgcgaga ctgggggcgt acactggatg 21900
gcctttgcct ggaacccgca ctcaaaaaca tgctacctct ttgagccctt tggcttttct 21960
gaccagcgac tcaagcaggt ttaccagttt gagtacgagt cactcctgcg ccgtagcgcc 22020
attgcttctt cccccgaccg ctgtataacg ctggaaaagt ccacccaaag cgtacagggg 22080
cccaactcgg ccgcctgtgg actattctgc tgcatgtttc tccacgcctt tgccaactgg 22140
ccccaaactc ccatggatca caaccccacc atgaacctta ttaccggggt acccaactcc 22200
atgctcaaca gtccccaggt acagcccacc ctgcgtcgca accaggaaca gctctacagc 22260
ttcctggagc gccactcgcc ctacttccgc agccacagtg cgcagattag gagcgccact 22320
tctttttgtc acttgaaaaa catgtaaaaa taatgtacta gagacacttt caataaaggc 22380
aaatgctttt atttgtacac tctcgggtga ttatttaccc ccacccttgc cgtctgcgcc 22440
gtttaaaaat caaaggggtt ctgccgcgca tcgctatgcg ccactggcag ggacacgttg 22500
cgatactggt gtttagtgct ccacttaaac tcaggcacaa ccatccgcgg cagctcggtg 22560
aagttttcac tccacaggct gcgcaccatc accaacgcgt ttagcaggtc gggcgccgat 22620
atcttgaagt cgcagttggg gcctccgccc tgcgcgcgcg agttgcgata cacagggttg 22680
cagcactgga acactatcag cgccgggtgg tgcacgctgg ccagcacgct cttgtcggag 22740
atcagatccg cgtccaggtc ctccgcgttg ctcagggcga acggagtcaa ctttggtagc 22800
tgccttccca aaaagggcgc gtgcccaggc tttgagttgc actcgcaccg tagtggcatc 22860
aaaaggtgac cgtgcccggt ctgggcgtta ggatacagcg cctgcataaa agccttgatc 22920
tgcttaaaag ccacctgagc ctttgcgcct tcagagaaga acatgccgca agacttgccg 22980
gaaaactgat tggccggaca ggccgcgtcg tgcacgcagc accttgcgtc ggtgttggag 23040
atctgcacca catttcggcc ccaccggttc ttcacgatct tggccttgct agactgctcc 23100
ttcagcgcgc gctgcccgtt ttcgctcgtc acatccattt caatcacgtg ctccttattt 23160
atcataatgc ttccgtgtag acacttaagc tcgccttcga tctcagcgca gcggtgcagc 23220
cacaacgcgc agcccgtggg ctcgtgatgc ttgtaggtca cctctgcaaa cgactgcagg 23280
tacgcctgca ggaatcgccc catcatcgtc acaaaggtct tgttgctggt gaaggtcagc 23340
tgcaacccgc ggtgctcctc gttcagccag gtcttgcata cggccgccag agcttccact 23400
tggtcaggca gtagtttgaa gttcgccttt agatcgttat ccacgtggta cttgtccatc 23460
agcgcgcgcg cagcctccat gcccttctcc cacgcagaca cgatcggcac actcagcggg 23520
ttcatcaccg taatttcact ttccgcttcg ctgggctctt cctcttcctc ttgcgtccgc 23580
ataccacgcg ccactgggtc gtcttcattc agccgccgca ctgtgcgctt acctcctttg 23640
ccatgcttga ttagcaccgg tgggttgctg aaacccacca tttgtagcgc cacatcttct 23700
ctttcttcct cgctgtccac gattacctct ggtgatggcg ggcgctcggg cttgggagaa 23760
gggcgcttct ttttcttctt gggcgcaatg gccaaatccg ccgccgaggt cgatggccgc 23820
gggctgggtg tgcgcggcac cagcgcgtct tgtgatgagt cttcctcgtc ctcggactcg 23880
atacgccgcc tcatccgctt ttttgggggc gcccggggag gcggcggcga cggggacggg 23940
gacgacacgt cctccatggt tgggggacgt cgcgccgcac cgcgtccgcg ctcgggggtg 24000
gtttcgcgct gctcctcttc ccgactggcc atttccttct cctataggca gaaaaagatc 24060
atggagtcag tcgagaagaa ggacagccta accgccccct ctgagttcgc caccaccgcc 24120

-continued

```
tccaccgatg ccgccaacgc gcctaccacc ttccccgtcg aggcaccccc gcttgaggag  24180
gaggaagtga ttatcgagca ggacccaggt tttgtaagcg aagacgacga ggaccgctca  24240
gtaccaacag aggataaaaa gcaagaccag gacaacgcag aggcaaacga ggaacaagtc  24300
gggcgggggg acgaaaggca tggcgactac ctagatgtgg gagacgacgt gctgttgaag  24360
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccacctat cacatctttt tccaaaactg caagataccc  24600
ctatcctgcc gtgccaaccg cagccgagcg gacaagcagc tggccttgcg gcagggcgct  24660
gtcatacctg atatcgcctc gctcaacgaa gtgccaaaaa tctttgaggg tcttggacgc  24720
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc ccaaggtcat gagcacagtc  24900
atgagtgagc tgatcgtgcg ccgtgcgcag cccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
gtggagcttg agtgcatgca gcggttcttt gctgacccgg agatgcagcg caagctagag  25140
gaaacattgc actacacctt tcgacagggc tacgtacgcc aggcctgcaa gatctccaac  25200
gtggagctct gcaacctggt ctcctacctt ggaattttgc acgaaaaccg ccttgggcaa  25260
aacgtgcttc attccacgct caagggcgag gcgcgccgcg actacgtccg cgactgcgtt  25320
tacttatttc tatgctacac ctggcagacg gccatgggcg tttggcagca gtgcttggag  25380
gagtgcaacc tcaaggagct gcagaaactg ctaaagcaaa acttgaagga cctatggacg  25440
gccttcaacg agcgctccgt ggccgcgcac ctggcggaca tcattttccc cgaacgcctg  25500
cttaaaaccc tgcaacaggg tctgccagac ttcaccagtc aaagcatgtt gcagaacttt  25560
aggaacttta tcctagagcg ctcaggaatc ttgcccgcca cctgctgtgc acttcctagc  25620
gactttgtgc ccattaagta ccgcgaatgc cctccgccgc tttggggcca ctgctacctt  25680
ctgcagctag ccaactacct tgcctaccac tctgacataa tggaagacgt gagcggtgac  25740
ggtctactgg agtgtcactg tcgctgcaac ctatgcaccc cgcaccgctc cctggtttgc  25800
aattcgcagc tgcttaacga aagtcaaatt atcggtacct ttgagctgca gggtccctcg  25860
cctgacgaaa agtccgcggc tccggggttg aaactcactc cggggctgtg gacgtcggct  25920
taccttcgca aatttgtacc tgaggactac cacgcccacg agattaggtt ctacgaagac  25980
caatcccgcc cgccaaatgc ggagcttacc gcctgcgtca ttacccaggg ccacattctt  26040
ggccaattgc aagccatcaa caaagcccgc caagagtttc tgctacgaaa gggacggggg  26100
gtttacttgg acccccagtc cggcgaggag ctcaacccaa tcccccgcc gccgcagccc  26160
tatcagcagc agccgcgggc ccttgcttcc caggatggca cccaaaaaga agctgcagct  26220
gccgccgcca cccacggacg aggaggaata ctgggacagt caggcagagg aggttttgga  26280
cgaggaggag gaggacatga tggaagactg ggagagccta gacgaggaag cttccgaggt  26340
cgaagaggtg tcagacgaaa caccgtcacc ctcggtcgca ttcccctcgc cggcgcccca  26400
gaaatcggca accggttcca gcatggctac aacctccgct cctcaggcgc cgccggcact  26460
```

-continued

```
gcccgttcgc cgacccaacc gtagatggga caccactgga accagggccg gtaagtccaa  26520
gcagccgccg ccgttagccc aagagcaaca acagcgccaa ggctaccgct catggcgcgg  26580
gcacaagaac gccatagttg cttgcttgca agactgtggg ggcaacatct ccttcgcccg  26640
ccgctttctt ctctaccatc acggcgtggc cttccccgt aacatcctgc attactaccg  26700
tcatctctac agcccatact gcaccggcgg cagcggcagc ggcagcaaca gcagcggcca  26760
cacagaagca aaggcgaccg gatagcaaga ctctgacaaa gcccaagaaa tccacagcgg  26820
cggcagcagc aggaggagga gcgctgcgtc tggcgcccaa cgaacccgta tcgacccgcg  26880
agcttagaaa caggattttt cccactctgt atgctatatt tcaacagagc aggggccaag  26940
aacaagagct gaaaataaaa aacaggtctc tgcgatccct cacccgcagc tgcctgtatc  27000
acaaaagcga agatcagctt cggcgcacgc tggaagacgc ggaggctctc ttcagtaaat  27060
actgcgcgct gactcttaag gactagtttc gcgccctttc tcaaatttaa gcgcgaaaac  27120
tacgtcatct ccagcggcca cacccggcgc cagcacctgt cgtcagcgcc attatgagca  27180
aggaaattcc cacgccctac atgtggagtt accagccaca aatgggactt gcggctggag  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataacctt aatccccgta gttggcccgc tgccctggtg taccaggaaa  27420
gtcccgctcc caccactgtg gtacttccca gagacgccca ggccgaagtt cagatgacta  27480
actcaggggc gcagcttgcg ggcggctttc gtcacagggt gcggtcgccc gggcagggta  27540
taactcacct gacaatcaga gggcgaggta ttcagctcaa cgacgagtcg gtgagctcct  27600
cgcttggtct ccgtccggac gggacatttc agatcggcgg cgccggccgt ccttcattca  27660
cgcctcgtca ggcaatccta actctgcaga cctcgtcctc tgagccgcgc tctggaggca  27720
ttggaactct gcaatttatt gaggagtttg tgccatcggt ctactttaac cccttctcgg  27780
gacctcccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acggcgtccg gcttaccgcc cagggagagc  28020
ttgcccgtag cctgattcgg gagtttaccc agcgcccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggctcctat  28200
cgccatcctg taaacgccac cgtcttcacc cgcccaagca aaccaaggcg aaccttacct  28260
ggtactttta acatctctcc ctctgtgatt tacaacagtt tcaacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagactttt tccggacaga cctcaataac tctgtttacc agaacaggag gtgagcttag  28500
aaaaccctta gggtattagg ccaaaggcgc agctactgtg ggtttatga acaattcaag  28560
caactctacg ggctattcta attcaggttt ctctagaatc ggggttgggg ttattctctg  28620
tcttgtgatt ctctttattc ttatactaac gcttctctgc ctaaggctcg ccgcctgctg  28680
tgtgcacatt tgcatttatt gtcagctttt taaacgctgg ggtcgccacc caagatgatt  28740
aggtacataa tcctaggttt actcaccctt gcgtcagccc acggtaccac ccaaaaggtg  28800
gattttaagg agccagcctg taatgttaca ttcgcagctg aagctaatga gtgcaccact  28860
```

-continued

```
cttataaaat gcaccacaga acatgaaaag ctgcttattc gccacaaaaa caaaattggc  28920
aagtatgctg tttatgctat ttggcagcca ggtgacacta cagagtataa tgttacagtt  28980
ttccagggta aaagtcataa aacttttatg tatacttttc cattttatga aatgtgcgac  29040
attaccatgt acatgagcaa acagtataag ttgtggcccc cacaaaattg tgtggaaaac  29100
actggcactt tctgctgcac tgctatgcta attacagtgc tcgctttggt ctgtacccta  29160
ctctatatta aatacaaaag cagacgcagc tttattgagg aaaagaaaat gccttaattt  29220
actaagttac aaagctaatg tcaccactaa ctgctttact cgctgcttgc aaaacaaatt  29280
caaaaagtta gcattataat tagaatagga tttaaacccc ccggtcattt cctgctcaat  29340
accattcccc tgaacaattg actctatgtg ggatatgctc cagcgctaca accttgaagt  29400
caggcttcct ggatgtcagc atctgacttt ggccagcacc tgtcccgcgg atttgttcca  29460
gtccaactac agcgacccac cctaacagag atgaccaaca caaccaacgc ggccgccgct  29520
accggactta catctaccac aaatacaccc caagtttctg cctttgtcaa taactgggat  29580
aacttgggca tgtggtggtt ctccatagcg cttatgtttg tatgccttat tattatgtgg  29640
ctcatctgct gcctaaagcg caaacgcgcc cgaccaccca tctatagtcc catcattgtg  29700
ctacacccaa acaatgatgg aatccataga ttggacggac tgaaacacat gttcttttct  29760
cttacagtat gattaaatga gacatgattc ctcgagtttt tatattactg acccttgttg  29820
cgcttttttg tgcgtgctcc acattggctg cggtttctca catcgaagta gactgcattc  29880
cagccttcac agtctatttg ctttacggat ttgtcaccct cacgctcatc tgcagcctca  29940
tcactgtggt catcgccttt atccagtgca ttgactgggt ctgtgtgcgc tttgcatatc  30000
tcagacacca tccccagtac agggacagga ctatagctga gcttcttaga attctttaat  30060
tatgaaattt actgtgactt ttctgctgat tatttgcacc ctatctgcgt tttgttcccc  30120
gacctccaag cctcaaagac atatatcatg cagattcact cgtatatgga atattccaag  30180
ttgctacaat gaaaaaagcg atctttccga agcctggtta tatgcaatca tctctgttat  30240
ggtgttctgc agtaccatct tagccctagc tatatatccc taccttgaca ttggctggaa  30300
acgaatagat gccatgaacc acccaacttt ccccgcgccc gctatgcttc cactgcaaca  30360
agttgttgcc ggcggctttg tcccagccaa tcagcctcgc cccacttctc ccaccccccac  30420
tgaaatcagc tactttaatc taacaggagg agatgactga caccctagat ctagaaatgg  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
aaaaaaaaat aataaagcat cacttactta aaatcagtta gcaaatttct gtccagttta  30900
ttcagcagca cctccttgcc ctcctcccag ctctggtatt gcagcttcct cctggctgca  30960
aactttctcc acaatctaaa tggaatgtca gtttcctcct gttcctgtcc atccgcaccc  31020
actatcttca tgttgttgca gatgaagcgc gcaagaccgt ctgaagatac cttcaacccc  31080
gtgtatccat atgacacgga aaccggtcct ccaactgtgc cttttcttac tcctcccttt  31140
gtatccccca atgggtttca agagagtccc cctggggtac tctctttgcg cctatccgaa  31200
```

-continued

```
cctctagtta cctccaatgg catgcttgcg ctcaaaatgg gcaacggcct ctctctggac  31260
gaggccggca accttacctc ccaaaatgta accactgtga gcccacctct caaaaaaacc  31320
aagtcaaaca taaacctgga aatatctgca cccctcacag ttacctcaga agccctaact  31380
gtggctgccg ccgcacctct aatggtcgcg ggcaacacac tcaccatgca atcacaggcc  31440
ccgctaaccg tgcacgactc caaacttagc attgccaccc aaggacccct cacagtgtca  31500
gaaggaaagc tagccctgca aacatcaggc cccctcacca ccaccgatag cagtacccct  31560
actatcactg cctcaccccc tctaactact gccactggta gcttgggcat tgacttgaaa  31620
gagcccattt atacacaaaa tggaaaacta ggactaaagt acggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
tatccgtttg atgctcaaaa ccaactaaat ctaagactag gacagggccc tctttttata  31920
aactcagccc acaacttgga tattaactac aacaaaggcc tttacttgtt tacagcttca  31980
aacaattcca aaaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aattggccat ggcctagaat ttgattcaaa caaggctatg  32160
gttcctaaac taggaactgg ccttagtttt gacagcacag gtgccattac agtaggaaac  32220
aaaaataatg ataagctaac tttgtggacc acaccagctc catctcctaa ctgtagacta  32280
aatgcagaga aagatgctaa actcactttg gtcttaacaa aatgtggcag tcaaatactt  32340
gctacagttt cagttttggc tgttaaaggc agtttggctc caatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
ttttcatggg actggtctgg ccacaactac attaatgaaa tatttgccac atcctcttac  32760
actttttcat acattgccca agaataaaga atcgtttgtg ttatgtttca acgtgtttat  32820
ttttcaattg cagaaaattt caagtcattt ttcattcagt agtatagccc caccaccaca  32880
tagcttatac agatcaccgt accttaatca aactcacaga accctagtat tcaacctgcc  32940
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctacatgg gggtagagtc ataatcgtgc atcaggatag ggcggtggtg  33240
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
```

-continued

```
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtt tctgtctcaa aaggaggtag acgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgccgct  34140
tagatcgctc tgtgtagtag ttgtagtata tccactctct caaagcatcc aggcgccccc  34200
tggcttcggg ttctatgtaa actccttcat gcgccgctgc cctgataaca tccaccaccg  34260
cagaataagc cacacccagc caacctacac attcgttctg cgagtcacac acgggaggag  34320
cgggaagagc tggaagaacc atgttttttt ttttattcca aaagattatc caaaacctca  34380
aaatgaagat ctattaagtg aacgcgctcc cctccggtgg cgtggtcaaa ctctacagcc  34440
aaagaacaga taatggcatt tgtaagatgt tgcacaatgg cttccaaaag gcaaacggcc  34500
ctcacgtcca agtggacgta aaggctaaac ccttcagggt gaatctcctc tataaacatt  34560
ccagcacctt caaccatgcc caaataattc tcatctcgcc accttctcaa tatatctcta  34620
agcaaatccc gaatattaag tccggccatt gtaaaaatct gctccagagc gccctccacc  34680
ttcagcctca agcagcgaat catgattgca aaaattcagg ttcctcacag acctgtataa  34740
gattcaaaag cggaacatta acaaaaatac cgcgatcccg taggtccctt cgcagggcca  34800
gctgaacata atcgtgcagg tctgcacgga ccagcgcggc cacttccccg ccaggaacct  34860
tgacaaaaga acccacactg attatgacac gcatactcgg agctatgcta accagcgtag  34920
ccccgatgta agctttgttg catgggcggc gatataaaat gcaaggtgct gctcaaaaaa  34980
tcaggcaaag cctcgcgcaa aaaagaaagc acatcgtagt catgctcatg cagataaagg  35040
caggtaagct ccggaaccac cacagaaaaa gacaccattt ttctctcaaa catgtctgcg  35100
ggtttctgca taaacacaaa ataaaataac aaaaaaacat ttaaacatta gaagcctgtc  35160
ttacaacagg aaaaacaacc cttataagca taagacggac tacggccatg ccggcgtgac  35220
cgtaaaaaaa ctggtcaccg tgattaaaaa gcaccaccga cagctcctcg gtcatgtccg  35280
gagtcataat gtaagactcg gtaaacacat caggttgatt catcggtcag tgctaaaaag  35340
cgaccgaaat agcccggggg aatacatacc cgcaggcgta gagacaacat tacagccccc  35400
ataggaggta taacaaaatt aataggagag aaaaacacat aaacacctga aaaaccctcc  35460
tgcctaggca aaatagcacc ctcccgctcc agaacaacat acagcgcttc acagcggcag  35520
cctaacagtc agccttacca gtaaaaaaga aaacctatta aaaaaacacc actcgacacg  35580
gcaccagctc aatcagtcac agtgtaaaaa agggccaagt gcagagcgag tatatatagg  35640
actaaaaaat gacgtaacgg ttaaagtcca caaaaaacac ccagaaaacc gcacgcgaac  35700
ctacgcccag aaacgaaagc caaaaaaccc acaacttcct caaatcgtca cttccgtttt  35760
cccacgttac gtaacttccc attttaagaa aactacaatt cccaacacat acaagttact  35820
ccgccctaaa acctacgtca cccgccccgt tcccacgccc cgcgccacgt cacaaactcc  35880
acccccctcat tatcatattg gcttcaatcc aaaataaggt atattattga tgatg       35935
```

-continued

<210> SEQ ID NO 6
<211> LENGTH: 145
<212> TYPE: DNA
<213> ORGANISM: Homo sapiens

<400> SEQUENCE: 6
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcct 145

<210> SEQ ID NO 7
<211> LENGTH: 20
<212> TYPE: DNA
<213> ORGANISM: Human adeno-associated virus 2

<400> SEQUENCE: 7
ctccatcact aggggttcct 20

<210> SEQ ID NO 8
<211> LENGTH: 165
<212> TYPE: DNA
<213> ORGANISM: Homo sapiens

<400> SEQUENCE: 8
tccttgggga tcactacctc ttggccactc cctctctgcg cgctcgctcg ctcactgagg 60
ccgggcgacc aaaggtcgcc cgacgcccgg gctttgcccg ggcggcctca gtgagcgagc 120
gagcgcgcag agagggagtg gccaactcca tcactagggg ttcct 165

<210> SEQ ID NO 9
<211> LENGTH: 23
<212> TYPE: DNA
<213> ORGANISM: T7 virus

<400> SEQUENCE: 9
taatacgact cactataggg cga 23

<210> SEQ ID NO 10
<211> LENGTH: 24
<212> TYPE: DNA
<213> ORGANISM: T3 virus

<400> SEQUENCE: 10
ttattaaccc tcactaaagg gaag 24

<210> SEQ ID NO 11
<211> LENGTH: 23
<212> TYPE: DNA
<213> ORGANISM: SP6 virus

<400> SEQUENCE: 11
atttaggtga cactatagaa tac 23

<210> SEQ ID NO 12
<211> LENGTH: 36741
<212> TYPE: DNA
<213> ORGANISM: Homo sapiens

<400> SEQUENCE: 12
gatctgggta aagggttttc caggtgtcag gatggaagtg actaaggtgc agaggctgga 60
gggctggggc aggtagaagc aagcattcct gttacctact gctgtgtgac aatctccccc 120

-continued

```
taaaacacaa tggcttaaaa taacatccat ttcattacat atctcaatac tataggtcag    180
gaatttgggc tgggcttact tgggtaattc ttctgtccca catggcattg accaaagcct    240
ggttttcagt gggcagctgg gctggatggc ccaacacagc ttcgctaaca tgattgctgt    300
cttcgtaggg atggtggaag cctgggctca gtgggactgt caactggaat ggccatatgt    360
ggactctctt agcatgatgg tctcttctag aagcttgggt tcccagagag aatgttcaag    420
aggccccaaa ggacaccaca aagcttcttt atgaccaagg ctcggaaatc caggaagctt    480
gctcccatca cgctctatta ctccaacaag tcactcaggc cagcccaggt ccaagaggag    540
gaaacctaga ctccatcttg caatgtgaag aattgcaaat aatttgtgtc acccttaagc    600
aaccagcaac tcatctaggt tgattggcat ttcagcaatg tggtgggaag tggtgggact    660
gatgttgaag agggacttga atgtcatgag aggctgggga ggcaataagg tggggagtga    720
agtttctcga gtcagattca aatttaaacc ccagttttgc cacttacaac ccatgagcca    780
agcaggctgt ctctctatct gaacctcagt gtcctcatct gtaaaatgag gagaacacct    840
cctacatctg aggatgactg taaagatgaa atgggatggg tgcttataaa gtgcttccca    900
gtgtacctgg ctccaaacct gtctcagtaa atggcagccc ctattattga acccgagtaa    960
cacagagagc caagaaagga tcttacaaaa aactcccctg gctttgacaa tgtatgagac   1020
ccactgatag ggtttggctt tgtgtcctca cccaaatctc atctagtagc tcccataatt   1080
cctacatgtt gtgggagaga ctcggcggga gataattgaa tcatggggga tggtctttcc   1140
catgctgttc ttgtgatagt aaataagtct cacaagatct gatggtttta aaaatgggag   1200
tttccctgca ggcgctctct ctttgtctac tgccatccat gtaagacgtg acttgctcct   1260
cctttgcctt ctgccatgat tgcaaggcct ccccaccatt gtggaactgt aagtctatta   1320
aagcctcttt cttttgtaaa ttacccagtc tcaggtatgt cttttttttt tttttcatga   1380
gatggagttt cgctcttgtt gcccaggctg gaatgcaatg gtgtaatctt ggctcaccac   1440
aacctccacc tcccaggttc aagcgattct cctgcctcag cctcccgagt agctgggatt   1500
acagtcatac accaccacgc ctggctaatt ttgtattttt tttttttttt ttagtagaga   1560
cggggtttca ccatgttggt caggctggtc tcaaactccc gacctcaggt gatcctcctg   1620
ccttggcctc ccaaagtcct gggattacag gcatgaacca ctgcgcccag gctcgggtat   1680
gtcttcatca gtagcatgaa aataatggac taatacagcc accctctccc tcactcccac   1740
atacaaccaa accccaaatc cagctgattt tacaccctaa atgcagcttg aatatgagtt   1800
tctccacttc ccccactgac atcactatgc cctacccaga ccatggcagt tgcctccttc   1860
ctggtatcct gtcctccctc acccccgctg gccccctgta atgccctccc ctcacagcag   1920
ggagcccagg cttctcaaag tgccctgtgg gtgcgaacca cctgggggtc ctgtttgtat   1980
aaaatacaga ttctacttca gtaggtctgg gatggggtct gaaagtctgc atttgtagtc   2040
agctcccagg tgatgtgggt gctgatgatc cctggatcac actttcagta gctggagaat   2100
attttttcca aataaaaggg tgattttgtc tcgcctccac ttaaaacact ccactgactt   2160
cctaggaatc ccacaccatc gctgggtccc acatccctgg caggattcag ctcccatcag   2220
accttctagc cccttgctct ccactctccc actctctctt tccccccttgt ttatgggttt   2280
gttaatttat ttatgatgaa atgaaatgaa gctaccatcc accccagtac tggaacatta   2340
tcaataacct gtgtgtggcc aggcgtggtg gctcatgcct gtaatcacgc cttgggaagc   2400
cgaggtgggt ggatcatgtg aggtcaggtg ttcgagacca gcctggccaa catggtgaaa   2460
```

-continued

```
ccccgtctct actacaaatc caaaacttag cagggcacgg tgccacgcgc ctgtaatccc   2520
agctactcgg gacgctgagg ccgagaactg cttaaaatcc aggaggtgga ggttgcagtg   2580
agccgagatt tcgccactgc actccagcct gggcgacaga gcaagagtcc atctcaaaaa   2640
aacaaaaaca aaaacaaaaa aacaaaaaac aaaaattagc caggcgtggt tgtgggcgcc   2700
tataatccca gctactcggg aggctgagac aggaaaatcg cttgaaacgc tgggggtgcg   2760
ggggggcggt ggggaggagg cgggccagag gggcagaggt tgcagtgagc ccagatcgcg   2820
ccacttcact gcagcctccg cgaaagagcg aaactccgtc tcagtaaata aataaataaa   2880
taaataaata aataaataaa taacctgtac ccgcgtgtta tttccctccg tccttacctc   2940
ctcccggctc cttccctttc acctgagata accactcttc tcgtatctat gctcatcttt   3000
cccttgcttt acatttttc caccgatgca tgtgtctaaa catacatact tttggttttg   3060
cttttacaca ttctaaaagt tgcaccattg tatgcagttt tccgcaactt agtttttttc   3120
actcaacatt gtttctgaga cattgtttct gttgttgtct ggctgaagtt cattccgttt   3180
cactgctgtc taacgtttca tggtgtgaat attccggttt atttgcccac tcgcccgtgg   3240
aggggcattt gagggtgttt ccaatgttcc tgttattcgg aatagcgctg gtgtgaacat   3300
tctgcacagg tctctggctg cgcctgggcg ggtttcttaa aggtgaatgc ccaggagggg   3360
actgtctgtg ttctccctcc ctccgagctc cagccttcct cgcctccttt cactcccagc   3420
tccctggagt ctctcacgta gaatgtcctc tccaccccca cccacccctg atgaactcct   3480
gcaggttctg caggccacgg ctggccccc tcgaaagttc cttaactata caattatggt   3540
gtgtgtttct gcgacgagcg tccgtctatc cggtggaagg cacgccgctc gaggcttgcg   3600
atgctcccgg ggtccccgct tctagcttgg gcctggcgca cagcagcgcc cagactgcag   3660
ggggacgctt gaaagttgct ggaggagccg gggggaaggc agcgcccagc gaggcggctg   3720
gagcgcgcgc ccacaggtgg gtccggtcgg gcgccgcggg gccgtagttt tcgggtcggc   3780
gggcgaggac gccgggtcca gaattccagg aaatgcgcga tccaggccgg cgggcggggc   3840
gggggctccg gcgagagggc gggccccggg aacggcggcg ggcggggcgg gaggcggggc   3900
ccggcccgtt aagaagagcg tggccggccg cggccaccgc tggccccagg gaaagccgag   3960
cggccaccga gccggcagag acccaccgag cggcggcgga gggagcagcg ccggggcgca   4020
cgagggcacc atggcccaga cgcccgcctt cgacaagccc aaagtgagcg cgcgcggggg   4080
ctccggggac gggggtccgg cgcctgggcg gcccgagggg cttagcgggg cccagcccgg   4140
ggcgtccaaa ccctgggaac gaacgggggc tcctgcaggc gagttcttcc ttcggcttag   4200
gccgtggctt gcttgcgggc taatcaggga caatggggca gagaaggtcc agaacccgga   4260
ggcctccaga gtctgcttct gcccctgact tgacccctct gggtctcagt ttcgctgtct   4320
gtcaagtggg catcctagca ccgctgagcg ctgtgtgggc ctgggcaggg acttgaggtc   4380
tctgaagctc agctgtatga tcaggcccga tgtctacgcc ggatagcgac ctagtgctgt   4440
gccccgcgcc tactgagtgc tcagtgaatg gaagcagctt tgtacgccag cgttatggtg   4500
gtgagcgcca aggagctcag gtttgtggat gcgccccggg gaagaaccgt gagccctgcc   4560
agaaagggga gggaggggag cagagcaccc cccttccccc gcgcgggaag aacaggagct   4620
aggtaggccc tgggtttggg gccctagcag ggttcactcg aggccaagcc atggcccact   4680
ggccccaggg gagaatcccc ttgtttctcc gcccaccagc tgtggcgtct tgggactgtt   4740
ggggtcaggg agggtctgga cccccttggc ctgtctcaga gtccgagagg aggggcccag   4800
gagtctgcca agcagggtga gtcagccagt agggtgtgag agtggttggg gaaggagtca   4860
```

-continued

```
gctgcagtca gcctcaactt acccttctaa gaaataggtg tgagtggccc aggaggttgg   4920
ctcacgcctg taatcccagc actttgtgag gctgaggcgg gaggatcatt tgagtccagg   4980
agtttgagac tagcctggac aacaaaacta gaccccgtct ctccaaaaaa taaaaaaagt   5040
taggggaagt gtgtgtggtg gtgcactccc gtagtcccag ctactcagga ggctgaggcg   5100
ggaggatcgc ttgagcccag gaggttgagg ctgcagtgag gtgtgatggt gccactgacc   5160
ttcagcctgg gagacagagc gagaccctgt ctcaaaaaaa aagagaagaa aaagaaaaga   5220
aaagaaatag gtgtgaatga tgatgacagc tatcacaaaa gtgccggtga gaatccagtg   5280
agtgtgcatg tgtcagtgag ggagacaggc tgtggagagc ccacctacct tctgaggagg   5340
gtgaggcctg gcccccacta ctgatgcccc cagcccaggg aaaatgctca gctactcccc   5400
gtcagaagct ggaacgactg aggtgctgta caagccctcc tacccccacc cctgcctcct   5460
tcacgtctta ctggagctgg ggcccatgat tggcgcctcc cctttgcagt ctttttatta   5520
aatgctctgg gctccctctg cccttgggct ggggacccac tgtaccctga tgtgaatcct   5580
atggcagtag caaagctctt tgattggcgg ggtgcagtgg ctcacgcctg taatcccagc   5640
actttgggag gcaaaggtgg gtggatcatg aggccaggag ttcgagacca gcctggccaa   5700
catggcaaaa ccccatttct actaaaaata caaaaaatta gctgggcatg gtgcgggcgc   5760
ctgtagtccc acgtacgcag aaggctgagg caggagaatg gcataaaccc gggaggtgga   5820
gcttgcagtg agccgagatc tcgccattgc actccagcct gggtgacaga gtgagactct   5880
gtctcaaaaa aaaaaaaaaa aaaaaaaagg ctccttgatt gcgaacatgt tgggagttat   5940
ggagagaaca gcagggccca cttctagagc acttgttgca gacacccatt ggatccttgc   6000
agttcttctg taacagccca tcaagggagg ggctcatatt attatcccca ttttttggcc   6060
ttgctcagtc ctcccatctg attcaagctg gcagatcatt ttccctattg ggacctcagt   6120
gtccacacct ggaggatgga acatcagctg cttatgtggg tgtcccgtgt cctgagtccc   6180
aaggccacaa ggtgatgctt gagagtgaag gtagaatgtt acctgccatg tgtttgaggc   6240
gtgacaaatc ttgtatgatt gtgaggagga acttgtgtga gctggcagga gaagtgggaa   6300
ggagtgtgaa tctcagagcc actgtgacca gagccagctc cctgccctct tgtgggaggg   6360
acagatgaca gttataatta ttagcattac tagctgcagc taatggagtg ttgatgtttc   6420
tgccaggcac cgttctaaac acattatctg catttttat ttaatccagg cacagagagg   6480
ttaactaggc ccaagatcac acagctagga aatgtccaac tctggggttt gagtccaagg   6540
gaggctggct tcgaaatccc atgcctctaa ccatctttcc taaactacct ctgcagaagc   6600
ctttggggat agaggtgcca gtgccccagg tgcaaacctc ctgagacagg agcctttgct   6660
gtgtccttca gcttctcata cctgccacca gctgaggcct gggacctggt cagctagaag   6720
aaagcagagc agggcagcgc ttttcaaact gcactcaagt ggcctgactt ttaatgttca   6780
cactgtgatt ctgtgtgggt cgggttgggg cctgcgatgc tgcactgctg accagctccc   6840
aggaaatgct aatgtcaacg atccaggaac acactttgct tagcaaggcc ctaggcagct   6900
gccttctgtt gtgcgggacc cctattgact ccaatggata tagcaccagg ttcaagaggc   6960
taccttcttt ggaagaggta gcaaacaaga tacggggttt tactgggggc ttagacacag   7020
ggaagagagt ccagtggcgg cagactgagc agaagaaccg caaccacttg caaatcatgc   7080
agtttatgta gcattttcat ttaacacctt ctcccaacca tctccaccta gtaaccttca   7140
tttaacccaa aacaaagggc ctcggtccct ataccccctgt atggtcagtg tcccgtggga   7200
```

-continued

```
atggggtggg gctcagatgt tcctcataga taacgactgg atctccaggt tggccactct   7260
tggattcctt cgctcagaac tctgaacacc cattcaagtg tgcctgccat gcagggtcat   7320
cgtcagggga tgcccaagtc aagtttgcct gtcgggtgtg cctcccatac ccccacctgg   7380
tttgacttag cacctgctgg gcactggaag aagtgcaaag gggggttgca ggggtggccc   7440
ttatcagcct atgttcacag gtggcaccag gcactcaggc attctgcatc ctggaggcca   7500
gtgctgatca catgcctgtt acaataatca taacaatagc tgtccttgaa gtagtcctgg   7560
gtaccaggtg ccttcagtga ctttttcttc tttgccagaa tctcactctg tcgcccaagc   7620
tggagtgcag tggcaagatt ttgggtccct gcaacctctg cctcctgggt tcatgcgatc   7680
ctcctgcctc agcctcccaa gtagctggga ctacaggcgt gtgccgcagt ctcactctgt   7740
tgcccaggct ggagtgcagt ggtgtgatcc tggctcacta caacctccac ctcccgagtt   7800
caagccattc ttctgcctca gcctccggag tagctgggat tacaggcgtc caccaccacg   7860
cccggctaat ttttgtattt ttagtagaga cagggtttca ccacgttagc cagctggtct   7920
cgaactcctg atctcaggtg atcctcccac cttggcttcc caaagcgctg ggattacagg   7980
tgtgagccac tgtgcccggc tagtaacttt tatctcacgg aatcctctgg acgacttgac   8040
aaggcatggg tcttcatccc catttacaga tgaagaaact gaagcttagg gagtggaggg   8100
acttgccagg gctacacaaa atctgagagc cttgaagctg tagactggca agtgaacagg   8160
tacaggctgg gacagcagtt tctttctttt tttctttttt tagacagagt ttcgctcttg   8220
ttgcccaggc tggagtgcaa tggcacgacc tcggctcact gcaaccttcg cctcccaggt   8280
tcaagtgatt cttctgcctc agcctcccaa gtagctggaa ttacaggcat gcaccaccat   8340
gcccggctaa tttttttgtat ttttagtaga gacggggttt ctccttgttg gccaggctgg   8400
tctcgaactc ccgacttcag gtgatccgcc cacctcagcc tcccaaagtg ccgggattac   8460
aggcatgagc caccgcaccc ggccaaggga cagcagtttc taaactgtcc ctctctgatg   8520
cagaggggaa ttggggctaa atcagcaatg tgccttttct gtctcatatt tgaatgtcta   8580
ctctgcacga ggcgctgtcc tgctttgcat acagtgactc atttaatgtt tatgtcagcc   8640
ctctgaggaa ggtcctgtcc tattattaac ttcacttatt atgaggaaac tgagactcag   8700
agaggggagg gaacttgcca aagtcacaca gctggcaagc agcagagcta gacttgaacc   8760
cagatctgcc tgcactcaag tagaagctgt tcattgcttt gctcatttgc caattccact   8820
ttatgcaaaa aagagggggc agtgtggggg gaagagttag aatcagggtg gcagggtggg   8880
ccagtgcatt agccctgggc ttcagatgta ctggggttga attcctgcct gccgcttagc   8940
agctagggta cctcaggtag acaactcctg aaactcagct tccccctctg taaaatgggg   9000
tgacaaaacc aagatcttgg ggttcttggg gaaactgaca tgctgattgg tttttgtaca   9060
gtgcctggct ggtaacagca ggccctcagg ggtgcgtttc cttcctgggg actggagtgg   9120
gggttgcagt agactctggg aggcctctcc agctgcagaa tctccctcct ccctcctcct   9180
ttttgtcttc ctgacacaaa acccaccagc tgcacttctt tgggcttgca gtggctttca   9240
gttaccagag ccacctgtta aaacaaaaat gtgcctagga agagcctgcc ttacccattt   9300
tgactcacat ggcagttggt ggtggagggg aacaaaggag actgagtttc atcgaagcct   9360
tttgcttcgg aggaggaagg gaggatcaga gagaggaagt ggtctgtgtt cacacaggga   9420
ggcaggggag gccaggcagc ttcccaatcc tgcattcaac ctcagggtgg gcttgacctg   9480
ggtggctggg ggccctgtga tccaggagag acttgtccac ctgctcaggt gtcttgaagg   9540
ggtccctgtg gtacccccctg ggcggggcaa ggtagtagga ccatggtctg gctggggagg   9600
```

-continued

```
tggagaggag caggctgtgg gcgcagagtg aggttggaat ctgtatttac ccaaggtgtt   9660
gggggtaggc ttgccctcag cccttaatgt tctcaggccc ctgagcagtt gtgggggata   9720
acctctgcac tcctagtgac cagggagcta gaacagcaag gaatttgaac ttggacacca   9780
gctggggtca ggctctctgg gtctgagtcc tgatttccca ctttccagct agaggagctt   9840
gaatgagtca tttaacttca cggtgcctca gtttcccctc tctaaaatga gaattatacc   9900
catacccacc tctcaaacac caagtgcagg cctggctcag agcaggtgct gcagcaatag   9960
ctgccattgg tcagcatcat catcatggtt ggtaatggtc ctactttgac ttttgagaca  10020
gagtctcact ctgtcgccca ggctggagtg cagtggtgca atctcggctc actacaacct  10080
ctgctcccgg gttcaagtga ttcttctgcc tcagtctccc aagtagttgg gattacaggt  10140
gtgcgccacc atgcctggct aatttttgtg tttttagtag agacagggtt tcaccatgtt  10200
ggccataaca atggctgtcc ttgaagtagt cctgggtacc aggtgccttc agtgactttt  10260
tttttttttt tttttttgag ctggagtctt cctctgtcac ccaagctgga gtgcagtggc  10320
acgattttgg ctcactgcaa cctctgcctc ctgggttcat gcgatcctcc tgcctcagcc  10380
tcccaagtag ctgggacttg ggatacactt gcccccgctg gtcctccctt ccacctctgt  10440
gaagaggagg tctcaaactc ctggcctcaa gtgatccacc cacctcagcc tcccaaagtg  10500
ctgggatttc aagagtgagc caccgcacct ggcccctgtt tagatgttag catcagtgac  10560
ccagcacctt gctatgtggc atgcagggag cgtgctgcta gacctccggg tttagagtca  10620
aatagcttcc tggctgtggt gtgcattaga ctttctaact caaggtcctc ccactctctg  10680
agcctcagtc ttgttgcctt taaaacgagt ttaagtgtgc tgagtcccta tgctgtggct  10740
ccacaggaat ttccccaggt ggaagacaca tcttgccttc tgtgaaacct ctcagcagca  10800
gagctgtcag gccccgtcag caggagacac tgtggggact gctcagtccc ttccactgtg  10860
tacctcggag ctggcggagc ctagatgagg ctgagcatag agggcttcct ggaggaagtg  10920
gagctgaaac agtttctcag cccagggctg ctctgtctcc tggcctcaca ctaaaagtca  10980
gttgagaggc catagtggca taagtcactg accctggcac tgcccagctc atcaccaaaa  11040
gcagggctag ggagggaggg gacattcgat tggcagtggg cacctgtggc tcatctgggt  11100
tctggccacg gtgctcaggt tctgtgagct gaccaggcag ccctggctcc tctgcccccg  11160
tgtgggttct gccaggtccc atggggcagg tcagcccctt ccttgttgca gggagagcac  11220
ccagcattgc tgacatggga cagggaaacg aggaaataac ggtgtggtca ttgaacacag  11280
agagcactag gtgctgtgcg aggtgctgag gacacgacat gatgacacag acaaggtccc  11340
ccctctcagc aaacggctca tgagggagac agacatgtta catacatgaa cccaaaaagt  11400
cagacgaaaa caaaacagag cgatgtgttt gggaggcaaa cccaactgcc ggagggcgag  11460
cagttgggaa cgtggaaaca tgagtcagat ctgggagtat ctgtcccagg agtccaagac  11520
ctgggtcctc atggtagctc tgccaccgac acactgagtg accttgggta agtgaaccca  11580
ccgccctgga cctctctggc acgcatctct tgagagcagg gacttagtgc atttcccgag  11640
ggcctccacg gtgcctggca catagtgggg cttagtaaat atttgttggt aactgaggat  11700
gcttcctgtt cacatcagcg ctgggaggat ttcctgctgt tcagacaaat gctgggctgg  11760
ctgtgagtca gccttgcaga gagcaaaggc agtgggaagg ggcgtgagat tcccctctgg  11820
agaggtcagg aggccaggca ctgtctcgac atgagtgcca gggagggggt gtggcctgtg  11880
ggcagggctt gggctgaggc agagggactt gagttccacc ctagctctac caccatcaat  11940
```

-continued

```
tttgtgtaac tctggacagg ccactgaact tctccgggct tagcctggca agtccatttc  12000
cccatctgta acatgggccg atatgtacat tgcctaggga ttaaatgaga taaagggtct  12060
gaaaacagta ggtagctgct ttatcattat tattatttct gtattattga tgtctgaggc  12120
taggcccaca gaggcagtac agtagagtgg ttaggagctc aagaatcaga ctagggttca  12180
aattctgact ccatcactga ctgttttggg gtacttcttt gaacctcagt ttcttcatca  12240
gtaaaatggg agtgaagtct ctaccttgct ggttgtaagg atgaaataag ataatgcata  12300
tagatggtct agcacatagt agatactcaa aagtttgagg ccactgctga cccttttccc  12360
tgaaaggaga caggagagcg gggtcgccac cccattgtca ttgtcatctg gaataggctg  12420
acagacttcc catggtgtgt tgcagttttc tagaaaattc agtaggaggc ctgcctgagc  12480
ttgagccacc tgtggaggtg cttcctgcct ctgctccaca cctgaaacgc gtctgggcct  12540
cttctcaggc agccgtgaga agggatgagt gctactggtc atggtgggca gctggctctg  12600
ctttcccccct tcccagaggc gctcctgcct cctgcccagc tccctgaacc cctagcttct  12660
gcaccccggc actgtctggc ttctgccccg ctgagcaccc actgtctctg acgctgcctt  12720
gagtacttcc cgcatgttat tcaaatccca atcagatctt ccctccccca gtagctggtc  12780
ttctgttctg gcttcctgcc atcctgtcct ccacacagca gccgggaaag gtttttttaa  12840
aggggactct ccgatttaac acacttgggt ggaaaaccct ttgcttcggc ctctgcaatc  12900
tccctgcccc ctctccactt tgccctggcc tcatttctca ccactaacct cactctgcac  12960
tctggccaac tccccgcctg cttcctgatt cagacactaa gcacacgcag ctcccctgcc  13020
tggagccatt ctccctctcc ttctttcttc tccctggaga actcccccctt taagtgatct  13080
tttcccaaca cactttctaa attgccccca ccccagtgtg atttttcttt atctcatagc  13140
acttggtctg cttcttatca cagtttgcaa ggctgagttc agaaaggtgt gtttgctcat  13200
tctgaggcag gagaggctac cttgtgctgc tgtggtaaca aacagccccc aggtctgagg  13260
ggtctgcaga gacccaggtt gacctcatac tgcttgtccc tccagggcct ccagtgaggt  13320
ttcggctcct tggatcactc agggccccag gcagatggga agattccact ctgaacattg  13380
ccaattgttg tgccagagta aagcagagct gggaggtggg ctcttgaatt ggcatttaaa  13440
tacttttgcc aggcagggta aggcagctca cgcctgtaat cataacactt tgggaggcct  13500
aggtgggtgg atcacctgag gtcaggagtt caaaaccagc ctggccaaca tggtgaaacc  13560
ctgtctctac taaaagtaca aaaattagcc gggcatggtg gtgggcgcct gtaatcccag  13620
ctacttggga ggctgaggca cgagaatccc ttgaacctgg gaggcagagg ctgcaatgag  13680
ctgagatctt gccactgcac tccagcctgg gcaacagagc cagactccat ctcaaaaaaa  13740
aaaaaacaac aacaacaaat aaataaatga ataaatactt tagccagaag tagccatgca  13800
gacctccccc caccagtccc acccacaagc ggacgtgact accgccccca ttcactgcct  13860
gatcctcctg ttctcagggg ctccaaggcc aggcctggtt tgaccttctg actttctgac  13920
ttcctcctac cttcccagta acctcatgca actcctttca ctcagcctca atcatcccca  13980
tgggtgttta aacttgccca agacatgccc ctttgaaaaa gcctgccatt ctcttgaccc  14040
acatgcacgt cctgcccccct ccaaggctgc tagttccttt aggggcaaaa ttgtgaaaga  14100
gtagtctaaa ccttcttcct cttcttacct ccacttcttt cttaccttat tcccatgtgg  14160
attctaccct cactcaggcc tctagaacgg ttcctctacg gcagtggttc ccaatcttga  14220
ctacgtgttt ttttaaaaaa agtcctccac ctgggcctgc caccaaggat ttttctttaa  14280
ttgacctcag atggggttga ggccttggga actggccaga acttcccgtg ctcctaactt  14340
```

-continued

```
gcagccgggg ttaagaacta ctcctctgaa gcccccagtg cctgcgcttt tagcccgacg  14400
gacaagtttc tgcccttcca tcctgtgacc tccagcaggg cctgaccatg tgagttttct  14460
gtggctgccg tgacaagttg ccacaccctg catggcttca accaacagaa acgtgtgccc  14520
tggcagttct gggggccaga agtccaacat caagatatca tcagagccac atgcccactg  14580
aaggctctcg ggggaatcca ttccttgcct cttctggttg ctggtggctc taggcattcc  14640
ttggcttgtg gctgcatcat tccagtctct gcctctgagg tcacgttgct gcttcctctt  14700
gtgtgtgttt ctcttaaaac tctctgcttc tgtcttataa ggatacatgt gattgcatct  14760
agggcccaac cagataatcc aggataaact cttcctgtca agacatttaa taatcacact  14820
ttgccatata aggtaatttt tttttttttt tgaggtggag ttttgcactt tcacccaggc  14880
tggagtaaag tgatttaatc tcggctcact ggaatctctg cccccaggtt caagcaattc  14940
tcctgcctca gcctcctgag tagctgggat tataggtacc tgccaccatg cccagctaac  15000
ttttgtattt ttagtagaca tggggtttca ccatgttggc caggctggtc tcgaactcct  15060
gacctcaggt gatccacccg ccataagtta atattttttt tttgagaggg agtattgctc  15120
tgttgcccag gctggagtgc tagtggctca atctcggctc actgcaacct ccgcctccca  15180
ggttcaaatg attctcctac ctcagtctcc tgagtagctg ggactacaga tgcatgccac  15240
catgcctggc tgatttttgt atttttaata gagaggggat ttcaccatgt tggccaggct  15300
ggtgttgaac tcctaacctc aagtgatcca cccacctcag cctcccaaag tgttgggatt  15360
acaggcatga accaccacgc ccgacccata taaggtaata tttacaggtt ctggggatta  15420
ggattagcat gtagacagct ttgtggggc caccattcag cccactatgc taaccctgtg  15480
aaccgttgct cgcttctcct tgacatctga cggcctggcc ttctgcatac cacacaccct  15540
cccacctctc tggccacagt tctgtaggct cagcctcctc cgtaaggcca ttaagtgctt  15600
gtgctggtca aagtttcatc ctaggccttt tccttacctc ccttgatatt ttctccctag  15660
gtgagctcct tcaagcccac agcttctgtg cttacccaca ctcctaccta cattcccagc  15720
ttgggcttct caggccagct ctagactctt gtatcccact gggttcttcc acttaccttt  15780
ggatatctca aaggcatctc cagttggctg ggcacgatgg ttcacacctg taaccccagc  15840
actttgggag gccgaggtgg gcagatcact tgaggtcagg agttcaagac cagcctggcc  15900
aatatggtga aaccccatct ctactaaaaa tacaaaaatt agctgggcat ggtggtgggt  15960
gcctgtagtc ccaactactc gggaggctga ggcaggagaa tcgcttgaac ccgggaggtg  16020
gaggtttccg tgagctgagc tggagccact gcactccagc ctgggcaaca gagtgaaact  16080
ccgtcttaaa aaaacaaaaa acaaaaggtg tctctagtgt aacataacta aaaccaaacc  16140
aatcatgcct ccctccccg catcctccct cctggaggga gctccaggac ttggtcttct  16200
cttccagagt tctctgtctc aaactgcggg aattgctccc cacccaggcc taacctgaag  16260
tgtgagcctt ggcatctctt tctatccacc tgttttcct ctatgcacct cacaaccctg  16320
gtccaagcca ccgtcatctt tcaaatggct gcagtagcct ctaactggcc ttggaggagc  16380
catcctcttt ctctaaccag ctgccaaccc tgcaatggcc tctgtgtgct ttccagataa  16440
agcctgactc ctcgtggccc gcacagccct gcctgggtgg tcctatcctg cagcctctcc  16500
agtaccatga accctccctt ctctgaacct ctatttaatc catttcatat accccgtttt  16560
ctcctgccat agggccttgc acatgctgtt ccttctgcct ggaattttct tcctgcctcc  16620
ctccgcaccc ctgccttgtg ttgtgggttc ctcgctatcc tctagctttt cgctcaggct  16680
```

-continued

```
cattgttggc cctctagatg tattcacttc tcttgtttgt taccctctgt cataggactg  16740
tgttcgtact tcccaaggag tcgtcttggt ttgtgactgt acattttccc atgtgacatt  16800
tgcttaatgc ctctcccact ctggggcctg tacaagcccc aggaacagga cttggaccct  16860
cctgtttaac tctacaatct agcatccagc aggcgcgcag gccttcgttg acttttattt  16920
tattcttatt ttttattttt gagatgcagt ttcgctcttg tcgcccaggc tggagtgcag  16980
tggcgtaatc tcggctcact gcagcctctg cctcccaggt tcaggtgatt ctcctgtctc  17040
agcctcccaa gtagctggga ttacaggtgt gcgccaccac gcctggctaa tttttttgcat  17100
ttttagtaga gatggggttt caccatgttg gccaggctgg tctcaaactc ctggcctcag  17160
gtgatccacc cacctcggcc tcccaaagtg gctggattac aggggtgagc ccccatgccc  17220
agccttcatt gacttttagt tgacaactat ttagcatttg ctatgtgcca agaactccct  17280
gcctactaat gcagttaacc ctcatgaagc ctagaaggaa ggactgccat tctccccact  17340
taacagatga ggatgccgag gcacaggaag tgaagtgact ttctcagggt caagcaggga  17400
gtgagtggag gagccgagat tccagctcta accgcatgat gctctataca gtgtgactcc  17460
ggctctctgg ctgggccctc tccatagccc tgtgagggtt aaggatagaa aacagaggct  17520
cagagagttg aggtcccttg cctgaggtca cacagctggt tggccgttcc ctgggctata  17580
agcttcagta ttcccaatgc tgagcatatt ttgagaaccc gagaaacaga cgtttggctg  17640
ggtgggaact gaactcattt tgtcagggaa ttcaacaact aagttggccc tgagactggg  17700
tgtgaagacc gctctgtccc ctgccagctg gatgacctca ggagagatct gatgactctg  17760
aggtcctgct gataggacct ctggtgtctc tgttccctgc tggcctcccc tgggcctggg  17820
ttgggtttcc tctgcaggag gcagctcatg tatgtgctcc tagacgccct tgggccagca  17880
gctccttggc tgttcctccc tgagccaggg cagccaactt tcttatccag ctctccatgc  17940
tccccacccc agcatgagat gtcagctgag agttttctgg atctccccta gctaggggga  18000
aagcttccat catttggaac aggaacagca ggaacagcaa agtccctttc cccaccatct  18060
cccactgcct gctgtgcttc tcctaacagc tcatggtaaa caccctgact gagcggcagg  18120
ggctgtttcc tttgggctat ccatgtccac ctacactgcc ctttttaatc cttacaattt  18180
ttcttggaca cgggggcata atattccatt gtttttcagt tgaggaaact gaggctcaga  18240
gaggtcaagt gtcttgtctg aggtcacaca gcagaactgg gagtcaagcc agatgggctg  18300
cctccaagga tcctactctt aaactctaga gtactagaaa gatcttccgt tgcctaatat  18360
tgattcctga taggctatgc ttgagtagca tctgcttttg aaaatggagc ctgggtcggt  18420
tgcggtggca catacctgta atcccagcac tttgggaggc tgaggtgggt ggacacctga  18480
ggtcaggagt tcgagactag cctgagcaac atggtgaaac cctgtctcta ctaaaaatac  18540
aaaaattaac tgggtgtggt ggcacctgcc tatagtccca gctactccgg aggctgaggc  18600
acaagaattg cttgaaccca ggaggtggag gttgcagtga gaggagatca cgtcactgca  18660
ctccagcctg ggagacagag cgagactcca tccgtctcaa aaaaaagaaa acgaaaatgg  18720
atcctgaatt ttgaaatatg ctgtgactct tccctagttt gggacatctg ggtcaatccc  18780
ttttgttaaa gtagtttatt tagttggctg agagcgggag ctgcctacgt gacctggagc  18840
acaagctttg gaattgggct tgggttagaa ttccgcctct gccactcacc agctgcgatt  18900
aagaacaaag atactgggtt gggctcctgc ctctattact tgcaatctgt gtggccttgg  18960
atgagatatt taacacctcc gaacctcagt gtcctcaatt gtgaaagaga tcgagataac  19020
agctgaaccc acatcccagg agcggattaa atgagatagt gcagtacaga gtttaccgaa  19080
```

-continued

```
gtatatgggg tcagcagcca gccagtaaaa tggtggctaa tggttatcat gattaatgtt  19140
aacattaagc tctgaaaggt ccttcgtgaa ctcataggta tttgttctct ctctcccttt  19200
ctctctctct tccccctgcc cccttgcagg tagaactgca tgtccaccta gacggatcca  19260
tcaagcctga aaccatctta tactatggca ggtaagtcca tacagaagag ccctctctcc  19320
ctgggatttg agtggggtcc ccagctccac ccagaggccc ctggggaatt ccagggtcac  19380
tgttccttcc tgtctccctg tgggaatcaa gccagctcca ggccagaagt gggactgtga  19440
ggacatggag gcctcggcac tgagctgcag acccgcagac caactcctga gctttctggg  19500
cctctgagtc ttgtcctcct ggtgtcaggt gagccaggcc tgagcctgct ctccccaccc  19560
acccacatac gtgcatgaag gtagttccca gggctgaatc cgtctttttt tttttctttt  19620
gagatagagt cttgctctgt cgcccaggct ggagtgcagt ggcatgatct cggctcactg  19680
caacctccac ctcctgggtt caagtgattc tcctgcctca gcctcctgag tagctgggat  19740
tacaagcaca tgccaccaca tccagctaat ttttgtattt ttagcggaga tggggtttca  19800
catgttggcc aggctggtct cgaactcctg acctcaagtg atccacccag cttggcctcc  19860
cacagtgctg ggattacagg catgagccac tgtgcctggc tcctgtcttt tgacttaact  19920
gagagcctat atatagcagg tgatgtgctc acatgagatg ccagtacaat ttcttgagca  19980
tctcctagag ctgggctggg ctttatcagc tcattgaatt cctccacgct tggaagagga  20040
ggatacgctc tctgcatttt actgaggagg gaatgggctc agccaagaca gttgtccacg  20100
gtcacacaaa ttaatagcag atcaagagtt gaacccaagg ctgtctgacc cctaaggctt  20160
tactacatca tcagggtcat aacctgctag gagtcacgga aaagtggctc cccaactctg  20220
ggcctaaatc tctgcatctt ccaagtgaga acacacttcc tgcctcagct ctcagagatg  20280
ctagggggcc agagggtccc cctgttcccc agcgaggaag gttcttccct tcctacccag  20340
acctcaaggg ctcacagcag ctcctctctt aggaccagct tttaagggca gggactttaa  20400
aggccagtgg atctggattc aaatttggac atattatctc ctgtctgcga acttggtctc  20460
tatcaactga ggctaagaac aggccctccc tagagagatg acctaggagc taggggctcc  20520
ttgtccaccc agccctgccc ccgcagacct gtgttcctcg gatgtttgca caacactcat  20580
tttgtttgga gctgaaagaa ctcagcctct ctgtcacagt cttgaaattc agctcgggac  20640
ccaaatttga acatttctgc tccataagcc agaatcctgt tattcagagg cctgccctca  20700
tggagagaat gagggatccc gggggttgcc cccaactctc gggagcatct ccaccaactc  20760
cctgagagat ttctggtaag tccactattc tccatctttt cacacttcca gggaccttct  20820
tctgccccag gaagctgcca ttgatttaat tcctatttaa ctgcaaggca taagcacagt  20880
agcacctcct gtgtgccaaa cactccttta agtgcgttac ccgggttaag ttattgaagc  20940
ctcacaacaa tttgtaagat aggaactcta ttgccgtcat ttacagatga ggagactgag  21000
ccgtggtagg tggagtaagg tgcccagtaa gcacagggcg gaggtttgaa cccagatagt  21060
ctgcccccga gtccatggcc ctggccatta ccccctgtca gttagaggtt ttggtaagtg  21120
atgcccgtaa aatgcttagt tcagggccta gcacacatta atgtgctcca taaatgtcac  21180
ttaatgataa tattcttatt aattggagct tatatctcta agtggggtga aacctcttgg  21240
cttatctctg cctggccttt gcccatgtca agccgccaac ttgccacaag gcccctaatg  21300
aggtcgttca gtggggcacc aagatgagat cgaacccagg cactcattaa ggggtcacgg  21360
agggctcatc agctgcagcc aggggctggg agcgccgggt ggggctaaga gaaaggggaa  21420
```

-continued

```
aggagccgcc gggaggggca ctggtctgat cgtccattcc tcacaccacc tctgggcctt  21480
ggagatggcg tgcggcaggt gccagctgga gcttggcctg aagtcagcag gcaggggact  21540
ggggagtttg tcacactcag atatgggtgt ctgtaaatgc acacaaatat gggctaagaa  21600
tggaaggagg aggggagccc ctggcctgag ccctgctagg cccaattcag tggccctttt  21660
tccagctctg ggactcaggc ctgcctcatt aactgtcctc acccatttct ccttcctcca  21720
gttcccagga ttctggcctt ttcaggggcc tctccaacct ctttctcagt cttgtttata  21780
accctgtcaa ctatttctac agagattctg aaactggctg ctctttcctc cgatcactgc  21840
cctggtctgg gccaccactg cccctccctg gtgctgtggc ctcctgattg gtctcagcca  21900
tctactctgg ccttcctctc tacgggccct gcagtgctgt agttggagca agagccttaa  21960
cccatggtct tcccagctca ttccccagct tccccatctc actcagagtc aaagccaaag  22020
tccacacatg ggccttaaag ttctgcaaag cctgcattgc ctctctgacc tctctaaggc  22080
tccttgctta gtccacactg gatgtttttc aaacatgcca gacctaggaa acagagagtc  22140
tgggttactt gcccaaggtc acacagcctt taagtcacag agctgggatt caaacccaga  22200
ccactgggct tcagagtctg ctctttctca tgacacacaa agtttcattt cttcctctgt  22260
gcacccctac atggaaaata ttatgtttta ctgacaaggg caccaagggc cttagagggg  22320
agcgctcctg cctgggatga tgtggtaaat aggggtggga gatggacttg acctgcaacc  22380
cctgcgctca tcctccctcc ctccctgggc tcctgatggt gggcttcttg tgactgtgtt  22440
gcccaccaag gccggaagag gaccagacag tgccccagca cagcagctgt ggctgaccag  22500
ggagtaggga tcatctaaga acagagcgtg catggtgctc acgcctgtaa tcccagcact  22560
ttgggaggcc aaggcgggtg gatcacctga ggtcaggagt tcaagaccag cgtggccaac  22620
atgggaaacc ccgtgtctac taaacataca aaaaattagc caggcatggt ggtgggcatc  22680
tataatccca gctacttgag aggctgaggc aggagaatca cttgaaccag ggaggtgaag  22740
gttgcagtga gtcgaggtcg tgccattgca ctccagcctg ggcaacaaga gcaagactcc  22800
gtctcaaaaa aacaaaacaa aagaaaaaac agagggtggc cctatgagga gccttcgctt  22860
gtgtgggtgg ccagggacag caagaggtgc cagggcccta ggaacagctc tttcctgctt  22920
caactttggg ctccagatgg gcgctttcca gctcagtctg agcagcttcg ggaagctgtg  22980
tcccatggga gacactggga gtcccctgtg ctctttgtct cctgtcgggc ccccacatta  23040
gctctctggc ctcagctctg gcttccctcc aatttgtttc ccacgcagca gccagaggag  23100
ctttcaaaaa ggtaaattat ttcatgctag tcccctgctt gaaatcctac agtgccttcc  23160
cagtgctttc agccaaagcc ccagtccctt cctaagccca gcctggccct gcctccctgg  23220
tgcatcatct gcacaaatgc ctgctctctg acctccagcc accctgcact tccaatgccc  23280
gcggcttcct gcctgcagct ttagtacaga cccctcccct gcccagaact gcccccaccc  23340
caaggcttct gctgaaatgt cacctcctca gagaggcctt ccctggctgc tctgtctaaa  23400
ctctgtgttg agaagttcct tcttgatggt tgttgaggag ggaggctgga gaagaagaat  23460
caaagaggag aaatagaaag caaaataatt tgttcttggg gacgggctgg tgctgggcac  23520
ggggaggcgc ccgtctctgg tgtgggcagc tgggtagatg gaggagccgt atttggaaat  23580
gtggaaccca ggaagggagt gatctagagg gaggggaaag gtggcgcgag atgcctgcct  23640
ctcaacaggt agccagacac atgggtctgt cttggtcact gctatctgcc cagtgcccag  23700
cacatcacag gccctcagtg gtggtgtgtg ggcatagaga attagaagct gtggacctct  23760
ggatccggag ctgaaaacca ccaaaggaga tgagttggcc tggccaggtg tgtaaaaggc  23820
```

-continued

```
agagtctgag agagaacgac cagagggcag agccccgcag gtggagtcct gggggctgga  23880
gggagaccat taggagaatc gcacatggct ggcgcagcag gtcccaggca aatgtggcca  23940
ctgggtttgg caatatggga gccagagccc tagtgtcatc tccctgcctt ctacccagca  24000
gttcccagag tgatatcccc aacagtgttt gacaactggt acaggctctt cagcggccac  24060
agttactggg caaggccttg tgagggtgac tttggggcag ctggccagca gtgggagggg  24120
aagcagtctc aggggtacct gaggcactga gctccgacct ccaggtgcca atgccgcacc  24180
agggcaccgt tcccctgcag gctcttacag ggattagggg ctggtaagga gcagtgatta  24240
ggggctgact agcaggctgg tgggcaccag catgacccct tggtggtacc ctctgggcac  24300
tcatggggac ttgggctaac agatggggaa gggagcacat tcaggggggct taggaaacat  24360
atttatgtag ggaagcattt taatatttta gtaacagaag ctattaaagg acttacaaac  24420
ttacttacat acactaaaac actatttggt caaacttctg tttctttggc actttcctcc  24480
tttattcttt tttatttttt tgagacaggg tcttgctctg tcacccaagc tggagtgcag  24540
tggtgcaatc ttggcccgca gtagccttga cttccaggct caggtggtcc tcccacctta  24600
gcctcccaag tagctgggac tacaggtgca cgccaccacg cctggtgaat ttttgttttg  24660
aaggggtttc actgtgttgc ccaggctggt ttcaaactcc tgggcttaag tgatccgcca  24720
gccttggctt cccaaagtac tgtgattaca ggtatgagcc actgcacccg gcctcctatt  24780
tttctgcttc tgctttgtgg ataattggat gcttggacct cctgatttaa tcttctaatt  24840
tccttaactg tttactccta tttttcatca tcttgtcttt ttgttctact ttgtggagga  24900
tttcttcact tttagcttcc agttcttttc ttacatcgtg acagttgctg ccgcattctc  24960
ttgtaaattt ccgagggctc gttcttgggt tctgaatgtt ccctcctttc aaggatcttc  25020
tcatctcttt gaggatattc atgtcttttt tgttttggtt cttaggtttt catctgttct  25080
ctgtgctgtt tcctcggagt gcttttgtct attctgttgt tttgtccctc atgttagaag  25140
catttctttt ttttttcttt ttttttttgt gatacagagt cttgctctgt caccaggctg  25200
gagtgcagta gcatgatctc ggctcaccac agcctctgac tccctggttc aagtgattct  25260
cctgcctcag cctcctgagt agctgggatt acaggcacac accaccacac ccaactaatt  25320
tttgtatttt tggtagagac ggggtttcac catgttggcc aggatagtct caatctcctg  25380
acctcatgat cctccgacct tgcctgggag gccaaagtgc tgggattaca ggcgtgagcc  25440
accatgccca gcctagaagc atttcttaat gtctggtgtt ctctggctgt tgtatcttaa  25500
aaaaaaaagg ggggggaaac tgaggctcga ggtgaccttg tgagctggag cagagccggg  25560
atgggatgag gaggcaggag cgtgtgcaga agagagggag ccccccctgag ctcgcaccct  25620
gcttcccgtg gctgggaggg gaggccgaga tgcttgggga gaaatggagg ctccaagcca  25680
gaggggctgt ttccagcacg ctcttactga gcgctgctgt agtccagctt ggtgtggcgg  25740
ctgtgggcag ggaggggaga gaggtctgag ctggctggcg gcccactggg cccctcccct  25800
gagcctccac cggccctctc ccagtgcgct gggctgggca agcctctgat gtgccagcca  25860
gatggagggt gaagtcctga tgcctgcccc taccctggga attgtgatgc tgcagttact  25920
gcccctgata acccctgact gggcatagga ccagctggct gagccagctc ctggggctga  25980
ggaggaagcc atgaacttga cctggcactt tccttgtctc caagcatcag tcaaccaagg  26040
atatggaggg ggtgtgtgca tgtgtgcaca catacacaca cacacacaca cacacttcaa  26100
cctgtttatc ccccttgaga tttgctgact tgtgcattgg gggtagaagg tgctggaaaa  26160
```

-continued

```
attccggtcc tggttctcag tttccccatc tgtccagtgg gagcagctgg actgagagac  26220
gcccatgtct cctgctgtgg tcctgcaagg aggctggcgc tcctgagtct gctccatcct  26280
ggcctgtcag gcctgcctgg atcctgcccc gggttggtcc accactcact gttttgtttc  26340
caggaggaga gggatcgccc tcccagctaa cacagcagag gggctgctga acgtcattgg  26400
catggacaag ccgctcaccc ttccagactt cctggccaag tttgactact acatgcctgc  26460
tatcgcgtga gttgccccca acccacaggt cctagggcag cattgatccc tatgactagg  26520
accaggcctg tccctcagcc tgtgggggcc agagaagttg ctctgaaacc acagctgtct  26580
ttctcaccat tgtgtacact tagtgagtct ctccagtgcc tttaggcctc agttttccct  26640
tctgagatgt gggtgtgatg gactgaaatt gcttcaagtt ctacagagaa atggcagaat  26700
atgggagcta agaacacagg gtcagaggca gtgcagggct tgaacccggg ccatctatct  26760
cctagttcag ggcttcgtgt tgtgagggga ggagaggcct gaatataggg tgggggcggg  26820
gagatgtggg gaagattctc caaaaggctt tttctttttc ttgtcttgag tcgccaggga  26880
acagcactag gtaccgaaaa ggccagaagg ggtatgggcg agtactagag agaaatttcc  26940
atgactgctt tatttattta tttatttatt tatttattta tttattgaga cagagtctca  27000
ctctgttgcc caggctgaag tgcagtggtg cgatctcagc tcactgcaac ctccacctcc  27060
cagtttaagg gattctcctg ctttagcctc ccaagtagct gggatcacag gcacccacca  27120
tcacacccaa ctaatggttt tgtatttta gtagagatgg ggttttacta tgtttgccag  27180
gctggtctcg aattcctgac ctcaggtgat ctgcccgcct cggcctccca aaatgctggg  27240
attacaggcg tgagccactg cgcctggcct ccatcctcat cctgaagatg caagaacttc  27300
tggtgacccc ttctcctgag agtggcctga tctcccctgg gcagggcact ttcttcccac  27360
gctgggctct cccacgactt gtgtgccttc cctcacacat tctagtaacc acttcatttt  27420
cactcttcat ggtgggaact tccagctaag cacagtccac cgttacgtga tcaacacagt  27480
ggccctggca ggccaatttg tgccttgctt ctggaacaaa catgcagtaa taacaacgaa  27540
aatgttttga gcatttgtcc gctctgctcc aagcactgac ccgggtgggg tttatgaagt  27600
ttgactcatt tgtccccgca ataactcctt gacctaggtg tcagagggtg actaaccagg  27660
ggtcacacag cagataagtg tgggcacaag gatccaagtc catgactgta tcccacgtgt  27720
ctcccacatc caggcatccc tctggacttg tccagctgtg tccttttctc tcatttctct  27780
tccctgccag ccttaactcc atcaccaaca aatattgggc tactctgtcc taggcatggt  27840
cctcagctga gaggtcgcag ccatcccaag acagaggggt ccttgccaca tggagactgc  27900
attctagtag ggaatacagc aaactggctg ataagccata tgacacacaa tgttgagtag  27960
tgataaggac ctgggagaaa aagaaagccc aggagaatgg tggaggggcc gttttaagat  28020
aaggcggtct gggccaggta cagtggctca cgcctgtatc cccagcactt tgggaggctg  28080
aggtgggcgg atcatgaggt caggagatcg agaccatcct ggctaacaca gcgaaacgct  28140
gtctctacta aaaatacaaa aaattagccg ggcgtggtgg catgcgcctg taatcccagc  28200
tacttgggag gctgaggcag acgaatcact tgaacccagg aggcagaggc tgcagtgagc  28260
tgagatggcg ccactgcact ccagcctggg cgacagagca agattctgtc tcaaaaaaaa  28320
aaaaaaaaga taaggtggtc agggaaggcc tctctgagga ggtgaagctt cagctggctc  28380
taaaccaggg gagcgggaga gacgcagtgt aggacagtat cggggaagag caggcctgtg  28440
tcttctccgg tggcctcagg gaatgaggga gaaggaaggt gctggggagg ctggcaaggc  28500
tggaggatgc aggcttgtgg gcaggacctg ggagttgcga tgtcactctc cgtggcagga  28560
```

-continued

```
agctactggg gcttcgaggg gagaagtgat atgctttgat ttaccttctt aaaagattgc  28620
cccaactgct gggtggagaa caggatgaca ggggcaagca tggagacagg gaggccagtt  28680
agagatggcg tgattcaggc caggatgagg ggtgagaact ggtatgcagt tccaaagtag  28740
agctgatagg acttgcccag tgtctggatc ttatccagtg gatgcccaga gcttgggtct  28800
ggggatgaag tgggtttaat ctgccaaggg ttggggatgt catttgctcc tggagctccc  28860
aagggacttg gggaaggttg ttcccaaccc ctttcttccc ttcccagggg ctgccgggag  28920
gctatcaaaa ggatcgccta tgagtttgta gagatgaagg ccaaagaggg cgtggtgtat  28980
gtggaggtgc ggtacagtcc gcacctgctg gccaactcca aagtggagcc aatcccctgg  29040
aaccaggctg agtgagtgat gggcctggaa ggggccatgc tgagggtgtg gctgggaggc  29100
tcagctctga gactggaagg gcgaactgct gggaatccct gacccaagca agaccttgtt  29160
cttgccccca gtctggtcca tggcctcaga aagatgggtt taactctgtc acaagagacg  29220
tggttcccat cctccctttg ccgttatgtt cttaccttgg gcacaagtgt ttggctgtgt  29280
cttgctctgg ccacaggcct gctgtccagg aatgttaacc tgcttagcca cccaggattt  29340
ctgaggggtc tcccttgtca ctgatgctga tcagatctct aaaggcccta aaggtcctgc  29400
tctaacttca taactgaagt gagtctggcc catttctagc cccctgcctg ggcccccatg  29460
gatctctaag tggtatcaca aaaccaccct gccccatttt ctgagccatg attctgatac  29520
atatagaatg tgaacatcat ggcaggccca agcttagcaa tgctgtccat ctgggggtgg  29580
ggagggccat gttgacaccc cacacctccc actaagatct aggagcaccc agctgcttta  29640
agagctagag ggacatgcta gggcctgggg gcatctctgc cagtctttcc tctgaggcag  29700
tgggtcagtg ggggaggagg gtcctcccca aagcctcctc ttcctcctct gtcccagtcc  29760
cagagctgcc ctttaggcct tccttttgcc tcaggcccat ccctactcct ctcctcacac  29820
agaggggacc tcaccccaga cgaggtggtg gccctagtgg gccagggcct gcaggagggg  29880
gagcgagact tcggggtcaa ggcccggtcc atcctgtgct gcatgcgcca ccagcccagt  29940
gagtaggatc accgccctgc ccagggccgc ccgtctcacc ctggccctga cctcctggcc  30000
tagcagtggg gctgtacctg atctcccctg tgccccacag ccccatggtg tccccttgag  30060
cccactggca tgaacttggg gcttcatgaa acaactggag acctcctagg caggctcaga  30120
acttctggag atgttctccc cagggacacc atgcctttat agccaccctg caggaagctc  30180
aacaccaaat aggaacgtaa ctattgaaaa aaaaatctag gctagattct gatcagccca  30240
tagtcctccc tcgagaccca gtggaccagg ccccatcctg tctgggcctg aataggtctg  30300
atttccaaga tttctgaggg gtctcccttg tcactgacgc agatcagatc tctagagttt  30360
gtgcctcatg gtgcacagcc tcactgtgtg atattgggca ggtcacactg ctgctctggt  30420
tatgcaccaa gacacctcag ttgtgcactg tcacaaggag atgatcacac ttacttcatt  30480
cctctaccct caggattagt aagaaccaaa gagctacctg cacgcatttc ctctaatcct  30540
cgcagcagcc tgcaaagcag aactaccatt gcttagtccc atttgacaga tgaggaaact  30600
gaggtggagt gaggtgcagc ctcttgcaag gcacaaaccc tggatttgta tccggggaca  30660
tctagttcca aagcctgtgt tcattcattc tttcttaaac acttcagaat aactttattg  30720
gttaagagta cctaatacat tagcgagata cttcccaata ctagtgtgag ttctatttta  30780
gatgacgtgt taaacggtcc tccgtttcct catctgcgca tgggaataag cctaccatga  30840
gtgttgttgg aaacaccagg tgagagaagg gtccgtgtca tttactgagc tcaggccccg  30900
```

-continued

```
tccttggtgc tttacacaca tggcctcggc aaagcctggc cgtgaccctg tgcaatagct  30960
ggcagggttc tttctgaaaa gggcggaaac tgaggccata agcagagcag ttttccgcag  31020
ccatgtggtt aggacatagc agttaggatt tgaagacact gagccctgtt ttgtgctggc  31080
ctcccatggg gggtttgggt gggacagcag gcaggtaggc tgggaggtct ctccatggtg  31140
ctggtgacag agcctgggtg ggcatctgcc cacagactgg tcccccaagg tggtggagct  31200
gtgtaagaag taccagcagc agaccgtggt agccattgac ctggctggag atgagaccat  31260
cccaggaagc agcctcttgc ctggacatgt ccaggcctac caggtgggtc ctgtgagaag  31320
gaatggagag gctggccctg ggtgagcttg tctcccaccc atagttggga gaaatcacaa  31380
gaaccaggga ccatggtgtc tcctgagttc tgaagtgtgt ctttgttggg tcttaaggct  31440
tggaactgga atccccctgg gccaggcgtg gtggttcatg cctgtgatcc cagcactttg  31500
ggaggcgagg caggaggatt gcttgagcct aggagtttga gaccagccag ggcaacatag  31560
tgagatccat ctctgcaaat acaaaaaaaa gtagtcaggc atggtggtgc atgcctgtag  31620
tcccagctac ttgggaggct gaggtgggag aattgcttga gtccaggaag tcaaagctgc  31680
agtgagctgt gataatgcga ctgcactcca gcctgggtga cagagggaga ccctgtctca  31740
aaaaaaaaaa aaaggaagaa agaagaaaga gaaaagaaag agaaagaaag agaggaagga  31800
aggaaaaaga ggaagggagg gagggaggaa ggaaggaaag aaggaaggaa gggagagaga  31860
aagaaaagcc tccacttggt gttgggagtc ctgtgctgag cctgcttctg gctgtgattt  31920
gctgtgtgaa cctgggcaac actgtgtctt ctctgggcct ctgtttcttc tattgggatg  31980
actgagttgg agccgacatc tcaaaagtcg cttccagcgt gatgatgaat gggcctcctg  32040
tggagggtgc agcatggtgg agaagtcagg gctctggagt cccactgccc gggctcagag  32100
cttggttcca cacttcctgt ctgaccttgg tcacattact tgaatctcct gagcttcagt  32160
ccttcatcat aaaatgggtg ggataatagt tgtgaatatt agataatgta tacaagtcac  32220
ttcatatact acctgacaca tggtaactgg ctaatgagtg acagctacca cttagataag  32280
gacttggagg gtaaaagacc aggtttcccc atgctgttga agcaggcagc atgactagga  32340
tggttcaatc tccacagcat ggtcaaggca ggctgccggg gccctcccgc tagggcaccc  32400
atgacctggc tctccccctt ccaggaggct gtgaagagcg gcattcaccg tactgtccac  32460
gccggggagg tgggctcggc cgaagtagta aaagaggtga gggcctgggc tggccatggg  32520
gtccctcctc actgcctcct cccatacttg gctctattct gcttctctac aggctgtgga  32580
catactcaag acagagcggc tgggacacgg ctaccacacc ctggaagacc aggcccttta  32640
taacaggctg cggcaggaaa acatgcactt cgaggtaagc gggccaggga gtggggagga  32700
accatccccg gctgtcccaa cttcctgtat agagaggcag aaagcagggc gggtcccagg  32760
aactcgaggg gtggccccag gcccagacat gggggggagga atcagcatgg cctggggcca  32820
tccctgccag ccacacacct gctcttccag atctgcccct ggtccagcta cctcactggt  32880
gcctggaagc cggacacgga gcatgcagtc attcggtgag ctctgttccc ctgggcctgt  32940
tcaattttgt tccaggaagg ccaaagaggg aagaaacttt agggattggg catcagccca  33000
tgccgcgtct tttagatatg aaatctcttc gacaccctgg gaagcaggca ttgccgtcct  33060
catcttacaa atgaggaatc cgaggcccag atgtgctgtg gcttgactgg gattacccag  33120
ctgctaacca gcagagctgg ggccctacag ctcatcagct ggagcagaac gctccattac  33180
tctgagggaa gcttccacac ttccaattct cccaactctg ccccctgggc atcgcatagg  33240
aagcaggagt ccctctggcc agcatgttct ctcttcctga cacctggccc ttgggacccc  33300
```

-continued

```
tgggcattcc cctgagcgcc atcttgaagc tttccaccgg aggtctgttc caccctgcct  33360
ggctcccatc ctggagtcta accagggtca aggccctcct tccgtcctgt cgccaagcca  33420
caggagcagt atcaggcctt aggaaaaagc cgccttcccc aagacaagga cagcaagaac  33480
tcagggtgac catggtcagg ccagcactta tccatctgcc aggcatatga gaagggggagg  33540
ggcttcggct ctgatgttct gatgacaagg gggtcttggg gcttgcttag ggacacgtgg  33600
cacctgtgga ggttcttgga ggcatgtggg tataccatgg gctggaaaaa gatccaggag  33660
tcatctgcac agatatggtg gctgaaggag aagcagtggc cccaggaggt ggtggagcaa  33720
gaagggccta ggatagaacc cagaaggaca atggtattta agggaccagc aaaagagaca  33780
agtaggagga aagtcaaaag tgtggtgtca cagaaatcca gggaaaaggt ttcaagaaac  33840
agtcaacagt gtgaaattct gctatgcaag tcgattatgg tcagagctag gaaagatcca  33900
ttagatacaa caagatggtg gtcagggatc gtgccaagaa cagcttccat ggtatgttgg  33960
agtagccagc tcccagtggg actgaggaac aagcagggta gggtgcagag gggaaggctg  34020
gagagggtgg cagccggagg gggatgttgc tttcttggct cccacccccca cgcccccacc  34080
ggctgccatt ctgcctggtt cccatgtctg gcccctctgc tgcctttgcc cagctctggt  34140
cttcaggatg ggctggattc tggactttct ggttacatag acttgaacaa gtcacctaag  34200
ttctgaattt atttccccct ctgcacaagg atcagatctt tcagatctgt ttgaggctgc  34260
tgtgaggatc aaaggcgggt gaacgtcaat gtgttctgac tatttatgta agagtaaaag  34320
gaggctgatt ctctcctcct ccctcttctg caggctcaaa aatgaccagg ctaactactc  34380
gctcaacaca gatgacccgc tcatcttcaa gtccaccctg gacactgatt accagatgac  34440
caaacgggac atgggcttta ctgaagagga gtttaaaagg ctggtgagtg ggtgtgagcc  34500
atactggcct tgactcgggt ttgggagtat ggtatctaca ggtccagtcc ggggcctgga  34560
atctttggag agagggagtg agtctgcctc aacagtccaa gacaagccca acctagacac  34620
tttccacaga gaagacatct ttgtgttgac gtcctgacct aggaccaggt ttttgatcct  34680
ttgcttgggt tgagtgcctt taaagaatcc agtgaaagct gtcaaccctc tccccagaaa  34740
ggtgtgtgca gcagctatga agtcttgcac actctcttca ggttgttctt aaatcccagg  34800
ctgaataagt ccattcctgc acgtgtctgc gaggtgtctc tggcccccta catgccaccc  34860
tgtctctcaa aggtttctcc aacttccttc tcacagccct ttttcatgta atgacaaatt  34920
aagaacacga cctcatggtc tctactctgg cacttgctgc cgtgtgacag tggacaaatc  34980
cttccccctc taagcgtatc tgcccatgtt gagtgaagag gatggactat cactacattg  35040
ctaagagctg ccttctttgt tctctggttc catgttgtct gccattctgg cctttccaga  35100
acatcaatgc ggccaaatct agtttcctcc cagaagatga aaagagggag cttctcgacc  35160
tgctctataa agcctatggg atgccacctt cagcctctgc aggtaggttc ctgtctgggc  35220
ttctgggcag ttgcctgtcc tggccccagt gtggctttct gtgggacttc tagcaagatg  35280
cccttccatt cttgggcagc gcatgaatgt gtgatgactc cctggtttct gggccctggc  35340
tgggagcagc gtctcattag atcggtttgt tttctataaa agttcttgag aggctgttct  35400
aaggggagac tttctgaagc ccagtcccaa aggtctgggc agttggggac acctccatgg  35460
ctgcccaaag ccaagggcag ggagaggggc ccaggctgtt ctgctccttt cttcctatgt  35520
ggtcttggca aggcatcttc ttgccatcat aggaaggagt tcctttctgg ttctggtgtt  35580
ctatgatttt tacaacatcc tgggtactac aagttgcctg atctttttgc ttctctgaac  35640
```

-continued

```
caacgagcag ggcagaacct ctgaagacgc cactcctcca agccttcacc ctgtggagtc  35700

accccaactc tgtggggctg agcaacattt ttacatttat tccttccaag aagaccatga  35760

tctcaatagt cagttactga tgctcctgaa ccctatgtgt ccatttctgc acacacgtat  35820

acctcggcat ggccgcgtca cttctctgat tatgtgccct ggccagggac cagcgccctt  35880

gcacatgggc atggttgaat ctgaaaccct ccttctgtgg caacttgtac tgaaaatctg  35940

gtgctcaata aagaagccca tggctggtgg catgcagcag gtggcatgta atttggtggt  36000

cttgggcggg ccgatgtggg caggatgagc atggagggag ctgggtcagc ctgctcagca  36060

gcagggcctg agcctaaggg tggctgtgaa tgccaggcca gagatcccaa tgctgtgggc  36120

caagaggggt ccagaggctg tcctccttcc agaagaaata aggcttctct ggttgttgct  36180

caaacattcc ctgaactctc agcccctcct aactctaggt tttaaggagt aaagcttcct  36240

tttgggttcc tgaagctggc agttggggtg agagcagatg agatggaaga gggctcatca  36300

gacactggcc ttggagggtg ctggcctctg cagaacgcca gcatcttctc agaatcgtat  36360

gttctagaag cctgggcgaa gtccggctaa ttgtggactt ggggaaaata aggcccaacc  36420

cctgtttttg caaggttaag gagaaataat cttaaaccag tcacacaaat catcggcatt  36480

tatttcctgg gtcctaggtg tcacttatcc tggtggacag ggcagaggtg gtcagatcgt  36540

tttgagccaa aatcccttcc ctaaaaatgg atctgtggag ctccatgagg gaacctcaga  36600

gatgcacaat gacagtttag ctaaaatggc ttaaaaaatg tgaattgatt gtcagctctc  36660

tccatatctg ctgaaaaaag gtttaaaatt tttaaaaagt ttaaaagtgt tttctaaaaa  36720

agggacaagc aggtctggac c                                            36741
```

<210> SEQ ID NO 13
<211> LENGTH: 1345
<212> TYPE: DNA
<213> ORGANISM: Homo sapiens

<400> SEQUENCE: 13

```
acatgtaatc gacaatgccg tcttctgtct cgtggggcat cctcctggca ggcctgtgct     60

gcctggtccc tgtctccctg gctgaggatc cccagggaga tgctgcccag aagacagata    120

catcccacca tgatcaggat cacccaacct tcaacaagat cacccccaac ctggctgagt    180

tcgccttcag cctataccgc cagctggcac accagtccaa cagcaccaat atcttcttct    240

ccccagtgag catcgctaca gcctttgcaa tgctctccct ggggaccaag gctgacactc    300

acgatgaaat cctggagggc ctgaatttca acctcacgga gattccggag gctcagatcc    360

atgaaggctt ccaggaactc ctccgtaccc taaaccagcc agacagccag ctccagctga    420

ccaccggcaa tggcctgttc ctcagcgagg gcctgaagct agtggataag tttttggagg    480

atgttaaaaa gttgtaccac tcagaagcct tcactgtcaa cttcggggat cacgaagagg    540

ccaagaaaca gatcaacgat tacgtggaga agggtactca agggaaaatt gtggatttgg    600

tcaaggagct tgacagagac acagtttttg ctctggtgaa ttacatcttc tttaaaggca    660

aatgggagag acccttttgaa gtcaaggaca ccgaggacga ggacttccac gtggaccagg    720

tgaccaccgt gaaggtccct atgatgaagc gtttaggcat gtttaacatc cagcactgta    780

agaagctgtc cagctgggta ctgctaatga aatacctggg caatgccacc gccatcttct    840

tcctacctga tgaggggaaa ctacagcacc tggaaaatga actcacccac gatatcatca    900

ccaagttcct ggaaaatgaa gacagaaggt ctgccagctt acatttaccc aaactgtcca    960

ttactggaac ctatgatctg aagagcgtcc tgggtcaact gggcatcact aaggtcttca   1020
```

-continued

```
gcaatggggc tgacctctcc ggggtcacag aggaggcacc cctgaagctc tccaaggccg   1080

tgcataaggc tgtgctgacc atcgacgaga aggggactga agctgctggg gccatgtttt   1140

tagaggccat accaatgtct atccccccag aggtcaagtt caacaaaccc tttgtcttct   1200

taatgattga acaaaatacc aagtctcccc tcttcatggg aaaagtggtg aatcccaccc   1260

aaaaataact gcctctcgct cctcaacccc tcccctccat ccctggcccc ctccctggat   1320

gacattaaag aagggttgag ctgga                                          1345
```

<210> SEQ ID NO 14
<211> LENGTH: 625
<212> TYPE: DNA
<213> ORGANISM: Homo sapiens

<400> SEQUENCE: 14

```
acatttgctt ctgacacaac tgtgttcact agcaacctca aacagacacc atggtgcacc     60

tgactcctga ggagaagtct gccgttactg ccctgtgggg caaggtgaac gtggatgaag    120

ttggtggtga ggccctgggc aggctgctgg tggtctaccc ttggacccag aggttctttg    180

agtcctttgg ggatctgtcc actcctgatg ctgttatggg caaccctaag gtgaaggctc    240

atggcaagaa agtgctcggt gcctttagtg atggcctggc tcacctggac aacctcaagg    300

gcacctttgc cacactgagt gagctgcact gtgacaagct gcacgtggat cctgagaact    360

tcaggctcct gggcaacgtg ctggtctgtg tgctggccca tcactttggc aaagaattca    420

ccccaccagt gcaggctgcc tatcagaaag tggtggctgg tgtggctaat gccctggccc    480

acaagtatca ctagctcgct ttcttgctgt ccaatttcta ttaaaggttc ctttgttccc    540

taagtccaac tactaaactg ggggatatta tgaagggcct tgagcatctg gattctgcct    600

aataaaaaac atttattttc attgc                                          625
```

<210> SEQ ID NO 15
<211> LENGTH: 3155
<212> TYPE: DNA
<213> ORGANISM: Homo sapiens

<400> SEQUENCE: 15

```
catgggcacg tccgcgctct gggcgctctg gctgctgctc gcgctgtgct gggcgccccg     60

ggagagcggc gccaccggaa ccgggagaaa agccaaatgt gaaccctccc aattccagtg    120

cacaaatggt cgctgtatta cgctgttgtg gaaatgtgat ggggatgaag actgtgttga    180

cggcagtgat gaaaagaact gtgtaaagaa gacgtgtgct gaatctgact tcgtgtgcaa    240

caatggccag tgtgttccca gccgatggaa gtgtgatgga gatcctgact gcgaagatgg    300

ttcagatgaa agcccagaac agtgccatat gagaacatgc cgcatacatg aaatcagctg    360

tggcgcccat tctactcagt gtatcccagt gtcctggaga tgtgatggtg aaaatgattg    420

tgacagtgga gaagatgaag aaaactgtgg caatataaca tgtagtcccg acgagttcac    480

ctgctccagt ggccgctgca tctccaggaa ctttgtatgc aatggccagg atgactgcag    540

cgatggcagt gatgagctgg actgtgcccc gccaacctgt ggcgcccatg agttccagtg    600

cagcacctcc tcctgcatcc ccatcagctg ggtatgcgac gatgatgcag actgctccga    660

ccaatctgat gagtccctgg agcagtgtgg ccgtcagcca gtcatacaca ccaagtgtcc    720

agccagcgaa atccagtgcg gctctggcga gtgcatccat aagaagtggc gatgtgatgg    780

ggaccctgac tgcaaggatg gcagtgatga ggtcaactgt ccctctcgaa cttgccgacc    840
```

-continued

```
tgaccaattt gaatgtgagg atggcagctg catccatggc agcaggcagt gtaatggtat    900
ccgagactgt gtcgatggtt ccgatgaagt caactgcaaa aatgtcaatc agtgcttggg    960
ccctggaaaa ttcaagtgca gaagtggaga atgcatagat atcagcaaag tatgtaacca   1020
ggagcaggac tgcagggact ggagtgatga gcccctgaaa gagtgtcata taaacgaatg   1080
cttggtaaat aatggtggat gttctcatat ctgcaaagac ctagttatag gctacgagtg   1140
tgactgtgca gctgggtttg aactgataga taggaaaacc tgtggagata ttgatgaatg   1200
ccaaaatcca ggaatctgca gtcaaatttg tatcaactta aaaggcggtt acaagtgtga   1260
atgtagtcgt ggctatcaaa tggatcttgc tactggcgtg tgcaaggcag taggcaaaga   1320
gccaagtctg atcttcacta atcgaagaga catcaggaag attggcttag agaggaaaga   1380
atatatccaa ctagttgaac agctaagaaa cactgtggct ctcgatgctg acattgctgc   1440
ccagaaacta ttctgggccg atctaagcca aaaggctatc ttcagtgcct caattgatga   1500
caaggttggt agacatgtta aaatgatcga caatgtctat aatcctgcag ccattgctgt   1560
tgattgggtg tacaagacca tctactggac tgatgcggct tctaagacta tttcagtagc   1620
taccctagat ggaaccaaga ggaagttcct gtttaactct gacttgcgag agcctgcctc   1680
catagctgtg gacccactgt ctggctttgt ttactggtca gactggggtg aaccagctaa   1740
aatagaaaaa gcaggaatga atggattcga tagacgtcca ctggtgacag cggatatcca   1800
gtggcctaac ggaattacac ttgaccttat aaaaagtcgc ctctattggc ttgattctaa   1860
gttgcacatg ttatccagcg tggacttgaa tggccaagat cgtaggatag tactaaagtc   1920
tctggagttc ctagctcatc ctcttgcact aacaatattt gaggatcgtg tctactggat   1980
agatggggaa aatgaagcag tctatggtgc caataaattc actggatcag agctagccac   2040
tctagtcaac aacctgaatg atgcccaaga catcattgtc tatcatgaac ttgtacagcc   2100
atcaggtaaa aattggtgtg aagaagacat ggagaatgga ggatgtgaat acctatgcct   2160
gccagcacca cagattaatg atcactctcc aaaatatacc tgttcctgtc ccagtgggta   2220
caatgtagag gaaaatggcc gagactgtca aaggatcaat gtgaccacag cagtatcaga   2280
ggtcagtgtt cccccaaaag ggacttctgc cgcatgggcc attcttcctc tcttgctctt   2340
agtgatggca gcagtaggtg gctacttgat gtggcggaat tggcaacaca agaacatgaa   2400
aagcatgaac tttgacaatc ctgtgtactt gaaaaccact gaagaggacc tctccataga   2460
cattggtaga cacagtgctt ctgttggaca cacgtaccca gcaatatcag ttgtaagcac   2520
agatgatgat ctagcttgac ttctgtgaca aatgttgacc tttgaggtct aaacaaataa   2580
tacccccgtc ggaatggaac cgagccagca gctgaagtct ctttttcttc ctctcggctg   2640
gaagaacatc aagatacctt tgcgtggatc aagcttgtgt acttgaccgt ttttatatta   2700
cttttgtaaa tattcttgtc cacattctac ttcagctttg gatgtggtta ccgagtatct   2760
gtaacccttg aatttctaga cagtattgcc acctctggcc aaatatgcac tttccctaga   2820
aagccatatt ccagcagtga aacttgtgct atagtgtata ccacctgtac atacattgta   2880
taggccatct gtaaatatcc cagagaacaa tcactattct taagcacttt gaaaatattt   2940
ctatgtaaat tattgtaaac tttttcaatg gttgggacaa tggcaatagg acaaaacggg   3000
ttactaagat gaaattgcca aaaaaattta taaactaatt ttgtacgtat gaatgatatc   3060
tttgacctca atggaggttt gcaaagactg agtgttcaaa ctactgtaca ttttttttca   3120
agtgctaaaa aattaaacca agcagcttaa ccatg                              3155
```

-continued

<210> SEQ ID NO 16
<211> LENGTH: 1792
<212> TYPE: DNA
<213> ORGANISM: Homo sapiens

<400> SEQUENCE: 16

```
ccttccagag aggaatgtcc caagcctttg agtagggtaa gcatcatggc tggcagcctc     60
acaggattgc ttctacttca ggcagtgtcg tgggcatcag gtgcccgccc ctgcatccct    120
aaaagcttcg gctacagctc ggtggtgtgt gtctgcaatg ccacatactg tgactccttt    180
gaccccccga cctttcctgc ccttggtacc ttcagccgct atgagagtac acgcagtggg    240
cgacggatgg agctgagtat ggggcccatc caggctaatc acacgggcac aggcctgcta    300
ctgaccctgc agccagaaca gaagttccag aaagtgaagg gatttggagg ggccatgaca    360
gatgctgctg ctctcaacat ccttgccctg tcaccccctg cccaaaattt gctacttaaa    420
tcgtacttct ctgaagaagg aatcggatat aacatcatcc gggtacccat ggccagctgt    480
gacttctcca tccgcaccta cacctatgca gacacccctg atgatttcca gttgcacaac    540
ttcagcctcc cagaggaaga taccaagctc aagatacccc tgattcaccg agcactgcag    600
ttggcccagc gtcccgtttc actccttgcc agcccctgga catcacccac ttggctcaag    660
accaatggag cggtgaatgg gaaggggtca ctcaagggac agcccggaga catctaccac    720
cagacctggg ccagatactt tgtgaagttc ctggatgcct atgctgagca caagttacag    780
ttctgggcag tgacagctga aaatgagcct tctgctgggc tgttgagtgg ataccccttc    840
cagtgcctgg gcttcacccc tgaacatcag cgagacttaa ttgcccgtga cctaggtcct    900
accctcgcca acagtactca ccacaatgtc cgcctactca tgctggatga ccaacgcttg    960
ctgctgcccc actgggcaaa ggtggtactg acagacccag aagcagctaa atatgttcat   1020
ggcattgctg tacattggta cctggacttt ctggctccag ccaaagccac cctaggggag   1080
acacaccgcc tgttccccaa caccatgctc tttgcctcag aggcctgtgt gggctccaag   1140
ttctgggagc agagtgtgcg gctaggctcc tgggatcgag ggatgcagta cagccacagc   1200
atcatcacga acctcctgta ccatgtggtc ggctggaccg actggaacct tgccctgaac   1260
cccgaaggag gacccaattg ggtgcgtaac tttgtcgaca gtcccatcat tgtagacatc   1320
accaaggaca cgttttacaa acagcccatg ttctaccacc ttggccattt cagcaagttc   1380
attcctgagg gctcccagag agtggggctg gttgccagtc agaagaacga cctggacgca   1440
gtggcattga tgcatcccga tggctctgct gttgtggtcg tgctaaaccg ctcctctaag   1500
gatgtgcctc ttaccatcaa ggatcctgct gtgggcttcc tggagacaat ctcacctggc   1560
tactccattc acacctacct gtggcgtcgc cagtgatgga gcagatactc aaggaggcac   1620
tgggctcagc ctgggcatta aagggacaga gtcagctcac acgctgtctg tgactaaaga   1680
gggcacagca gggccagtgt gagcttacag cgacgtaagc ccaggggcaa tggtttgggt   1740
gactcacttt cccctctagg tggtgccagg ggctggaggc ccctagaaaa ag           1792
```

<210> SEQ ID NO 17
<211> LENGTH: 56737
<212> TYPE: DNA
<213> ORGANISM: Homo sapiens

<400> SEQUENCE: 17

```
gaattctcgt aaaactcttc atggcagtag ttattattct ctctctctct ctttttcttt     60
tttcttgaga caggatattt ctctgttgcc caggctggag tgcagtggca cagtcttggc    120
```

-continued

```
tcactgcagc ctggacctcc tgggctcaag ccatcctccc acctcagcct cccaagtagc    180
tggggctaca ggcacatggc caccaggcca gataattttt catttttgta gagactgagt    240
ctcaccatgt tacccaggtt tattattctc attttttaga tgaagagact gaggtccaga    300
gaagctcaat gacttgccta gttttacaaa tctcctgcca tcacataccc ctcagcgtcc    360
ttaataagag ggaggccacc aactatgtgc tgggcactgt ggtggatgct ggagctatag    420
ggttgagtat ataagaaatg gtgttgctgg agcaactgtt gcttgcttac ctgacctatc    480
tgagaattaa ttagcagggg aacatatttt tgttttcaga ttcaatataa gaacttgtgt    540
gggcaaaaat aaagatcagt agtaataaca gtagttccca tttgctgact gtactgtcct    600
aagtgcatat atatatacat acacacacgc atacctatac tcctctaata ctcaaaatga    660
tcctgtttat gtattgttaa tatgctcatt ttatttttaa atttttattt atttttattt    720
ttatttattt ttgagacgga gtctcattct gtcgcggagg ctgaagtgca gtggtgcgat    780
ctcagctcag tgcgacctcc gcctcccggg ttcaagtgat tctcctgcct cagctccgga    840
ctagctggga ttacaggcgc ccgcctccac gcccagctaa tttttgtatt tttagtagag    900
atggggtttc gccatgttgg ccaggctggt ctcgtactcc tgaccttgag tgatccacct    960
gcctcggcct cccaaagtgc tgggattaca ggcatgagcc accgcgccgg gctaatatgc   1020
tcattttagt gaggcaaaaa tagaggctca gagtctgatt tgtacaaaac tacagagcag   1080
ttaagtgtcc tctcagatgt gtaccctgat ctgggtgact ctaggactct aggtctcaac   1140
tgttacaacc agttaagggt ttggggaagc actgggccaa gagtcaggaa aatggaagcc   1200
acaggtagtg caaggtcttg ggaatgggac gtctggtcca aggattcacg cgatgactgg   1260
aacccgaaga gccggggccc ggtttacggc cgccatgaag caacgcgcgc cggtaggttt   1320
gggaatcagg gagccctctg aataggagac tgagttggga gggaaagggg cttcgctggg   1380
ggagcctcgg cttcttctgg gagaaaattc ccacggctac ctagtgagcc tgcaaactgg   1440
taggcgccgg cgtaggcgcg cgggcggggc cgggggcggg gcctgcgggg cgtggcgggg   1500
cgggcagagg gcggggcctg cttctcctca gcttcaggcg gctgcgacga gccctcaggc   1560
gaacctctcg gctttcccgc gcggcgccgc ctcttgctgc gcctccgcct cctcctctgc   1620
tccgccaccg gcttcctcct cctgagcagt cagcccgcgc gccggccggc tccgttatgg   1680
cgacccgcag ccctggcgtc gtggtgagca gctcggcctg ccggccctgg ccggttcagg   1740
cccacgcggc aggtggcggc cggccctga ggcgcgggat ccgcagtgcg ggctcgggcg   1800
gccgggccca gggaaccccg caggcggggg cggccagttt cccgggttcg gctttacgtc   1860
acgcgagggc ggcagggagg acggaatggc ggggtttggg gtgggtccct cctcggggga   1920
gccctgggaa aagaggactg cgtgtgggaa gagaaggtgg aaatggcgtt ttggttgaca   1980
tgtgccgcct gcgagcgtgc tgcggggagg ggccgagggc agattcggga atgatggcgc   2040
ggggtggggg cgtgggggct ttctcgggag aggcccttcc ctggaagttt ggggtgcgat   2100
ggtgaggttc tcggggcacc tctggagggg cctcggcacg gaaagcgacc acctgggagg   2160
gcgtgtgggg accaggtttt gcctttagtt ttgcacacac tgtagttcat ctttatggag   2220
atgctcatgg cctcattgaa gccccactac agctctggta gcggtaacca tgcgtatttg   2280
acacacgaag gaactaggga aaaggcatta ggtcatttca agccgaaatt cacatgtgct   2340
agaatccaga ttccatgctg accgatgccc caggatatag aaaatgagaa tctggtcctt   2400
accttcaaga acattcttaa ccgtaatcag cctctggtat cttagctcca ccctcactgg   2460
ttttttcttg tttgttgaac cggccaagct gctggcctcc ctcctcaacc gttctgatca   2520
```

-continued

```
tgcttgctaa aatagtcaaa accccggcca gttaaatatg ctttagcctg ctttattatg   2580
attatttttg ttgttttggc aatgacctgg ttacctgttg tttctcccac taaaactttt   2640
taagggcagg aatcaccgcc gtaactctag cacttagcac agtacttggc ttgtaagagg   2700
tcctcgatga tggtttgttg aatgaataca ttaaataatt aaccacttga accctaagaa   2760
agaagcgatt ctatttcata ttaggcattg taatgactta aggtaaagag cagtgctatt   2820
aacggagtct aactgggaat ccagcttgtt tgggctattt actagttgtg tggctgtggg   2880
caacttactt cacctctctg ggcttaagtc attttatgta tatctgaggt gctggctacc   2940
tcttggagtt attgagagga ttataagaca gtctatgtga atcagcaacc cttgcatggc   3000
ccctggcggg gaacagtaat aatagccatc atcatgttta cttacatagt cctaattagt   3060
cttcaaaaca gccctgtagc aatggtatga ttattaccat tttacagatg aggaaccttt   3120
gaagcctcag agaggctaac agacataccc taggtcatac agttattaag agaaggagct   3180
ctgtctcgaa cctagctctc tctctctcga gtaataccag ttaaaaaata ggctacaaat   3240
aggtactcaa aaaaatggta gtggctgttg tttttattca gttgctgagg aaaaaatgtt   3300
gatttttcat ctctaaacat caacttactt aattctgcca atttcttttt tttgagacag   3360
ggtctcactc tgtcacctag gatggagtgc agtggcacaa tcactgctca ctgcagcctc   3420
gacttcccgg gctcgggtga ttctccccag gctcagggga ttctcccact tcagcctccc   3480
aagtagctgg gactacaggt gcgcaccacc atccctggct aatatttgta ctttatttta   3540
tttatttatt tatttatttt ttgagatgga gtttcgctct tgttgcccgg gctggagtac   3600
agtggcatga tctcggctca gtgcaacctc tgcctcccgg gttcaagcga ttctcctacc   3660
tcatccccct gagtagctgg gattacaggc gcctgccacc atgcctggct aatttttttgt   3720
atttttaata gagacgaggt ttcaccatgt tggccaggct actctcgaac tcctgatctc   3780
aggtgatcca cccgccttgg cctcccaaag tgctgggatt acaggcgtga gccactgcgc   3840
ccggcctaat atttgtattt tttgtagaga tggtgttttg ccatgttgtc caggctggtc   3900
ttgaactcct gagctcaagc gatctgcccg cctctgcttc ccaaagtgct gggattacag   3960
gcatgagcca ccgtgcctgg cctaggtaga cgcttttagc tttggggtgt gatgcctgcc   4020
ccagtatata gtgaatttaa ttattgctag agctggctgt ttgttagttt tctttgaaca   4080
taagatactc attgttttta gtttgcaaat ccctcttcct ttttaaaaaa tttctttccc   4140
ttaaattgtt tgcatgttag caataacaaa tgcttaaatg gtgctatgtg ctagatactc   4200
ttctaagccc tgttatgtat attaactaat tttttaaatt acacaaatca gagaggttaa   4260
gtaacttgcc caagattacc caacaatact aggatttgaa cctaagtttg tctcacccca   4320
gattctgctc ttaatctcta aacttttaag ttagtagtga caatagtagg tatttattga   4380
atacttaact atgttttagg cgttgaagta aatattttgc aggcattatc taatgtaaac   4440
accctaaagt tacataacag gtacccttta ggtaaataaa cactagtatg accttggagg   4500
cacagatagt tgaagtaact tgcccaatat cacttacatg aaattggccc tcaaatgtgt   4560
ctgatacaac ccatgctgct tgtaactatc gttttaaact gccagggtaa acttggacac   4620
acttgagcta agaaaaagct tttagatttt tgcaaattaa tgtgaaagat atgctttatg   4680
tggatataat atcttctaaa tttcggggat ggtagtccta gaaatgtaat cctgccctag   4740
ccgagcttac cctgccaata attttttaca gaattggtaa aacggagcac cttttttttg   4800
tccttggcca cactgttatc aacagggtgt agattgacat caatctgtag gtgtaaacca   4860
```

-continued

```
gaattactct ttgtgaccac caggaaatag agcagttcag ttcaggggtt tctttctgtg   4920
aatttagcac tgtgacctgc atactacaag tctactttgt tttctatcca ttgtttgtat   4980
ctgggtattg caaaaggtag gaaaaggacc aaccagatca gcagagaaga gttgccttgg   5040
agttttcttt tagttttctg cagttcatta gatagtaact aggccatgtc attttactcc   5100
cttgtagtga agatatgttg aagttgtact ggtatactct tctacctttc tgtaatttta   5160
tattgtgtag acttgataaa atttatgtgt caatcaccac cattaatatc aatattgagc   5220
ctcaattctt atttttctgc ccagtggctg ccaaattact aacatttaca ataattcact   5280
actactaaga taatctacta gttcgatcac atacttcaaa ttgttatgga actactgtct   5340
tcagcattgt gcttctgata actgataagt ataatttttt ttttgtccag agtgaacatg   5400
tctattcttc cactgtacac actaataaaa ggaaaaattg taatattggg taaattcatg   5460
tccttacaca tgtagtagtt atgagcccat gtccctagaa tgagtaataa tttatccctc   5520
ccttggttga atagtcaaga atgctgattt taattcttct aacagcttta tccctcagaa   5580
gggaaggcaa gcaagttata tatgtagttt atttgtaaga ctgatatgaa attggaagat   5640
gaatctacta ttagctttaa ttatttttac atttaggaat attgcatcag taactcataa   5700
ttttggtttt ctgttatcct gagttaacac aaattatcca aggagatggc ggatcatctg   5760
ctttgaggtg tttttttttg agaattttaa tgtatctgaa tataaaaggt aaaaatatgc   5820
caactagcaa tttctgccca ttccagaagt ttggaaatat tactcattac taggaattaa   5880
ataaaatatg gtttatctat tgttatacct cttttaattc acatagctca tttttatctt   5940
ttatttttgt ttgttttttt tgagatggag tcttgctctg tcaccaggca ggagtgcagt   6000
gatgcaaatc tcggctcact ctagccaccg actccctggt tcaagcgatt ctcctgcctg   6060
agccttctga gtagctggga ttacaggcag gcaccaccac gcccagctaa tttttgtaga   6120
gacaggattt caccgtgttg gccaggatgg tctccatctc ctgacctcat gatctgcctg   6180
cttcggcctc ccaaagtgct gggattacag gtgggagcca ctacgcctgg cccacatagc   6240
tcatttttag actcacttcc attaagtctt gtttggaccc acgaacattg tctttttttt   6300
tttaagatgg agtttcactt ttgttgccca gactgtagtg caatggtgca atctcagctc   6360
actgcaatct ctgcctcctg ggttctagca attctcctgc ctcagcctcc cgagtagctg   6420
gaattacagg cgcccgccac cacgcccagc taatttttgt gtttttagta gagacggggt   6480
ttcaccatgt tgggcaggcc aggggtgatc cgcccacctc agcctcccaa agtgctggga   6540
ttacaggtgt gagccaccgc atctggccaa catgtctttt tttttttttt ccttttttaac  6600
cacaaagaga cttaagcagt ccttgtcaca gatgatgaat tgatgttgca agtattgtct   6660
tagcttggat taattttctt gcttactgta attttagata atatagcttt gtaattagag   6720
attttatgtg taaaccacaa aaatgtttac atgaaggcca ttattacaga tgtgacgtgc   6780
ataattatta gtaatttgta tgtttacatg ggtcagtctg gcaaaaaatt atgaagtttt   6840
aaaaattaaa aaaaattata atgccagttt tactggaaag taaaattatt tcagtaatcg   6900
attatagcaa aagtattgat tttcattcca gacaaaagtc agaatgaaag gtaatttctc   6960
aatactcttt cagattaata aaagtacctg tagcgatttt tatcattcac aagtatatca   7020
caagtaagtt agaatttgag aactgtgttc tagatctctg aggagatgca gtcagatttc   7080
tgaactgtct cagcaaatgg taagtaactt agagctagta attaataacc tgtcctttga   7140
tttctgattc agccaagaat ggccatattt gggaaaggca gatctggaga gtaaccacgt   7200
tttcattcat ttaccacttc taggcccctc cagagctctc agatattttg gggttgagcc   7260
```

-continued

```
cttccccaaa gccatacagg accttttttt tgtgatctgt tctagccatt tttatgttgg   7320
gtgcttgtta tggactgagc atttatgtcc tcccacaccc cccccatacc tttttgaag   7380
tcctaacccc cagtgtgatg gtatttggag acagggcctt tggaaggtaa ttacagttag   7440
aagaagtcgg gagggttggg cccaggtctg attggattag tgcccttata tgaaaagaca   7500
ccaggacggg cgcagtggct cacacctgta atcccagcac tttgggaggc caaggtgggt   7560
ggatcacgag gtcaggagtt tgagaccagc ctggccaatg tagtgaaaca ccatctctac   7620
taaaaataca aaaattagct gggtgtggta gcgggctcct gtcatccaag ctactcggga   7680
gggtgaggca tgagaatcac ttgaacccgg gagttggagg ttgcagtgag cccagattgt   7740
gccactgtac tccagcctgg gtgacagagt gagactctgt ctcaaaaaag aaaaaaaaaa   7800
aaaaagagac accagagagc ttgttagaag aggtcatgtg agcacacagt tagaagacct   7860
tcaagccaaa gaagaggcct gagattgaaa cctaccttgc aggtacctta attttggact   7920
tcccagcctc caaaactgtg agaaataagt ttctgttaag tcactcagtc tgtggtattt   7980
tgttatggca gcctgagcag gtagttgttc tttcagaagg tgttgataat aaccacatgc   8040
aacaccaagt cacaaataat aaaacagatg taacttatat tcatacagaa agttgggcac   8100
tgccattgcc ttgttggttt acacggctgt gctagttcag tagcagaaag gtgctggtct   8160
cctttactca gtttacaatc taggcagtag aatgtaatca ctgctttaaa cttgatactg   8220
cttagggaga gaatcattgg tgctgggtaa ctttgggttc taggtttact ttttgtgtat   8280
atataactgt ttttggtaaa tcacaagttt ctgggcttgt cgaattagat tttgttacag   8340
attatgagct ttattatgct atacagttag ttgtatgtat atatgccttt cccactagat   8400
tttaagcttt tttttttttt ttttttttgt gacggagtct tgctcttgtc gcccaggctg   8460
aagtggagtg cagtggcaca atctcggctc actgcagcct ccacctccta ggttcaagcg   8520
attctcctgc ctcggcctcc caagtaactg ggactacagg cacgtgccac cacacccggc   8580
taatttttgt atttttgta gagacagggt ttcgccatgt tggctaggct ggtcttgaac   8640
ttctggcctc aggtgatcca cccgcctcag cctcccaaag tgctgggatt tacaggcatg   8700
agccaccacg cccagctata gctctttaag ggttgtaaat ttataatcat tcttttactc   8760
tcctgcaaat tctgttgcac actgccttaa tcaaggtaga tgctgaatgc atttttgtat   8820
aattgaatat gttgcaatcc ccaactctct ccaactgttc ctgtcaaagc agccactgga   8880
ttgttaacta atccatatta gatggggtta attaatatca gatgggacaa gtaagggcta   8940
ataagattat aggccaccaa gtagatttct gtctagctct tatagagatt gagtttattg   9000
gacctgtttg ataggaagtt ttggtgtttg ggatgattaa aactgaagtt cctatttatt   9060
gaattatacc tatttatatt atttcatatc agtggtccac atgcaagtga ggcttctgag   9120
acagagtttg agttctctct tcaactacca taacacttaa cctgtatctt tttttttttt   9180
ttttttttta gacaggagtc tcgctctgtc actcaggctg gagtgtagtg gtatgatctc   9240
ggctcactgt aacctctgcc tcctggattc aagcagttct ccatgtctca gcctccctag   9300
tagctgggat tacaggcctg tgccaccatg cctggctaat tttttttttg tatttttagt   9360
agagacgggg ttttaccacg ttggccaggc tggtctcgaa ctcttgacct cgagcgatca   9420
acttgccttg gcctcccaaa gtgctgggat tacaggcatg agccacagcg cccagccgtc   9480
ttttttttta aatagcaatt taacactgtt cacagttact catgtacatg tcatgccatc   9540
tattacactg taagttctgt gagggtagct gtatcaaatt tatctaactc tctctagtat   9600
```

-continued

```
gcatgacata gtaagtattc aataaatatt tgcatattag tgataaggat acaggttctg   9660
aatagtgggt ccttaccatt taagaattag tatttgatgg ccgggcgggg tggctcacgc   9720
ctgtaatccc agcactttgg gaggctgagg cgggcggatc atgagatcag gagatcgaga   9780
ccatcctggc taacatggtg aaatcccgtc tttacaaaaa aaatacaaaa gaattaacca   9840
agtgtggtgg tgggtgcctg tagtcccagc tactgctttg tgaggctgag gcaggcagat   9900
cacctgaggt gggaaattca agaccagcct gaccaacatg gagaaacccc atctctacta   9960
aaaatacaaa attagccggg cgtggtggcg catgtctgta atcccagcta ctcgggaggc  10020
tgaggcagga gaatggcgtg aacccgggag gcggagcttg cagtgagcca ggatcgcgcc  10080
actgcactcc agcctgggcg acagagcgag actccgtctc aaaaaaaaaa aaaaaaaaaa  10140
aattagtatt tgatatttga tcattaaata tgaattaaga ggacttagac tttttgttaa  10200
atgtcaagct gggaaaagtt gtcatttaaa tgaattgcct cttatttaat ttcgtctgat  10260
gatacatttt gtttttattt tgtaaaaaat tattttttttt ctttttggag acagggtctt  10320
gctctgttgc ccaggctggt cacaaactcc tgacctcaag caatcctcct gccttagcct  10380
cccaaaatgc tgggattaca ggcgtgacga cctcgcccgg ccttgtatta tgatacattt  10440
tgaacaacta caagtagact tggtataatg aacctgcacg tacccattgc caagttctga  10500
caactgtctg tctatagcca attatgcatt tcttaaatta gaaccccccc aatataccca  10560
aatatatata tatgtgtgca tatatatagt aagttgtaac aaagttgtga attcatacct  10620
gaagtatctc aagtgatgca agttttatga atttttgttt atgccttttg ggaagagttg  10680
tattgacaaa ttttttatgc ttaaagtaaa ccataaatca aaaaaataaa atctaggatg  10740
caataaaaca aaacaacttc ttgacataag tatggtatgt aaatctgttt tgattggaaa  10800
tcaatttgtt atattgccag aattcctgtt ttagaataca tctctgctga tctgtctgta  10860
ttcttagact gcatatctgg gatgaactct gggcagaatt cacatgggct tcctttgaaa  10920
taaacaagac ttttcaaatt cttagtcgat ctgcagaacc tgtagccagg cactgaacca  10980
ttttgataga tgcagtaatc gttgcaagtg tatatttcaa gggagttctg gctgggtcct  11040
agtttatgct tgtggcagaa gcagtgagta actgggagga agttggtgag taagcttcaa  11100
ggaagaagtc atttttagta ctctggatct tcctgatttt aaagcactac aaaatggtgc  11160
attttcattc ttgtcaagtg ataacagata tattctgatg agcctgaaat gaatatatat  11220
tgtatcattt ttataatatc tagcaaggtt tgtattttcc tagaacttga actaaatttc  11280
agttcataaa atttataaaa tacttagttg ttgtaaaata tttttggaat gttcacatag  11340
gtgacacaca aatgtcccat tttcattctt tctatagtaa atatgttctg atatgtgaag  11400
gtttagcaga tgcatcagca tttaatccta gaggatctgg cataatcttt tcccccaaga  11460
atagaaattt tttctgctta tgaaagtagt acatgtttct ttaaaaacaa atcaatattg  11520
acttctgcct gctgtatagc actatgcctc cacctggcca tgaccagggg catgtcctgg  11580
tccacctacc tgaaaatgtt tgcaaccagc ctcctggcca tgtgcacagg ggctgaagtt  11640
gtcccacagg tattacgggc caacctgaca atacatgaag ttccaccaaa gtctgagaac  11700
tcagaactga gctttgggga ctgaaagaca gcacaaacct caaatttctc agcactggaa  11760
acctcaaaat ataactgaat tccataaata agattttaag tcttaaatat gtatttttaa  11820
atgtattaaa agtcaagctg cttgtattta agcacctaat acaatgctta ggttgtaaaa  11880
ggagatgctc aataggtact aactgatata ttgagattta attatggttt gaccaatatt  11940
tattggaaac cgccaaagct taaatcatca gcttcttgaa tgtgatttga aaggtaattt  12000
```

-continued

```
agtattgaat agcatgtgag ctagagtatt tcattctttc tggtttattt cttcaaatag  12060
actttgaata taatggtgaa tgggtattat aaattaacta ataaaaatga cattgaaaat  12120
gaaaaaatat atatattaaa gtgtagaaag tgaccaggcg tggtggctca cacctgtaat  12180
ccaagcacct tgggaggctg aggcaggagg atctcttgat cccaggagtt caagaccagc  12240
ctgggcaaca tagcgagact tcgtctctaa aaaaaaaaaa gagagagaaa aaaatttttt  12300
ttatttaaaa aaagtgtaga aagtgtcaag accccacttc ttaccattat ttggtatatt  12360
tctctatacc cacccaccct tcctccttac tccctccctc ccttcccaat ctttttatct  12420
ttttgtattc tgatttttttg tttgtatatt ttgctttaat ttaatgtatc ctttaaaaat  12480
ttcccataca ttttatatgt atatataaaa acgcatgctg ccaaagataa tttataagaa  12540
agaccattga atttttttaa aagtgatata tattcattga aaaaaattta gaatatatag  12600
caaagcaata aagaactaaa taaaattgct gtaactcctc tttcaaagat aagtgctttt  12660
atgattttgt tgtatttttt tctgtatata ggtacatata tagtatttat aaagctgtac  12720
tcatagtaca ttttcacatc acaggtacca tatcagtgtt attaaatatt ttgtatgcca  12780
ggggctagac ataccaagac aaccaatatg tggttctact taaataatat tagagtatct  12840
tttatgatga cacttcatga gttgactata ataatcttag acttctaaga gtttgggttt  12900
tcaaaagatc acttagcttt tttgggtgat ttttccccct tactgtgaga tgagagaggc  12960
tgtttggatt tgggattggg gtagcgggga cagcaacttt tcttttcttt ttcttttta  13020
ttttgaggta gggtattgct gtgtcaccca ggctggagtg cagtggtgtg atctcggctc  13080
actgcaacct ccacctcccg ggctcaggtg atcctcctgc ttcagcctcc cagtaactgg  13140
gactacaggc gcgtgccaca tgcctggcta attttgtatt tttagtagag atggggtttc  13200
accatgttgg ccaggctggt ctctaactcc tgacctcagg tgatacgccc acctgggcct  13260
cccaaaatac tgggattaca ggcatgagcc gctgcatcag ccagcagttt ttcttgtggt  13320
tttttttgtt tgttttgttt tgttttgttt ttgagatagg gtcttactct gttgtccacg  13380
ctggagtgct gtggtatgat cgtagctcac tgcagcctca aactcctggg ctcaagtgat  13440
tccttctgcc tccgcctccc gagtagctgg gactacaggt atgcaccacc atacctggca  13500
aatttttaca aagtttttttg tagggacggg gtcttgctac attccccatg tcggtcttga  13560
actcctggcc tcaagcaact ctcctgtctc agcctcccaa agcactggga ttacaagtgt  13620
gagccaccac accatgccag tttttcctgt tcagtgtgat attttatctt gttagactac  13680
agtgtgttaa aacttgtttt actaaatttt caaacatact caaaagtgga gagaatagta  13740
taatgaatac ccgtatgttc atcacccatg tttagaatat tattaaatat aaagattttg  13800
ctgcgtttgt cttagctctt taaaattttt ctttttctct ttgtgaccta aaggaaattc  13860
catatcttat cactttactt ctacattctt gactaagatg actaagacat atagttacat  13920
ggttttttgt tttgtttttg ttttttaaag acgaaatctc gctcttgtcc cccaggctgg  13980
agtgcaatgg tgccatctca gctcagtgca acctctgcct tctgggtaca agcgattctc  14040
ctgcctcagc ctcccaagta gctgggatta caggctcctg ccaccacgcc tggctaattt  14100
ttgtattttt agtagagacg gcggggggag gtttcaccat gttgacaagg ctggtctgga  14160
actcctgacc tcaggtgatc cacccgcctc ggcctcccaa agtgctggga ttacaggcgt  14220
gagccaccgc gcccagcctg tttttttgtt tgtgtgtttt gtttttttttg agacagagtc  14280
ttgctctgtt tcccaggctg gagtgaagtg gtgccatctc agctcagaga cagagtcttg  14340
```

-continued

```
ctctgtttcc caggctggag tgaagtggtg ccatcttggc tcactgcaac cttcacctcc  14400
caggttcaag tgattctcct gcctcagcct cccaagtagc tgggactaca ggcatgtgtc  14460
accacacccg gctaattttt ttgtattttt agtagagacg ggatttcacc gtgttgccca  14520
ggctggtctc gaactcctga gctcaggcag tctgcctgcc tcagcctccc aaagtgctgg  14580
gattacacgt gtgaaccaac ccgcccggcc tgttgttttc ttacataatt cattatcata  14640
cctacaaagt taacagttac taatatcatc ttacacctaa atttctctga tagactaagg  14700
ttatttttta acatcttaat ccaatcaaat gtttgtatcc tgtaatgctc tcattgaaac  14760
agctatattt ctttttcaga ttagtgatga tgaaccaggt tatgaccttg atttattttg  14820
catacctaat cattatgctg aggatttgga aagggtgttt attcctcatg gactaattat  14880
ggacaggtaa gtaagatctt aaaatgaggt tttttacttt ttcttgtgtt aatttcaaac  14940
atcagcagct gttctgagta cttgctattt gaacataaac taggccaact tattaaataa  15000
ctgatgcttt ctaaaatctt ctttattaaa aataaaagag gagggcctta ctaattactt  15060
agtatcagtt gtggtatagt gggactctgt agggaccaga acaaagtaaa cattgaaggg  15120
agatggaaga aggaactcta gccagagtct tgcatttctc agtcctaaac agggtaatgg  15180
actggggctg aatcacatga aggcaaggtc agatttttat tattatgcac atctagcttg  15240
aaaattttct gttaagtcaa ttacagtgaa aaaccttacc tggtattgaa tgcttgcatt  15300
gtatgtctgg ctattctgtg tttttatttt aaaattataa tatcaaaata tttgtgttat  15360
aaaatattct aactatggag gccataaaca agaagactaa agttctctcc tttcagcctt  15420
ctgtacacat ttcttctcaa gcactggcct atgcatgtat actatatgca aaagtacata  15480
tatacattta tattttaacg tatgagtata gttttaaatg ttattggaca cttttaatat  15540
tagtgtgtct agagctatct aatatatttt aaaggttgca tagcattctg tcttatggag  15600
ataccataac tgatttaacc agtccactat tgatagacac tattttgttc ttaccgactg  15660
tactagaaga aacattcttt tacatgtttg gtacttgttc agctttattc aagtggaatt  15720
tctgggtcaa ggggaaagag tttattgaat attttggtat tgccaaattt tcctctaaga  15780
agttgaatca ttttatactc ctgatgttat atgagagtac ctttctcttc acaatttgtc  15840
tctttttttt ttttttttga gacaaggtct ctgttgccca ggctggggtg cagtgcagca  15900
gaatgatcac agttcactgc agtctcaacc tcctgggttc aagcgatcct tccacctcag  15960
cctcctgagt agctgggact ataggtgtgc gccaccactc ccagctaata tttttatttt  16020
gtagaaacag ggttcgccat gttacccagc ctcccaaagt gctgggatta caggcatgag  16080
ccactggccc agtttctaca gtctctctta atattgtata ttatccagaa aatttcattt  16140
aatcagaacc tgccagtctg ataggtgaaa atggtatctt gtttttattt gcatttaaaa  16200
aaaattatga tagtggtatg cttggttttt ttgaaggtat caaatttttt accttatgaa  16260
acatgagggc aaaggatgtg atacgtggaa gatttaaaaa aaatttttaa tgcatttttt  16320
tgagacaagg tcttgctcta ttgtccaggc tggagtgcag tggcacaatc acagttcact  16380
ccagcctcaa catcctgcac taaagtgatt ttcccacctc acctctcaag tagctgggac  16440
tacaggtaca tgctaccatg cctggctaat tttttttttt ttgcaggcat ggggtctcac  16500
tatattgccc aggttggtgt ggaagtttaa tgactaagag gtgtttgtta taaagtttaa  16560
tgtatgaaac tttctattaa attcctgatt ttatttctgt aggactgaac gtcttgctcg  16620
agatgtgatg aaggagatgg gaggccatca cattgtagcc ctctgtgtgc tcaagggggg  16680
ctataaattc tttgctgacc tgctggatta catcaaagca ctgaatagaa atagtgatag  16740
```

-continued

```
atccattcct atgactgtag attttatcag actgaagagc tattgtgtga gtatatttaa  16800
tatatgattc tttttagtgg caacagtagg ttttcttata ttttctttga atctctgcaa  16860
accatacttg ctttcatttc acttggttac agtgagattt ttctaacata ttcactagta  16920
ctttacatca aagccaatac tgttttttta aaactagtca ccttggagga tatatactta  16980
ttttacaggt gtgtgtggtt ttttaaataa actcctttta ggaattgctg ttgggacttg  17040
ggatactttt ttcactatac atactggtga cagataccct ctcttgagct acatcggttt  17100
gtggggagtc aaaagtcctt tggagctagg tttgacaaat aaggtgggtt aacacttgtt  17160
tcctagaaag cacatggaga gctagagtat tggcgaattg aagaaatccc cctttttttt  17220
taacacactt aagaaagggg actgcaggta tactcaagag agtaagtcgc accagaaacc  17280
acttttgatc cacagtctgc ctgtgtcaca caattgaaat gcatcacaac attgacactg  17340
tggatgaaac aaaatcagtg tgaattttag tagtgaattt cattcataat ttgatcgtgc  17400
aaacgtttga tttttattac tttagactat tgtttctgat tttatgttgg gttggtattt  17460
cctgtgagtt actgttttac ctttaaaata ggaatttttc atactcttca aagattagaa  17520
caaatgtcca gtttttgctg tttcatgaat gagtcctgtc catctttgta gaaactcgcc  17580
ttatgttcac atttttattg agaataagac cacttatcta catttaacta tcaacctcat  17640
cctctccatt aatcatctat tttagtgacc caagtttttg accttttcca tgtttacatc  17700
aatcctgtag gtgattgggc agccatttaa gtattattat agacattttc actatcccat  17760
taaaaccctt tatgcccata catcataaca ctacttccta cccataagct ccttttaact  17820
tgttaaagtc ttgcttgaat taaagacttg tttaaacaca aaatttagac ttttactcaa  17880
caaaagtgat tgattgattg attgattgat tgatggttta cagtaggact tcattctagt  17940
cattatagct gctggcagta taactggcca gcctttaata cattgctgct tagagtcaaa  18000
gcatgtactt tagagttggt atgatttatc tttttggtct tctatagcct ccttccccat  18060
ccccatcagt cttaatcagt cttgttacgt tatgactaat ctttggggat tgtgcagaat  18120
gttattttag ataagcaaaa acgagcaaaa taggggagtt taactttaat attttctttt  18180
aaaaagcatt tcatgttata agatcaattc tgagtggtag aaaatgcttt gacattttat  18240
ttccattttc tacttttagt ttttttccta tttgtttaag atcttagagg attattaagc  18300
tgaactcctc aactgataaa aagcatgaca tcttaaacat aagcaaagca tatttttagg  18360
ttaattttca catagaaaac agtttatttt atgtgaaatt ctatgtagat atactatttt  18420
tttggtattt attgatatgt ttattttatt ttattttatt ttattttatt ttattttatt  18480
ttatttattt attttttttt ttgagacaga gtctcactct gttgcccagg ctggagtgca  18540
gtggcatgat cgtagctcac tgcaacctcc actcccgggt tcaagcaatt cttctgtctc  18600
agcctcccga gtagctggga ctacaggtgc ctgccactat gcccggctaa tttttgtgtt  18660
tttagtagag atggggtttc accttgttgg tcaggctggt ctcgaacccc tgacctcagg  18720
tgatccaccc acctcagcct cccaaagtgc tgggattata ggcatgagcc acgtgcccgg  18780
ccgacatgtt aatttttttaa aaaaggcttt actggggtat attttatata atataataat  18840
cacatgtttt aactatacaa ttccaagctt tttagtatat ttatagggct atgcaaggaa  18900
gatatactgt taaacagtag aaattgagaa agctcttctg ataatatctc ttgatttgat  18960
gatggctcat gcctgtaatc tcagtgcttt ggaaggccaa gacagcagaa tcacttgagg  19020
ccaggggttc gagaccagcc tgggcaacac agcaataccc tatctttaca aataataaaa  19080
```

-continued

```
atatctgttg atttgaagta aagttttttt ttaaagacaa ggtctcattc tgtcacccag  19140
gctggaatgc agtagcaaga tcacagctca ctgtggcctt gaccttctgg gctcaagtga  19200
ttctcccact tcggcctccc gagtagctgg gactaacagg tgtgcaccac catggctggc  19260
taattttttt ttatgtttgt agagattggg tcttactgtg ttgcccaggc tgatcccgaa  19320
ctcctgggct caagcagtct tcctgcctca gcctctaaaa ttgctgggat tacaggcttg  19380
agtcaccatg cccagcctga agtagcattt ctaccctgtt taataattca gcagcttgtc  19440
atgtaagata ttcatatatg catataaaca ttaggcagct taatttggta aaactgtaaa  19500
atggaaattt taaattgttt gcagcatcaa taacattgat gtcagtatga tttttacatg  19560
ctgatcttga ccaatttgaa acagtgagtt aaaatctggc tgatccgtac taatcctaaa  19620
gaaatattct atgaactatt aaatgtttcc agaatatata aagaaacatt atgatgtcaa  19680
cacacccatc tatttttttt tggaaataaa aactccattt ttcttattaa agaaaacatg  19740
cttattagaa aacatacggc tgggtgcagt ggcacacatg taattccagt gctttgggag  19800
atcgaggtgg gagaatcact tgaggccagg agtttgagac cagcctagac aacataatga  19860
gaccccctct ctacacaaaa agaattagtt gtgcatggtg gcgtgcacct gtagtcccag  19920
ctacttggga ggcagaggca ggagcatccc ttgagcctag gagtttgaga ctgcaggagt  19980
tcgagactga gtggaatgca gtggaactgc attccagcct gagtgacaga gggagaccct  20040
gtcttaaaaa aataagaaag aaaacacaac tgcagaaaat tataaaggat ttaagtcatt  20100
ccaaatatca ctgccacttt ttatttagaa tattctaaag aattctctct ctgtgtacac  20160
acacacatat gcgtactctt aatccaagta gcttggtagg attttattta cctagtgcct  20220
agatgggaaa ttgcctgggg attccaaata cctatttcat taaattaaag atgtcactga  20280
ttttaagact taacactatt tttcatactg ccaagaaaga aaacactacc agttataaat  20340
gtaaattgcc atcaattgta atacatcaat tttagagcta ttattaataa aatgtgaatg  20400
tgcatcttag agcaatgaaa tatagtacta tatatttgat gaccttttct gccctgtgat  20460
attcagaaag tgaaagttaa atatgggctg agcatggtgg ctcacacctg taatcccagt  20520
actttgggaa gtcaagacgg gaggctggct tgaacccagg agttcaagac cagcctaggc  20580
aatgtagcga gacgccatct caaaatatta aaaataagta aataagtaaa taaaaagaag  20640
gttaagtata caaatgtatt tcctttgttg tgaatttatt tcaattttat agtgattttt  20700
tttttttgag acgaagtctc actcttgtcc cccaggctgg agtgcgatgg cgtgatctca  20760
gctcactgca acctctgcct cccaggttca agctatactc ctgccttggc cccccgagta  20820
gctgggatta caggcgcctg ctaccatgcc tggctaattt ttgtattttt agttgagatg  20880
gggtttcacc atgttggcca ggctggtcta gaactcttga cctctggtga tccacccgcc  20940
tcggactccc aaaatgctgg gattacaggc gtgagccacc gtgcctggcc agtggttttt  21000
tgttgttgtt gttgttgttt tgttttgttt ttgtttttgt ttttgttttg agacaggatc  21060
ttgctctgtc acccaggctg gagtgcagtg gtgccatctt ggttcactgc aacctctgcg  21120
tgggctcaag caatcctccc acctcccttt ccagagtagc ggggaccaca ggtgtgtgcc  21180
accacacctg actaattttt gcattttttt ttgtagaaac agggttttgc catgttgccc  21240
aggttggtct gaaactcctg agctcaaaca atccaactgc cttggcttcc ctaagtgaaa  21300
ttacaggcat gggccactgt acccagtcta gtgatttttt tatttttatt tttattttat  21360
tttattttat ttttttacca aaaaaacaac aaagcctcag gaggaaaagt tgatacacaa  21420
gtaaatttta ttggaaatgt ttttgtgtgg accttaagca gagggaaaat tagtctgcat  21480
```

-continued

```
tatggtgtat ccagactaaa tgactgatat taaaatgaaa ttattcttag gatttgcaat  21540
cttagagaaa actttttcat ttttattttt ttgagttaca aattatcttc atttacattt  21600
gagaacagtg agtcacagag ggattaagta acttactcaa gatcatacaa gtctttgatt  21660
tgaacccaat cttttaactc tgcagaactc agagtcactc ttatttggaa aaacttttta  21720
actgatgtgg atcctctaat atgggcttcc tattattcat tctctattag tcagaagttt  21780
tgcaagcaga cagaattcat tttgccaatt acgggatttt ccctcagttg cagtcaaggt  21840
tcataaaact ataactcttt atctttaatt agaaatgttt ttttttttga gacaaggtct  21900
tgctctgttg cccagactgg aatgcagtgg catagtggcc cattgcagct ttgaactcct  21960
gggctcaagg gatcctctgc ctcagcctcc caagtatctg agactacaag tgcgtgccat  22020
cacccatggc tattttaaaa aaaaaaaaaa ttgtagagat agggtcttgc tgtgttgccc  22080
aggctggtct caaactcctg gtctcaagca atccttctgc cttggtctcc caaagtgctg  22140
agattacagg tgtcagccgt tgcacctggc caaaacgata acttaaaata cacacacaca  22200
cacacacaca caaacacata tgtgtatttg tgtgtgtgtg tgtgtgtgtg tgtctcaaaa  22260
ggtatcaaaa gagaatagct ataactttag tgttgatctt gatagtgact tgattaggct  22320
ctgtttaaca tcaaagatgc aaattaatac tttctttgaa catattaaaa atgcagaaaa  22380
tattggagta ttttatttta aataaattgt attctgtata tttaaggtat acaacatgat  22440
gttatgggat acatataggt ggttaaaaga ttactgcagt gaagcaaatt aacgtatccc  22500
tcaactcaca tagttaccca tttttttttt gttttggtgg caagaggagc ttaaaatctc  22560
atttagtgtg aatcccaaat acagcacaat tttattacct atatacttca tgttgtacat  22620
tatatttcta gacttgttca tcctacatat ctgctacttt gtatcctctg agctacatct  22680
ccccatttc tcacttgccc cccaagtagt ttcttaaagt gtctcatgta agagggcagt  22740
agctttcagc ttaaactttt tctctgtatg tagtcgattt ctttgaggta tacttttctc  22800
tccagaatag ttagatgtag gtataccact ttgatgttga cactagttta cctagaactt  22860
atcttctgta aatctgtctc tatttccatc tctgtctcca tctttgtctc tatctctatc  22920
tgtctatctc tatctatcta tctatctatc tatctatcta tctatctatc tatctatcta  22980
aagcaaattc atgcccttct cctatttatt gaatcgagac catagacagg ggtgagagaa  23040
agaatttggc aggaatgggg atgtgtatta tctgtggcat aaggaaactt tacagaacta  23100
ggttcaaaag tatactttct agttctttcc catggctttt cactttgatg tagtccttat  23160
caggtaactg aggttttata taagtcccct gattcttaga acatgaaggt gtagtagtca  23220
aggttggtcc cttgaaacca caaattttgt gaaaaaaaat taagaaaatt tgaataattt  23280
cctcagcaaa tacatattga tcatctgtta tacagccatg agaagtggtt ctgttgcaca  23340
cgtttatttt atcagatcct aatcccaaac caggcataaa atggaaacca tgaagatagg  23400
atgaaataac ttctgaatgt ttgaatgttt gaaaatagtg tacttaaaaa taccaggtgg  23460
tttttgtttg ttttttgttt ttttcttttt ttgagacagg gtctcactct gtcacccagg  23520
ctggagtgta gtggtgcaat ctcatctcat tgcagtcttg acctcccagg ctcaggttat  23580
ctcccacctc agcctcccaa gtagctggga ctacaggcac atgccaccac gcccagctaa  23640
tttttgtat tttttgtaga gacggggttt caccctgttg cccaggctgg tctagaactc  23700
ctgggcttaa gcgatcctcc cacctcagcc tcccaaagtg ctaggattac aggcatgagc  23760
caccatgcct ggcagaaaat accaggtttt taagtatcag cacttactct tcaatctttt  23820
```

-continued

```
ctattactat gttgtgctaa atggtatttt ttatttaatt agagcaatgc tgttcaatag  23880
aactttcttt gaggatggaa atcttttatg tttctgctat gtggtacaga gccactagtg  23940
acatgtggct tttgagcgct tgacacatct tgtgcaacac aggaactgaa tttttaagta  24000
atttatattg ccacatgtgg ctaccgtatg ggacagtgta gtactagatg atctgtaagg  24060
gctgtgcttc atcagtgtcg ttttttaact gacaaaaacc tttagttttt tttttagtaa  24120
tgtgtttatt taaaagaatt cataaaatac aagtaaacaa attaacttgt tacctgagca  24180
tatgtccttt catacttatt ttttctgcat acatattttg gaaaatggaa tatctgcccc  24240
ttttttttta tctgagatac agtctacctc taaaaataca tgattctaac attctcactt  24300
tttgttggca tttgatcagg gtatagaaaa acagttaaaa ggacagagaa tggttgagag  24360
attatgatat gaagagaaaa tgtgattgag tgtggtagac ttggggcctg cttgaatgtt  24420
gagagaatga ctgttttccg ataaaaaaaa aaagtccatt ctaggatcct aaaagaaggg  24480
tctgaagttc actgcagaaa gcaagctaca tagtactaag ccactaaggg gacatggagc  24540
ccttagtaat tcctacctta gtaatagtct catcatgccc tcttgggaac ccagccttgt  24600
tgattagcct ctctgctttc tctccttata gttcaacctc cctgtttgtt ccaagcagtt  24660
cttttcctgc ccatttatta tgcatttcta tacagctttc ctcctctttt tctataccat  24720
gctgcagttc ttattgctac ctagaggttt tcaaaattcc taggggcgga taagtaggca  24780
taaacaaagt tcttccctat tatccttcct attttttcac ctagactgaa gaggtagaca  24840
aaatagaaat aaagacatta agggtatgtg tttgtagtcc caaagagctt ctctggcaat  24900
tttgatgtag ttgacagtga cgctctgagt tcaggacaga ttggactcct tggctgagag  24960
gagtgaggag ataggacggt agaggagagg gtagagcaac tctggaggaa gctttcccct  25020
cacctttgcc agtcctgtta tcctagactt aaccataatt aaagatgagg gaggcactca  25080
gtaaagggat ctagtgggaa gcttgttcca gacagccaag gagggaggtt cgcgcagttc  25140
ctttggccac ccaggtgggg taattgatcc atgtatgcca ttcatgtaca atgtaggcac  25200
ttatacctgt attccaatgt agtgaactat accattactc ttaaattaat attctttatt  25260
agcttccatg gtggctatag gccaggcaag agagttaaga aaaaataaat agccaggtat  25320
ggtgactcaa gcctgtaatc tcggcacttt aggaggccga ggcaggagga tagcttgagt  25380
ccaggagttc aagaccagcc tgagcaaaat agtgagatcc tgtctctatt ttttaaaaaa  25440
gccttggggc aaacaggagt atggaggttt ggatgctaat agaacagcag tgtcttactg  25500
cttggagttc tcttgtttct tgtcctatca ccgtagcctt tggatcacag caatttttcc  25560
atgactccat acttttcagt tcttgaatat tttttccttt attcctcttg tctctgtaaa  25620
gacatcaact ggagttggac tgtaatacca ggtatctcca gaagatggca ctatttaaca  25680
gattttataa ataatttgat gtgagtcact gtcatctgaa gcttgttgcc ttttctttct  25740
ttcttctttc ttttttttcc ccatcaattc tgtatgtttg aaatgctggg atttaagtta  25800
gttagaataa gggatgtctg taatttccct aaattgagaa gtaatatgca aaggttgata  25860
tcagaagtca tatgctcacc ttgcaacacc aaataatact ggcccatttg tgatttttga  25920
aagtaacact ccataataaa tggatgtata tatagaagca taacaaaaat agaagcacat  25980
aaaagtgaaa agtctcataa acgccattgt cactactcat gtaattgctg ttacaaattt  26040
gtttaaatgt tgaataaaaa tggtgtcata ggcaacacag tgttccacta cttggtgttt  26100
ttaatagcat tattctgtct cagtgtgctt tggattatca ggtgcttttt aatagttgca  26160
tggtattaca ttgtgtagat gaacttgatt aatttaaatg gttccctgtt aatggacatg  26220
```

-continued

```
ttggtttgtt tttgtgaaca actgatacag tgaacattta ttttttaaat aaaaaaaaga  26280
gagacagggt cttgctgtgt ttctcgggct ggccttgaac tcctggggtc aagcgatcgt  26340
cttgcctctg cctccctggg attacaggca tgaagccacc gcacccggcc cagtgaacac  26400
tcttgaatgt atctttgtat acttgtcaag tgtttttgta gcaattgatt cccagaagtg  26460
ggaattacat ggaattaagt gacatgcatg tttgcaattt taacaggtat tgctatgtca  26520
ttttcaaaag aagctatgcc aattaatact ctcaccaaca agagtgctta tttcccctca  26580
gcatattatc aggcttaagt tttgccagta tgggtgggag aacagtagaa tcacattgtt  26640
ttagtgtttg tttctcagat agatataatt ttacacctta taaccttctc ttctataaat  26700
tgtctatttg tgttcattct ccattttcct atgggttctt attgttggag cccaatatat  26760
aaaaggggt atttgttaca gaacctcttc agttttggtt catgtcatgc ctgggttttt  26820
accctttcta cggatgttaa aaaaaattct ctattttctt ccagtccact tatggcttta  26880
ttttttacat ttagatttta atccgtctgg aatttatttt tgtgtatgct gtgaggtagg  26940
gaccatactt ttattttttc ccaaatgggt tactagttgg ccaaacatca tttattgaat  27000
aattcatctt ttccctactg actcgaaata ccatctttat tgtatactaa atcctcatat  27060
agttctgggt ctgtttctgg gctctacttt gttcatttac tgtgctggta ctgcaccgtt  27120
gtaattgctg tggctttgtg gtatggtatg gcttgctctc tgctagggca agtcgaagct  27180
cttttgttca cctgctcttt cacccaaatt ttctgtcctg aatccagcac agccaaatta  27240
tggtcattgt caccaccaac tacagtgggt gttgagcatt tcccattgaa tctcctgtaa  27300
gggttttatt ggattctgtg atagcagtaa aatgggagcc taagaggtat tccttaaagg  27360
actactaatc agacctggtt tcccagatga tgctgaagat gacggggcct gggctagact  27420
tttgagggac atatccttgg ggttgggtgt gatatagacc agcccttaca atttgcttga  27480
ctcatgggaa tcgtacaggg ccagaaccag acacctgtca tgctaataac ttccctcaca  27540
attcagaaat cactgtgatt gaagatgggt ggctgttata atactaccca cttaaaaatg  27600
gatgtaaccc attttttagg actcttaaaa acatcaaatc agtaatggcc gattaggact  27660
ttttaatttt tactaatctc tacttgaaag ttttctagtc attcatttca ggaaacctaa  27720
ttcttataat tcatatcatt tagaatatca taatgctatg gatattagct agctaacttc  27780
tcaaatcttc tagttctcat ttaatttgaa gtttgtgtgt gtacataagg atatacatat  27840
acatatgtgt gtgtagatat atatatatat agtttttttt tttttaacta gaatgaccag  27900
tcaacagggg acataaaagt aattggtgga gatgatctct caactttaac tggaaaggta  27960
tgtatcttga aagggaagaa aaaaaagcac ttcataccga gtcaattagt aacagtgtgc  28020
tttcaatcaa tcactaagag ataatttaca tagtataact aaatgggtta tttaaccctt  28080
ggaagcagtc taggttaatt atcgttccct aggtcatgta gtaaaaagac agtagaatcc  28140
aacattaacc ttaaatgtcc atattgtcaa gtactgctgt ctgcctctgt gggactctaa  28200
tttgggatcc ttcaaaaaac attgatgggg gaaaagatag cctttaaaaa aaaaaaaaaa  28260
acaaacctat gtgagtctat gtgaggtaga ctcacatagt ttcctaaaag atagcaaagc  28320
agtattatgt agtggctgaa agtgtgagtt ccggagcctg acaactgatt caaagcatgg  28380
cttagtactt cctaactctg accttgggca agttacttaa cctctctgtg tcccatatgt  28440
gattagggtg aggttgataa tagcagccat agagttaaga ggattaagtg ctataatgca  28500
agtagagctc ttacaacagt ttctggtaaa tcactcaata aattcagaca tactattatt  28560
```

-continued

```
ttaagaaatc tcaaagagtt ttcttgtacc ttaaaattct cctagtgtga accattggtt  28620
ttggtatatt gtgcttccat gtagtttaat atcaagatgt ttttagattt ccctttttaat  28680
ttatttgttg acccattggt tgttcaggag catgctgttt acctgaaaat aatggagata  28740
ttaaggtatt tgaatattta tcttctagta cattgaaaaa ctttttgaga gtaaccaata  28800
ataaatgatg gaatgctact gctttttttt tttgaagctg ccagttattg tttacttaca  28860
ctatgccaaa tataaaggca ttaatctcat aaaagtttca caacaatcct gtgagggaga  28920
cgatatcccc attttacaaa tcaggaaatt aagacttaat aaggttaaaa gacttgcccc  28980
aaagtcacag aaccagtaag tggtagagct tgaatttgaa tacagacctg actctaaagc  29040
tcttttcttt ctttagattt tagtgttcat tgcttacttg aatgagtatc tataagaaaa  29100
ctttaacatg taaaacttct gtgaaattat cttgtcccat atcagggtca tgtcaaacta  29160
atgtcctcct cagcatcttt ggaaaacttc agaggagaaa tgagctttgc ccctcctgtt  29220
catttcatat accactgtta gacctgtcct tccctttcag catgctttgt ccatatttag  29280
aagctgttga agccattact tgtctggtca gtttttagtg ctggaatgga cctagccttt  29340
taggccttct gagatttagt ttgatctcgt ctttcccacc taatggctct gttctactac  29400
atagatttga tctgaaacag ttctctgttt ctaaaataac tttcttttca tgatagtcac  29460
agtaaagtac atttattatg gaaaaatcaa taagtataac gagtgaaagt tatttcttgg  29520
tggtaagatt atgggattat ttgaactttc tgtttcattg tattttattt atttatttat  29580
ttttgtgatg gagtctcact ctgctgccca ggctggagtg cagtagtacg atcttggctc  29640
actgcaacct cccccttccca gttcaagtga ttctcctgcc tcagactccc aagtagctgg  29700
gattacaggc gcacgccacc atgcctggct aattttttta tctttagtag agacagggtt  29760
tcaccatgtt gaccaggctg atctccaact cctgatctca ggtatccacc tgcctcagcc  29820
tcccaaagta ccgggattac gggtgtgagc caccctgcct ggcctcattt tgtcttttgg  29880
gggtattttt gtgtgcagat atatatgtat ataaatattt ttccctcttt tccccagtta  29940
gtatttgagc agatgaactt tggacccgaa tacctgtatt caagtctcta ataccacttc  30000
ttggctattt tcattttatc aaatggcctc ttatcctcgt tttctcatt tattaagtag  30060
agatgtaact acttgatata attcaaaaac tcaataatgg cattcttttg ttttttagac  30120
tctagtgtct gtactccttg taccatgctg ggattcattt gaacaattgc atggcttttt  30180
tagtgtatta ttaaatttgc agtttactta gaatttactg ggacctcata caaatgggaa  30240
aaaaacataa ctgtgttact catttgctgt gtgcctttgg attgacccta ttttttgtat  30300
tcattttctc cccatgtcct gagttccact ttgaataaaa aagtaatttt tttcctgcct  30360
gtaaaatagg ctaccaatag gctgcagttg tctatagtag ctgcttcact gaggagagct  30420
cagcatgaga gaaatagtat gaattgcttg ccacaagtta tgggctagcc ttacttcatt  30480
ctgtacttgg acctgtttag gcttctaaga gatcttacct ccaacaataa actgctttga  30540
gacatgaaaa ggtggaagct ttacttggtt ataactttac ttttaatacc tagaacagtg  30600
agtcttcaaa cttgtatttg catgcccaat ttataaaaag tttcctgagc atttacccct  30660
aatatatgca ttttaaatta tatatgattt atggtaataa taatatatat gttacaaaat  30720
acatacaaaa atatagatta aacaaggtga ggttaaaaaa tttaaaagtt ctaatctttc  30780
ttgcaaacca gtggatcttt tgtgccttac tctggtaaac actgtcttag aagaatatat  30840
agaacattaa aatcttaatg ctatagttat atgacagagt atgatgagag ctacagataa  30900
acaacacatc atgaatcttc ttgtggcagt gtttataacc attatgtgaa atgctgcctc  30960
```

-continued

```
attcttataa ctagcataag aacagatagg actttctcga ttttgagggg taattattag  31020
atggtatttt ctgttaagga ctcttccagc tataaaattc ttaaatgtag aaagcgaagt  31080
gagggtttat ggtgagagga agcattggta tcatgtttta gtgtagtcca agaatatgga  31140
cacatccaga aaatgcagat caagtttagc ctaatgagaa aatatatttt ggagtccata  31200
tggtaaatta aattatgtga tttttgagtt attgtacaaa tataattctt agaatgttag  31260
agtcaggaga ctataagaga ccaactgctt caagtttcat ttaacacatg ggaaactaag  31320
gcgagagaaa tttcaagact tgcccaagat tagacctctt gttaagtaat gaaagtgttt  31380
taaaaacagg tgggtcaaat tctgttttta aaatttccat tatgatgaaa atttcagtat  31440
tacaggcttc caaatcccag cagatgggcc acttgtttaa aggagagttt gatataataa  31500
agcatctaaa aacaagagtt tggataattc cttagggttg ttatgatgtg atttgactta  31560
taattggaaa taccgtttta ttcattgtac tgattttcat ttctcttttt cttctagaat  31620
gtcttgattg tggaagtaag ttcacattta cttttaatat aacatttatg actttctaa   31680
cttagtatgc accatcctaa aggtaagcca gggagagaaa ttcctctgca tcagttttaa  31740
tggtgggctt gtgttctaaa ggagtgagat tggtttttg taaagactac ttagtaattt   31800
gtttttacca ataatggaat ggtatacttc ctacctctct ttttttagtt tgaagtattt  31860
tctttctaaa cataactctc tctctctatt tatctatata taatatatac atatatatct  31920
tatattttat gtatatatat atatatcttg cttagatttt gtcttatgta atatttggta  31980
cataaaaaat aatatttata atttatagac tattttccat gtgttattat gtgctaaagt  32040
attttgtatc ttagcaccga gaggctaagc agtttcctag ggttaccagc tagtaaacta  32100
agggaaacct ttacttcctt tagctcagtg gttctcaaaa tgtggttccc tagaccaaaa  32160
gtattaatat cagacaagaa cctaccgaat caaaatatct gtgatgaggc ccagcaagct  32220
atgctttaac aagtttccga gtgattctga tgcatgctaa ggtttaggat cccttgtttt  32280
tactcataag tcactttctc attaaggcct tccctggcca tcctatataa aatctcatgt  32340
tttcacaccg tcaacttcgt attcctcctc aatactttta ttttcctgat cacttatcac  32400
taacagcctc tctctctctc tctctctctc tctatgtata tatatatata tatcacttat  32460
cactgtctaa cagcctctct ttatatatat ataatctata gattatatat atatgcagca  32520
ttgtgcaatc attatcacgc tcaattttaa aacattttca tttccccaca aagaaaccca  32580
atccccttag ccatcactcc caatttttccc ttccccccagc acctagcaaa ctgatcatct  32640
acctacttgc tgtctataag atttgcctat tctggacatt ttgtataaat agaatcatac  32700
aatatgtggc cttttgtatc tggcttctct cacttaatgt tttcaaggtt cattcatgtt  32760
gtggagtata tctgcactca tttccttttt attgccaaat tgtatggata gacaggtgtt  32820
cctcaactgt gtcctgataa acccatctga agttgaaaat atcataagtt gaaaatggat  32880
ttactacttt gataaatcta tcctaaagtc agaaaaatct catgttggaa ccatcgtaag  32940
ttggatacca tctgaattac atttttgtta tccattcact ggttgacaga cgttaggttg  33000
tttccactga tgctccttat ttctcgtacc tgaaatgtcc ttattccctc ccttcttatc  33060
ccatgtttaa gtcatttaag acccagctca aacgtcacct ccacaaaacc ttccttgata  33120
ccccttttcct cttcaattca cttggacctt ttgcatttaa ttttaatttt tattttttttt  33180
aagacagagt ctcactctgt caccaggctg gagtgcagtg gtatgatctc agctcactaa  33240
ctactctgcc tcccaggttc aagcaattct catgtctcag cctcccaagt agctgggact  33300
```

-continued

```
acaggtgtgc gccaccatgc ctggctaatt gtgtgtgtgt gtgtgtgtat gtatgtatgt  33360
atatatgtgt gtgtgtgtat atatatatat acacaaacat atataaatat atatacatat  33420
atatatatac acacatatat aaatatatat acatatatat atatacacac acacacacat  33480
atatatatat atagtttttt tttttttaag tagagatggg gttttgccat gttggccagg  33540
ctggtctggc ctcaagccat cctcccacct cggcctcgca aagtgctggt attataggca  33600
tgagccactg tgcctggcct gcatttcatt ttaattataa aatattttga actcagaaaa  33660
aagggtatgc tgaataccta cgtacccaca aaagtattaa cattttgcca tatttgcttc  33720
tgatcttatt tttttgaga aattaaagat cataatacaa ctaaagcccc atttctttcc  33780
cttcattccc agaagtatga caattatcct taaagttgat atatatcatt cccatgcatg  33840
ttttttatac ttccctagta caagttagct gtatcctctg ctcaggggct catcaagctg  33900
aatcaaggga ctcatgatcc tcttcaaagt tccttcaggt tgttggcaga atttagttcc  33960
ttgtgattgt aggactgagg gcccgttttc tcactggctg ctggccaggg gttgctccca  34020
gatatttaaa ggctcatgcc ctagcccatg acagtctcac aacatggcag ctgacttctt  34080
caaaaccagc aggagaatct tgctctagtc taccacataa cctaatcaca ggagcggcta  34140
tcccgttatt ttcacagatc ctggtcacat tcaaggggag ggaacccttc tgtgtgtgta  34200
caccaggagg caggaatttt tttttcttt ttctttttg ttaaaaagtc ttaaagtctt  34260
ttatccctaa aggaggcagg aattttgaga gccatcagaa ttctgcctac cacagcccag  34320
aaatctgcat ttttcacaag tctccagcca tgatgtttct gatggctcac actgctttat  34380
tccattttta aagagtattt ttattgaaaa gcattagggt tatggtttaa aaaatatttt  34440
ccctaacaaa gatgggtttg tttagagtcc tacttttgac taaatagctg agattcactt  34500
ttatgtaaag ttcattttat agcgttatta atttgggtgc ctttaaaaat agtataaagc  34560
atgtttctcg agtgtagtct gttagccacc tatattggag agttgggagg agagagtctc  34620
tatcttgaat ttatgggaaa aattctaaaa tactttttat aatgaaggac aacatcataa  34680
ctccctaata aaatgtgcat gtatatattc aaatttgctg tcattgatcc tgcacctaca  34740
aaatccagtc ctgggggctg gcattcttac tgcttgctga gggccagatg atatagattc  34800
cagaatatct ccatgtagat tttggtgaga attactgtgc tgaaaagaat gacagtattg  34860
cagttataca tgggggtttt ggtactttat attgtgactc tgaatttaaa gctatgcaat  34920
gtcttctttt ttgaaaggat ataattgaca ctggcaaaac aatgcagact ttgctttcct  34980
tggtcaggca gtataatcca aagatggtca aggtcgcaag gtatgtatga cattttgaca  35040
cagaatattt tcctcatttg aagggggatt aagtgattgc ttctttttaa ggataaatgt  35100
tttcaactgt cattttatct tcgaaaagta atgtaatctc atataagact taagatataa  35160
tccttttaaa taattttgtc atgtgttaat aaagctcata attacagtca cttccttgct  35220
aatattaaca tttggttttc agcatgctaa ttatatcagt ttgtcctgaa tagcatggca  35280
gaggattttg ggcccccttg caaaattaag aataaggatt ccaaagcggg tgaggaagtg  35340
ataggaaggg gtgggccctg aagatctgga cctcctggaa ttgagtgatg aatgctgcat  35400
cttctttgtg tctgtagtga aattttataa tgcctgcttc cttttttatt aagtcggcct  35460
cacctcctca ccttacctat gctgttttac ttttgctttt atagttctac ctgtgtttat  35520
ttctcatttt cgtttcatct ctcaacaact ctggggtggc attattattc ccacttttca  35580
gataaggtta ctgaggcata gggaattgtc caaaggtaca gagctagtcc gctatagaga  35640
tgagatttga acccagggaa cctggctcac agtttatgct tttgcctacc ttaagttttt  35700
```

-continued

```
aatagagtga catcaaacaa acatttaaga atatgttttt cttttccttt tataatttca  35760
ttaaaaacat taagtctctg atcagtctgc agtttttatg taggggtcag gtaatgttct  35820
aacttctgct ttttcctaag tgattaacag gtttttataa gccctttttga aaaaatcacg  35880
gtatctgtcg agcatctttg aatcagagta agccttctag tgagtcatat gtcagcagtt  35940
tgactgtatg ggcttttcta atatccagtt caagtgttta tcagtgagtt tttcttttaa  36000
atagatttgg gacaggtact atgagagtat ataagtgata cgttatagga cactaactag  36060
tatcctatga aatggcaaaa actgcaatca cttttgcacc aaccaaatag aaactaatca  36120
gtgcacttgc ttatttttct acatgctctt tagggtttta aatgtcaacc tactgtggca  36180
tagactttaa tcctctgggt attcttttgt tgttctttcc tggtatatgc tgtggaattg  36240
agatagactg gttcgtgagc gagagatttt gtgttgccac aggtaggaca tgctcaaaca  36300
atacttgggt catttcttga cccaagtcat ctattcacca tagttttgta gcaccgatct  36360
tgcatacatt tcatgtatct tctttgaacc ccacgtcagt gctgcttata tgatactcag  36420
aaattaaaca ctaaggaata agattttcag gtaggattga gttttggagg gtcacaaatc  36480
ttgtaatgtc taatatttcc actctccctg ctgagaatta gttttggctt ccttggaggt  36540
gatatcgcct ctgttgagta taagtggcct actgtgatca caccactgca ctccagcctg  36600
ggtgacagag tgagaccctg tctcagaaaa aaaaaaaaaa aaaaagaatg catggcctag  36660
atgacttcta aggtttttcc cacccagttc cagttttcat gttctaggca gagcagtaaa  36720
gtgagaaaca catggacttg ggagtttagt ctcgcatttc actgccactt aatctgagcg  36780
actattccat atttaatctc tctgaatgta tttactcatc tttaaagggg aatgattatt  36840
aacatctttt tctcagggaa actatatgag tcaaggagat aatatatttg aaaatctttt  36900
taactgcaaa gcgctgtttc actgttggtt ataatgtgat tgatctcatt gtagtgagca  36960
gctgcttaat tgcgttttag aatgtaggga agatagtaat atttttcaca ttatatatgt  37020
agctggttct ggaactgtaa acatactcct tttttatgga gatctgagtc acgtaccata  37080
aaattcactc ttttaaagtt gtacaatcca gtggtttttg atatattcag agttgtgcat  37140
ctgctaccac tatttcattt tggaacccaa agaaaccttg tacccattag cagtcattct  37200
cccttctccc agcccctggc aactactaat ctactttcta cagaaagtcc gtacagattt  37260
gtgtattatg gacattccat ataaatggac tcatgcaata tcctgtcttc tttcacttag  37320
catagtgttt tcaaggttca tctaggttgg ggcatgtatc agtacttcat cccttgtttt  37380
ggctgaataa tatttcattg tacaaatata tcacattttg cttatccatc tgttggtgaa  37440
catttgagtt tctacctgtt ggcttttatg aataatgttg atttgaatgt ttgtgtacaa  37500
gtatgaatac ctgttttcag gtctcttgag tatatagttg ctaggtcata tagtaactct  37560
gtgtttaaca ttttgaggaa ttgcccgact atttaacaag gtatatgtac tgttttacac  37620
cagtaacata tgagggttcc aatatctcca catccttgac aacacttgtt actgtccttt  37680
ttattgtagc catcctagtg gctatgatgt ggtatctcat tgtggttttg atttgtgttt  37740
ctctgatgct gatgatgttg aacatgtttt catctgctta ttggccattt acatatatct  37800
tcttaagaac ggttacccat ttacagtatg gaaaatgctt cagatgcaac tctagtcatg  37860
ccttagagat ggagctttat taaacattca gatctctagg catatgaagt gctgagttct  37920
cttgaactcc taatacagat tgcactgagt ttagtgatac cttttctgga gcattcctga  37980
gttcaggtag ggagaagggt ttttgctgtg attggcttgt tatgttcttt ctaaatggaa  38040
```

-continued

```
atagaattga agtgtctcct ctctccattt attggaagag tcatgaggga cataattaga  38100
tgatcccttg gagtctccgg cttaggtcag tggttatcta cttaggctgc acattggaat  38160
cacctgagag ttaaaaaacc aggataacct ctgcctgtgt ctcatctcca gcaattctga  38220
tgtaattggt caggctgtgg cccgagtagg tgagttctgg ttttttaaag ctcccaggtg  38280
attctgatgt gcaatccagg ttgagatcac tttgggccct ttccagctct ttaaacatat  38340
atatttatct aggaaggtat gaaagcataa gttttcttga gactgccttt aacatctgta  38400
aaggctttca aagcagcttc tgtagttttt tttaaatggc tgaatatttt tcaacaggca  38460
gcatttgggt tataaaatta gcttttggta gagttgactt ataccacctc cagcttttgt  38520
tccaaaaata aatactggtt cttttggcac actagttgtt ttaccctaaa gttcctcttt  38580
gtaagccagt tattaaaagt tgtgatgcag ccagggcgaa gtggtacaca tctgtagtcc  38640
cagctactcg gaaggctgag gggggaggat cgctagagcc caagaagtca aggctgcagt  38700
gaactgtgat tacaccactg cactgcagcc tgggccacag agcgagactc atctctttaa  38760
aaaaagaatg ttgtgaggcc gggcgcagtg ctcacgcctg tgatcccagc actttgggag  38820
gccgaggtgg acggatcacc tgaggttggg agttcgagac cagcctgacc aacatggaga  38880
aaccctgtct ctactaaaaa aaatacaaaa ttagccgggc gtggtggcac atgcctgtag  38940
tcccagctac tcggcaggct gaggcaggag aatcgcttga acctgggagg cagaggttgt  39000
ggtgagttgg gcgagccatt gcactccagc ctgggcaaca agagcaaaac tccatctcaa  39060
aaaaaagaaa agaaaagaaa agaatgttgt ggccaggcgc ggtggcttac gcctgtaatt  39120
tcagcacttt gggagaccga ggtgggcgga tcacgaggtc aggagatcaa gaccatcctg  39180
gctaacacag taaaacccca tctctactaa atacaaaaaa aaattagccg ggagtgctgg  39240
cgggtgcctg tagtcccagc tactcaggag gctgaggcgg gagaatggcg tgaacccagg  39300
aggcagagct tgcagtgagc ggagatcgcg ccactgcact ccagcctggg caacagagcg  39360
agattccgtc taaaaaaaaa aaaaaagaat gttgtgataa aaggtgatgc tcacctctcc  39420
cacacccttt tatagtttag ggattgtatt tccaaggttt ctagactgag agcccttttc  39480
atctttgctc attgacactc tgtacccatt aatcctcctt attagctccc cttcaatgga  39540
cacatgggta gtcagggtgc aggtctcaga actgtccttc aggttccagg tgatcaacca  39600
agtgccttgt ctgtagtgtc aactcattgc tgccccttcc tagtaatccc cataatttag  39660
ctctccattt catagtcttt ccttgggtgt gttaaaagtg accatggtac actcagcacg  39720
gatgaaatga aacagtgttt agaaacgtca gtcttctctt ttgtaatgcc ctgtagtctc  39780
tctgtatgtt atatgtcaca ttttgtaatt aacagcttgc tggtgaaaag gaccccacga  39840
agtgttggat ataagccaga ctgtaagtga attacttttt ttgtcaatca tttaaccatc  39900
tttaacctaa aagagtttta tgtgaaatgg cttataattg cttagagaat atttgtagag  39960
aggcacattt gccagtatta gatttaaaag tgatgttttc tttatctaaa tgatgaatta  40020
tgattctttt tagttgttgg atttgaaatt ccagacaagt ttgttgtagg atatgccctt  40080
gactataatg aatacttcag ggatttgaat gtaagtaatt gcttcttttt ctcactcatt  40140
tttcaaaaca cgcataaaaa tttaggaaag agaattgttt tctccttcca gcacctcata  40200
atttgaacag actgatggtt cccattagtc acataaagct gtagtctagt acagacgtcc  40260
ttagaactgg aacctggcca ggctagggtg acacttcttg ttggctgaaa tagttgaaca  40320
gctttaatat acaataattg ttgcattatt atttcagatg ataaatgtgg tcataagtaa  40380
gaaataaatg atcgagttta gtcttttaat tcactgtcct ttgaatacct gcctcttact  40440
```

-continued

```
ctggaggcag aagtcccatg gatgtgttta tgaacatggt tgaggaagat ttaggaagac  40500
tgcaacagta cactacctaa agcaggtttt ttactccatc tttttttgcc acgtacactg  40560
gcctcccact ttgatatgct tgaaattatc tccttgattt gtctttcaaa actacatatt  40620
gaggctggtt gcggtggctc acacctgtaa tcctagcact ttgggaggcc aagccggaca  40680
gatcacttga ggtcaggagt tcgagaccag cctggcaaac atgatgaaac cccaccttta  40740
ctaaaaatac aaaaattagc caggcgtagt ggtgtgtgcc tgtaacccag ctacctggga  40800
ggctgaggca ggagaatcac tggaacccgg gaggcagagg ctacagtgag ccaacatcac  40860
gccactgcac tccagcctgg gtgacagagc aagactctgt ctcaaaacaa aacaaaaaac  40920
aaaaaactac gtattaagac aagaaacaga ctgggcgcgg tggctcacgc ctgtaatccc  40980
agcactttgg gaggctgagg cgggcggatc acaaggtcag gagatcgaga ccatcctggc  41040
taacacggtg aaaccccgtc tctactaaaa aatagaaaaa attagctggg gtggtggcgg  41100
gcgcctatag tctcagctac tcgggaggct gaggcaggag aatggcgtga acccgggagg  41160
cagagcttgc agtgagcaga gatcgtgcca ctgcactcca gtctgggtga cagagcaaga  41220
ctccgtctca aaaaaaaaaa caaaaacaag aaacaaatta aactaatgtg atagactact  41280
gctttgtttt caaaagatac actccccaaa agttactgat ctaaatacag tagtactatc  41340
tctgtttagt aagaaccctg acaactaata gtgttcttat atgtaaaatg ctattcttgc  41400
ctttcatttc agaatatact ttttaaatgt gaatttctgg attttttttt atagcatgtt  41460
tgtgtcatta gtgaaactgg aaaagcaaaa tacaaagcct aagatgagag ttcaagttga  41520
gtttggaaac atctggagtc ctattgacat cgccagtaaa attatcaatg ttctagttct  41580
gtggccatct gcttagtaga gctttttgca tgtatcttct aagaatttta tctgttttgt  41640
actttagaaa tgtcagttgc tgcattccta aactgtttat ttgcactatg agcctataga  41700
ctatcagttc cctttgggcg gattgttgtt taacttgtaa atgaaaaaat tctcttaaac  41760
cacagcacta ttgagtgaaa cattgaactc atatctgtaa gaaataaaga gaagatatat  41820
tagtttttta attggtattt taatttttat atatgcagga aagaatagaa gtgattgaat  41880
attgttaatt ataccaccgt gtgttagaaa agtaagaagc agtcaatttt cacatcaaag  41940
acagcatcta agaagttttg ttctgtcctg gaattatttt agtagtgttt cagtaatgtt  42000
gactgtattt tccaacttgt tcaaattatt accagtgaat ctttgtcagc agttcccttt  42060
taaatgcaaa tcaataaatt cccaaaaatt taactgcttt atgaattcaa tttaaaaatc  42120
cttaaaataa gtcctgtctc tttaaaaaaa cctatgcata gttatcattt ctctacaaat  42180
taacctagtt tagttttctg ttggttccat tttccttgtt tgttaagttt tagtagctag  42240
tttaattgta atctcaatga ttatgtggta gaatgggttg gcggacgtac aaaaattcct  42300
agctacttca gagacattaa atttcagaca catggtacac tttatattac attttactat  42360
gctaaaataa cacggctttc ttttggaatt ctgttcagtt tttcagattg taatctcagc  42420
tacatctcaa cagattgttc tcagatatgt cctattacct tctttgtgta gatagtgctt  42480
tattgactaa gaacaatgac aacaacacct tttgttttct gggaatagga gaaaagtttt  42540
aagccaaaac tcttaattgc ttatctgctc cacgtgaggt atgaactatc aaacttagga  42600
gccatctagc ttacacgtgt tccttaaaaa gtttgctgta ggccgggcac agtggctcgt  42660
acctgtagtc ccagcacttt tgggagccca gggtggggga tcacttgagc tcaggagttc  42720
aagaccagcc tgggcaacat ggcaaaacgc catctctaca aaaatacaaa aaaaaaaaaa  42780
```

-continued aacgctgggt gtggtggcgc acaactgtag tcccagctac ttgggaggct gaggtgggag 42840
gattgcttga gcttgggagg tgaaggctgc agtgagcctt gacagtgcca ctacactcca 42900
gcctggatga cagagtgaga ccctgtctca aaaaaaagag tttgctgtaa ttcccagcaa 42960
caaagtagga gactcaaact aaataatttt ctatagtcct agaacttctt agtttacaaa 43020
acatttttac ttctgttatc tcatttgatc ttcataccca tgtaagggtt gaggtagatg 43080
ttaccacatg tgagtgcaat atccagaact ctgaatccct tcttccccta aaatgtcagc 43140
ccgctgaggt ccacttggct accctcttga atactgcatc cagcttccca ctgctgaacc 43200
tctttactct tttttttca gttgcactta ccgccttcta gtaagttgaa ccatatgaaa 43260
ttaccatttt tgcaggtaaa aaatggccgg tgataggcag tttggcgtcg tataacccaa 43320
taacatgtta tataatttac ccacaagtgg tgggttgcta tgtcctggag gagtcagctt 43380
cagactctag ctaaatgatt gtataacctt gcagctctcc cctaagtgag gaggcaatgt 43440
tgaaagtccc atgtcttatc agaaccaggg aggcagatga gaaactgcct tatggcagct 43500
cccacaacat agggaggtgg gtgacaaatg gccttgggac agcttcttcc caagactggt 43560
tatgttacag tgttcctggg aggatcacat ggcattcctc caagatgggt cagactgctg 43620
ttggccttgt ctgtgtggcg tatgtgaaga cattcatggc cagagctgtt cccttagaag 43680
catctactaa attgatcttt tcctttctta cttactgtct gtctccctta gtaggctgtc 43740
agctccgtga gtgcaggacc ttgccagtcc tggtcactgc tatatcccca gcacctacaa 43800
gagtgcctgg aaaattgtag tgctcaataa atatttgttg gataaatgat agaatgatag 43860
gaagttaaaa agcaattaaa atacttgaaa agaagcaaaa catttttcat gttaagcaaa 43920
aaaaaaaaaa aaacttatta aggatagcta acatgtattg aattctatat gcaatggaat 43980
gatacttagc gcctttgaat ccttatgata accctataag gtaggttgtt tgggtttttt 44040
taattgtccc aactttacag atgaagaagt gcaggtccag agaggtcaca taatttgccc 44100
aggatcacac agctagtaag tagcagatga ggaatttgaa cccaggcagt tgtattccac 44160
catctgccct cttagttcat tgccacttaa cctataatgc ccagctcttg tgtagaaatt 44220
aatacactga taacatagag gaaaacatta agctcattga atgtaataag tccagatgac 44280
ttgtacatta aacacagctt tttgaggtca cagctgatct ctaagaatgt aaactgattt 44340
cctctggcac taaaaagcat tttcaaagac tgttaagaga gtttctccaa cattctcttc 44400
agatttttct gctggcttat tttatgattc tgtggacagc ttcagacaaa ataactttct 44460
ggtatgaagg attgtgttta ctctgctttt tttttgttg ttttttgggt tttttgtttt 44520
gttttgtttt gtttttgaga cagtgccttg ctctgctgct gcccaggctg agtgcaatgg 44580
catgatctcg gctcactgca acctctgcct ccctgggctc aggccaggtg tatgctacca 44640
ctctcagcta atttttaatt tattttttta gagatacggt cccactctgt ttcccaggct 44700
ggtctcagaa ctcctgggct cagacagtcc cccgccatgg cctcccacag tgctgggatt 44760
acaggcatca gccaccatgc tcagcttgtt ctgccatttt caaatgtgaa ttttatagac 44820
actttaaacc acttgaaaga gtgatgatgt tttaatgatt ttcattatta tttgcaactt 44880
caagcattaa acactgccaa attaagtttc aagttttctc tttacacaat atggatgtac 44940
ttcataatgg acttcctcat catgattaat gagtgaagtg acattcaaac ttggtagctt 45000
ttcagtagaa cttcctttcc caacattttt tctgttcctt taattatggc aatatctgag 45060
agctctgaac ataagtcaaa ggtttgatta tttttcatgt ggcttcctct gcttggaact 45120
ttctgccccg catcttcccg ttgccccctg tgtcctcttg tcatgcccct accctttttt 45180

-continued

```
gagtgtgtct attttctggc actacaagac ataacaggct catcttgtgt tttccctacc  45240
ctgacccaga atcagccatt acttcaagga gccctggttc cattattgga gaatactatt  45300
agaaaccagg atctggtgct aggcatgctc atttctattg gagtgtcata caaacaattt  45360
gtaaattgtt tgtaggtcct cccagtggat aggattagga aataaaacat gcatactaac  45420
catgcataca cacacatcta cgtctatttc tgtatctgtc tgtatacata ttaaaataaa  45480
catgggttga taactaatgt ttctgctgta atccacagcc ttcatcctag cctgccactc  45540
ttcttctttt tagcttttc aacagtggga aatgtggctc ttgttatgta cactttattc  45600
acttatttgt ttgaccctag tatcataaag tagttccgta tgcctgtaac agatcgacta  45660
actagagtcc attatttgcg gaaagatctt tttgtccgaa cgttaccgca ggggtgtcca  45720
atcttttggc ttccctgggc cacactagaa aaagaagaat tgtcttgggc cacacgtaaa  45780
atacactaac actaacgata gctgataagc taaaaaaaaa aaatcaaaaa aatttcatga  45840
tgttttaaga aagtttacta atttgtgttg ggccacgttt aaagccatcc cgggtcgcag  45900
gttggacaag cttgccttac agtatccagt caaaataatg ttttccaaaa ttacttcttt  45960
tctttttcat ccctttcagt gtggccgtta tttataatgc agtttggttc attagtgttt  46020
ttattacaaa tacaccctca gccttcatat cctagtttta atgaattatt acggtgaaac  46080
ataataagag tcagagctat acagaaaggt ctactcagag gtgctttgtt ccctcctatt  46140
ctgttcccac tactcctact ttccactgac cctgtaagca tcatatttat ttttaatggc  46200
agttacattt ttaccaagtg cttactatct gtaggcactt ggtgtgtatt gcttcttttg  46260
gtgttcacag caacctcttg aggtaagcac tattattatc ccccttttt ctttttcttt  46320
tctttctttc tttttttttt tttttttttt tgacagtctt actctgttgc ccaggcagga  46380
gtgcagtggc gcaatctcgg ctcactgcaa cctctgcctc ccaggttcaa gtgattctcc  46440
tgcctcagcc tcctgagtag ctgcgagtac aggcacaagc caccacgccc ggctaatttt  46500
tgtattttta gtagggatga ggttttgcca tgttggccag ggtggtctcg aactcctgac  46560
ctcaggtgat ctgcccgcct cgacctccca aagtgctggg attacaggca cgaaccactg  46620
cacccggcta ttatccccat tttttagatg agaaagctga atcccagaga gcataagaag  46680
cttgtccaga gtgacatctc tgatgcataa ccagtactca aacctatttt tctgacacca  46740
aggcctgtgt gtaaactgta aaggggctgc ttggcaccta ctttcctaaa gttgtcctat  46800
cccttctctg tctgggtctt cctgaagctt ggcacttctg aagtcacctc tctgaaaaca  46860
ttctggtaac tgttaaatcc cttgttctag ctattcatgt gttctgtgtg gttaaacaag  46920
gttcacaatg gccacctggc ctttggaact tgggtgaaga ggctgccttc agttgatcct  46980
ccccactccc attttcaaaa catgggttta catgagttat ttgtgaatta ggaaacataa  47040
ccatgttttg agccttcata gaaaacaaac gtctggggtc atacaggtta aaaggagtaa  47100
ccaaattcgg cactatcatt gttctattca gtagacaatt ctggggcctt tctgtgtctc  47160
aggttctgta ctagttgttt caggactttg ggataaatac aaactatccc tgccctcagg  47220
gggcttaagg tcaggtgtac aagtgactct aatgtgaggc aaggctggat tcagtgctgc  47280
atatctaatg ctatgggaat tcaaagagga agtgatcaga atgagaaggg agggatggat  47340
cattccagga gaagcttcag ggaaaagcaa catttaaaat gagacttttg agagtgaggg  47400
aaatttggac aggtggatat agaggatgca aggctagagg aaaggtttta gccagaaagt  47460
ctgcttgggc aaatgcctgg gtaaaaaaag aaaatccact ttgggaggac aaggcgggca  47520
```

-continued

```
atcgcctgag gtcaggagtt cgagaccagc ctggccaaca tggtgaaacc ccgtctctac  47580
taaaaataca aaaattagct gggcgtggtg gtgggtgcct gtaatcccag ctacttggaa  47640
ggctgaggca ggagaatcac ttgaacccag gaggcagagg tttcagtgag ccgagattgc  47700
gccactgcac tccagcctgg gcaacaagag tgaaacatct aaaaaaaaaa aaaagaaaat  47760
cacagggcag tgtggggaat ggtgagtatt ctaatttggt tgtggcagag aggatgtaga  47820
aggaagtgat aagagagaaa gccggatagg agggcctttg tgccagttag gatgttctag  47880
acttccagcc aggttgccca gctcaaactg gcttaaacaa tgaggggtt tattggctat  47940
gtaattggga agtgcagagg tagctcaggc cagatcagtt tgatccactg ctccattatg  48000
atgtcaaaga cccatgcgat ttccacctca ttattctgct gtccatagag ccaacttcat  48060
cctaaggcca gtccttgtgg tcagacaagg gctgccaata gtaatctggg tgcaagtttc  48120
tttgagaaaa tctttctgtg tcaactctct taaaaggggt gaaaaatctc tccttaagtc  48180
ccactggcca gaatgggccc atgcacccat ttcttaacca gtcactggca actgggggtg  48240
ggattgccgt ttgcccaatc aggtccattt ctggagctaa gattaaactc catttccctt  48300
gggacacatt gaacagaatc agaattcgat gaagaaggaa gaagcggaga attggtttgg  48360
tgttgggtag gcaaccaaaa ataacctctg ttgcctcaag tgccaagaaa gtggtgtttt  48420
gtgcttgtta gggtaaaaat ggggatcatg gaaaatattt taagtttcat agaccaaaaa  48480
atattccagt gtttcatcaa atctaagagg ctatcaatta taagatatac cattatttta  48540
tgtaccacca aggaagaaaa aatgctgcca gtgaagttag gatgtattgc aggttgggtt  48600
ctctgggaag caggctgaaa aggaggtgag aatgcaggac atttatggga gaacaccctt  48660
gggattaata ctggaggagg agaaccaagc agggttggtg gggcacaggg agaagttggg  48720
atgccatgca gtcacaacaa aggcctcagc caaccccacg gggagctcga gaagctgaga  48780
tggcccttca gtgttgccct gccttgtggt gagtgaattg ggtcttcata tccccatgtt  48840
gactggtcat tggatgtggg ctcccttagg aatgggcatc tcttcagcag aggtagcttt  48900
cttcaaaaga ggtgattcca aagagtcacc cactcactga gggctgtctg ctggcagcat  48960
tctcagccac tactcaaaga tgacctgtcc aggaagggga acctaggtgg catgacacat  49020
tgtctattac aacatgctac tgattataag agccgggagg tgggggcaa cacaatgtct  49080
gagatattaa aatggaagtc tcttagaaga aatggataat tctataatta tagttaatca  49140
gaaaggggaa gaagtgggga aatggaccaa gggcctgaga gagaaaacag acgcaacagg  49200
ccactagaaa gataggacac tggagggtgg gaagccctag cagtttcttc cagggtgggc  49260
tgggcacggt ggctcattcc tgtaatccca gaactttggg aggccgaggc gggcagatca  49320
tttgaagtca ggagttggag accagcctgg ccaactcctg tttcaccctg tctctgccaa  49380
aaatataaaa aattagccgg gtgtggttgc atgcgcctgt aatcccagct acttgggaag  49440
ctgaggcagg agaatcgctt gaacccagga ggcagaggtt gcagcgagga aaaatcgtgc  49500
cactgcactt gagcctgggt gacagagtga gactgtctca aaaaaaaaaa aagtttcttc  49560
cagggtggct tctgtgccag agtcaggtgc cccagctacc tctaatttat ggtcctcctg  49620
cactgggaaa cagattttct acttttggtt tcatgataaa taacatttcc ccctgatttt  49680
aaaagttatg gatttggctg ggcatggtgg ctcatgcctg taatcctagc actttgggag  49740
gtcaaggcag gcagatcact taaggtcagg agttccagac cagactgggc aacatggtga  49800
aaacccgtgt ctaccaaaaa aaaaaaaaaa aaaaaaatta gccaagtgtg gtggtacatg  49860
ccagtagccc tagctactca ggagactgag gtgggaggat tacctgagcc caggagatca  49920
```

-continued ggcctgcagt gagctgtgat tgtgccattt tactccagcc tgggtgacag agtaagaccc 49980
tgtctcaaaa ataatagtaa taggctgggc gcggtggctc aagcctgtaa tcccaacact 50040
ttgggaggcc aaggcgggcg atcaattgag gtcaggaact caagaacagc cttgccaaaa 50100
tggtgaaact ccgtctctac taaaaataca aaaatgagcc gggtgtggtg gcgcatgctg 50160
cattcccagc tactcaggag gctgaggcag gagaatcgct tgaactcggg aggcagaggt 50220
tgcagtgagc cgagattgca ccactgcact ccagcctggg tgacagagtg agactccatc 50280
ttaataataa taaaataata aaaattttaa aaagttatgg atctggatgg agggaaatgg 50340
aatgtataaa agaagtaaac atacacaaga agatacaaat acagaataaa agtaaaatgc 50400
aaccatcatc ccactacccc gataccaggg tatccgtttt tacatctttt ctttcattct 50460
ttctgtcttt atataattgt ataaatgctg cataaacctc ctcttgcctg ctgcctcctc 50520
aaagacctcc ctccctcctt cactgccctt ctgctcctgg agagccaccc tctctccatt 50580
tatccttcct atcagcttca ggttcttacc atgttaacaa aaagaaaatc ttataagcct 50640
gtcactctct acatacgccg cacctccttt cattcatagc ctttaaaaca tatatatagc 50700
agttattgtg gttatttttc tgttcacaaa ataaaaaaac actctttcta gaaaactgga 50760
atatagaggc aagctttttt tttttttcag acggagtttc gttctgtcgc cccaggctgg 50820
agtgcagtaa cgaaattaca gcttactgta acctctgcct cctgggttca agatattctc 50880
ttgcctcagc ctcctgagta gctgggatta taggtgcctg ccaccacacc cggctaattt 50940
ttgtattttt agtggaaatg gggtttcgcc atgttggtca ggctggtctc gaactcctga 51000
ccttgtgatc tgcccatctc ggccttccaa agtgctggga ttacaggtgt gagccactgc 51060
accctgccga ggcaagattt tttttttttt ttttaagaaa acccagttat tccattaccc 51120
aatgaaactc taaacatgtt gatgtacatc cttccaaaat ttctttttat gacaacatgc 51180
tttttatttt taattatttt tattttattt taaggtccgg ggtacatgtg aaggatgtgc 51240
aggtttgtta cataggtaaa cgtgtgcctt ggtggtttgc tgcaccctgt caacccatca 51300
cctacgtatt aagccccaca tgcattagct attgatcctg atgctctctc tccctgctgg 51360
ctccccagca ggccccggtg tgtgttgttc ccctccctgt ttatgagaac actttcttga 51420
cataaagatt tcatttattc ccatggaatt ctaaaggctt ttcatacttg tgaaggaata 51480
atagtttaga aataaactga actttaaaag ataccatttt gaaaaataat atacagccat 51540
caaaaattat atttatggga actatgcaat aatattaaac tctatcatct gttgactgcc 51600
tcctatattc cagaaacttt acatacacca attctaatcc ttacaagaac gctgtgtagg 51660
ctttagcatt agatggacca ggtttcacca actgtatggt cttggataag tacccaacct 51720
cctgtcccta agtttcctca cctgtgaaaa cacggtttct accagctttc aaataagatg 51780
atcaatataa ggcacttgga acagaacctg acacatcata agcactctat aaatgtctat 51840
tatcaccaaa taattccagg tgccttgaaa atttaaatga aaaacaaaat caaaccatga 51900
caatactaga agcaaattta ggtgaacact tttctaatcc gggggtgggc gggggctggg 51960
gggaggcagg gagaagacct tttttttttc tttttgagat ggagtcttgc tctgtcccca 52020
agctggagtg cagaggcgtg atctcagctc actgcaacct ctgcctcctg gattcaagtg 52080
attctcctgc ctcagcctcc cgagtagctg ggactataca ggtgcacacc accacggcca 52140
gctaattttt gtatttttag tagagatggg gtttacaccc tgttagccag gatggtctca 52200
atttcttgac ctcgtgatcc catccgcgtt ggccttccaa agtgctggga ttaccagcat 52260

-continued

```
gagccaccgt gcccggctgg gagaagacct ttctaagcat gataccaaag gcagagacaa  52320
taaaggcaaa gaattgacag aattcactat ccgataaaaa tcacttctgt ggccgggcgc  52380
ggtggctcac acctgtaatc ccagcactgg gaagccgagg tgggcggatt gcttgaggcc  52440
aggagttcaa gaccagcctg gccaacatgg caaacctcct gtctctacta aaaatacaaa  52500
aaattagcta ggcatggtgg catgcctgta gtcccagcta ctcaggaagc tgaggcatga  52560
gaatcacttg aacctgggag gtagaggttg cagtgagcca agatcatgcc actgcactcc  52620
aacctgggtg acaaagtgag actctgtctc aaaaaaaata acaattaaaa taaaatcact  52680
tctgaatggt ggaaagcacc acaaagttag aggtcaagca ataatttgga gaaaagaatt  52740
agtaatttgt tggacagaca aaagactttt ttaatataac aaaaacttta aaaattaaaa  52800
aaatacacat tcgaggacat tttcctaaaa acacaggcaa aggacataaa cagcaaagca  52860
agaagacagc ttgatgtggc cattttatcc aggggggacat tttggtgagc cctatggaca  52920
cagctgccat gatgccaaca atgtgacagc tgtccccttc aaaatgcgtt agccccagct  52980
cttcctctcc cccaacctcc agtccaaagg acttgcactt tctactttac tcctttctgc  53040
attgtttaat tttcttttac aaatatgtta cttgtcatca gaaaaaataa agaaataaat  53100
aaactgttag agtgttagcc ccttaaaggg gagcaagaat cacctttcta aaagaaagtt  53160
tatgttaaat ataatattag catatgtgaa tcctgagaga aaagttaaca gtttagttga  53220
gttatttcct ctgtagtctg gagctaaaaa tagggaatct tattctgtcc taaatctttt  53280
ccttcctcca cccagtgtct gtctggatcg aattcattca ttcactcagt aggcactcac  53340
tcagccaggc atggtgctag gcctcaggac ctcgctgtga accagaaact gtccctaccc  53400
ccatggtgca ggcattctgc ttgggagttg gaggaggaac aggtaaaaaa taattaaata  53460
ttcaggttaa cgatatattg tcaggtttga ggattgagga aagggcgcag agagtggcaa  53520
gggctgctgt ttagatacag tggccaggag gctccgatga ggtgaccttt gaggagagac  53580
atgcaggaga tgaggggaca gtgaagagga tttctaagaa cactccaggc agacagaaca  53640
gcgacagcca aggccctgaa gtgggtaggg gcctggtgtg tgtgaggaac ctcaggattg  53700
ccatcatggc tggagcagag acatgaagca agaaggccat ggagatgagg gcagggagat  53760
cccggagtgg ggagatcaga tggggctctg tgtatcatgc aaaggacttt gcattctgtt  53820
ccaagagctg ggaaggttga cataattagg aaaaaagccc agaaaagcag aggtatccat  53880
ttttcatggt aaagatgata atttcaatta aaacacgatt cctggatata tgtaatttgt  53940
aggccaaatg gtgcccaatc cctacctccc tcacccctc acttccctat ccctaaaacc  54000
tgtacctcaa ctcccgttcg taagtgatgg gagttaggaa tagagaaatc tcccggttgg  54060
gttttctgag caaagaggta acatagcagc tctgttattt ctttcacgtc tccaagggaa  54120
ccatgactca cccttagcta tccccccggga atgtggccct cagagtgttc ttttactgat  54180
tcgtgatttt gttatgtaca cctggagtga tggaacatac cataccagct tgtcagggtt  54240
gctttgtgca aagatcgatg acgtgtgtga acccggatcc atgcttgggg tcctgagttt  54300
caggtgccat ggccagttgc tagcaggttg tatgtgtgtg accagcccct atgtgagtct  54360
ctcagaccct gaaactccaa acaggcttcc ctgggcagag acattctgtc catgctctgt  54420
ggcttgctgc tcgagaggga tagatcacat cctgtgtggc ttcttcttaa atgaagaagg  54480
acattggaag cctgtgctgg gcttctctgg accccccgat gtatatgtat gtatattaaa  54540
gagagaccag ggtctcactc tgttggccag gctggtcttg aactgctagc ctcaagaaat  54600
cctcccgctt tggcctccca aagtgctggg attacaggca tgagtcacca tgcctgatgt  54660
```

-continued

```
atatattttt ccagctccct tcttttctgt atcatttgct attactacct cttagctatt  54720

agtataaact gatcttgagt tgtgtaaatc tttctggtga ttcactgtga tgggatgatt  54780

gtgtcctctc aaaattccta tgttggagtc ctgacccatg gtacctcaga aagtgactgt  54840

atttgaagat aggtctttaa agaggtcatt gtaaattaat taataaggtc attagggtgg  54900

actctaatcc gatatgactg gtatccttat aagaaaagga aattagcaca cagacacaca  54960

atcagaggga gaagacagcc agtcatctac aagccgagga gacagacctc agaagaaacc  55020

aaccctgcct gcaccttgat cttggacttc tagtcgccag aactgtgaga aaacaaatct  55080

catgtttaag ccagaaccta gcacgtggta cttgttaagg catccctaga aaactaatac  55140

actcactgaa tgaggcaggt agctgtttct tttatttttt gagacagagt ctcactttgt  55200

ctccaaggcc agagtgcagt ggagcgatca cagctcactg cagcccctgc cttccaggct  55260

caagccatcc tcccacctca gcttctcaag tagctgggac tacaggcatg caccaccacg  55320

cccagctaat ttttgtattt tttttttttt tttgtagaga cggggttcac cgtgttgcct  55380

aggctggtct caaacccctg agctcaagca atctgccctc cttggcctcc caaagtgttg  55440

gatttacagg cgtgagccac tgtgcctgga tatggtaact ttttcatatg ctatttgctt  55500

gatgattatt tttctgtttc tgatataatg ctttttatta gagagttatc tgtttgtttt  55560

tattttttaa tgtttgaatt taaaaaatta gtataatttg cataattgaa aaattatatt  55620

tgaataattg aaatatattt gtataacctt aaatttaaaa actatgatag cgtatacagt  55680

gaaattttcc tctcatccct tttttccatt taaccagtgc acttcccaac agccaacaga  55740

taattttagt ttcctcactc cctgagctat tttatgtata tgcaagtaga tatgtacata  55800

catatttctg ccttgtaaca caaatagtag catactatac aactgctctg cttcttcctt  55860

tttttagcta agaatattaa aagagtgaaa aagatgtacg ctaacaaaaa tcaaaagaaa  55920

actagagtga cattataaga actgatgatg tagatttcag agcaatgatt actgctagga  55980

aaaaagggtc attttacatt gatcaaagag gtcaactcat caggaagaca taataatcct  56040

aaacacttat gtacttaaca gagcatcaaa atacatgaag cataaatgaa agaaccgtgg  56100

gagaaagtag acaaattaat gactgtagtt gaagatttca gtatccctct atgaaaatca  56160

gggtagtaca agtacacaga aaattggtaa agatatatga cttgaacaac attatcaacc  56220

aaattgacct catttacatt tgtggaatgt tccaactaag aacgtcagaa aacatactct  56280

tttcaagtgc acatggaaca tttaccaaga tagacaatat tttgggtcac cgcaagtctc  56340

aacacattga aaggattcag atcatataaa gtatgctcca tgaccatgat ggaattgaat  56400

tagaaaccaa taatgtatct ctggaaaata cacaaatatt tggaaattaa tatgcccttc  56460

taaaaaattt atgcatcaag aagaaatcaa aaagggatat ttgaaaagta ctatgaaact  56520

gatggccagg catggtgctc atcgcctgta atcccagcac tttgggaggc cgagaaagat  56580

ggatgaagtc aggagttcaa gaccagcctg ggcaacatgg cagaaccccg tctctactaa  56640

aaatacaaaa aattagccgg gcgtggtggt gggcgcctgt aatcccagca gtccacgtgt  56700
cgccgcccct ggtgatggac cagcggggct tcgacga                           56737
```

<210> SEQ ID NO 18
<211> LENGTH: 2039
<212> TYPE: DNA
<213> ORGANISM: Homo sapiens

<400> SEQUENCE: 18

```
cggaagcgcc cgcagcccgg taccggctcc tcctgggctc cctctagcgc cttccccccg     60
```

-continued

```
gcccgactcc gctggtcagc gccaagtgac ttacgccccc gaccctgagc ccggaccgct    120
aggcgaggag gatcagatct ccgctcgaga atctgaaggt gccctggtcc tggaggagtt    180
ccgtcccagc ccgcggtctc ccggtactgt cgggccccgg ccctctggag cttcaggagg    240
cggccgtcag ggtcggggag tatttgggtc cggggtctca gggaagggcg gcgcctgggt    300
ctgcggtatc ggaaagagcc tgctggagcc aagtagccct ccctctcttg ggacagaccc    360
ctcggtccca tgtccatggg ggcaccgcgg tccctcctcc tggccctggc tgctggcctg    420
gccgttgccc gtccgcccaa catcgtgctg atctttgccg acgacctcgg ctatggggac    480
ctgggctgct atgggcaccc cagctctacc actcccaacc tggaccagct ggcggcggga    540
gggctgcggt tcacagactt ctacgtgcct gtgtctctgt gcacaccctc tagggccgcc    600
ctcctgaccg gccggctccc ggttcggatg ggcatgtacc ctggcgtcct ggtgcccagc    660
tcccgggggg gcctgcccct ggaggaggtg accgtggccg aagtcctggc tgcccgaggc    720
tacctcacag gaatggccgg caagtggcac cttggggtgg ggcctgaggg ggccttcctg    780
ccccccatc agggcttcca tcgatttcta ggcatcccgt actcccacga ccagggcccc    840
tgccagaacc tgacctgctt cccgccggcc actccttgcg acggtggctg tgaccagggc    900
ctggtcccca tcccactgtt ggccaacctg tccgtggagg cgcagccccc ctggctgccc    960
ggactagagg cccgctacat ggctttcgcc catgacctca tggccgacgc ccagcgccag   1020
gatcgcccct tcttcctgta ctatgcctct caccacaccc actaccctca gttcagtggg   1080
cagagctttg cagagcgttc aggccgcggg ccatttgggg actccctgat ggagctggat   1140
gcagctgtgg ggaccctgat gacagccata ggggacctgg ggctgcttga agagacgctg   1200
gtcatcttca ctgcagacaa tggacctgag accatgcgta tgtcccgagg cggctgctcc   1260
ggtctcttgc ggtgtggaaa gggaacgacc tacgagggcg gtgtccgaga gcctgccttg   1320
gccttctggc caggtcatat cgctcccggc gtgacccacg agctggccag ctccctggac   1380
ctgctgccta ccctggcagc cctggctggg gccccactgc ccaatgtcac cttggatggc   1440
tttgacctca gcccccctgct gctgggcaca ggcaagagcc ctcggcagtc tctcttcttc   1500
tacccgtcct acccagacga ggtccgtggg gtttttgctg tgcggactgg aaagtacaag   1560
gctcacttct tcacccaggg ctctgcccac agtgatacca ctgcagaccc tgcctgccac   1620
gcctccagct ctctgactgc tcatgagccc ccgctgctct atgacctgtc caaggaccct   1680
ggtgagaact acaacctgct gggggtgtg gccggggcca ccccagaggt gctgcaagcc   1740
ctgaaacagc ttcagctgct caaggcccag ttagacgcag ctgtgacctt cggccccagc   1800
caggtggccc ggggcgagga ccccgccctg cagatctgct gtcatcctgg ctgcaccccc   1860
cgcccagctt gctgccattg cccagatccc catgcctgag ggcccctcgg ctggcctggg   1920
catgtgatgg ctcctcactg ggagcctgtg ggggaggctc aggtgtctgg agggggtttg   1980
tgcctgataa cgtaataaca ccagtggaga cttgcacatc tgaaaaaaaa aaaaaaaaa    2039
```

<210> SEQ ID NO 19
<211> LENGTH: 1917
<212> TYPE: DNA
<213> ORGANISM: Homo sapiens

<400> SEQUENCE: 19

```
gagccccagg actgagatat ttttactata ccttctctat catcttgcac ccccaaaata     60
gcttccaggg cacttctatt tgtttttgtg gaaagactgg caattagagg tagaaaagtg    120
```

-continued

```
aaataaatgg aaatagtact actcagggct gtcacatcta catctgtgtt tttgcagtgc     180

caatttgcat tttctgagtg agttacttct actcaccttc acagcagcca gtaccgcagt     240

gccttgcata tattatatcc tcaatgagta cttgtcaatt gattttgtac atgcgtgtga     300

cagtataaat atattatgaa aaatgaggag gccaggcaat aaaagagtca ggatttcttc     360

caaaaaaaat acacagcggt ggagcttggc ataaagttca aatgctccta caccctgccc     420

tgcagtatct ctaaccaggg gactttgata aggaagctga agggtgatat tacctttgct     480

ccctcactgc aactgaacac atttcttagt ttttaggtgg cccccgctgg ctaacttgct     540

gtggagtttt caagggcata gaatcgtcct ttacacaatt aaaagaagat gctgtttaat     600

ctgaggatcc tgttaaacaa tgcagctttt agaaatggtc acaacttcat ggttcgaaat     660

tttcggtgtg gacaaccact acaaaataaa gtgcagctga agggccgtga ccttctcact     720

ctaaaaaact ttaccggaga agaaattaaa tatatgctat ggctatcagc agatctgaaa     780

tttaggataa aacagaaagg agagtatttg cctttattgc aggggaagtc cttaggcatg     840

atttttgaga aaagaagtac tcgaacaaga ttgtctacag aaacaggctt tgcacttctg     900

ggaggacatc cttgttttcc taccacacaa gatattcatt tgggtgtgaa tgaaagtctc     960

acggacacgg cccgtgtatt gtctagcatg gcagatgcag tattggctcg agtgtataaa    1020

caatcagatt tggacaccct tgctaaagaa gcatccatcc caattatcaa tgggctgtca    1080

gatttgtacc atcctatcca gatcctggct gattacctca cgctccagga acactatagc    1140

tctctgaaag gtcttaccct cagctgtttc ggggatggga acaatatcct gcactccatc    1200

atgatgagcg cagcgaaatt cggaatgcac cttcaggcag ctactccaaa gggttatgag    1260

ccggatgcta gtgtaaccaa gttggcagag cagtatgcca aagagaatgg taccaagctg    1320

ttgctgacaa atgatccatt ggaagcagcg catggaggca atgtattaat tacagacact    1380

tggataagca tgggacgaga agaggagaag aaaaagcggc tccaagcttt ccaaggttac    1440

caagttacaa tgaagactgc taaagttgct gcctctgact ggacattttt acactgcttg    1500

cccagaaagc cagaagaagt ggatgatgaa gtcttttatt ctcctcgatc actagtgttc    1560

ccagaggcag aaaacagaaa gtggacaatc atggctgtca tggtgtccct gctgacagat    1620

tactcacctc agctccagaa gcctaaattt tgatgttgtg ttacttgtca agaaagaagc    1680

aatgttggtc agtaacagaa tgagttggtt tatggggaaa agagaagaga atctaaaaaa    1740

taaaccaatc cctaacacgt ggtatgggcg aatcgtacga tatgctttgc cattgtgaaa    1800

ctttccttaa gccttcaatt taagtgctga tgcactgtaa tacgtgctta actttgctta    1860

aactctctaa ttcccaattt ctgagttaca tttagatatc atattaacta tcatata       1917
```

<210> SEQ ID NO 20
<211> LENGTH: 2680
<212> TYPE: DNA
<213> ORGANISM: Homo sapiens

<400> SEQUENCE: 20

```
cagctggggg taaggggggc ggattattca tataattgtt ataccagacg gtcgcaggct      60

tagtccaatt gcagagaact cgcttcccag gcttctgaga gtcccggaag tgcctaaacc     120

tgtctaatcg acggggcttg ggtggcccgt cgctccctgg cttcttccct ttacccaggg     180

cgggcagcga agtggtgcct cctgcgtccc ccacaccctc cctcagcccc tcccctccgg     240

cccgtcctgg gcaggtgacc tggagcatcc ggcaggctgc cctggcctcc tgcgtcagga     300

caagcccacg aggggcgtta ctgtgcggag atgcaccacg caagagacac cctttgtaac     360
```

-continued

```
tctcttctcc tccctagtgc gaggttaaaa ccttcagccc cacgtgctgt ttgcaaacct    420
gcctgtacct gaggccctaa aaagccagag acctcactcc cggggagcca gcatgtccac    480
tgcggtcctg gaaaacccag gcttgggcag gaaactctct gactttggac aggaaacaag    540
ctatattgaa gacaactgca atcaaaatgg tgccatatca ctgatcttct cactcaaaga    600
agaagttggt gcattggcca aagtattgcg cttatttgag gagaatgatg taaacctgac    660
ccacattgaa tctagacctt ctcgtttaaa gaaagatgag tatgaatttt tcacccattt    720
ggataaacgt agcctgcctg ctctgacaaa catcatcaag atcttgaggc atgacattgg    780
tgccactgtc catgagcttt cacgagataa gaagaaagac acagtgccct ggttcccaag    840
aaccattcaa gagctggaca gatttgccaa tcagattctc agctatggag cggaactgga    900
tgctgaccac cctggtttta aagatcctgt gtaccgtgca agacggaagc agtttgctga    960
cattgcctac aactaccgcc atgggcagcc catccctcga gtggaataca tggaggaaga   1020
aaagaaaaca tggggcacag tgttcaagac tctgaagtcc ttgtataaaa cccatgcttg   1080
ctatgagtac aatcacattt ttccacttct tgaaaagtac tgtggcttcc atgaagataa   1140
cattccccag ctggaagacg tttctcaatt cctgcagact tgcactggtt tccgcctccg   1200
acctgtggct ggcctgcttt cctctcggga tttcttgggt ggcctggcct tccgagtctt   1260
ccactgcaca cagtacatca gacatggatc caagcccatg tataccccccg aacctgacat   1320
ctgccatgag ctgttgggac atgtgccctt gttttcagat cgcagctttg cccagttttc   1380
ccaggaaatt ggccttgcct ctctgggtgc acctgatgaa tacattgaaa agctcgccac   1440
aatttactgg tttactgtgg agtttgggct ctgcaaacaa ggagactcca taaaggcata   1500
tggtgctggg ctcctgtcat cctttggtga attacagtac tgcttatcag agaagccaaa   1560
gcttctcccc ctggagctgg agaagacagc catccaaaat tacactgtca cggagttcca   1620
gcccctgtat tacgtggcag agagttttaa tgatgccaag gagaaagtaa ggaactttgc   1680
tgccacaata cctcggccct tctcagttcg ctacgaccca tacacccaaa ggattgaggt   1740
cttggacaat acccagcagc ttaagatttt ggctgattcc attaacagtg aaattggaat   1800
cctttgcagt gccctccaga aaataaagta aagccatgga cagaatgtgg tctgtcagct   1860
gtgaatctgt tgatggagat ccaactattt ctttcatcag aaaaagtccg aaaagcaaac   1920
cttaatttga aataacagcc ttaaatcctt tacaagatgg agaaacaaca aataagtcaa   1980
aataatctga aatgacagga tatgagtaca tactcaagag cataatggta aatcttttgg   2040
ggtcatcttt gatttagaga tgataatccc atactctcaa ttgagttaaa tcagtaatct   2100
gtcgcatttc atcaagatta attaaaattt gggacctgct tcattcaagc ttcatatatg   2160
ctttgcagag aactcataaa ggagcatata aggctaaatg taaaacacaa gactgtcatt   2220
agaattgaat tattgggctt aatataaatc gtaacctatg aagtttattt tctattttag   2280
ttaactatga ttccaattac tactttgtta ttgtacctaa gtaaattttc tttaggtcag   2340
aagcccatta aaatagttac aagcattgaa cttctttagt attatattaa tataaaaaca   2400
tttttgtatg ttttattgta atcataaata ctgctgtata aggtaataaa actctgcacc   2460
taatccccat aacttccagt atcattttcc aattaattat caagtctgtt ttgggaaaca   2520
ctttgaggac atttatgatg cagcagatgt tgactaaagg cttggttggt agatattcag   2580
gaaatgttca ctgaataaat aagtaaatac attattgaaa agcaaatctg tataaatgtg   2640
aaatttttat ttgtattagt aataaaacat tagtagttta                          2680
```

-continued

<210> SEQ ID NO 21
<211> LENGTH: 1418
<212> TYPE: DNA
<213> ORGANISM: Homo sapiens

<400> SEQUENCE: 21

```
aactgtgcga accagacccg gcagccttgc tcagttcagc atagcggagc ggatccgatc     60
ggatcggagc acaccggagc aggctcatcg agaaggcgtc tgcgagacca tggagaacgg    120
atacacctat gaagattata agaacactgc agaatggctt ctgtctcata ctaagcaccg    180
acctcaagtt gcaataatct gtggttctgg attaggaggt ctgactgata aattaactca    240
ggcccagatc tttgactaca gtgaaatccc caactttcct cgaagtacag tgccaggtca    300
tgctggccga ctggtgtttg ggttcctgaa tggcagggcc tgtgtgatga tgcagggcag    360
gttccacatg tatgaagggt acccactctg gaaggtgaca ttcccagtga gggttttcca    420
ccttctgggt gtggacaccc tggtagtcac caatgcagca ggagggctga accccaagtt    480
tgaggttgga gatatcatgc tgatccgtga ccatatcaac ctacctggtt tcagtggtca    540
gaaccctctc agagggccca atgatgaaag gtttggagat cgtttccctg ccatgtctga    600
tgcctacgac cggactatga ggcagagggc tctcagtacc tggaaacaaa tgggggagca    660
acgtgagcta caggaaggca cctatgtgat ggtggcaggc cccagctttg agactgtggc    720
agaatgtcgt gtgctgcaga agctgggagc agacgctgtt ggcatgagta cagtaccaga    780
agttatcgtt gcacggcact gtggacttcg agtctttggc ttctcactca tcactaacaa    840
ggtcatcatg gattatgaaa gcctggagaa ggccaaccat gaagaagtct tagcagctgg    900
caaacaagct gcacagaaat tggaacagtt tgtctccatt cttatggcca gcattccact    960
ccctgacaaa gccagttgac ctgccttgga gtcgtctggc atctcccaca caagacccaa   1020
gtagctgcta ccttctttgg ccccttgctg gagtcatgtg cctctgtcct taggttgtag   1080
cagaaaggaa aagattcctg tccttcacct ttcccacttt cttctaccag acccttctgg   1140
tgccagatcc tcttctcaaa gctgggatta caggtgtgag catagtgaga ccttggcgct   1200
acaaaataaa gctgttctca ttcctgttct ttcttacaca agagctggag cccgtgccct   1260
accacacatc tgtggagatg cccaggattt gactcgggcc ttagaacttt gcatagcagc   1320
tgctactagc tctttgagat aatacattcc gaggggctca gttctgcctt atctaaatca   1380
ccagagacca aacaaggact aatccaatac ctcttgga                           1418
```

<210> SEQ ID NO 22
<211> LENGTH: 13957
<212> TYPE: DNA
<213> ORGANISM: Homo sapiens

<400> SEQUENCE: 22

```
gggattccct cactttcccc ctacaggact cagatctggg aggcaattac cttcggagaa     60
aaacgaatag gaaaaactga agtgttactt tttttaaagc tgctgaagtt tgttggtttc    120
tcattgtttt taagcctact ggagcaataa agtttgaaga acttttacca ggtttttttt    180
atcgctgcct tgatatacac ttttcaaaat gctttggtgg gaagaagtag aggactgtta    240
tgaaagagaa gatgttcaaa agaaaacatt cacaaaatgg gtaaatgcac aattttctaa    300
gtttgggaag cagcatattg agaacctctt cagtgaccta caggatggga ggcgcctcct    360
agacctcctc gaaggcctga cagggcaaaa actgccaaaa gaaaaaggat ccacaagagt    420
tcatgccctg aacaatgtca acaaggcact gcgggttttg cagaacaata atgttgattt    480
```

-continued

```
agtgaatatt ggaagtactg acatcgtaga tggaaatcat aaactgactc ttggtttgat    540
ttggaatata atcctccact ggcaggtcaa aaatgtaatg aaaaatatca tggctggatt    600
gcaacaaacc aacagtgaaa agattctcct gagctgggtc cgacaatcaa ctcgtaatta    660
tccacaggtt aatgtaatca acttcaccac cagctggtct gatggcctgg ctttgaatgc    720
tctcatccat agtcataggc cagacctatt tgactggaat agtgtggttt gccagcagtc    780
agccacacaa cgactggaac atgcattcaa catcgccaga tatcaattag gcatagagaa    840
actactcgat cctgaagatg ttgataccac ctatccagat aagaagtcca tcttaatgta    900
catcacatca ctcttccaag ttttgcctca acaagtgagc attgaagcca tccaggaagt    960
ggaaatgttg ccaaggccac ctaaagtgac taaagaagaa cattttcagt tacatcatca   1020
aatgcactat tctcaacaga tcacggtcag tctagcacag ggatatgaga gaacttcttc   1080
ccctaagcct cgattcaaga gctatgccta cacacaggct gcttatgtca ccacctctga   1140
ccctacacgg agcccatttc cttcacagca tttggaagct cctgaagaca agtcatttgg   1200
cagttcattg atggagagtg aagtaaacct ggaccgttat caaacagctt tagaagaagt   1260
attatcgtgg cttctttctg ctgaggacac attgcaagca caaggagaga tttctaatga   1320
tgtggaagtg gtgaaagacc agtttcatac tcatgagggg tacatgatgg atttgacagc   1380
ccatcagggc cgggttggta atattctaca attgggaagt aagctgattg gaacaggaaa   1440
attatcagaa gatgaagaaa ctgaagtaca agagcagatg aatctcctaa attcaagatg   1500
ggaatgcctc agggtagcta gcatggaaaa acaaagcaat ttacatagag ttttaatgga   1560
tctccagaat cagaaactga aagagttgaa tgactggcta acaaaaacag aagaaagaac   1620
aaggaaaatg gaggaagagc ctcttggacc tgatcttgaa gacctaaaac gccaagtaca   1680
acaacataag gtgcttcaag aagatctaga acaagaacaa gtcagggtca attctctcac   1740
tcacatggtg gtggtagttg atgaatctag tggagatcac gcaactgctg ctttggaaga   1800
acaacttaag gtattgggag atcgatgggc aaacatctgt agatggacag aagaccgctg   1860
ggttctttta caagacatcc ttctcaaatg gcaacgtctt actgaagaac agtgcctttt   1920
tagtgcatgg ctttcagaaa aagaagatgc agtgaacaag attcacacaa ctggctttaa   1980
agatcaaaat gaaatgttat caagtcttca aaaactggcc gttttaaaag cggatctaga   2040
aaagaaaaag caatccatgg gcaaactgta ttcactcaaa caagatcttc tttcaacact   2100
gaagaataag tcagtgaccc agaagacgga agcatggctg gataactttg cccggtgttg   2160
ggataattta gtccaaaaac ttgaaaagag tacagcacag atttcacagg ctgtcaccac   2220
cactcagcca tcactaacac agacaactgt aatggaaaca gtaactacgg tgaccacaag   2280
ggaacagatc ctggtaaagc atgctcaaga ggaacttcca ccaccacctc cccaaaagaa   2340
gaggcagatt actgtggatt ctgaaattag gaaaaggttg gatgttgata taactgaact   2400
tcacagctgg attactcgct cagaagctgt gttgcagagt cctgaatttg caatctttcg   2460
gaaggaaggc aacttctcag acttaaaaga aaaagtcaat gccatagagc gagaaaaagc   2520
tgagaagttc agaaaactgc aagatgccag cagatcagct caggccctgg tggaacagat   2580
ggtgaatgag ggtgttaatg cagatagcat caaacaagcc tcagaacaac tgaacagccg   2640
gtggatcgaa ttctgccagt tgctaagtga gagacttaac tggctggagt atcagaacaa   2700
catcatcgct ttctataatc agctacaaca attggagcag atgacaacta ctgctgaaaa   2760
ctggttgaaa atccaaccca ccaccccatc agagccaaca gcaattaaaa gtcagttaaa   2820
```

-continued

```
aatttgtaag gatgaagtca accggctatc aggtcttcaa cctcaaattg aacgattaaa   2880
aattcaaagc atagccctga aagagaaagg acaaggaccc atgttcctgg atgcagactt   2940
tgtggccttt acaaatcatt ttaagcaagt cttttctgat gtgcaggcca gagagaaaga   3000
gctacagaca atttttgaca ctttgccacc aatgcgctat caggagacca tgagtgccat   3060
caggacatgg gtccagcagt cagaaaccaa actctccata cctcaactta gtgtcaccga   3120
ctatgaaatc atggagcaga gactcgggga attgcaggct ttacaaagtt ctctgcaaga   3180
gcaacaaagt ggcctatact atctcagcac cactgtgaaa gagatgtcga agaaagcgcc   3240
ctctgaaatt agccggaaat atcaatcaga atttgaagaa attgagggac gctggaagaa   3300
gctctcctcc cagctggttg agcattgtca aaagctagag gagcaaatga ataaactccg   3360
aaaaattcag aatcacatac aaaccctgaa gaaatggatg gctgaagttg atgtttttct   3420
gaaggaggaa tggcctgccc ttggggattc agaaattcta aaaaagcagc tgaaacagtg   3480
cagactttta gtcagtgata ttcagacaat tcagcccagt ctaaacagtg tcaatgaagg   3540
tgggcagaag ataaagaatg aagcagagcc agagtttgct tcgagacttg agacagaact   3600
caaagaactt aacactcagt gggatcacat gtgccaacag gtctatgcca gaaaggaggc   3660
cttgaaggga ggtttggaga aaactgtaag cctccagaaa gatctatcag agatgcacga   3720
atggatgaca caagctgaag aagagtatct tgagagagat tttgaatata aaactccaga   3780
tgaattacag aaagcagttg aagagatgaa gagagctaaa gaagaggccc aacaaaaaga   3840
agcgaaagtg aaactcctta ctgagtctgt aaatagtgtc atagctcaag ctccacctgt   3900
agcacaagag gccttaaaaa aggaacttga aactctaacc accaactacc agtggctctg   3960
cactaggctg aatgggaaat gcaagacttt ggaagaagtt tgggcatgtt ggcatgagtt   4020
attgtcatac ttggagaaag caaacaagtg gctaaatgaa gtagaattta aacttaaaac   4080
cactgaaaac attcctggcg gagctgagga aatctctgag gtgctagatt cacttgaaaa   4140
tttgatgcga cattcagagg ataacccaaa tcagattcgc atattggcac agaccctaac   4200
agatggcgga gtcatggatg agctaatcaa tgaggaactt gagacattta attctcgttg   4260
gagggaacta catgaagagg ctgtaaggag gcaaaagttg cttgaacaga gcatccagtc   4320
tgcccaggag actgaaaaat ccttacactt aatccaggag tccctcacat tcattgacaa   4380
gcagttggca gcttatattg cagacaaggt ggacgcagct caaatgcctc aggaagccca   4440
gaaaatccaa tctgatttga caagtcatga gatcagttta gaagaaatga agaaacataa   4500
tcaggggaag gaggctgccc aaagagtcct gtctcagatt gatgttgcac agaaaaaatt   4560
acaagatgtc tccatgaagt ttcgattatt ccagaaacca gccaattttg agctgcgtct   4620
acaagaaagt aagatgattt tagatgaagt gaagatgcac ttgcctgcat tggaaacaaa   4680
gagtgtggaa caggaagtag tacagtcaca gctaaatcat tgtgtgaact tgtataaaag   4740
tctgagtgaa gtgaagtctg aagtggaaat ggtgataaag actggacgtc agattgtaca   4800
gaaaaagcag acggaaaatc ccaaagaact tgatgaaaga gtaacagctt tgaaattgca   4860
ttataatgag ctgggagcaa aggtaacaga aagaaagcaa cagttggaga aatgcttgaa   4920
attgtcccgt aagatgcgaa aggaaatgaa tgtcttgaca gaatggctgg cagctacaga   4980
tatggaattg acaaagagat cagcagttga aggaatgcct agtaatttgg attctgaagt   5040
tgcctgggga aaggctactc aaaaagagat tgagaaacag aaggtgcacc tgaagagtat   5100
cacagaggta ggagaggcct tgaaaacagt tttgggcaag aaggagacgt tggtggaaga   5160
taaactcagt cttctgaata gtaactggat agctgtcacc tcccgagcag aagagtggtt   5220
```

-continued

```
aaatcttttg ttggaatacc agaaacacat ggaaactttt gaccagaatg tggaccacat   5280
cacaaagtgg atcattcagg ctgacacact tttggatgaa tcagagaaaa agaaacccca   5340
gcaaaaagaa gacgtgctta agcgtttaaa ggcagaactg aatgacatac gcccaaaggt   5400
ggactctaca cgtgaccaag cagcaaactt gatggcaaac cgcggtgacc actgcaggaa   5460
attagtagag ccccaaatct cagagctcaa ccatcgattt gcagccattt cacacagaat   5520
taagactgga aaggcctcca ttcctttgaa ggaattggag cagtttaact cagatataca   5580
aaaattgctt gaaccactgg aggctgaaat tcagcagggg gtgaatctga aagaggaaga   5640
cttcaataaa gatatgaatg aagacaatga gggtactgta aaagaattgt tgcaaagagg   5700
agacaactta caacaaagaa tcacagatga gagaaagaga gaggaaataa agataaaaca   5760
gcagctgtta cagacaaaac ataatgctct caaggatttg aggtctcaaa gaagaaaaaa   5820
ggctctagaa atttctcatc agtggtatca gtacaagagg caggctgatg atctcctgaa   5880
atgcttggat gacattgaaa aaaaattagc cagcctacct gagcccagag atgaaaggaa   5940
aataaaggaa attgatcggg aattgcagaa gaagaaagag gagctgaatg cagtgcgtag   6000
gcaagctgag ggcttgtctg aggatggggc cgcaatggca gtggagccaa ctcagatcca   6060
gctcagcaag cgctggcggg aaattgagag caaatttgct cagtttcgaa gactcaactt   6120
tgcacaaatt cacactgtcc gtgaagaaac gatgatggtg atgactgaag acatgccttt   6180
ggaaatttct tatgtgcctt ctacttattt gactgaaatc actcatgtct cacaagccct   6240
attagaagtg gaacaacttc tcaatgctcc tgacctctgt gctaaggact ttgaagatct   6300
ctttaagcaa gaggagtctc tgaagaatat aaaagatagt ctacaacaaa gctcaggtcg   6360
gattgacatt attcatagca agaagacagc agcattgcaa agtgcaacgc ctgtggaaag   6420
ggtgaagcta caggaagctc tctcccagct tgatttccaa tgggaaaaag ttaacaaaat   6480
gtacaaggac cgacaagggc gatttgacag atctgttgag aaatggcggc gttttcatta   6540
tgatataaag atatttaatc agtggctaac agaagctgaa cagtttctca gaaagacaca   6600
aattcctgag aattgggaac atgctaaata caaatggtat cttaaggaac tccaggatgg   6660
cattgggcag cggcaaactg ttgtcagaac attgaatgca actggggaag aaataattca   6720
gcaatcctca aaaacagatg ccagtattct acaggaaaaa ttgggaagcc tgaatctgcg   6780
gtggcaggag gtctgcaaac agctgtcaga cagaaaaaag aggctagaag aacaaaagaa   6840
tatcttgtca gaatttcaaa gagatttaaa tgaatttgtt ttatggttgg aggaagcaga   6900
taacattgct agtatcccac ttgaacctgg aaaagagcag caactaaaag aaaagcttga   6960
gcaagtcaag ttactggtgg aagagttgcc cctgcgccag ggaattctca aacaattaaa   7020
tgaaactgga ggacccgtgc ttgtaagtgc tcccataagc ccagaagagc aagataaact   7080
tgaaaataag ctcaagcaga caaatctcca gtggataaag gtttccagag ctttacctga   7140
gaaacaagga gaaattgaag ctcaaataaa agaccttggg cagcttgaaa aaaagcttga   7200
agaccttgaa gagcagttaa atcatctgct gctgtggtta tctcctatta ggaatcagtt   7260
ggaaatttat aaccaaccaa accaagaagg accatttgac gttcaggaaa ctgaaatagc   7320
agttcaagct aaacaaccgg atgtggaaga gattttgtct aaagggcagc atttgtacaa   7380
ggaaaaacca gccactcagc cagtgaagag gaagttagaa gatctgagct ctgagtggaa   7440
ggcggtaaac cgtttacttc aagagctgag ggcaaagcag cctgacctag ctcctggact   7500
gaccactatt ggagcctctc ctactcagac tgttactctg gtgacacaac ctgtggttac   7560
```

-continued

```
taaggaaact gccatctcca aactagaaat gccatcttcc ttgatgttgg aggtacctgc   7620
tctggcagat ttcaaccggg cttggacaga acttaccgac tggctttctc tgcttgatca   7680
agttataaaa tcacagaggg tgatggtggg tgaccttgag gatatcaacg agatgatcat   7740
caagcagaag gcaacaatgc aggatttgga acagaggcgt ccccagttgg aagaactcat   7800
taccgctgcc caaaatttga aaaacaagac cagcaatcaa gaggctagaa caatcattac   7860
ggatcgaatt gaaagaattc agaatcagtg ggatgaagta caagaacacc ttcagaaccg   7920
gaggcaacag ttgaatgaaa tgttaaagga ttcaacacaa tggctggaag ctaaggaaga   7980
agctgagcag gtcttaggac aggccagagc caagcttgag tcatggaagg agggtcccta   8040
tacagtagat gcaatccaaa agaaaatcac agaaaccaag cagttggcca aagacctccg   8100
ccagtggcag acaaatgtag atgtggcaaa tgacttggcc ctgaaacttc tccgggatta   8160
ttctgcagat gataccagaa aagtccacat gataacagag aatatcaatg cctcttggag   8220
aagcattcat aaaagggtga gtgagcgaga ggctgctttg gaagaaactc atagattact   8280
gcaacagttc cccctggacc tggaaaagtt tcttgcctgg cttacagaag ctgaaacaac   8340
tgccaatgtc ctacaggatg ctacccgtaa ggaaaggctc ctagaagact ccaagggagt   8400
aaaagagctg atgaaacaat ggcaagacct ccaaggtgaa attgaagctc acacagatgt   8460
ttatcacaac ctggatgaaa acagccaaaa aatcctgaga tccctggaag gttccgatga   8520
tgcagtcctg ttacaaagac gtttggataa catgaacttc aagtggagtg aacttcggaa   8580
aaagtctctc aacattaggt cccatttgga agccagttct gaccagtgga agcgtctgca   8640
cctttctctg caggaacttc tggtgtggct acagctgaaa gatgatgaat taagccggca   8700
ggcacctatt ggaggcgact ttccagcagt tcagaagcag aacgatgtac atagggcctt   8760
caagagggaa ttgaaaacta aagaacctgt aatcatgagt actcttgaga ctgtacgaat   8820
atttctgaca gagcagcctt tggaaggact agagaaactc taccaggagc ccagagagct   8880
gcctcctgag gagagagccc agaatgtcac tcggcttcta cgaaagcagg ctgaggaggt   8940
caatactgag tgggaaaaat tgaacctgca ctccgctgac tggcagagaa aaatagatga   9000
gacccttgaa agactccagg aacttcaaga ggccacggat gagctggacc tcaagctgcg   9060
ccaagctgag gtgatcaagg gatcctggca gcccgtgggc gatctcctca ttgactctct   9120
ccaagatcac ctcgagaaag tcaaggcact tcgaggagaa attgcgcctc tgaaagagaa   9180
cgtgagccac gtcaatgacc ttgctcgcca gcttaccact ttgggcattc agctctcacc   9240
gtataacctc agcactctgg aagacctgaa caccagatgg aagcttctgc aggtggccgt   9300
cgaggaccga gtcaggcagc tgcatgaagc ccacagggac tttggtccag catctcagca   9360
ctttctttcc acgtctgtcc agggtccctg ggagagagcc atctcgccaa acaaagtgcc   9420
ctactatatc aaccacgaga ctcaaacaac ttgctgggac catcccaaaa tgacagagct   9480
ctaccagtct ttagctgacc tgaataatgt cagattctca gcttatagga ctgccatgaa   9540
actccgaaga ctgcagaagg ccctttgctt ggatctcttg agcctgtcag ctgcatgtga   9600
tgccttggac cagcacaacc tcaagcaaaa tgaccagccc atggatatcc tgcagattat   9660
taattgtttg accactattt atgaccgcct ggagcaagag cacaacaatt tggtcaacgt   9720
ccctctctgc gtggatatgt gtctgaactg gctgctgaat gtttatgata cgggacgaac   9780
agggaggatc cgtgtcctgt cttttaaaac tggcatcatt tccctgtgta aagcacattt   9840
ggaagacaag tacagatacc ttttcaagca agtggcaagt tcaacaggat tttgtgacca   9900
gcgcaggctg ggcctccttc tgcatgattc tatccaaatt ccaagacagt tgggtgaagt   9960
```

-continued

```
tgcatccttt gggggcagta acattgagcc aagtgtccgg agctgcttcc aatttgctaa  10020
taataagcca gagatcgaag cggccctctt cctagactgg atgagactgg aaccccagtc  10080
catggtgtgg ctgcccgtcc tgcacagagt ggctgctgca gaaactgcca agcatcaggc  10140
caaatgtaac atctgcaaag agtgtccaat cattggattc aggtacagga gtctaaagca  10200
ctttaattat gacatctgcc aaagctgctt tttttctggt cgagttgcaa aaggccataa  10260
aatgcactat cccatggtgg aatattgcac tccgactaca tcaggagaag atgttcgaga  10320
ctttgccaag gtactaaaaa acaaatttcg aaccaaaagg tattttgcga agcatccccg  10380
aatgggctac ctgccagtgc agactgtctt agagggggac aacatggaaa ctcccgttac  10440
tctgatcaac ttctggccag tagattctgc gcctgcctcg tcccctcagc tttcacacga  10500
tgatactcat tcacgcattg aacattatgc tagcaggcta gcagaaatgg aaaacagcaa  10560
tggatcttat ctaaatgata gcatctctcc taatgagagc atagatgatg aacatttgtt  10620
aatccagcat tactgccaaa gtttgaacca ggactccccc ctgagccagc ctcgtagtcc  10680
tgcccagatc ttgatttcct tagagagtga ggaaagaggg gagctagaga gaatcctagc  10740
agatcttgag gaagaaaaca ggaatctgca agcagaatat gaccgtctaa agcagcagca  10800
cgaacataaa ggcctgtccc cactgccgtc ccctcctgaa atgatgccca cctctcccca  10860
gagtccccgg gatgctgagc tcattgctga ggccaagcta ctgcgtcaac acaaaggccg  10920
cctggaagcc aggatgcaaa tcctggaaga ccacaataaa cagctggagt cacagttaca  10980
caggctaagg cagctgctgg agcaacccca ggcagaggcc aaagtgaatg gcacaacggt  11040
gtcctctcct tctacctctc tacagaggtc cgacagcagt cagcctatgc tgctccgagt  11100
ggttggcagt caaacttcgg actccatggg tgaggaagat cttctcagtc ctccccagga  11160
cacaagcaca gggttagagg aggtgatgga gcaactcaac aactccttcc ctagttcaag  11220
aggaagaaat acccctggaa agccaatgag agaggacaca atgtaggaag tcttttccac  11280
atggcagatg atttgggcag agcgatggag tccttagtat cagtcatgac agatgaagaa  11340
ggagcagaat aaatgtttta caactcctga ttcccgcatg gtttttataa tattcataca  11400
acaaagagga ttagacagta agagtttaca agaaataaat ctatattttt gtgaagggta  11460
gtggtattat actgtagatt tcagtagttt ctaagtctgt tattgttttg ttaacaatgg  11520
caggttttac acgtctatgc aattgtacaa aaaagttata agaaaactac atgtaaaatc  11580
ttgatagcta aataacttgc catttcttta tatggaacgc attttgggtt gtttaaaaat  11640
ttataacagt tataaagaaa gattgtaaac taaagtgtgc tttataaaaa aaagttgttt  11700
ataaaaaccc ctaaaaacaa aacaaacaca cacacacaca catacacaca cacacacaaa  11760
actttgaggc agcgcattgt tttgcatcct tttggcgtga tatccatatg aaattcatgg  11820
ctttttcttt ttttgcatat taaagataag acttcctcta ccaccacacc aaatgactac  11880
tacacactgc tcatttgaga actgtcagct gagtggggca ggcttgagtt ttcatttcat  11940
atatctatat gtctataagt atataaatac tatagttata tagataaaga gatacgaatt  12000
tctatagact gactttttcc attttttaaa tgttcatgtc acatcctaat agaaagaaat  12060
tacttctagt cagtcatcca ggcttacctg cttggtctag aatggatttt tcccggagcc  12120
ggaagccagg aggaaactac accacactaa aacattgtct acagctccag atgtttctca  12180
ttttaaacaa ctttccactg acaacgaaag taaagtaaag tattggattt ttttaaaggg  12240
aacatgtgaa tgaatacaca ggacttatta tatcagagtg agtaatcggt tggttggttg  12300
```

-continued

```
attgattgat tgattgatac attcagcttc ctgctgctag caatgccacg atttagattt  12360

aatgatgctt cagtggaaat caatcagaag gtattctgac cttgtgaaca tcagaaggta  12420

ttttttaact cccaagcagt agcaggacga tgatagggct ggagggctat ggattcccag  12480

cccatccctg tgaaggagta ggccactctt taagtgaagg attggatgat tgttcataat  12540

acataaagtt ctctgtaatt acaactaaat tattatgccc tcttctcaca gtcaaaagga  12600

actgggtggt ttggtttttg ttgctttttt agatttattg tcccatgtgg gatgagtttt  12660

taaatgccac aagacataat ttaaaataaa taaactttgg gaaaaggtgt aagacagtag  12720

ccccatcaca tttgtgatac tgacaggtat caacccagaa gcccatgaac tgtgtttcca  12780

tcctttgcat ttctctgcga gtagttccac acaggtttgt aagtaagtaa gaaagaaggc  12840

aaattgattc aaatgttaca aaaaaaccct tcttggtgga ttagacaggt taaatatata  12900

aacaaacaaa caaaaattgc tcaaaaaaga ggagaaaagc tcaagaggaa aagctaagga  12960

ctggtaggaa aaagctttac tctttcatgc cattttattt ctttttgatt tttaaatcat  13020

tcattcaata gataccaccg tgtgacctat aattttgcaa atctgttacc tctgacatca  13080

agtgtaatta gcttttggag agtgggctga catcaagtgt aattagcttt tggagagtgg  13140

gttttgtcca ttattaataa ttaattaatt aacatcaaac acggcttctc atgctatttc  13200

tacctcactt tggttttggg gtgttcctga taattgtgca cacctgagtt cacagcttca  13260

ccacttgtcc attgcgttat tttctttttc ctttataatt ctttcttttt ccttcataat  13320

tttcaaaaga aaacccaaag ctctaaggta acaaattacc aaattacatg aagatttggt  13380

ttttgtcttg cattttttttc ctttatgtga cgctggacct tttctttacc caaggatttt  13440

taaaactcag atttaaaaca aggggttact ttacatccta ctaagaagtt taagtaagta  13500

agtttcattc taaaatcaga ggtaaataga gtgcataaat aattttgttt taatcttttt  13560

gtttttcttt tagacacatt agctctggag tgagtctgtc ataatatttg aacaaaaatt  13620

gagagcttta ttgctgcatt ttaagcataa ttaatttgga cattatttcg tgttgtgttc  13680

tttataacca ccgagtatta aactgtaaat cataatgtaa ctgaagcata aacatcacat  13740

ggcatgtttt gtcattgttt tcaggtactg agttcttact tgagtatcat aatatattgt  13800

gttttaacac caacactgta acatttacga attatttttt taaacttcag ttttactgca  13860

ttttcacaac atatcagact tcaccaaata tatgccttac tattgtatta tagtactgct  13920

ttactgtgta tctcaataaa gcacgcagtt atgttac                           13957
```

```
<210> SEQ ID NO 23
<211> LENGTH: 10302
<212> TYPE: DNA
<213> ORGANISM: Homo sapiens

<400> SEQUENCE: 23
```

```
atggccaagt atggagaaca tgaagccagt cctgacaatg ggcagaacga attcagtgat     60

atcattaagt ccagatctga tgaacacaat gacgtacaga agaaaacctt taccaaatgg    120

ataaatgctc gattttcaaa gagtgggaaa ccacccatca atgatatgtt cacagacctc    180

aaagatggaa ggaagctatt ggatcttcta gaaggcctca caggaacatc actgccaaag    240

gaacgtggtt ccacaagggt acatgcctta aataacgtca acagagtgct gcaggtttta    300

catcagaaca atgtggaatt agtgaatata gggggaactg acattgtgga tggaaatcac    360

aaactgactt tggggttact ttggagcatc attttgcact ggcaggtgaa agatgtcatg    420

aaggatgtca tgtcggacct gcagcagacg aacagtgaga agatcctgct cagctgggtg    480
```

-continued

```
cgtcagacca ccaggcccta cagccaagtc aacgtcctca acttcaccac cagctggaca    540
gatggactcg cctttaatgc tgtcctccac cgacataaac ctgatctctt cagctgggat    600
aaagttgtca aaatgtcacc aattgagaga cttgaacatg ccttcagcaa ggctcaaact    660
tatttgggaa ttgaaaagct gttagatcct gaagatgttg ccgttcggct tcctgacaag    720
aaatccataa ttatgtattt aacatctttg tttgaggtgc tacctcagca agtcaccata    780
gacgccatcc gtgaggtaga gacactccca aggaaatata aaaaagaatg tgaagaagag    840
gcaattaata tacagagtac agcgcctgag gaggagcatg agagtccccg agctgaaact    900
cccagcactg tcactgaggt cgacatggat ctggacagct atcagattgc gttggaggaa    960
gtgctgacct ggttgctttc tgctgaggac actttccagg agcaggatga tatttctgat   1020
gatgttgaag aagtcaaaga ccagtttgca acccatgaag cttttatgat ggaactgact   1080
gcacaccaga gcagtgtggg cagcgtcctg caggcaggca accaactgat aacacaagga   1140
actctgtcag acgaagaaga atttgagatt caggaacaga tgaccctgct gaatgctaga   1200
tgggaggctc ttagggtgga gagtatggac agacagtccc ggctgcacga tgtgctgatg   1260
gaactgcaga agaagcaact gcagcagctc tccgcctggt taacactcac agaggagcgc   1320
attcagaaga tggaaacttg ccccctggat gatgatgtaa aatctctaca aaagctgcta   1380
gaagaacata aaagtttgca aagtgatctt gaggctgaac aggtgaaagt aaattcacta   1440
actcacatgg tggtcattgt tgatgaaaac agtggtgaga gcgctacagc tatcctagaa   1500
gaccagttac agaaacttgg tgagcgctgg acagcagtat gccgttggac tgaagaacgc   1560
tggaataggt tacaagaaat caatatattg tggcaggaat tattggaaga acagtgcttg   1620
ttgaaagctt ggttaaccga aaaagaagag gctttaaata aagtccagac aagcaacttc   1680
aaagaccaaa aggaactaag tgtcagtgtt cgacgtctgg ctattttgaa ggaagacatg   1740
gaaatgaagc gtcaaacatt ggatcagctg agtgagattg gccaggatgt gggacaatta   1800
cttgataatt ccaaggcatc taagaagatc aacagtgact cagaggaact gactcaaaga   1860
tgggattctt tggttcagag actagaagat tcctccaacc aggtgactca ggctgtagca   1920
aagctgggga tgtctcagat tcctcagaag gaccttttgg agactgttcg tgtaagagaa   1980
caagcaatta caaaaaaatc taagcaggaa ctgcctcctc ctcctccccc aaagaagaga   2040
cagatccatg tggatattga agctaagaaa aagtttgatg ctataagtgc agagctgttg   2100
aactggattt tgaaatggaa aactgccatt cagaccacag agataaaaga gtatatgaag   2160
atgcaagaca cttccgaaat gaaaaagaag ttgaaggcat tagaaaaaga acagagagaa   2220
agaatcccca gagcagatga attaaaccaa actggacaaa tccttgtgga gcaaatggga   2280
aaagaaggcc ttcctactga agaaataaaa aatgttctgg agaaggtttc atcagaatgg   2340
aagaatgtat ctcaacattt ggaagatcta gaaagaaaga ttcagctaca ggaagatata   2400
aatgcttatt tcaagcagct tgatgagctt gaaaaggtca tcaagacaaa ggaggagtgg   2460
gtaaaacaca cttccatttc tgaatcttcc cggcagtcct tgccaagctt gaaggattcc   2520
tgtcagcggg aattgacaaa tcttcttggc cttcacccca aaattgaaat ggctcgtgca   2580
agctgctcgg ccctgatgtc tcagccttct gccccagatt ttgtccagcg gggcttcgat   2640
agctttctgg gccgctacca agctgtacaa gaggctgtag aggatcgtca acaacatcta   2700
gagaatgaac tgaagggcca acctggacat gcatatctgg aaacattgaa aacactgaaa   2760
gatgtgctaa atgattcaga aaataaggcc caggtgtctc tgaatgtcct taatgatctt   2820
```

-continued

```
gccaaggtgg agaaggccct gcaagaaaaa aagacccttg atgaaatcct tgagaatcag   2880
aaacctgcat tacataaact tgcagaagaa acaaaggctc tggagaaaaa tgttcatcct   2940
gatgtagaaa aattatataa gcaagaattt gatgatgtgc aaggaaagtg gaacaagcta   3000
aaggtcttgg tttccaaaga tctacatttg cttgaggaaa ttgctctcac actcagagct   3060
tttgaggccg attcaacagt cattgagaag tggatggatg gcgtgaaaga cttcttaatg   3120
aaacagcagg ctgcccaagg agacgacgca ggtctacaga ggcagttaga ccagtgctct   3180
gcatttgtta atgaaataga aacaattgaa tcatctctga aaaacatgaa ggaaatagag   3240
actaatcttc gaagtggtcc agttgctgga ataaaaactt gggtgcagac aagactaggt   3300
gactaccaaa ctcaactgga gaaacttagc aaggagatcg ctactcaaaa aagtaggttg   3360
tctgaaagtc aagaaaaagc tgcgaacctg aagaaagact tggcagagat gcaggaatgg   3420
atgacccagg ccgaggaaga atatttggag cgggattttg agtacaagtc accagaagag   3480
cttgagagtg ctgtggaaga gatgaagagg gcaaaagagg atgtgttgca gaaggaggtg   3540
agagtgaaga ttctcaagga caacatcaag ttattagctg ccaaggtgcc ctctggtggc   3600
caggagttga cgtctgagct gaatgttgtg ctggagaatt accaacttct ttgtaataga   3660
attcgaggaa agtgccacac gctagaggag gtctggtctt gttggattga actgcttcac   3720
tatttggatc ttgaaactac ctggttaaac actttggaag agcggatgaa gagcacagag   3780
gtcctgcctg agaagacgga tgctgtcaac gaagccctgg agtctctgga atctgttctg   3840
cgccacccgg cagataatcg cacccagatt cgagagcttg gccagactct gattgatggg   3900
gggatcctgg atgatataat cagtgagaaa ctggaggctt tcaacagccg atatgaagat   3960
ctaagtcacc tggcagagag caagcagatt tctttggaaa agcaactcca ggtgctgcgg   4020
gaaactgacc agatgcttca agtcttgcaa gagagcttgg gggagctgga caaacagctc   4080
accacatacc tgactgacag gatagatgct ttccaagttc cacaggaagc tcagaaaatc   4140
caagcagaga tctcagccca tgagctaacc ctagaggagt tgagaagaaa tatgcgttct   4200
cagcccctga cctccccaga gagtaggact gccagaggag gaagtcagat ggatgtgcta   4260
cagaggaaac tccgagaggt gtccacaaag ttccagcttt tccagaagcc agctaacttc   4320
gagcagcgca tgctggactg caagcgtgtg ctggatggcg tgaaagcaga acttcacgtt   4380
ctggatgtga aggacgtaga ccctgacgtc atacagacgc acctggacaa gtgtatgaaa   4440
ctgtataaaa ctttgagtga agtcaaactt gaagtggaaa ctgtgattaa aacaggaaga   4500
catattgtcc agaaacagca aacggacaac ccaaaaggga tggatgagca gctgacttcc   4560
ctgaaggttc tttacaatga cctgggcgca caggtgacag aaggaaaaca ggatctggaa   4620
agagcatcac agttggcccg gaaaatgaag aaagaggctg cttctctctc tgaatggctt   4680
tctgctactg aaactgaatt ggtacagaag tccacttcag aaggtctgct tggtgacttg   4740
gatacagaaa tttcctgggc taaaaatgtt ctgaaggatc tggaaaagag aaaagctgat   4800
ttaaatacca tcacagagag tagtgctgcc ctgcaaaact tgattgaggg cagtgagcct   4860
attttagaag agaggctctg cgtccttaac gctgggtgga gccgagttcg tacctggact   4920
gaagattggt gcaatacctt gatgaaccat cagaaccagc tagaaatatt tgatgggaac   4980
gtggctcaca taagtacctg gctttatcaa gctgaagctc tattggatga aattgaaaag   5040
aaaccaacaa gtaaacagga agaaattgtg aagcgtttag tatctgagct ggatgatgcc   5100
aacctccagg ttgaaaatgt ccgcgatcaa gcccttattt tgatgaatgc ccgtggaagc   5160
tcaagcaggg agcttgtaga accaaagtta gctgagctga ataggaactt tgaaaaggtg   5220
```

-continued

```
tctcaacata tcaaaagtgc caaattgcta attgctcagg aaccattata ccaatgtttg   5280
gtcaccactg aaacatttga aactggtgtg cctttctctg acttggaaaa attagaaaat   5340
gacatagaaa atatgttaaa atttgtggaa aaacacttgg aatccagtga tgaagatgaa   5400
aagatggatg aggagagtgc ccagattgag gaagttctac aaagaggaga agaaatgtta   5460
catcaaccta tggaagataa taaaaaagaa aagatccgtt tgcaattatt acttttgcat   5520
actagataca acaaaattaa ggcaatccct attcaacaga ggaaaatggg tcaacttgct   5580
tctggaatta gatcatcact tcttcctaca gattatctgg ttgaaattaa caaaatttta   5640
ctttgcatgg atgatgttga attatcgctt aatgttccag agctcaacac tgctatttac   5700
gaagacttct cttttcagga agactctctg aagaatatca aagaccaact ggacaaactt   5760
ggagagcaga ttgcagtcat tcatgaaaaa cagccagatg tcatccttga agcctctgga   5820
cctgaagcca ttcagatcag agatacactt actcagctga atgcaaaatg ggacagaatt   5880
aatagaatgt acagtgatcg gaaaggttgt tttgacaggg caatggaaga atggagacag   5940
ttccattgtg accttaatga cctcacacag tggataacag aggctgaaga attactggtt   6000
gatacctgtg ctccaggtgg cagcctggac ttagagaaag ccaggataca tcagcaggaa   6060
cttgaggtgg gcatcagcag ccaccagccc agttttgcag cactaaaccg aactggggat   6120
gggattgtgc agaaactctc ccaggcagat ggaagcttct tgaaagaaaa actggcaggt   6180
ttaaaccaac gctgggatgc aattgttgca gaagtgaagg ataggcagcc aaggctaaaa   6240
ggagaaagta agcaggtgat gaagtacagg catcagctag atgagattat ctgttggtta   6300
acaaaggctg agcatgctat gcaaaagaga tcaaccaccg aattgggaga aaacctgcaa   6360
gaattaagag acttaactca agaaatggaa gtacatgctg aaaaactcaa atggctgaat   6420
agaactgaat tggagatgct ttcagataaa agtctgagtt tacctgaaag ggataaaatt   6480
tcagaaagct taaggactgt aaatatgaca tggaataaga tttgcagaga ggtgcctacc   6540
accctgaagg aatgcatcca ggagcccagt tctgtttcac agacaaggat tgctgctcat   6600
cctaatgtcc aaaaggtggt gctagtatca tctgcgtcag atattcctgt tcagtctcat   6660
cgtacttcgg aaatttcaat tcctgctgat cttgataaaa ctataacaga actagccgac   6720
tggctggtat taatcgacca gatgctgaag tccaacattg tcactgttgg ggatgtagaa   6780
gagatcaata agaccgtttc ccgaatgaaa attacaaagg ctgacttaga acagcgccat   6840
cctcagctgg attatgtttt tacattggca cagaatttga aaaataaagc ttccagttca   6900
gatatgagaa cagcaattac agaaaaattg gaaagggtca agaaccagtg ggatggcacc   6960
cagcatggcg ttgagctaag acagcagcag cttgaggaca tgattattga cagtcttcag   7020
tgggatgacc atagggagga gactgaagaa ctgatgagaa aatatgaggc tcgactctat   7080
attcttcagc aagcccgacg ggatccactc accaaacaaa tttctgataa ccaaatactg   7140
cttcaagaac tgggtcctgg agatggtatc gtcatggcgt tcgataacgt cctgcagaaa   7200
ctcctggagg aatatgggag tgatgacaca aggaatgtga aagaaaccac agagtactta   7260
aaaacatcat ggatcaatct caaacaaagt attgctgaca gacagaacgc cttggaggct   7320
gagtggagga cggtgcaggc ctctcgcaga gatctggaaa acttcctgaa gtggatccaa   7380
gaagcagaga ccacagtgaa tgtgcttgtg gatgcctctc atcgggagaa tgctcttcag   7440
gatagtatct tggccaggga actcaaacag cagatgcagg acatccaggc agaaattgat   7500
gcccacaatg acatatttaa aagcattgac ggaaacaggc agaagatggt aaaagctttg   7560
```

-continued

```
ggaaattctg aagaggctac tatgcttcaa catcgactgg atgatatgaa ccaaagatgg   7620
aatgacttaa aagcaaaatc tgctagcatc agggcccatt tggaggccag cgctgagaag   7680
tggaacaggt tgctgatgtc cttagaagaa ctgatcaaat ggctgaatat gaaagatgaa   7740
gagcttaaga aacaaatgcc tattggagga gatgttccag ccttacagct ccagtatgac   7800
cattgtaagg ccctgagacg ggagttaaag gagaaagaat attctgtcct gaatgctgtc   7860
gaccaggccc gagttttctt ggctgatcag ccaattgagg cccctgaaga gccaagaaga   7920
aacctacaat caaaaacaga attaactcct gaggagagag cccaaaagat tgccaaagcc   7980
atgcgcaaac agtcttctga agtcaaagaa aaatgggaaa gtctaaatgc tgtaactagc   8040
aattggcaaa agcaagtgga caaggcattg gagaaactca gagacctgca gggagctatg   8100
gatgacctgg acgctgacat gaaggaggca gagtccgtgc ggaatggctg gaagcccgtg   8160
ggagacttac tcattgactc gctgcaggat cacattgaaa aaatcatggc atttagagaa   8220
gaaattgcac caatcaactt taaagttaaa acggtgaatg atttatccag tcagctgtct   8280
ccacttgacc tgcatccctc tctaaagatg tctcgccagc tagatgacct taatatgcga   8340
tggaaacttt tacaggtttc tgtggatgat cgccttaaac agcttcagga agcccacaga   8400
gattttggac catcctctca gcattttctc tctacgtcag tccagctgcc gtggcaaaga   8460
tccatttcac ataataaagt gccctattac atcaaccatc aaacacagac cacctgttgg   8520
gaccatccta aaatgaccga actctttcaa tcccttgctg acctgaataa tgtacgtttt   8580
tctgcctacc gtacagcaat caaaatccga agactacaaa aagcactatg tttggatctc   8640
ttagagttga gtacaacaaa tgaaattttc aaacagcaca agttgaacca aaatgaccag   8700
ctcctcagtg ttccagatgt catcaactgt ctgacaacaa cttatgatgg acttgagcaa   8760
atgcataagg acctggtcaa cgttccactc tgtgttgata tgtgtctcaa ttggttgctc   8820
aatgtctatg acacgggtcg aactggaaaa attagagtgc agagtctgaa gattggatta   8880
atgtctctct ccaaaggtct cttggaagaa aaatacagat atctctttaa ggaagttgcg   8940
gggccgacag aaatgtgtga ccagaggcag ctgggcctgt tacttcatga tgccatccag   9000
atcccccggc agctaggtga agtagcagct tttggaggca gtaatattga gcctagtgtt   9060
cgcagctgct tccaacagaa taacaataaa ccagaaataa gtgtgaaaga gtttatagat   9120
tggatgcatt tggaaccaca gtccatggtt tggctcccag ttttacatcg agtggcagca   9180
gcggagactg caaaacatca ggccaaatgc aacatctgta aagaatgtcc aattgtcggg   9240
ttcaggtata gaagccttaa gcattttaac tatgatgtct gccagagttg tttcttttcg   9300
ggtcgaacag caaaaggtca caaattacat tacccaatgg tggaatattg tatacctaca   9360
acatctgggg aagatgtacg agacttcaca aaggtactta agaacaagtt caggtcgaag   9420
aagtactttg ccaaacaccc tcgacttggt tacctgcctg tccagacagt tcttgaaggt   9480
gacaacttag agactcctat cacactcatc agtatgtggc cagagcacta tgacccctca   9540
caatctcctc aactgtttca tgatgacacc cattcaagaa tagaacaata tgccacacga   9600
ctggcccaga tggaaaggac taatgggtct ttttctcactg atagcagctc caccacagga   9660
agtgtggaag acgagcacgc cctcatccag cagtattgcc aaacactcgg aggagagtcc   9720
ccagtgagcc agccgcagag cccagctcag atcctgaagt cagtagagag ggaagaacgt   9780
ggagaactgg agaggatcat tgctgacctg gaggaagaac aaagaaatct acaggtggag   9840
tatgagcagc tgaaggacca gcacctccga agggggctcc ctgtcggttc accgccagag   9900
tcgattatat ctccccatca cacgtctgag gattcagaac ttatagcaga agcaaaactc   9960
```

-continued ctcaggcagc acaaaggtcg gctggaggct aggatgcaga ttttagaaga tcacaataaa 10020
cagctggagt ctcagctcca ccgcctccga cagctgctgg agcagcctga atctgattcc 10080
cgaatcaatg gtgtttcccc atgggcttct cctcagcatt ctgcactgag ctactcgctt 10140
gatccagatg cctccggccc acagttccac caggcagcgg gagaggacct gctggcccca 10200
ccgcacgaca ccagcacgga tctcacggag gtcatggagc agattcacag cacgtttcca 10260
tcttgctgcc caaatgttcc cagcaggcca caggcaatgt ga 10302

<210> SEQ ID NO 24
<211> LENGTH: 6129
<212> TYPE: DNA
<213> ORGANISM: Homo sapiens

<400> SEQUENCE: 24
aattggaagc aaatgacatc acagcaggtc agagaaaaag ggttgagcgg caggcaccca 60
gagtagtagg tctttggcat taggagcttg agcccagacg gccctagcag ggaccccagc 120
gcccgagaga ccatgcagag gtcgcctctg gaaaaggcca gcgttgtctc caaacttttt 180
ttcagctgga ccagaccaat tttgaggaaa ggatacagac agcgcctgga attgtcagac 240
atataccaaa tcccttctgt tgattctgct gacaatctat ctgaaaaatt ggaaagagaa 300
tgggatagag agctggcttc aaagaaaaat cctaaactca ttaatgccct tcggcgatgt 360
tttttctgga gatttatgtt ctatggaatc tttttatatt taggggaagt caccaaagca 420
gtacagcctc tcttactggg aagaatcata gcttcctatg acccggataa caaggaggaa 480
cgctctatcg cgatttatct aggcataggc ttatgccttc tctttattgt gaggacactg 540
ctcctacacc cagccatttt tggccttcat cacattggaa tgcagatgag aatagctatg 600
tttagtttga tttataagaa gactttaaag ctgtcaagcc gtgttctaga taaaataagt 660
attggacaac ttgttagtct cctttccaac aacctgaaca aatttgatga aggacttgca 720
ttggcacatt tcgtgtggat cgctcctttg caagtggcac tcctcatggg gctaatctgg 780
gagttgttac aggcgtctgc cttctgtgga cttggtttcc tgatagtcct tgcccttttt 840
caggctgggc tagggagaat gatgatgaag tacagagatc agagagctgg gaagatcagt 900
gaaagacttg tgattacctc agaaatgatt gaaaatatcc aatctgttaa ggcatactgc 960
tgggaagaag caatggaaaa aatgattgaa aacttaagac aaacagaact gaaactgact 1020
cggaaggcag cctatgtgag atacttcaat agctcagcct tcttcttctc agggttcttt 1080
gtggtgtttt tatctgtgct tccctatgca ctaatcaaag gaatcatcct ccggaaaata 1140
ttcaccacca tctcattctg cattgttctg cgcatggcgg tcactcggca atttccctgg 1200
gctgtacaaa catggtatga ctctcttgga gcaataaaca aaatacagga tttcttacaa 1260
aagcaagaat ataagacatt ggaatataac ttaacgacta cagaagtagt gatggagaat 1320
gtaacagcct tctgggagga gggatttggg gaattatttg agaaagcaaa acaaaacaat 1380
aacaatagaa aaacttctaa tggtgatgac agcctcttct tcagtaattt ctcacttctt 1440
ggtactcctg tcctgaaaga tattaatttc aagatagaaa gaggacagtt gttggcggtt 1500
gctggatcca ctggagcagg caagacttca cttctaatga tgattatggg agaactggag 1560
ccttcagagg gtaaaattaa gcacagtgga agaatttcat tctgttctca gttttcctgg 1620
attatgcctg gcaccattaa agaaaatatc atctttggtg tttcctatga tgaatataga 1680
tacagaagcg tcatcaaagc atgccaacta gaagaggaca tctccaagtt tgcagagaaa 1740

-continued

```
gacaatatag ttcttggaga aggtggaatc acactgagtg gaggtcaacg agcaagaatt   1800
tctttagcaa gagcagtata caaagatgct gatttgtatt tattagactc tccttttgga   1860
tacctagatg ttttaacaga aaaagaaata tttgaaagct gtgtctgtaa actgatggct   1920
aacaaaacta ggattttggt cacttctaaa atggaacatt taaagaaagc tgacaaaata   1980
ttaattttga atgaaggtag cagctatttt tatgggacat tttcagaact ccaaaatcta   2040
cagccagact ttagctcaaa actcatggga tgtgattctt tcgaccaatt tagtgcagaa   2100
agaagaaatt caatcctaac tgagacctta caccgtttct cattagaagg agatgctcct   2160
gtctcctgga cagaaacaaa aaaacaatct tttaaacaga ctggagagtt tggggaaaaa   2220
aggaagaatt ctattctcaa tccaatcaac tctatacgaa aattttccat tgtgcaaaag   2280
actcccttac aaatgaatgg catcgaagag gattctgatg agcctttaga gagaaggctg   2340
tccttagtac cagattctga gcagggagag gcgatactgc ctcgcatcag cgtgatcagc   2400
actggcccca cgcttcaggc acgaaggagg cagtctgtcc tgaacctgat gacacactca   2460
gttaaccaag gtcagaacat tcaccgaaag acaacagcat ccacacgaaa agtgtcactg   2520
gcccctcagg caaacttgac tgaactggat atatattcaa gaaggttatc tcaagaaact   2580
ggcttggaaa taagtgaaga aattaacgaa gaagacttaa aggagtgcct ttttgatgat   2640
atggagagca taccagcagt gactacatgg aacacatacc ttcgatatat tactgtccac   2700
aagagcttaa tttttgtgct aatttggtgc ttagtaattt ttctggcaga ggtggctgct   2760
tctttggttg tgctgtggct ccttggaaac actcctcttc aagacaaagg gaatagtact   2820
catagtagaa ataacagcta tgcagtgatt atcaccagca ccagttcgta ttatgtgttt   2880
tacatttacg tgggagtagc cgacactttg cttgctatgg gattcttcag aggtctacca   2940
ctggtgcata ctctaatcac agtgtcgaaa attttacacc acaaaatgtt acattctgtt   3000
cttcaagcac ctatgtcaac cctcaacacg ttgaaagcag gtgggattct taatagattc   3060
tccaaagata tagcaatttt ggatgacctt ctgcctctta ccatatttga cttcatccag   3120
ttgttattaa ttgtgattgg agctatagca gttgtcgcag ttttacaacc ctacatcttt   3180
gttgcaacag tgccagtgat agtggctttt attatgttga gagcatattt cctccaaacc   3240
tcacagcaac tcaaacaact ggaatctgaa ggcaggagtc caattttcac tcatcttgtt   3300
acaagcttaa aaggactatg gacacttcgt gccttcggac ggcagcctta ctttgaaact   3360
ctgttccaca aagctctgaa tttacatact gccaactggt tcttgtacct gtcaacactg   3420
cgctggttcc aaatgagaat agaaatgatt tttgtcatct tcttcattgc tgttaccttc   3480
atttccattt taacaacagg agaaggagaa ggaagagttg gtattatcct gactttagcc   3540
atgaatatca tgagtacatt gcagtgggct gtaaactcca gcatagatgt ggatagcttg   3600
atgcgatctg tgagccgagt ctttaagttc attgacatgc caacagaagg taaacctacc   3660
aagtcaacca aaccatacaa gaatggccaa ctctcgaaag ttatgattat tgagaattca   3720
cacgtgaaga aagatgacat ctggccctca gggggccaaa tgactgtcaa agatctcaca   3780
gcaaaataca cagaaggtgg aaatgccata ttagagaaca tttccttctc aataagtcct   3840
ggccagaggg tgggcctctt gggaagaact ggatcaggga agagtacttt gttatcagct   3900
tttttgagac tactgaacac tgaaggagaa atccagatcg atggtgtgtc ttgggattca   3960
ataactttgc aacagtggag gaaagccttt ggagtgatac cacagaaagt atttattttt   4020
tctggaacat ttagaaaaaa cttggatccc tatgaacagt ggagtgatca agaaatatgg   4080
aaagttgcag atgaggttgg gctcagatct gtgatagaac agtttcctgg gaagcttgac   4140
```

-continued

```
tttgtccttg tggatggggg ctgtgtccta agccatggcc acaagcagtt gatgtgcttg   4200

gctagatctg ttctcagtaa ggcgaagatc ttgctgcttg atgaacccag tgctcatttg   4260

gatccagtaa cataccaaat aattagaaga actctaaaac aagcatttgc tgattgcaca   4320

gtaattctct gtgaacacag gatagaagca atgctggaat gccaacaatt tttggtcata   4380

gaagagaaca aagtgcggca gtacgattcc atccagaaac tgctgaacga gaggagcctc   4440

ttccggcaag ccatcagccc ctccgacagg gtgaagctct ttccccaccg gaactcaagc   4500

aagtgcaagt ctaagcccca gattgctgct ctgaaagagg agacagaaga agaggtgcaa   4560

gatacaaggc tttagagagc agcataaatg ttgacatggg acatttgctc atggaattgg   4620

agctcgtggg acagtcacct catggaattg gagctcgtgg aacagttacc tctgcctcag   4680

aaaacaagga tgaattaagt tttttttaa aaaagaaaca tttggtaagg ggaattgagg   4740

acactgatat gggtcttgat aaatggcttc ctggcaatag tcaaattgtg tgaaaggtac   4800

ttcaaatcct tgaagattta ccacttgtgt tttgcaagcc agattttcct gaaaaccctt   4860

gccatgtgct agtaattgga aaggcagctc taaatgtcaa tcagcctagt tgatcagctt   4920

attgtctagt gaaactcgtt aatttgtagt gttggagaag aactgaaatc atacttctta   4980

gggttatgat taagtaatga taactggaaa cttcagcggt ttatataagc ttgtattcct   5040

ttttctctcc tctccccatg atgtttagaa acacaactat attgtttgct aagcattcca   5100

actatctcat ttccaagcaa gtattagaat accacaggaa ccacaagact gcacatcaaa   5160

atatgcccca ttcaacatct agtgagcagt caggaaagag aacttccaga tcctggaaat   5220

cagggttagt attgtccagg tctaccaaaa atctcaatat ttcagataat cacaatacat   5280

cccttacctg ggaaagggct gttataatct ttcacagggg acaggatggt tcccttgatg   5340

aagaagttga tatgcctttt cccaactcca gaaagtgaca agctcacaga cctttgaact   5400

agagtttagc tggaaaagta tgttagtgca aattgtcaca ggacagccct tctttccaca   5460

gaagctccag gtagagggtg tgtaagtaga taggccatgg gcactgtggg tagacacaca   5520

tgaagtccaa gcatttagat gtataggttg atggtggtat gttttcaggc tagatgtatg   5580

tacttcatgc tgtctacact aagagagaat gagagacaca ctgaagaagc accaatcatg   5640

aattagtttt atatgcttct gttttataat tttgtgaagc aaaatttttt ctctaggaaa   5700

tatttatttt aataatgttt caaacatata ttacaatgct gtattttaaa agaatgatta   5760

tgaattacat ttgtataaaa taatttttat atttgaaata ttgacttttt atggcactag   5820

tatttttatg aaatattatg ttaaaactgg gacaggggag aacctagggt gatattaacc   5880

aggggccatg aatcaccttt tggtctggag ggaagccttg ggctgatcg agttgttgcc   5940

cacagctgta tgattcccag ccagacacag cctcttagat gcagttctga agaagatggt   6000

accaccagtc tgactgtttc catcaagggt acactgcctt ctcaactcca aactgactct   6060

taagaagact gcattatatt tattactgta agaaaatatc acttgtcaat aaaatccata   6120

catttgtgt                                                            6129
```

<210> SEQ ID NO 25
<211> LENGTH: 34125
<212> TYPE: DNA
<213> ORGANISM: Human adenovirus type 12

<400> SEQUENCE: 25

```
cctatctaat aatatacctt atactggact agtgccaata ttaaaatgaa gtgggcgtag     60
```

-continued

```
tgtgtaattt gattgggtgg aggtgtggct ttggcgtgct tgtaagtttg ggcggatgag     120
gaagtggggc gcggcgtggg agccgggcgc gccggatgtg acgttttaga cgccatttta     180
cacggaaatg atgtttttg ggcgttgttt gtgcaaattt tgtgttttag gcgcgaaaac     240
tgaaatgcgg aagtgaaaat tgatgacggc aattttatta taggcgcgga atatttaccg     300
agggcagagt gaactctgag cctctacgtg tgggtttcga tacgtgagcg acggggaaac     360
tccacgttgg cgctcaaagg gcgcgtttat tgttctgtca gctgatcgtt tgggtattta     420
atgccgccgt gttcgtcaag aggccactct tgagtgccag cgagaagagt tttctctgcc     480
agctcatttt cacggcgcca ttatgagaac tgaaatgact cccttggtcc tgtcgtatca     540
ggaagctgac gacatattgg agcatttggt ggacaacttt tttaacgagg tacccagtga     600
tgatgatctt tatgttccgt ctctttacga actgtatgat cttgatgtgg agtctgccgg     660
tgaagataat aatgaacagg cggtgaatga gtttttttccc gaatcgctta ttttagctgc     720
cagtgagggg ttgtttttac cggagcctcc tgtactttct cctgtctgtg agcctattgg     780
gggcgaatgt atgccacaac tgcaccctga agatatggat ttattgtgct acgagatggg     840
ctttccctgt agcgattcgg aagacgagca agacgagaac ggaatggcgc atgtttctgc     900
atccgcagct gctgctgccg ctgataggga acgtgaggag tttcagttag accatccaga     960
gttgcccgga cacaattgta agtcctgtga gcaccaccgg aatagtactg gaaatactga    1020
cttaatgtgc tctttgtgct atctgcgagc ctacaacatg ttcatttaca gtaagtgtgc    1080
tatgggaggt gggaggtgat tttttttttct taagcagtga aaaataatat tttgttgttt    1140
ttaggtcctg tttccgataa tgagcctgaa cctaatagca ctttggatgg cgatgagcga    1200
ccctcacccc cgaaactagg aagtgcggtt ccagaaggag taataaaacc tgtgcctcag    1260
cgggtgactg ggaggcgtag atgtgctgtg gaaagcattt tggatttgat tcaagaggaa    1320
gaaagagaac aaacagtgcc tgttgatctg tcagtgaaac gccctagatg taattaatgg    1380
actttgagca cctgggcaat aaaatagggg taatgtggtt tttgtgagtc atgtataata    1440
aaactggttt cggttgaagt gtcttgttaa tgtttgtttg ggcgtggtta aacagggata    1500
taaagctggg ttggtgttgc tttgaatagt tcatcttagt aatggagttg gaaactgtgc    1560
tgcaaagttt tcagagcgtt cgccagctct tgcagtatac ctctaaaaac acttcaggtt    1620
tttggaggta tctgtttggc tctaccttaa gcaaggtggt aaatagggtg aaagaagact    1680
atagagagga atttgaaaac atattggccg actgtccagg gcttttggct tcactagacc    1740
tttgttacca cttggtgttt caggaaaaag tggtcagatc cttagatttt tcatctgtgg    1800
gacgaacggt tgcttctatt gctttttttgg caaccatatt ggataaatgg agcgagaaat    1860
cccacctgag ttgggattac atgctggatt acatgtcaat gcagctgtgg agggcatggc    1920
tgaagaggag ggtttgcatt tactcgctgg cgcggccttt gaccatgccg ccgctgccga    1980
cgttgcaaga ggagaaggag gaggagcgga accctgcggt ggtggagaag taaacatgga    2040
acaacaggtg caagaaggcc atgtacttga ctctggcgaa gggcctagtt gcgcagatga    2100
tagagataag caggaaaaaa aagaaagttt aaaggaagct gctgttctta gtaggctaac    2160
tgttaatctg atgtcccgcc cgcgtttgga aactgtatat tggcaggagt tgcaggatga    2220
atttcagcgg ggtgatatgc atttacagta caaatacagt tttgaacaat taaaaaccca    2280
ctggttagag ccatgggagg atatggagtg tgctattaaa gcttttgcta aattggcctt    2340
acgtcctgat tgtagctaca gaattactaa aacagtaacc attacttcat gcgcctatat    2400
tataggtaac ggggcaatag ttgaggtaga tacaagcgac agagttgctt ttagatgtcg    2460
```

-continued

```
aatgcagggt atgggcccag gggtggtggg tttggatgga attacattta taaatgttag   2520
gtttgctgga gataagttta aaggcattat gttcgaagct aatacctgtc ttgtcttgca   2580
tggtgtttac tttcttaact ttagtaacat ttgtgtagag tcttggaata aggtttctgc   2640
taggggctgt actttttatg gatgttggaa gggtttggtg ggtagaccaa aaagtaaact   2700
gtctgtaaaa aagtgtttgt ttgaaaaatg tgtacttgct ttaattgtag agggggatgc   2760
acatattagg cataatgcag cttcagaaaa tgcctgtttt gtattattga agggaatggc   2820
tattttaaag cataatatgg tttgtggggt gtctgatcaa actatgcgac gttttgttac   2880
ctgtgctgat ggaaattgtc ataccttaaa aactgttcat attgtgagcc acagtagaca   2940
ttgttggcct gtatgtgatc ataacatgtt tatgcgctgt accatacatt taggcttaag   3000
gcggggtatg tttagacctt cccaatgtaa cttcagccac tcaaacatta tgctggaacc   3060
tgaagtgttt tctagagtgt gtttaaatgg ggtatttgat ttatctgtgg aattatgtaa   3120
ggttataaga tataatgatg atactcgaca tcgttgccga cagtgtgagt gtggtagcag   3180
tcatctagaa cttcgtccca ttgtgctaaa tgtaactgag gagctgagaa gtgaccacct   3240
taccctgtct tgcctgcgga ctgactatga gtcaagtgat gaagacgaca actgaggtaa   3300
gtgggtggag ctaggtggga ttataaaagg ctggaagtca actaaaaatt gtttttgttc   3360
ttttaacagc acgatgaacg gaactactca gaacaacgct gcgctttttg atggaggggt   3420
ttttagccct tatttgactt ccaggttacc atattgggcc ggagtacgtc agaatgtggt   3480
aggatctaca gtggacggtc gacctgtggc acctgcaaat tcatcaacat taacctatgc   3540
aactattgga ccctcgcctt tggataccgc cgccgccgct gcagcttccg cggccgcttc   3600
tacggctcgc agtatggcag ctgatttcag cttctacaat cacttggctt cgaatgctgt   3660
gacacgcacc gcagttcgag aggacattct gactgttatg cttgccaagc ttgaaactct   3720
aactgctcag ctggaagagc tatcgcaaaa ggttgaggaa ttagctgatg ctactaccca   3780
taccccagcc caacctgtaa cccaataaag aaaaaactta aattgagatg gtgttatgaa   3840
tctttattga tacttgtttt ttctgacatg gtaagctctt gaccaccgtt ccctatcatt   3900
aagaacacgg tgaatgtgtt ccagtatttt gtaaagatga gcctgtatat taaggtacat   3960
tggcattagg ccatctttgg gatgaaggta ggaccattga agggcttcat gttccgggtt   4020
agtgttgtag ataatccagt catagcaaca acgctgggca tggtgattaa atatatcttt   4080
taacaacaag ctaattgcta atggaagacc tttagtatag gtattgataa aacggttaag   4140
ctgggtggga tgcatccgag gtgacatgat atgaagtttt gattgtattt tgagattggc   4200
aatgttacct gccaaatctc ttcttggatt catattgtgg agaaccacga aaacggtgta   4260
gccagtacac ttgggaaatt tgtcatggag tttagaagga aaggcatgga aaaacttgga   4320
aacgcctttg tgacttccca aattttccat acactcatcc attattatgg caattggacc   4380
gcgagcagcg gcttgagcaa aaatgttttc tggatcagaa acatcatagt tgtggtctag   4440
agttaggtca tcgtaggaca acttaacaaa tttaggacac agcgttccag attgtggaat   4500
aatagttccc tctggtcctg ggacataatt tccctcacaa atttgcattt cccaagattt   4560
aatttcagat gggggaatca tgtccacttg cggaacaata aaaaaaacag tttctggagc   4620
aggtgtaacc agctgggcag aaagcaaatt acgcaacaac tgagacttcc cacagccagt   4680
gggtccataa attaccccaa ttacaggttg caagtgatag tttaacgagg tgcagctgcc   4740
gtcttcgtgg agaagcggag ccacttcatt catcatttgt cggacgcgga tgttttgctt   4800
```

-continued

```
ggccagttcc cctaacagac gctctccgcc taaggaaagt aactcttgta aagatttgaa   4860
atttttaagt ggctttaggc catcggccat aggcatgtgg tccagggttt gcttcagcag   4920
ttgcaagcga tcccatagct cagttatatt ttctatgcca tctcgatcca gcaaacttcc   4980
tcgttgcggg ggtttggctg gctgttgctg taaggaacga ggcggtgagc atccaaatgg   5040
acgagggttt tgtccttcca gggacgtaat gtgcgcgtca gggttgtttc ggtcacggtg   5100
aatggatgcg ctcctggttg agcgctggcc agtgtgcgct ttaaactgag gcggctggtg   5160
ctgaagcgcg tgtcttctcc ctgtgcttcg gcaaggtagc attttaacat aagatcataa   5220
gacaaagcct ctgtagcgtg gcctttagcc cgtatttttc ctttggaggt gctcccgcag   5280
tgaggacact gaaggcattt aagggcgtac agttttggag ccaaaaaaac agattctgga   5340
gaataagcat ctgcgccaca ataactacaa acagtttcac attcaactga ccaggtcagc   5400
tcaggacatg atggatcaaa aacaagtttc cctccgtact ttttgatgcg tttcttacct   5460
tgcgactcca taaggcggcg tcctttctct gtgacaaaaa gactgtcagt gtctccgtat   5520
acagatttaa ggggtctatc cttcagtggt attccgcggt cctcctcgta caggaattct   5580
gaccactctg acacaaaagc tctagtccaa gcaagtacaa aggaagccac atgggaaggg   5640
taccgatcgt tgttaattaa agggttagaa ctttctaagg tgtgtaaaca catgtctcct   5700
tcttcagcgt ccatgaatgt gattggtttg taggtgtaag tcacgtgttc acaattttct   5760
ggtggtgggc tataaaaagg ggcgggtcct tggtcttcat cgctttcttc tgcttcgctg   5820
tttacgagcg ccaactggtt gggtgagtac acgcgctcaa aggcaggcat tacctctgta   5880
ctcaacgtgt cagtttctat aaacgatgag gatttgatgt ttaatcgccc cgctgcaatt   5940
tctttcatta ggctttcttc catttgatca gaaaaaacta ttttttttgtt atctagtttg   6000
gtagcaaaag atccgtacaa ggcattggaa agcagcttgg ctatagatct tagggtttga   6060
tttttgtccc tatcggcccg ttcttttgcg gcaatattga gttgcacata ttcgcgtgcc   6120
aggcatttcc aggtggggaa aatggtggtg cgctcgtcag atagcaagcg taagcgccac   6180
ccgcgattat gcagtgtaac cagatctacg ctggtaacta cttcaccgcg caagctttca   6240
ttggtccagg ctaaacgacc gccttttcta gaacaaaaag gaggaagaac atccaactga   6300
ttttcatctg gggggtcggc atctatagta aaaatgccag gacaaagatt tttgtcaaaa   6360
taatcaattt tgcaagtgta attttccagc gccacctgcc attgccgcac ggccaatgcc   6420
cgctcatagg ggttaagggg aggaccccaa ggcatggggt gtgtgagggc cgatgcatac   6480
atgccgcaaa tatcatatac atatatgggc tcttttagta ctcctatgta agtaggatag   6540
cacctgccgc cacgaatgct ggcgcgaacg tagtcatata gctcatgtga aggcgccagg   6600
atgttgggcc caagatgtgt gcgctgtggt ttttcggcgc ggtacaaaat ttgtctgaaa   6660
attgcatgag agttagagga aatggtagga cgctgaaaca cattaaaatg tgccgcgtca   6720
agacccactg cgtcagtaac aaactgggcg tatgagctac gcagtttttc taccaatgag   6780
gcagtcacaa gtacatccag ggcacaatag tttaatgttt ccccgataag attgtaattt   6840
ttttctcctt ttttttcca tagttcttga tttaggaggt attcctcctt atccttccag   6900
tactcctcca ggggaaaccc atttgcatct gcacggtaag aaccaagcat ataaaactga   6960
tttaccgcct tgtacggaca acatcctttt tctacaggca gggcatacgc ttgtgcagcc   7020
tttcttaaag atgtatgagt aagagcaaag gtatctctga ccattacttt taaatactgg   7080
tatttaaaat cttggtcgtc acaccctccg tgttcccaca gtaggaagtt agttcgcttt   7140
ttgtagtggg gattgggaag ggcaaaagta atatcattaa ataatatttt gccagctctt   7200
```

-continued

```
ggaataaaat ttctagaaat tttaaagggt ccagggacgt ccaagcggtt attgattacc   7260
tgagcggcaa gaacaatttc atcaaatcca ttaatattgt gtcctactat atacaactct   7320
acaaatcttg gctcaccctt aattgcaggg gctcttttaa gatcttcgta ggaaagatct   7380
tcaagcgcga ctagtccgtt ttcttcttga gcccattgag acaagtgtgg atttttttgt   7440
aaaaaagtca tccaaagatc agtagctaag gaggtttgta agcggtttct ataggtacga   7500
aactgttgac cgaccttcat tttttctggg gttaagcagt agaaagtagt agagtctttt   7560
tcccattggt cccatccaag ttctaatgca agttgtaagg catgtttgac aagattgtca   7620
tccccagaca gtttcatcac cagcataaat gggacaagtt gctttccaaa tgcccccatc   7680
caggtgtagg tttctacatc ataggtaata aaaaggcgct cagtgcgagg atgcgaaccg   7740
attgggaaaa agtggatctc ctgccaccag ttggaagaat ggctgttgat gtgatgaaag   7800
tagaaatctc gtcggcggac agagcattca tgctgatgtt tgtaaaagcg tgcgcagtgt   7860
tcgcatcgtt gcacgggctg tatctgttga atgaggtgta cctggcggcc tcgcaccaga   7920
aagcagatgg gaaaatcaat accacttggc agctgccgtt cgtcctcttc ctcttctgct   7980
gcattgccac taccgtttgg atcctcgaaa gcgagaacgg agagggtgac ggtgcccctc   8040
gacctgcatg tccagatttc agcacgagag gggcggaaac gggaaatcag ggcgtacagc   8100
ctggagctgt ccatggtatc agtcagagag aaaagcatgt ccgcggggac agcgcgcaag   8160
ttgacttcgc acaggcgggt aagagcaggc tggaggtgca ggtaatactt aatttctaga   8220
ggcgtgccgt tggcagagtc tattgcgtga agtattccat gagcccgggg actaaccacg   8280
gttccacggt gcacttttcc aatgcgcctg cttaaaatcg gcggcgcgga cgagctcccg   8340
gaggaagcgg cggttcgggt cctgcgggaa gcgggggaag cggtatgtcg gcctgacgct   8400
ctggcagggg aaggtgttga gcccgaagtt gactggcatg ggcgactacc cggcgattga   8460
tatcttgaat ctgtcggcgt tgtgtaaaca ctaccggccc tgttgttttg aacctgaaag   8520
aaagttcaac agaatcaatc tcagtgtcat ttactgcagc ctgtcttaaa atctcctgaa   8580
cgtcgcctga gttatcttgg taggcaattt ctgccattaa ttgatcaatt tcttcctcct   8640
ggaggtctcc atgtcccgca cgttcaatag tggctgcaag gtcattagat atccgactca   8700
taagctgtga aaatgcgttt agtccaattt cgttccagac tcggctgtat actacccctc   8760
cttcgctgtc ccgagcgcgc ataaccactt gcgccaagtt gagttccacg agccgtgcga   8820
acacgccgta gttgcgcaag cgctgaaaca ggtagtttaa ggtggtggca acgtgttctg   8880
agacgaagaa atacagaatc caccgacgaa gcgtcagctc gttgatgtca cctaaggctt   8940
caagacgttc catggcttcg taaaagtcta ctgcaaaatt gaaaaactgg gagttgcgag   9000
ctgccaccgt caattcttct tccaacagac gaataagctc ggccaccgtc tcgcgcactt   9060
cttgctgaaa tgcgcccgga actatttctt gttcttcctc ttctacctcc attatttctt   9120
cctcgaccac aggtggtggg ggttgtcttc ttcgacgccg gcgaacgggc agcctgtcta   9180
caaatctttc aatcatttcg ccgcgacggc ggcgcatagt ttcggttact gctcgaccgt   9240
tttcacgtgg tcgtaactca aaaactccac ctctaagttc tgtttcatgt aaaatgggaa   9300
atgaggcgtt gcgaggggcg ttaggtaggg atacagcgct gattatgcat tttattattt   9360
gctgcgtagg aactccgcgc aaggagctaa gcgtctgcat atccaccggg tcggagaacc   9420
tttcaagaaa ggcatctagc cagtcacagt cacaaggtag gctaagtttt gtttcttcta   9480
aagtaccagg aagctgagca atgctactaa taatgtaatt gaagtaagct gttttaagcc   9540
```

-continued

```
cacgaatggt tttaagaagc accacatctt tgggtccggc ttgttgaatt cgcaggcggt   9600
ctgccattcc ccacacgtca ctttgacatc gtccaagatc tttgtagtag tcttgcatta   9660
acctttccac ctctacctcg cggtttccgc gatcagccat gtgcgtgctt ccgtagcctt   9720
gcagcggttg taataaagct aaatctgcca ctacccgttc cgcaagcact gcctgttgaa   9780
tttgggtaag ggtggttgca aagtcatcca catctacaaa gcggtgataa gctcctgcat   9840
taatggtgta gctgcagttt gtcattactg accaattaac agtttgcgtg cctggctgta   9900
cagtttctgt gtatcgcaag cgtgagtaag cccgagagtc aaaaacatag tcattgcagg   9960
tgcgcactag gtattgatag cccacaagga aatgaggagg aggttcgcga tacaacggcc  10020
agccaagcgt agccgcagca cctggagcga gatcttccaa catgaggcgg tggtattcat  10080
atatgtatct ggacatccat gtgatgccgg cagcggtagt tgttgctcgc ataaattcgc  10140
gggctcggtt ccaaatattg cgcaggggta aaaagcgttc aatagttgcc acgctttgac  10200
cggtcaggcg tgcgcagtct tgaatgctct ggacatggaa aaaatgaaag ttggtaagcg  10260
actcccttcc gtggtttggt ggaaaagtca caagggtacc atagcgagga accccggttc  10320
gaaaccggca ggatccgcta tgagcacaag tgaggcgctt gcgcgttgaa cccggccaag  10380
gacccccaga cacggagagg agtctttttt tatttatttt ttcttagatg catcctgtcc  10440
tgcgacaaat gcgacctcag cccagggcaa ccacggcctc agcagcggtg gcgctttcgg  10500
gctctggcga acaggaagag cctcaatgtc ctacattgga gttggaagaa ggagaaggca  10560
tagcccgatt gggcgcccac tctcctgagc gtcacccaag ggtgcagctc gcccgggaca  10620
gtcgcgtggc atttgtgcct cgtcagaaca tgtttcgcga caacagcggg gaggaagctg  10680
aggaaatgcg agactgcagg tttagggccg gtcgcgagct gcgccgcgga tttaatcgcg  10740
agcgactgct gcgtgaggag gactttgagc cagatgaaca ttcggggatt agttctgcac  10800
gggcccatgt atcagcagcc aacttagtaa cagcatatga acaaacggtt acagaggaac  10860
gtaactttca aaaaagcttt aataaccatg tgcgcacact aatagcgcga gaagaagtag  10920
ccattggttt aatgcatctt tgggactttg tagaagctta tgtacataat ccagcaagta  10980
aacccctaac tgcccagctg ttcttaatag ttcaacatag tagagacaat gaaactttta  11040
gggatgcaat gcttaacata gctgaacccc agggtcggtg gttactcgat ttaattaaca  11100
ttctgcagag cattgtggtt caggaacgca gtcttagttt ggcagacaag gtggccgcca  11160
ttaattactc catgttaagt ttgggaaagt tttatgctcg taaaatctac aaaagtccgt  11220
atgttcccat tgacaaggaa gtgaagatag acagctttta tatgcgcatg gctttaaagg  11280
tactaacatt aagcgacgat cttggagtgt accgcaatga ccgaatccac aaagcagtaa  11340
gcgccagtcg ccgcagagag ctaagcgaca aagagcttat gcatagctta caaagggcgc  11400
tgacgggagc aggaacagag gacgagtcgt tctttgatat gggcgcagac ctacggtggc  11460
agccaagcgc tcgcgctttg gaggcagctg gagtggcgtc tgctgacgtc actggcgatg  11520
acgatgacga agaccagtac gaggactgat cggccgtacc ttttgttaga tgcagcgacc  11580
ggcgatcatc gcggagaggg ctcctaacct ggatcccgcg gttttggcgg ccatgcaaag  11640
ccagccttct ggcgttacag cttcagatga ctggacagcg gccatggatc gtattatggc  11700
tttaacggcg cgcagtcctg atgcttttcg ccagcagccc caagctaacc gcttttcggc  11760
cattttggaa gcagtagtgc cgtctcgtac taaccctact cacgagaaag tgttaaccat  11820
tgtaaatgct ttgttggata gcaaagccat ccgcaaagat gaggctggtt taatatacaa  11880
cgctttgctt gagcgcgtgg cacgctataa cagtaccaat gtgcaggcta acttagaccg  11940
```

-continued

```
gatgggtaca gatgtaaagg aggcgctggc tcaacgagag cgctttcatc gcgatggtaa  12000
tcttggttcg ctagtagcat taaacgcttt tttgagtact cagccggcta atgttccgcg  12060
tggtcaggaa gattatacaa acttcatcag cgccttgcga ctaatggtta ctgaagtgcc  12120
tcaaagtgaa gtgtatcagt ctggacccga ttactttttt caaacgtcca ggcagggttt  12180
gcaaaccgta aacttaactc aggcttttaa aaatttgcaa ggtttgtggg gggttcgtgc  12240
tccagtaggc gatcgttcaa ctttgtccag tttactaaca ccaaactcgc gcctattact  12300
gttgctaatt gcccccttta ccaacaccaa cagtttaagt cgagattcat acctgggtca  12360
cttagttact ttgtaccgcg aagccattgg tcaagcgcag gtagacgaac aaacttatca  12420
agaaataacc agtgttagtc gcgcactggg ccaggaggac actggcagtt tagaggccac  12480
acttaacttt ttactaacta accgtcgcca gcaagtgcct cctcagtaca ctttaaatgc  12540
ggaagaagaa cgcatattgc gctatgtaca gcaatctgta agtttgtatc ttatgcgtga  12600
gggtgccacc cccagtgccg ccttagacat gacagcgcgc aatatggagc cgtccttcta  12660
cgcttccaat cgagctttca ttaatcgctt gatggattac cttcaccgcg ctgcggccat  12720
gaacggggaa tactttacaa atgcaattct aaatccgcat tggttgcccc ctcctggatt  12780
ttacactggt gaatttgatt tgccggaagg aaatgatggc tttttgtggg atgatgttac  12840
ggacagtctg tttagtcctg cagttattgg acaccatggt aaaaaggaag caggtgatga  12900
aggtcccttg cttgactctc gggcgagttc tccattcccc agtttaacta gtttacccgc  12960
cagtgttaac agcggtcgta ccaccagacc ccgactaaca ggtgaaagtg aatacttaaa  13020
tgaccccatc ttgtttccag tgcgcgacaa aaattttccc aacaatggca tagaaagttt  13080
ggtagataaa atgtctcgct ggaaaacata tgcacaagag cggcgagaat gggaggaaag  13140
acagccaaga ccagttcgcc ctcctaggca acgttggcag cgacgcaaaa aaggggcaca  13200
tgcgggggat gaaggaagcg atgactcagc tgacgacagt agtgtattag atttaggagg  13260
gtcaggaaac ccatttgctc atttgcgccc acagggttgc atagggtcat tgtattaaat  13320
tgaataaaag catacttacc aaagccatgg cgaccagtgt tcgtcttatt ttccttcttc  13380
cgttagctgt gaaatgaggc gcgcggtgga actgcagaca gtggcttttc ctgagacacc  13440
acctccctct tacgaaaccg tgatggcagc ggcgccaccc tacgtgcctc cccgctattt  13500
gggtcctacg gagggaagaa acagtatccg ttactcggaa ttgtcaccgt tgtacgatac  13560
cactcgagtg tacttggtgg acaacaagtc ttctgacatt gcttcattga attaccagaa  13620
tgatcacagc aactttttaa ccactgtagt gcaaaataat gactattccc ctatagaggc  13680
tggcacgcaa actattaact ttgatgaaag gtctagatgg ggtggagatt taaaaaccat  13740
cttacatacc aacatgccaa acgtgaacga ttttatgttt accaccaaat ttaaggccag  13800
ggtaatggtg gctaggaaaa caaacaacga aggccaaacc attttagaat atgagtgggc  13860
agaatttgtg ctacccgagg gtaactattc ggaaaccatg actattgact taatgaacaa  13920
tgctattatt gagcattatt tgcgagtagg aagacagcat ggagtgctgg aaagtgacat  13980
tggagttaag tttgacacca gaaactttcg tctgggttgg gaccccgaaa cccaattagt  14040
aactccggga gtgtacacta atgaggcttt tcatccagat atagtactgc ttccaggttg  14100
cggggttgat tttacagaga gcagattaag caacatacta ggtataagaa agaggcagcc  14160
gtttcaggaa ggatttgtga ttatgtatga acacttagag ggaggcaata ttccagctct  14220
tttggatgta aaaaaatacg aaaacagtct gcaggatcaa aacactgtaa gaggagacaa  14280
```

-continued

```
ctttattgcc ttaaataagg ctgctaggat tgaaccggtt gaaacagacc ccaaaggacg  14340
cagttacaac ttgcttccag acaaaaaaaa tactaaatat cgcagctggt atttggcata  14400
caactacgga gacccagaaa aaggagttcg gtcatggact ctactaacaa ctccagatgt  14460
aacaggcggc tccgaacagg tgtactggtc cctacccgat atgatgcaag atccggtgac  14520
ttttcgctcc tcgcgtcaag ttagcaacta tcctgtagtt gcagcagaat tactgccagt  14580
tcatgctaaa agcttctaca acgagcaagc cgtctactca cagcttattc gccagtcaac  14640
cgcgcttacg cgcgtgttta atcgctttcc cgagaaccag atactggtgc gtccaccagc  14700
cgctaccatc actaccgtca gtgaaaacgt tcccgccctt acagatcacg ggaccctgcc  14760
gctgcgtagc agtatcagtg gagttcagcg agtcaccatc actgacgccc gccgccggac  14820
ctgtccctac gtttacaaag cactgggcat agtttctcca cgagtgcttt ctagtcgcac  14880
tttttaaaaa agtgtggtaa catgtccatt ttggtttcgc caagtaacaa cacgggctgg  14940
ggactgggtg ccgcccgcat gtatggagga gctaaaacaa ggtctagcca acatccagtg  15000
cgcgtacgcg gacattaccg agctccatgg ggcgcgcata cccgaggacg cactggtcgc  15060
accactgtag acgatgttat tgactcggta gtggccgatg ctcgcaagta ccgcgcgccc  15120
gctgaaacag cagggtctac tgttgatgca gtaattgatg aggtagtggc aaacgcgcgg  15180
gcttatgcaa ggcgccgcag acggctgcgt cgccggcgta gaccaaccac cgccatgcgc  15240
gcggccagag cgttggttcg acgggccagg cgcattgggc ggcgagctat gatgcgggca  15300
gccaggcggg ctgcaacgcc tgccggtcga gcgcggagac gggccgcagc tgcggccgca  15360
acagctattg caaacctagc tgctccgcga cgaggaaatg tatactgggt gcgcgactca  15420
gtgaccggga cgcgtgtgcc agttcgtacg cgtccacctc acccttagaa gacaaagagt  15480
gactcaatgt ctgttatgta tgcccagcat gaccaaacgc aagttcaaag aagagctgct  15540
gcaggcctta gcgcctgaaa tatatggccc atcggataac cttaccaagc gcgatatcaa  15600
gcatgttaaa aaacgggaaa aaaaagagga agaagtcgcc gcggcgtcag cagacggcgt  15660
cgagtttgtg cgctcatttg cgcccagacg tagggtacag tggaagggac ggcaagtaaa  15720
acgcattttg cgaccgggca ccacagtggt tttttctccc ggagagcgaa cgattatgcg  15780
tcccctaaag cgcgagtacg acgaagtgta cgcagacgat gacattttgg agcaagcggc  15840
acaacagact ggggaatttg catatggaaa aaaagggcgt tacggagaca aaattgctat  15900
tcctttggac gagggaaatc caacacccag tttaaaggct gtcactttgc aacaagtgtt  15960
gcccgtcctt gggccttcgg aagaaaagcg tggaattaaa agggaagcca tggatgaatt  16020
gcagcctaca atgcaactga tggtgcctaa gcggcaaaag ttagaggacg tactagagca  16080
catgaaggtg gatcctagcg tacagccaga tgtaaaagta cgtccgataa aaaaggtagc  16140
tccaggattg ggagttcaaa cagtggacat tcaaattcct gtgcaaactg cattgggtga  16200
aactatggaa atccaaactt cgccaataaa aacaacggtg aacgcaagcg tgcaaacaga  16260
cccttggtac ccgccagtgc tttcaacaaa aaaaaagcgt cactacagac aaacaagttc  16320
gcttttgcca gactacgttt tacatccttc cattgtgccc acgcctgggt accgtgggac  16380
aacttttcag cgccgagcca cagcccctag ccgtagacga ggtccatcac gccgtagacg  16440
tcgacgcaaa gccactttag ccccagcggc agtacgtcgc gttgtacaaa gggggcgcac  16500
actaatactt ccatccgtgc gttaccaccc tagcattctc taacaagctg cgctgccgtt  16560
ttttcagatg gctcttactt gccgaatgcg catacccatt ccaggataca gaggacgacc  16620
ccgccggagg aaagggctga ccgggaacgg tcgatttcgg cggcgtagta tgcgcagacg  16680
```

-continued

```
catgaagggt ggggtgctgc ccttcctaat tccacttatt gctgcggcca ttggagccgt  16740
tcccggaatt gcctcagtag ccttgcaggc ttctcgaaaa aattaaaata aaataaaact  16800
tccaacttat tactggtact atgactgttt tatgcagact aaatggaaga catcaatttt  16860
tcgtcgctgg ccccgcgaca cggcacgcgg ccgtacatgg gcacctggaa cgagatcggc  16920
acgagccagc tgaacggggg cgccttcaat tggaacagta tctggagcgg tcttaaaaat  16980
tttggttcca cgattaagac atatggcacc aaggcgtgga acagccaaac cggccagatg  17040
ctaagggaca agttaaaaga ccaaaatttt caacagaaag ttgtagatgg tctggcttcg  17100
ggaattaatg gagttgtaga catagccaat caggctgtac agaaaaaaat tgccaaccgt  17160
ttagagccgc ggcccgacga ggtaatggta gaggaaaagc tgccacctct agaaactgtg  17220
cccggatccg ttccaaccaa aggagaaaag cggccacggc cggatgcaga ggaaacctta  17280
gtaacgcaca caacagaacc gccgtcctat gaggaagcaa taaaacaagg agccgctctg  17340
tcacctacca cctatcccat gaccaagcct attttaccca tggctactag agtgtatgga  17400
aaaaacgaaa atgtgcctat gacccttgag ctgcctcctt tgccagaacc cactatcgcg  17460
gatcccgtag gttccgttcc tgttgcatct gttccagttg catcgacagt gagccgtcca  17520
gcagtgcggc ctgttgccgt ggctagcttg cgaaacccac gatccagtaa ttggcaaagt  17580
accctaaaca gtattgtggg actgggagta aagtctctca aacgccgacg ctgctactaa  17640
cattaaaaga cgagtgttaa ttcccatctg tgtatacgcc tcctatgtta gcgccagagg  17700
accaacgcgt gaatcgcagt caccaccagc gctttcaaga tggccactcc ctcgatgatg  17760
ccgcagtggt cttacatgca catcgccggt caggatgcct cggagtacct gagtcccggt  17820
ctggtgcaat tcgcccgcgc cacggacacc tacttcaccc tgggaaacaa gtttagaaac  17880
cccaccgtgg ctcccaccca tgatgttacc accgatcgct cgcagcgtct gacgctgcgt  17940
tttgtgcccg tggatcggga agatactacc tactcctaca aggctcgctt tacgctggct  18000
gtgggtgaca accgcgtgtt agacatggct agttcttact ttgacattcg aggggtactg  18060
gatcgtggtc ccagttttaa gccctattcc ggaaccgcct acaattcttt ggcaccaaaa  18120
ggcgctccta atgcttcaca atggtcagat aacgctaagc ttaatacctt tgctcaggcg  18180
ccgtatctta gcgacactat caccgccgcc gatggtatta aagttggaac agacaccgcc  18240
caggcaggcg cggcggtgta tgccaacaaa acttatcagc cagagccgca agtaggacca  18300
agtgaatgga acaccagcat tgaaaacgtt aaagctggcg ggagggcatt aaagcaaacc  18360
actgcaatgc agccgtgcta tggctcctac gctcgtccaa ccaacgaaca cggaggacaa  18420
tccaaggatg acaacattga acttaagttc tttgattcag ctaacaatgc agcaaacact  18480
gctcaagttg tgttctatac cgaagacgta aaccttgaaa tgccagacac gcatcttgtg  18540
tttaagccta ctgttaccaa tggaacaatt gcttctgagt cgctgttggg acagcaagca  18600
gcgccaaata gagcaaacta cattgcattc agagataatt ttattggcct gatgtattac  18660
aacagtacag gcaacatggg tgtattggcc gggcaagctt cccaacttaa cgcagtagta  18720
gacctgcaag acagaaatac agagctgtca taccagttaa tgctggatgc tttgggagac  18780
agaacacggt acttttcctt gtggaattcc gcagtggaca gttacgaccc tgacgttcgc  18840
gttattgaga atcacggggt agaggatgaa ctaccaaatt attgctttcc tcttagcgca  18900
gtaggtgaaa taaaaaatta caaaggcatt aagccagata acggaggagg aggtggctgg  18960
actgccgaca acactgtcag tgaagcaaac cacataggca ttgggaatat agccgccatg  19020
```

-continued

```
gaaattaatt tgcaggctaa tttgtggaga agcttcttgt actcaaatgt gggcttatac  19080
ctaccagacg acttaaaata cactccagga aacataaaac tacctgataa caagaacacc  19140
tacgagtaca tgaacgggcg tgtgactgcc ccggggttgg tggataccta tgtcaatatc  19200
ggcgctcgct ggtccccaga tgtgatggat aatgtaaacc cttttaacca ccaccgaaac  19260
gcagggttgc gctacagatc catgttgcta ggcaatggga gatttgttcc ttttcacatt  19320
caggtgccgc aaaaattttt tgccatcaga aatttgttgc tgttgcccgg ttcctacact  19380
tacgaatgga actttagaaa ggatgtaaac atgattcttc agagcacact gggaaatgat  19440
cttcgggtgg acggagccag cgttcgcttt gacaacattg ccctgtatgc taactttttt  19500
cccatggcac ataacacagc ttctacttta gaagccatgt taagaaatga caccaacgac  19560
cagtctttta acgattattt gtgtgctgca aacatgctgt atcccatccc agctaacgcc  19620
accagcgtgc ccatttcaat accttcgcga aattgggcgg catttagagg ctggagcttt  19680
actcgcctaa aaactaaaga aactccttcc ctgggttcag ggtttgaccc ctactttgta  19740
tactctggaa ccattcccta tttagacggc accttttacc taaaccacac ttttaagaag  19800
gtgtcaatca tgtttgactc ctccgtgagt tggcctggaa atgaccgttt gctaacccca  19860
aatgaatttg aaataaagcg ttctgtggat ggggagggat acaatgtggc ccaatgcaat  19920
atgactaagg attggttcct aatacaaatg cttagtcatt acaacattgg ataccaaggt  19980
ttttacattc cagagagcta caaggaccgc atgtattctt tctttagaaa ctttcagccc  20040
atgagtaggc aagttgtgga taccacagaa tataagaact acaaaaaagt aaccgtagag  20100
tttcaacata acaactcagg attcgtggga tacctgggcc ccactatgcg ggagggacaa  20160
gcttaccccg ccaactatcc ctaccctctt ataggccaaa cagctgtgga aagcatcaca  20220
cagaaaaagt ttctatgcga tcgtgttatg tggcgcatcc cattttctag taacttcatg  20280
tctatggggg cgctaacgga tcttgggcaa aatatgctgt acgcaaactc agcccatgct  20340
ctagacatga catttgaggt ggatccaatg gatgagccta cccttcttta tgttttattt  20400
gaagttttcg acgtggtacg cattcaccag ccacaccgcg gcgtcattga agcggtctac  20460
ctgcgcacgc ccttctcggc gggtaacgct accacctaag aaggcaccct cccagactgc  20520
tgtaatgggt tcaagcgaac aggagctgac ggccattgtt cgagatctag gctgtggacc  20580
ctattttttg ggaacctttg acaaacgttt tccgggtttt gtgtctcgcg accgcttatc  20640
atgtgctatt gttaacactg ccggtcgcga aactgggggc gtacactggc tggcttttgg  20700
atggaacccc aaatcgcaca cttgctattt attcgatcca tttggatttt ctgatcaacg  20760
actaaaacaa atctatcagt ttgagtacga aagtctgttg cgccgtagtg cgctagcggc  20820
cactaaagac cgatgcgtta ccctagaaaa gtcaacccaa actgtacaag gaccgttttc  20880
tgcagcgtgc ggcctgtttt gttgtatgtt cttacacgct tttactcact ggcctgacca  20940
tccaatggat aaaaatccca ctatggacct acttactggg gtgcctaatt gtatgctaca  21000
aagtcctcag gtagtgggca cattgcaacg caatcagaat gaattgtata aattcttaaa  21060
caatctgtcc ccttactttc gtcacaaccg cgagcgcata gaaaaagcta catcttttac  21120
taaaatgcaa aatggactca aataaacgtg tacacaatgc attaataata aaaccatttt  21180
attagctcat tggagtacaa gcttgactgt tttattaaaa atcaaatggc tcttcgcgac  21240
agtcgccgtg gttggtgggc agggatatgt ttctgtactg caaacgctga tgccacttga  21300
attctggaat aacaagccta gggggggagc cgtcaaaatt ttctccccac agctggcgca  21360
caagttgcag ggcgcccata acatcaggag cagaaatctt gaagtcgcaa ttagggccag  21420
```

-continued

```
cattgccgcg cgcattgcga taaactggat ttgcgcactg aaaaaccaac aaacacggat  21480
acttaatact ggctaacgct ccagggtcgg ttacttcgtt gatatcaatg ttatccacat  21540
tgctgaggtt aaaaggagtg attttacaca gttgacgccc catccgtggc aggccatctt  21600
gcttgtttaa acattcgcag cgcactggca taaggagacg tttttgccca tgtcgcatgt  21660
gagggtagtc ggccagcata aaagcttcaa tttgcctaaa agctatttga gccttcattc  21720
cttcagaata aaacaagccg caggactttc cggagaaaga attattcccg cagccaacat  21780
catgaaaaca gcagcgggca tcgtcgtttt taatttgaac tacattacgc ccccagcggt  21840
tttgcgccac cttggctttc gaggggttct ctttcaacgc tcgttgccca ctttcgctgg  21900
ttacatccat ttccaccaaa tgctctttgc gcaccatctc cattccatgc aggcatctaa  21960
gctccccttc gcgctcggta cacttatgct cccacacgca gcaaccggtg ggttcccagg  22020
aattctgttg gacaccggca taagcttgca tatatccttg caaaaagcgt cccatgagct  22080
cctgaaaggt tttttgggat gaaaaagtca gctgcaaacc gcgcttttct tcgttgagcc  22140
atgttgtgca tattttcttg tacacgctgc cctgatccgg caaaaaacga aaggtggcgc  22200
gctcgtcgtg atccacatgg tacttttcca ttagcatagc catggcttcc atgccttttt  22260
cccaagctga aactaggggc tggcttgccg gattgcgaac aacaacaaca ttcttttcat  22320
tttcgtcgct gttttgagcg gaagccttca aaacgtgtac ctgcctggtt tccatttttt  22380
gaaaagactg agaaccgtct gcatgatgca taatgcggac gggcggcatg ctgaaaccca  22440
ttactcctaa aactgctctt ggtggttctg cctcttcttc ttctgcactc tctggggaaa  22500
gaggtatcgc agccatagat ttcttgactt ttttctttgg aggtaaaggc acagcttcca  22560
gttcttcttc gctttcggaa tccagaaagt atctgcccat ttttggcggc ggcggctgag  22620
cgctgcggtc tggggtgcgc tccctctgtg agtgctgatt gctggccatt atttaatcct  22680
aggcaaagaa acacatgatg gatctggagc cacaggaaag cttaaccgcc cccaccgctc  22740
ccgccattgg cgctacggct gtcatggaga aggacaaaag tctactcata ccccaagacg  22800
caccggttga gcagaacttg ggctacgaga ctcccccgga ggaatttgaa ggctttcttc  22860
aaatccaaaa gcaaccaaat gagcaaaacg ctgggctcga ggaccatgac tacctaaacg  22920
agggagatgt cctgtttaaa catctacagc gacaaagcac tatcgttcgc gacgccatat  22980
ctgatcgctc ttcaatacca gtttcaattg cagaactatc ttgcatctac gaacgcaacc  23040
tgttctcccc acgtgtgccc cctaaacggc aagccaacgg cacatgcgag ccaaatcctc  23100
gccttaactt ctacccagtt tttgcagtgc cagaagcact ggcaacatac catattttct  23160
ttaaaaatca caaaataccc ctatcctgtc gagctaaccg cagccgcgca gatgagcttc  23220
ttgctttaag ggctggcgct tccatacctg ggattgtgtc cttggaagag gtgcctaaaa  23280
tttttgaagg tttaggtcgg gatgaaaaac gagcagcaaa tgccctgcaa aaagaaaatg  23340
aacaaaatca ccatgggaat agtgctctaa tagaactgga aggtgacaat gcccgcctgg  23400
cagttttaaa gcgcaatatt gaggttactc actttgccta cccggcagta aatcttccgc  23460
caaaggtaat gagcgcagtg atgaatcagc tactaattaa gcgagcccaa cccattgaca  23520
aagatgcaaa cttgcaagac ccggaggcaa cagatgatgg aaagccggtt gtaagcgacg  23580
agcaattaac taagtggttg ggaacagaca attccaacga actacaacag cggcgtaaac  23640
tcatgatggc cgccgtactt gtaactgtgg aactcgagtg catgcatcgt tttttctccg  23700
acatcaccac attgcgcaaa attgaggaat gtcttcacta cactttccgc catggctacg  23760
```

-continued

```
tgcgccaagc ctgtaaaatt tctaatgtgg agctgagcaa tctagtttct tacatgggca  23820
tcttgcatga aaaccgattg ggacagaacg tgctacactc aacactacgc gatgaagcac  23880
gcagagatta cgtgcgagac tgcatttacc ttttcctgtt acatacctgg caaactggga  23940
tgggtgtttg gcagcaatgc ttggaagaaa aaaaccttcg agaactaaac aaactgttag  24000
acagagcact aaaatcccta tggaccggtt ttgacgaacg gacagtagct gcagagctag  24060
ctgacataat tttcccagaa aggttaatga taaccttgca aaacggcttg cctgacttta  24120
tgagtcaaag tatgctgcac aattatcgct cttttatatt agagcgttct gggatgcttc  24180
ctagcatgtg ttgtgcactt ccttcagatt ttgtgcctat atattttaga gagtgccccc  24240
ctcccctgtg gagccactgc tacttactac gacttgctaa ctacctagct taccactcag  24300
accttatgac agattcaagc ggcgaaggcc taatggagtg tcactgccgc tgcaatcttt  24360
gcacccccca ccgttctttg gtttgcaata ctgaactatt aagtgaaagt caagtcattg  24420
gtaccttcga aatgcaggga ccgcagtctg acagcaattt cacgacgaac ctaagactta  24480
cccctgggct ttggacttct gcctacctgc gcaaatttga accccaagat taccacgccc  24540
acagtatcaa tttttacgaa gaccaatcca aacccccaaa agcgccacta acggcttgcg  24600
tcattacgca gggaaaaatt ctagcccaat tgcatgctat taagcaagcg cgcgaagagt  24660
ttttacttaa aaaaggacac ggagtgtacc ttgatcccca aaccggcgag gaactaaacc  24720
ttccatcacc tttgtgtgct actgcgtctc cccattcgca gcatgtcccc gaaagccgca  24780
aaacaggcta ttgcgcagca acgctcaaag aaacagcagc aacggcagga aatctgggag  24840
gaagaatctt gggagagtca ggcagaggac gaggtcgagg acttggaaga atgggaggag  24900
gaggaggcgg acagcctaga cgaggatcca gaggaggagg aggaaggttc caaggacgga  24960
gcgaccgccg ccaaaccgtc gctttcaacc aagccctctc caatgaaacc cgctgtgagc  25020
aaatctcaga aagccaaccg tagatgggac accattgaaa ccagcgccgc aaacttgggt  25080
aagaatcgca agcaggcgcg tcggggctac tgctcatggc gggctcacca aagtaatatt  25140
gtagcctgct ttcagcactg cgggggggaat atctcatttg caaggcggta tttgctatac  25200
catgatggag tggcgattcc aaggaatgtc ctccattact accgtcatct ctacagcccc  25260
tttgaagagc tcgacaagga accgacctgc aacagccaag cggcccacta gaatcggcaa  25320
cagcagcaac aaggaaagtc ctgaggcgcg cgagttaaga aaacgcattt ttcccacttt  25380
atatgctatt tttcagcaga gtcgaggtca agaacacgaa ctgaaaataa aaaaccgttc  25440
cctgcgttca cttacccgca gctgtctcta cctcaaaagc gaagatcagt tgcaacgcac  25500
cttgcaggac gcagaagctc tgttcaataa atactgctcc ctctcgctta aagagtaaaa  25560
aaagcccgcg cgcggacttt caacaggcgg gaaaagtgac gtcacaacaa gatgagtaaa  25620
gatattccca cgccttacat gtggagcttt caaccccaaa tgggactggc ggccggcgcg  25680
gctcaagact attctagcaa aatgaattgg ttaagcgccg gaccccacat gatttccagg  25740
gtgaatgggg tacgagcccg gcgtaaccaa atactgctag aacaagccgc tctcaccgct  25800
acaccacgta atcaacttaa ccctccctct tggccagctg ccctgatata tcaggaaaat  25860
ccccctccta ccactgtact tttgcctcgc gacgcccagg ccgaagtcca tatgactaac  25920
gctggggcac agcttgcggg cggtgcacgt cacagtttca ggtataaagg tcgcactgag  25980
ccctatccgt ctccagctat aaaaagagta ctcatcagag ggaaaggtat tcagctgaac  26040
gacgaagtca catcgccatt gggagtcaga cccgacggag tgtttcagct cggagggtcc  26100
ggacgttcct cctttaccgc tcgtcaagcc tacctgacac tacagagctc atcctcagct  26160
```

-continued

```
ccgagatctg gtggtattgg aactctccaa tttgtggagg aatttactcc atctgtttac  26220
ttcaatcctt tttcgggctc gcctggacac tatcctgacg ccttcatacc caactttgac  26280
gcagtgagtg aatctgtgga tggctatgat taatgtctaa tggagcggct gacagagcgc  26340
ggctgcgaca tttagaccac tgtcgccaac ctcactgctt tgctcgagac atctgtgtct  26400
ttacctactt tgagcttcca gaggagcacc cccaggggcc agctcacggt gtcagaataa  26460
cagttgaaaa aggaattgat acacacctca ttaaattttt caccaaacgc ccgctattgg  26520
tggaaaaaga tcaaggaaat actatattaa ctttatattg catttgtcct gttcccggat  26580
tacatgaaga tttctgctgt catttgtgtg ctgaatttaa tcatctgtag tggcgctgta  26640
ccgcctgaag aagaacctaa ctgtcatccg catttaagca acattaaaat caacctttcg  26700
atccctcata tcactcttcg ctgcagtttt ttttccacac atctcacctg gacctttaac  26760
ggaaaacacg ttaccaatac agatataaag tttaaactac acaaagaaaa catcactcta  26820
tttcaaccta ttaacctggg atactaccgc tgctcagctc caccctgtac gcaagcattt  26880
tttgttgctc cagttattga caaacgccct gctccgacaa cagctgctgt cactgagcac  26940
atcaccgagg cagtttctcc ttctaaaggt acagaggaaa ttgtgtactt ttcaaacttt  27000
acaaaccact tagttttaaa ttgttcctgt tctaactcct taatttcatg gtttgctaac  27060
agctctctgt gcaaaacttt ctaccaagga aaacttttgt attctgctaa actcacattg  27120
tgtaaccaga gcaccccttc ccaccttact ctattgccac cttttgttgc cggtcgttac  27180
ttttgcatag gagctgcacg tactagcccc tgtcaacagc attggaattt aacttactgt  27240
cccccaccag tgtcgccctt tgtgatcaat actgaatatt tagactataa tcccttgctt  27300
gcttacggcg gtctcgcagc tcttatttta ttcctgattt ctaacttgtt tctagtgcaa  27360
catttgtatt catactaaca atgctttcca tttttctttt atttctcttt tctttacctt  27420
ctggcttgta tgctcaaaca gccgaaagac cactaaaagt cgtggtggaa gctggccata  27480
atgtaaccct tccccacctt tctggttcac accaaactgg ccatgttact tggctagtag  27540
agacatcaga ttatggttca gcttctccag acaacttcat tttcagtgga caaaaactat  27600
gccagtttac tgacagaacc atggtgtggc cttattacaa tttacatttt aactgtgaaa  27660
attatgacct taatctgttt tggcttaagg tggaaaattc ggctatttac aacgttaaaa  27720
atacagtcaa tgcttctgaa acaaatattt actatgattt aagagtagta caaatttttc  27780
cacctaaatg catcattact tcaaagtacc ttacaaacga ttattgtcac attacaatta  27840
actgcactaa ctctgattac cccaataagg ttgtgtttaa taatgtcagt cgatggtact  27900
acggatacgg taagggcagc ccaacccttc ccaactactt tataactaac tttaatgttt  27960
caggtattac taaaagcttt aatcacactt accctttttaa tgagctctgt gattatccca  28020
catcccaatc tcaacacagt ttaacacata cagtaagcac agtaatcttt ttaggaataa  28080
ttggcttcag cattttgatt attatagcag cctttattta tctgtgctgg catagaaaat  28140
ctttgtgtgt ttctaaaaca gaacctctta tgccgattcc ttactagttt tcttttttct  28200
tacagtatgg tgacggttct tctcatcttt ttatgcctgc cagtcatttt ttcttcttcg  28260
acttttgccg cagtcagtga ccttgatccc gagtgtttag cccccctttgc ggtgtacctg  28320
attttcacat ttgtgactgc tacctgcgtc tgcagtatta ttactctgct aatcacctcg  28380
ctccaatttt ttgattacta ctacgtgaga attgtttacc gcagacacca cccccgttac  28440
caaaaccctc aaattgcggc tcttttgcag ctccaaccat gaaaacagca ttagttcttt  28500
```

-continued

```
tctttatgtt aatcccagtt tgggctagtt cttgtcaact acataaacca tggaattttt  28560
tagattgtta tactaaagaa acaaactaca taggctgggt ttatggaatt atgtctggct  28620
tagtatttgt ctcctctgta gtttctttac aactgtatgc gcgccttaat tttagttgga  28680
ataagtatac tgatgatctt cccgaatatc caaacccccca ggatgattta cccctaaata  28740
ttgtatttcc agagcccccg cgtcctcctt ctgttgttag ctattttaag ttcaccggtg  28800
aagatgattg aacctgatct agaaattgat ggaagaatca ccgaacagag gctcctcact  28860
gatcgcgcta ggcgacgcca acaggatcaa aaaaataaag agttaattga tttacaaacc  28920
gtgcatcagt gtaaaaaagg actttttgc ctggtaaaac aagctaccct tcgctatgaa  28980
tctttaccag gcaaagaaca tcaactgtgc tacacgctgc ccactcagcg acaaaccttt  29040
actgcaatgg tgggctcggt acctattaaa gtgtcccaac aagcaggaga acaagaaggc  29100
tctattcggt gcctatgtga taaccctgaa tgtttgtaca ctttaataaa aacactgtgc  29160
ggtttaagaa atcttttacc aatgaattaa ataaattact taccggaaat ctgaaaatac  29220
atcatggtct ccgtgtactc ttataaaatt tccctcttcc caactgtcaa acctgacaga  29280
cttgcaaaca gcaaactttc tccaaatctt aaatggaagg tcagattctt cttcccaatc  29340
cctacccacc atcttcatct tttctagatg aagcgcagca gaacccagta tgctgaagaa  29400
acagaagaaa atgatgactt caaccccgtt taccctttttg acccatttga cacatcagac  29460
gtaccctttg ttacaccccc ttttacttct tccaatggtc ttcaagaaaa accaccaggt  29520
gtattagcac ttaattacaa agaccccatt gtaactgaaa atggaaccct tacactcaag  29580
ctaggggacg gaataaaact taatgcccaa ggtcaactta cagctagtaa taatatcaat  29640
gttttggagc cccttaccaa cacctcacaa ggtcttaaac tttcttggag cgccccccta  29700
gcagtaaagg ctagtgccct cacacttaac acaagagcgc ccttaaccac aacggatgaa  29760
agcttagcct taataaccgc ccctcccatt acagtagagt cttcgcgttt gggcttggcc  29820
accatagccc ctctaagctt agatggaggt ggaaacctag gtttaaatct ttctgctccc  29880
ctggacgtta gtaacaacaa tttgcatctc accactgaaa ctcccttagt tgtaaattct  29940
agcggtgccc tatctgttgc tactgcagac cccataagtg ttcgcaacaa cgctcttacc  30000
ctacctacgg cagatccgtt aatggtgagc tccgatgggt tgggaataag tgtcactagt  30060
cccattacag taataaacgg ttccttagcc ttgtctacaa ctgctcccct caacagcaca  30120
ggatccactt taagtctgtc tgttgccaat cctctgacta tttcacaaga cacattgact  30180
gtttccactg gtaacggtct tcaagtgtcg ggtctcaat tagtaacaag aatagggggat  30240
ggtttaacat tcgataatgg ggtcatgaaa gtaaacgttg ccgggggaat gagaacttct  30300
ggcggtagaa taattttaga tgttaattat ccctttgatg cgagcaataa cctgtcctta  30360
agacggggat tgggactaat ttataaccaa tctacaaact ggaacttaac aactgatatt  30420
agtaccgaaa aaggtttaat gtttagtggc aatcaaatag ctcttaatgc aggtcagggg  30480
cttacattta ataatggcca acttagggtt aagttgggag ctggacttat ttttgattca  30540
aacaataaca ttgccttagg cagcagcagc aacactccat acgaccctct gacactgtgg  30600
acaactcctg acccaccacc aaactgcagc ctcatacaag agctagatgc aaaactcacc  30660
ctgtgcttaa caaaaaacgg atctattgtt aatggcattg taagtttagt gggtgttaag  30720
ggtaatctcc taaatatcca aagtactact accactgtag gagtgcattt agtgtttgat  30780
gaacagggaa gattaatcac atcaacccct actgccctgg ttccccaagc ttcgtgggga  30840
tatagacaag gccaatcagt gtctaccaat actgttacca atggtctagg ttttatgcct  30900
```

-continued aatgtgagtg cttaccctag accaaatgcc agtgaggcta aaagccaaat ggtaagtctc 30960
acgtacttac agggagatac atctaaacct ataacaatga aagttgcatt taatggcatt 31020
acgtcgctaa atggatactc tttaacattc atgtggtcag gtctatcaaa ctatataaat 31080
cagcctttct ctacaccatc ctgctccttt tcttacatta cccaagaata aaaacacaca 31140
caaaacacaa attgcgtact tattgtttat tttttttttt ttttacacta tacgcgtggt 31200
taaactgcct ccttcccatt ttaccttgta tacctccctt tccccctttg tagctgaaaa 31260
caactgcact tgaatatttc gacttaggtt ttttggcgtt agcgtccaca cagtttcttt 31320
acgggcaaag cgagggtcgg tgatggaaac gaatccctcg cccgcacagt cactcaagcg 31380
gcattcccca tccaaaacca ggtccatgat tttatcctac aaaaagtaac aacagtcagt 31440
gtccatcagc cgcccaagga ttctctcgtt gattataatc tccaaataaa attgctcgat 31500
gatgcataat taaacccttt agcagttgct gacgataacg ttcatgccga ctatgtttta 31560
gagggcgaac agtgttttca gcaattactt gaacaacttt taacattagc agtctggtac 31620
gacgagcgca acagcgcatg cgtatctcac ttaagtcttt acaataatca caacacagca 31680
ctaacatgtt atttaaaatt ccataattaa aggcgctcca tccaaaacta actttttcta 31740
acgctaacca ggcatggcca tcatacataa ttttaaagta aattaaatgg cgacctctaa 31800
caaaggtgct tcccacatac atcacctctt taggcattaa atggttaaca acctcccgat 31860
accaaaaaca ccttttgtta attaaggcgc catatacggc cattttgaac cagcgtccca 31920
aaagcatccc agctgacata cactgtagtg aacccggacg ctggcaatga caatgaataa 31980
gccaccgctc atgaccatgt aataattgag taacttcaac atttatagtg gcacaacaca 32040
tacatacact catgtatttt ttcaaaataa acatctcata atcagttaga atcatatccc 32100
acggtattgg ccattcctgc agcactgtaa aacctacaca tgaaggaatg cctcttacct 32160
cacttacatt atgtaaagtc agactattac actcaggcca taaagaattt tccgaagtac 32220
tcaacgtagc ttttgactgt tcctcacagg gcggtagttg gtacttgttg tatggtgcca 32280
atctgtagcg ataccgtctg tcgcgctgca tcgtaaacaa cagacttgcg agcgtcttcg 32340
tacttaaaaa aacaaaacca cgtacgacca ctggttatcg cacctcgtcc tttttgtttg 32400
cagcgttggc gttccgtcaa aaaagcaaag tacaaccact ctcgcaggct tgctaaaatg 32460
tattcagctt caggtgttat cttcaaatca tgatgtttaa taaagcgcag agtatccaca 32520
caggatgcat gggctaaacc aagccatgct atgcaggcag ccgtgtcccg acttacagga 32580
ggaggaggaa tacaaggtag aggcataaaa acttaatcaa gacggtcagc aaggatttga 32640
atgcgtaaat ctcgcaggtg gcagcgatcg cctccgctgt gctggtgaaa gatcacagcc 32700
agatcaaatt gtaagcgatt ttccaaatgt tcaacaacag cttctaaaag agccacagct 32760
ctgatttcga taaacaaaag caaagcaaat gcattatcat gaaactcttc tatcatcaaa 32820
ctgcctgact gaaccattcc caggtaattt tcattcttcc actgttgtat tatttgaaca 32880
cactgatttt gcaggtttaa accgtgaata ttaaaaagct ctgtaagggc gccctccacc 32940
gccatccgca ggcagtactt catatttgct gaaaaaagtc tggatcttca aacacctgca 33000
gtaaattcag tagatttaca ttaggctcca caccttggtc tcgcagctga catcttaatg 33060
ccagttgtat aaaatcatac aaatcagaag ccagcagcaa agaaagttca cctccaggta 33120
caagttccgg agttcccaca gaacatacaa cttgcacaaa tggacccata ttagtaagcg 33180
tggcgccaac gtagacatcg cgcataggag gagttaaata atgcattacc agcagccaaa 33240

-continued

```
actcaggtag cacgtcttta agaaacgtca ccacctcaaa atctaagcca tgcaaatagt  33300

tccgtaaaga ctccggaaac aacacggagt aatgaacaag cgacctctga aacatgcttt  33360

aggttagcct gaaaaataaa aatatgttaa attaaagatg cctggcaaac gggtggaaaa  33420

acaactctac ttaaaagcaa gcgcgcgact ggctgctttg cgcgaacatc gcaaaacacg  33480

tcggaatgat taaacaacaa aacactgagc tccattcttg agcctggata aagcgtttca  33540

gcgccaacaa aaacccctct ggcgttcatg tcgcataatg aaaacaatgt tcccaaatat  33600

ccaggaggaa tatcaactgc tatgtgcaaa tataaaagca caactccatg tggaggtata  33660

acaaaattcg caggagaaaa taacacataa gcattagagt cgccctcttg tttaggcaac  33720

atagccccag gtcccgtaaa atacacataa agagtctcaa aagcagccat aatgccttac  33780

cagaaaaaca gtacaaagcc aggcacagca gacacaatct gccgcaagtg cgcaccttta  33840

atactgaaaa atagtgacgt aaatggccaa agttcgccta cacaacacaa aaaaaacccc  33900

aaaagcccgc gaaaaaaatc acttccgcat atgactcggc ataatacggt gttctcacga  33960

cacgtcacat ccggcgcgcc cggctcccac gccgcgcccc acttcctcat ccgcccaaac  34020

ttacaagcac gccaaagcca cacctccacc caatcaaatt acacactacg cccacttcat  34080

tttaatattg gcactagtcc agtataaggt atattattag atagg                34125
```

<210> SEQ ID NO 26
<211> LENGTH: 35100
<212> TYPE: DNA
<213> ORGANISM: Human adenovirus type 17
<220> FEATURE:
<221> NAME/KEY: misc_feature
<222> LOCATION: (25184)..(25184)
<223> OTHER INFORMATION: The n at this position can be a, c, t, or g.

<400> SEQUENCE: 26

```
catcatcaat aatatacccc acaaagtaaa caaaagttaa tatgcaaatg aggttttaaa     60

tttagggcgg ggctactgct gattggccga gaaacgttga tgcaaatgac gtcacgacgc    120

acggctaacg gtcgccgcgg aggcgtggcc tagcccggaa gcaagtcgcg gggctgatga    180

cgtataaaaa agcggacttt aaacccggaa acggccgatt ttcccgcggc cacgcccgga    240

tatgaggtaa ttctgggcgg atgcaagtga aattaggtca ttttggcgcg aaaactgaat    300

gaggaagtga aaagtgaaaa ataccggtcc cgcccagggc ggaatattta ccgagggccg    360

agagactttg accgattacg tgtgggtttc gattgcggtg ttttttcgcg aatttccgcg    420

tccgtgtcaa agtccggtgt ttatgtcaca gatcagctga tccacagggt atttaaacca    480

gtcgagcccg tcaagaggcc actcttgagt gccagcgagt agagatttct ctgagctccg    540

ctcccagagt gtgagaaaaa tgagacacct gcgcctcctg cctggaactg tgcccttgga    600

catggccgca ttattgctgg atgactttgt gagtacagta ttggaggatg aactgcaacc    660

aactccgttc gagctgggac ccacacttca ggacctctat gatttggagg tagatgccca    720

ggaggacgac ccgaacgaag atgctgtgaa tttaatattt ccagaatctc tgattcttca    780

ggctgacata gccagcgaag ctctacctac tccacttcat actccaactc tgtcacccat    840

acctgaattg gaagaggagg acgagttaga cctccggtgt tatgaggaag gttttcctcc    900

cagcgattca gaggacgaac agggtgagca gagcatggct ctaatctcag actatgcttg    960

tgtggttgtg gaagagcatt ttgtgttgga caatcctgag gtgcccgggc aaggctgtaa   1020

atcctgccag taccaccggg ataagaccgg agacacgaac gcctcctgtg ctctgtgtta   1080

catgaaaaag aacttcagct ttatttacag taagtggagt gaatgtgaga gaggctgagt   1140
```

-continued gcttaagaca taactgggtg atgcttcaac agctgtgcta agtgtggttt attttgtttc 1200
taggtccggt gtcagaggat ggtcatcacc ctcagaagaa gaccacccgt gtccccctga 1260
tctgtcaggc gaaacgcccc tgcaagtgca cagacccacc ccagtcagac ccagtggcga 1320
gaggcgagca gctgttgaaa aaattgagga cttgttacat gacatgggtg gggatgaacc 1380
tttggacctg agcttgaaac gtcccaggaa actaggcgca gctgcgctta gtcatgtgta 1440
aataaagttg tacaataaaa attatatgtg acgcatgcaa ggtgtggttt atgactcatg 1500
ggcggggctt agttctatat aagtggcaac acctgggcac tggagcacag accttcaggg 1560
agttcctgat ggatgtgtgg actatccttg cagactttag caagacacgc cggcttgtag 1620
aggatagttc agacgggtgc tccgggttct ggagacactg gtttggaact cctctatctc 1680
gcctggtgta cacagttaaa aaggattata acgaggaatt tgaaaatctt tttgctgatt 1740
gctctggcct gctagattct ctgaatctcg gccaccagtc ccttttccag gaaagggtac 1800
tccacagcct tgatttttcc agcccagggc gcactacagc cggggttgct tttgtggttt 1860
ttctggttga caaatggagc cagaacaccc aactgagcag ggctacatt ctggacttcg 1920
cagccatgca cctgtggagg gcatgggtca ggcagcgggg acagagaatc ttgaactact 1980
ggcttctaca gccagcagct ccgggtcttc ttcgtctaca cagacaaaca tccatgttgg 2040
aggaagaaat gaggcaggcc atggacgaga acccgaggag cggtctggac cctccgtcgg 2100
aagaggagtt ggattgaatc aggtatccag cctgtaccca gagcttagca aggtgctgac 2160
atccatggcc aggggagtga agagggagag gagcgatggg ggcaataccg ggatgatgac 2220
cgagctgacg gccagtctga tgaatcgcaa gcgcccagag cgccttacct ggtacgagct 2280
acagcaggag tgcagggatg agttgggcct gatgcaggat aaatatggcc tggagcagat 2340
aaaaacccat tggttgaacc cagatgagga ttgggaggag gctattaaga agtatgccaa 2400
gatagccctg cgcccagatt gcaagtacat agtgaccaag accgtgaata tcagacatgc 2460
tgctacatct cggggaacgg ggcagaggtg gtcattgata ccctggacaa ggccgccttt 2520
aggtgttgca tgatgggaat gagagccgga gtgatgaata tgaattccat gatctttatg 2580
aacatgaagt tcaatggaga gaagtttaat ggggtgctgt tcatggccaa cagccacatg 2640
accctgcatg gctgcgactt tttcggcttt aacaatatgt gcgcagaggt ctggggcgct 2700
tccaagatca ggggatgtaa gttttatggc tgctggatgg gcgtggtcgg aagacccaag 2760
agcgagatgt ctgtgaagca gtgtgtgttt gagaaatgct acctgggagt ctctaccgag 2820
ggcaatgcta gagtgaggca ctgctcttcc ctggagacgg gctgcttctg cctggtgaag 2880
ggcacagcct ctctgaagca taatatggtg aagggctgca cggatgagcg catgtacaac 2940
atgctgactg cgactcgggg gtctgtcata tcctgaagaa catccatgtg acctcccacc 3000
ccagaaagaa gtggccagtg tttgagaata acatgctgat caagtgccac atgcacctgg 3060
gcgccagaag ggcaccttc cagccgtacc agtgcaactt tagccagacc aagctgctgt 3120
tggagaacga tgccttctcc agggtgaacc tgaacggcat ctttgacatg gatgtctcgg 3180
tgtacaagat cctgagatac gatgagacca agtccagggt gcgcgcttgc gagtgcgggg 3240
gcagacacac caggatgcag ccagtggccc tggatgtgac cgaggagctg agaccagacc 3300
acctggtgat ggcctgtacc gggaccgagt tcagctccag tggggaggac acagattaga 3360
ggtaggtttg agtagtgggc gtggctaagg tgactataaa ggcgggtgtc ttacgagggt 3420
ctttttgctt ttctgcagac atcatgaacg ggaccggcgg ggccttcgaa gggggcttt 3480

-continued

```
ttagccctta tttgacaacc cgcctgccag gatgggccgg agttcgtcag aatgtgatgg   3540
gatcgacggt ggacgggcgc ccagtgcttc cagcaaattc ctcgaccatg acctacgcga   3600
ccgtggggaa ctcgtcgctt gacagcaccg ccgcagccgc ggcagccgca gccgccatga   3660
cagcgacgag actggcctcg agctacatgc ccagcagcag cagtagcccc tctgtgccca   3720
gttccatcat cgccgaggag aactgctggc cctgctggcc gagctggaag ccctgagccg   3780
ccagctggcc gccctgaccc agcaggtgtc cgagctccgc gaacagcagc agcaaaataa   3840
atgattcaat aaacacatat tctgattcaa acagcaaagc atctttatta tttatttttt   3900
cgcgcgcggt aggccctggt ccacctctcc cgatcattga gagtgcggtg gatttttttcc   3960
aagacccggt agaggtggga ttggatgttg aggtacatgg gcatgagccc gtcccggggg   4020
tggaggtagc accactgcat ggcctcgtgc tctggggtcg tgttgtagat gatccagtca   4080
tagcaggggc gctgggcgtg gtgctggatg atgtccttga ggaggagact gatggccacg   4140
gggagcccct tggtgtaggt gttggcaaag cggttgagct gggagggatg catgcggggg   4200
gagatgatgt gcagtttggc ctggatcttg aggttggcga tgttgccacc cagatcccgc   4260
cgggggttca tgttgtgcag gaccaccagg acggtgtagc ccgtgcactt ggggaactta   4320
tcatgcaact tggaagggaa tgcgtggaag aatttggaga cgcccttgtg cccgcccagg   4380
ttttccatgc actcatccat gatgatggcg atgggcccgt gggctgcggc tttggcaaag   4440
acgtttctgg ggtcagagac atcataatta tgctcctggg tgagatcatc ataagacatt   4500
ttaatgaatt ttgggcggag ggtgccagat tgggggacga tggtttccct cgggccccgg   4560
ggcgaagttc ccctcgcaga tctgcatctc ccaggctttc atctcggagg gggggatcat   4620
gtccacctgc ggggcgatga aaaaaacggt ttccggggcg ggggtgatga gctgcgagga   4680
gagcaggttt ctcaacagct gggacttgcc gcacccggtc gggccgtaga tgaccccgat   4740
gacgggttgc aggtggtagt tcaaggacat gcagctgccg tcgtcccgga ggaggggggc   4800
cacctcgttg agcatgtctc taacttggag gttttcccgg acgagctcgc cgaggaggcg   4860
gtccccgccc agcgagagga gctcttgcag ggaagcaaag tttttcaggg gcttgagtcc   4920
gtcggccatg ggcatcttgg cgagggtctg cgagaggagt tcgagacgtc ccagagctcg   4980
gtgacgtgct ctacggcatc tcgatccagc agacttcctc gtttcggggg ttgggacgac   5040
tgcgactgta gggcacgaga cgatgggcgt ccagcgcggc cagcgtcatg tccttccagg   5100
gtctcagggt ccgcgtgagg gtggtctccg tcacggtgaa ggggtgggcc cctggctggg   5160
cgcttgcaag ggtgcgcttg agactcatcc tgctggtgct gaaacgggca cggtcttcgc   5220
cctgcgcgtc ggcgagatag cagttgacca tgagctcgta gttgagggcc tcggcggcgt   5280
ggcccttggc gcggagcttg cccttggaag agcgtccgca ggcgggacag aggagggatt   5340
gcagggcgta gagcttgggc gcaagaaaga ccgactcggg agcaaaagcg tccgctccgc   5400
agtgggcgca gacggtctcg cactcgacga gccaggtgag ctcgggctgc tcggggtcaa   5460
aaaccagttt tcccccgttc tttttgatgc gcttcttacc tcgcgtctcc atgagtctgt   5520
gtccgcgctc ggtgacaaac aggctgtcgg tgtccccgta gacggacttg attggcctgt   5580
cctgcagggg cgtcccgcgg tcctcctcgt agagaaactc ggaccactct gagacaaagg   5640
cgcgcgtcca cgccaagaca aaggaggcca cgtgcgaggg gtagcggtcg ttgtccacca   5700
gggggtccac cttttccacc gtgtgcagac acatgtcccc ttcctccgca tccaagaagg   5760
tgattggctt gtaggtgtag gccacgtgac caggggtccc cgacgggggg gtataaaagg   5820
gggcgggtct gtgctcgtcc tcactctctt ccgcgtcgct gtccacgagc gccagctgtt   5880
```

-continued

```
ggggtaggta ttccctctcg agagcgggca tgacctcggc actcaggttg tcagtttcta   5940
gaaacgagga ggatttgatg ttggcttgcc ctgccgcaat gctttttagg agactttcat   6000
ccatctggtc agaaaagact atttttttat tgtcaagctt ggtggcaaag gagccataga   6060
gggcgttgga gagaagcttg gcgatggatc tcatggtctg atttttgtca cggtcggcgc   6120
gctccttggc cgcgatgttg agctggacat attcgcgcgc gacacacttc cattcgggaa   6180
agacggtggt gcgctcgtcg ggcacgatcc tgacgcgcca gccgcggtta tgcagggtga   6240
ccaggtccac gctggtggcc acctcgccgc gcaggggctc gttagtccag cagagtctgc   6300
cgcccttgcg cgagcagaac gggggcagca catcaagcag atgctcgtca gggggtccg    6360
catcgatggt gaagatgccg ggacagagtt tcttgtcaaa atagtctatt tttgaggatg   6420
catcatccaa ggccatctgc cactcgcggg cggccattgc tcgctcgtag ggttgaggg    6480
gcggacccca cggcatggga tgcgtgaggg cggaggcgta catgccgcaa atgtcgtaaa   6540
catagatggg ctccgagaag atgccgatgt tggtgggata acagcgcccc ccgcggatgc   6600
tggcgcgcac gtattcatac aactcgtgcg aggggccaag aaggccgggg ccgaaattgg   6660
tgcgctgggg ctgctcggcg cggaaaacaa tctggcgaaa gatggcgtgc gagttggagg   6720
agatggtggg ccgttggaag atgttaaagt gggcgtgggg caagcggacc gagtcgcgga   6780
tgaagtgcgc gtaggagtct tgcagcttgg cgacgaactc ggcggtgacg agaacgtcca   6840
tggcgcagta gtccagcgtt tcgcggatga tgtcataacc cgcctctcct ttcttctccc   6900
acagctcgcg gttgagggcg tattcctcgt catccttcca gtactcccgg agcgggaatc   6960
ctcgatcgtc cgcacggtaa gagcccagca tgtagaaatg gttcacggcc ttgtagggac   7020
agcagccctt ctccacgggg agggcgtaag cttgtgcggc cttgcggagc gaggtgtgcg   7080
tcagggcgaa ggtgtccctg accatgactt tcaagaactg gtacttgaaa tccgagtcgt   7140
cgcagccgcc gtgctcccat agctcgaaat cggtgcgctt cttcgagagg gggttaggca   7200
gagcgaaagt gacgtcattg aagagaatct tgcctgctcg cggcatgaaa ttgcgggtga   7260
tgcggaaagg gcccgggacg gaggctcggt tgttgatgac ctgggcggcg aggacgatct   7320
cgtcgaagcc gttgatgttg tgcccgacga tgtagagttc catgaatcgc gggcggcctt   7380
tgatgtgcgg cagctttttg agctcctcgt aggtgaggtc ctcggggcat tgcaggccgt   7440
gctgctcgag cgcccattcc tggagatgtg ggttggcttg catgaaggaa gcccagagct   7500
cgcgggccat gagggtctgg agctcgtcgc gaaagaggcg gaactgctgg cccacggcca   7560
tcttttcggg tgtgacgcag tagaaggtga gggggtcccg ctcccagcga tcccagcgta   7620
agcgcgcggc tagatcgcga gcaagggcga ccagctctgg gtcccccgag aatttcatga   7680
ccagcatgaa ggggacgagc tgcttgccga aggaccccat ccaggtgtag gtttctacat   7740
cgtaggtgac aaagagccgc tccgtgcgag gatgagagcc gattgggaag aactggattt   7800
cctgccacca gttggacgag tggctgttga tgtgatgaaa gtagaaatcc cgccggcgaa   7860
ccgagcactc gtgctgatgc ttgtaaaagc gtccgcagta ctcgcagcgc tgcacgggct   7920
gtacctcatc cacgagatac acagcgcgtc ccttgaggag gaacttcagg agtggcggcc   7980
ctggctggtg gttttcatgt tcgcctgcgt gggactcacc ctggggctcc tcgaggacgg   8040
agaggctgac gagcccgcgc gggagccagg tccagatctc ggcgcggcgg gggcggagag   8100
cgaagacgag ggcgcgcagt tgggagctgt ccatggtgtc gcggagatcc aggtccgggg   8160
gcagggttct gaggttgacc tcgtagaggc gggtgagggc gtgcttgaga tgcagatggt   8220
```

-continued

```
acttgatttc tacgggtgag ttggtggccg tgtccacgca ttgcatgagc ccgtagctgc   8280
gcggggccac gaccgtgccg cggtgcgctt ttagaagcgg tgtcgcggac gcgctcccgg   8340
cggcagcggc ggttccggcc ccgcgggcag gggcggcaga ggcacgtcgg cgtggcgctc   8400
gggcaggtcc cggtgttgcg ccctgagagc gctggcgtgc gcgacgacgc ggcggttgac   8460
atcctggatc tgccgcctct gcgtgaagac cactggcccc gtgactttga acctgaaaga   8520
cagttcaaca gaatcaatct cggcgtcatt gacggcgggc tgacgcagga tctcttgcac   8580
gtcgcccgag ttgtcctggt aggcgatctc ggacatgaac tgctcgatct cctcctcctg   8640
gagatcgccg cgacccgcgc gctccacggt ggcggcgagg tcattcgaga tgcgacccat   8700
gagctgcgag aaggcgccca ggccgctctc gttccagacg cggctgtaga ccacgtcccc   8760
gtcggcgtcg cgcgcgcgca tgaccacctg cgcgaggttg agctccacgt gccgcgcgaa   8820
gacggcgtag ttgcgcaggc gctggaagag gtagttgagg gtggtggcga tgtgctcggt   8880
gacgaagaag tacatgatcc agcggcgcag ggcatctcg ctgatgtcgc cgatggcctc   8940
cagcctttcc atggcctcgt agaaatccac ggcgaagttg aaaaactggg cgttgcgggc   9000
cgagaccgtg agctcgtctt ccaggagcct gatgagctcg gcgatggtgg cgcgcacctc   9060
gcgctcgaaa tccccggggg cctcgtcctc ttcctcttct tccatgacaa cctcttctat   9120
ttcttcctct gggggcggtg gtggtggcgg ggcccgacga cgacggcgac gcaccgggag   9180
acggtcgacg aagcgctcga tcatctcccc gcggcggcga cgcatggttt cggtgacggc   9240
gcgaccccgt tcgcgaggac gcagcgtgaa gacgccgccg gtcatctccc ggtaatgggg   9300
cgggtccccg ttgggcagcg agagggcgct gacgatgcat cttatcaatt gcggtgtagg   9360
ggacgtgagc gcgtcgagat cgaccggatc ggagaatctt tcgaggaaag cgtctagcca   9420
atcgcagtcg caaggtaagc tcaaacacgt agcagccctg tggacgctgt tagaattgcg   9480
gttgctaatg atgtaattga agtaggcgtt tttgaggcgg cggatggtgg cgaggaggac   9540
caggtccttg ggtcccgctt gctggatgcg gagccgctcg gccatgcccc aggcctggcc   9600
ctgacaccgg cttaggttct tgtagtagtc atgcatgagc ctctcgatgt catcactggc   9660
ggaggcggag tcttccatgc gggtgacccc gacgcccctg agcggctgca cgagcgccag   9720
gtcggcgacg acgcgctcgg cgaggatggc ctgttgcacg cgggtgaggg tgtcctggaa   9780
gtcgtccatg tcgacgaagc ggtggtaggc ccctgtgttg atggtgtaag tgcagttggc   9840
catgagcgac cagttgacgg tctgcaggcc gggctgcacg acctcggagt acctgagccg   9900
cgagaaggcg cgcgagtcga agacgtagtc gttgcaggtg cgcacaaggt actggtatcc   9960
gactaggaag tgcggcggcg gctggcggta gagcggccag cgctgggtgg ccggcgcgcc  10020
cggggccagg tcctcgagca tgaggcggtg gtagccgtag aggtagcggg acatccaggt  10080
gatgccggca gcggtggtgg aggcgcgcgg gaactcgcgg acgcggttcc agatgttgcg  10140
cagcggcagg aaatagtcca tggtcggcac ggtctggccg gtgagacgcg cgcagtcatt  10200
gacgctctag aggcaaaaac gaaagcggtt gagcgggctc ttcctccgta gcctggcgga  10260
acgcaaacgg gttaggccgc gcgtgtaccc cggttcgagt cccctcgaat caggctggag  10320
ccgcgactaa cgtggtattg gcactcccgt ctcgacccga gcccgatagc cgccaggata  10380
cgcgggaaga gccctttttg ccggccgarg ggagtcgcta gacttgaaag cggccgaaaa  10440
ccccgccggg tagtggctcg cgcccgtagt ctggagaagc atcgccaggg ttgagtcgcg  10500
gcagaacccg gttcgcggac ggccgcggcg agcgggactt ggtcaccccg ccgatttaaa  10560
gacccacagc cagccgactt ctccagttac gggagcgagc cccctttttt ctttttgcca  10620
```

-continued

```
gatgcatccc gtcctgcgcc aaatgcgtcc cacccccccg gcgaccaccg cgaccgcggc  10680
cgtagcaggc gccggcgcta gccagccaca gccacagaca gagatggact tggaagaggg  10740
cgaagggctg gcgagactgg gggcgccttc cccggagcga caccccccgcg tgcagctgca  10800
gaaggacgtg cgcccggcgt acgtgcctgc gcaaaacctg ttcagggacc gcagcgggga  10860
ggagcccgag gagatgcgcg actgccggtt tcgggcgggc agggagctgc gcgagggcct  10920
ggaccgccag cgcgtgctgc gcgacgagga tttcgagccg aacgagcaga cggggatcag  10980
ccccgcgcgc gcgcacgtgg cggcggccaa cctggtgacg gcctacgagc agacggtgaa  11040
gcaggagcgc aacttccaaa agagtttcaa caaccatgtg cgcaccctga tcgcgcgcga  11100
ggaggtggcc ctgggcctga tgcacctgtg ggacctggcg gaggccatcg tgcagaaccc  11160
ggacagcaag cctctgacgg cgcagctgtt cctggtggta cagcacagca gggacaacga  11220
ggcgttcagg gaggcgctgc taaacatcgc cgagcccgag ggtcgctggc tgctggagct  11280
gatcaacatc ttgcagagca tcgtagttca ggagcgcagc ctgagcttgg ccgagaaggt  11340
ggcggcaatc aactactcgg tgcttagcct gggcaagttt tacgcgcgca agatttacaa  11400
gacgccgtac gtgcccatag acaaggaggt gaagatagac agcttttaca tgcgcatggc  11460
gctcaaggtg ctgacgctga gcgacgacct gggcgtgtac cgcaacgacc gcatccacaa  11520
ggccgtgagc gcgagccggc ggcgcgagct gagcgaccgc gagctgatgc tgagcctgcg  11580
ccgggcgctg gtagggggcg ccgccggcgg cgaggagtcy tacttcgaca tgggggcgga  11640
cctgcattgg cagccgagcc ggcgcgcctt ggaggccgcc tacggtccag aggacttgga  11700
tgaggaagag gaagaggagg aggatgcacc cgctgcgggg tactgacgcc tccgtgatgt  11760
gtttttagat gcagcaagcc ccggaccccg ccataagggc ggcgctgcaa agccagccgt  11820
ccggtctagc atcggacgac tgggaggctg cgatgcaacg catcatggcc ctgacgaccc  11880
gcaaccccga gtcctttaga caacagccgc aggccaacag actctcggcc attctggagg  11940
cggtggtccc ttctcggacc aaccccacgc acgagaaggt gctggcgatc gtgaacgcgc  12000
tggcggagaa caaggccatc cgtcccgacg aggccgggct agtgtacaac gccctgctgg  12060
agcgcgtagg ccgctacaac agcacaaacg tgcagtccaa cctggaccgg ctggtgacgg  12120
acgtgcgcga agccgtggcg cagcgcgagc ggttcaagaa cgagggcctg ggctcgctgg  12180
tggcgctgaa cgccttcctg gcgacgcagc cggcgaacgt gccgcgcggg caggatgatt  12240
acaccaactt tatcagcgcg ctgcggctga tggtgaccga ggtgccccag agcgaggtgt  12300
accagtcggg cccggactac tttttccaaa ctagcagaca gggcctgcaa acggtgaacc  12360
tgagccaggc tttcaagaac ctgcgcgggc tgtggggcgt gcaggcgccc gtgggcgacc  12420
ggtcgacggt gagcagcttg ctgacgccca actcgcggct gctgctgctg ctgatcgcgc  12480
ccttcaccga cagtggcagc gtaaaccgca actcgtacct gggtcacctg ctaacgctgt  12540
accgcgaggc cataggccag gcgcaggtgg acgagcagac cttccaggag atcactagcg  12600
tgagccgcgc gctggggcag aacgacaccg acagtctgag ggccaccctg aacttcttgc  12660
tgaccaatag acagcagaag atcccggcgc agtacgcgct gtcggccgag gaggagcgca  12720
tcctgagata tgtgcagcag agcgtagggc ttttcctgat gcaggagggg gccactccca  12780
gcgccgcgct ggacatgacc gcgcgcaaca tggaacctag catgtacgcc gccaaccggc  12840
cgtttatcaa taagctaatg gactacctgc atcgcgcggc gtccatgaac tcggactact  12900
ttaccaatgc cattttgaac ccgcactggc ttccgccgcc ggggttctat acgggcgagt  12960
```

-continued

```
acgacatgcc cgaccccaac gacgggtttt tgtgggacga cgtggacagc gcggtgtttt  13020
caccgacctt gcaaaagcgc caggaggcgg tgcgcacgcc cgcgagcgag ggcgcggtgg  13080
gtcggagccc ctttcctagc ttagggagtt tgcatagctt gccgggctct gtgaacagcg  13140
gcagggtgag ccggccgcgc ttgctgggcg aggacgagta cctgaacgac tcgctgctgc  13200
agccgccgcg ggtcaagaac gccatggcca ataacgggat agagagtctg gtggacaaac  13260
tgaaccgctg gaagacctac gctcaggacc atagggagcc tgcgcccgcg ccgcggcgac  13320
agcgccacga ccggcagcgg ggcctggtgt gggacgacga ggactcggcc gacgatagca  13380
gcgtgttgga cttgggcggg agcggtgggg tcaacccgat atcgcgcatc ctgcagccca  13440
aactggggcg acggatgttt tgaatgcaaa ataaaactca ccaaggccat agcgtgcgtt  13500
ctcttccttg ttagagatga ggcgtgcggt ggtgtcttcc tctcctcctc cctcgtacga  13560
gagcgtgatg gcgcaggcga ccctggaggt tccgtttgtg cctccgcggt atatggctcc  13620
tacggagggc agaaacagca ttcgttactc ggagctggct ccgttgtacg acaccactcg  13680
cgtgtacttg gtggacaaca agtcggcgga catcgcttcc ctgaactatc aaaacgacca  13740
cagcaacttc ctgaccacgg tggtgcagaa caacgatttc acccccgccg aggctagcac  13800
gcagacgata aattttgacg agcggtcgcg gtggggcggt gatctgaaga ccattctgca  13860
caccaacatg cccaatgtga acgagtacat gttcaccagc aagtttaagg cgcgggtgat  13920
ggtggctaga aaacacccac aggggtaga agcaacagat ttaagcaagg atatcttaga  13980
gtatgagtgg tttgagttta ccctgcccga gggcaacttt tccgagacca tgaccataga  14040
cctgatgaac aacgccatct tggaaaacta cttgcaagtg ggcggcaaa atggcgtgct  14100
ggagagcgat attggagtca agtttgacag cagaaatttc aagctgggct gggaccctgt  14160
gaccaagctg gtgatgccag ggtctacac ctacgaggcc tttcacccgg acgtggtgct  14220
gctgccgggc tgcggggtgg acttcacaga gagccgcctg agcaacctcc tgggcattcg  14280
caagaagcaa cctttccaag agggcttcag aatcatgtat gaggatctag aaggggcaa  14340
catccccgcc ctgctggatg tgcccaagta cttggaaagc aagaagaagt tagaggaggc  14400
attggagaat gctgctaaag ctaatggtcc tgcaagagga gacagtagcg tctcaagaga  14460
ggttgaaaag gcagctgaaa aagaacttgt tattgagccc atcaagcaag atgataccaa  14520
gagaagttac aacctcatcg agggaaccat ggacacgctg taccgcagct ggtacctgtc  14580
ctatacctac cgggaccctg agaacggggt gcagtcgtgg acgctgctca ccaccccgga  14640
cgtcacctgc ggcgcggagc aagtctactg gtcgctgccg gacctcatgc aagaccccgt  14700
caccttccgt tctacccagc aagtcagcaa ctaccccgtg gtcggcgccg agctcatgcc  14760
cttccgcgcc aagagctttt acaacgacct cgccgtctac tcccagctca tccgcagcta  14820
cacctccctc acccacgtct tcaaccgctt ccccgacaac cagatcctct gccgtccgcc  14880
cgcgcccacc atcaccaccg tcagtgaaaa cgtgcctgct ctcacagatc acgggacgct  14940
accgctgcgc agcagtatcc gcggagtcca gcgagtgacc gtcactgacg cccgtcgccg  15000
cacctgtccc tacgtctaca aggccctggg catagtcgcg ccgcgtgtgc tttccagtcg  15060
caccttctaa aaaatgtcta ttctcatctc gcccagcaat aacaccggct ggggtattac  15120
taggcccagc agcatgtacg gaggagccaa gaaacgtccc agcagcaccc cgtccgcgtc  15180
cgcggccact tccgcgctcc gtggggcgct tacaagcgcg ggcggactgc caccgccgcc  15240
gccgtgcgca ccaccgtcga cgacgtcatc gactcggtgg tcgccgacgc gcgcaactat  15300
actcccgccc cttcgaccgt ggacgcggtt cattgacagc gtggtggcga cgcggcggcg  15360
```

-continued

```
atatgccaga cgcaagagcc ggcgggcgga cggatcgccc aggcgccatt cggagcacgc  15420
ccgccatggg gcgccgcccg agctctgctg cgccgcgcca gacgcacggg ccgccgggcc  15480
atgatgcgag ccgcgcgccg cgccgccact gcaccccccg caggcaggac tcgcagacga  15540
gcggccgccg ccgccgccgc ggccatctct agcatgacca gacccaggcg cggaaacgtg  15600
tactgggtgc gcgactccgt cacgggcgtg cgcgtgcccg tgcgcacccg tcctcctcgt  15660
ccctgatcta atgcttgtgt cctcccccgc aagcgacgat gtcaaagcgc atctacaaga  15720
gagatgctcc aggtcgtcgc cccggagatt tacggaccac cccaggcgga ccagaaaccc  15780
cgcaaaatca agcgggttaa aaaaaaggat gaggtggacg agggggcagt agagtttgtg  15840
cgcgagttcg ctccgcggcg gcgcgtaaat tggaaggggc gcaggtgcac gcgtgttgcg  15900
gcccggcacg gcggtggtgt tcacgcccgg cgagcggtcc tcggtcagga gcaagcgtag  15960
ctatgacgag gtgtacggcg acgacgacat cctggaccag gcggcagagc gggcgggcga  16020
gtttgcctac gggaagcggt cgcgcgaaga ggagctgatc tcgctgccgc tggacgagag  16080
caatcccacg ccgagcctga agcccgtgac ctgcagcagg tgctgcccca ggcggtgctg  16140
ctgccgagcc gcgggatcaa gcgcgagggc gagaacatgt acccgaccat gcagatcatg  16200
gtgcccaagc gccggcgcgt ggaggaagtg ctggacaccg tgaaaatgga tgtggagccc  16260
gaggtcaagg tgcgccccat caagcaggtg gcgccgggcc tgggcgtgca gaccgtggac  16320
attcagatcc ccaccgacat ggatgtcgac aaaaaaccct cgaccagcat cgaggtgcag  16380
accgacccct ggctcccagc ctccaccgct accgcttcca cttctaccgt cgccacggtc  16440
accgagcctc ccaggaggcg aagatggggc cccgccaacc ggctgatgcc caactacgtg  16500
ttgcatcctt ccattatccc gacgccgggc taccgcggca cccggtacta cgccagccgc  16560
aggcgcccag ccagcaaacg ccgccgccgc accgccaccc gccgccgtct gccccccgcc  16620
cgcgtgcgcc gcgtaaccaa cgcgccgggg ccgctcgctc gttctgccca ccgtgcgcta  16680
ccaccccagc atcctttaat ccgtgtgctg tgatactgtt gcagagagat ggctctcact  16740
tgccgcctgc gcatccccgt tccgaattac cgaggaagat cccgccgcag gagaggcatg  16800
gcaggcagcg gcctgaaccg ccgccggcgg cgggccatgc gcaggcgcct gagtggcggc  16860
tttctgcccg cgctcatccc cataatcgcg gcggccatcg gcacgatccc gggcatagct  16920
tccgttgcgc tgcaggcgtc gcagcgccgt tgatgtgcga ataaagcctc tttagactct  16980
gacacacctg gtcctgtata tttttagaat ggaagacatc aattttgcgt ccctggctcc  17040
gcggcacggc acgcggccgt tcatgggcac ctggaacgag atcggcacca gccagctgaa  17100
cgggggcgcc ttcaattgga gcagtgtctg gagcgggctt aaaaatttcg gctcgacgct  17160
ccggacctat gggaacaagg cctggaatag tagcacgggg cagttgttga gggaaaagct  17220
caaagaccag aacttccagc agaaggtggt ggacggcctg gcctcgggca ttaacggggt  17280
ggtggacatc gcgaaccagg cagtgcagcg cgagataaac agccgtctgg acccgcggcc  17340
gcccacggtg gtggagatgg aagatgcaac tcttccgccg ccgaagggcg agaagcggcc  17400
gcggccagat gcggaggaga cgatcctgca ggtggacgag ccgccttcgt acgaggaggc  17460
cgtgaaggcc ggcatgccca ccacgcgcat catcgcgcca ctggccacgg gtgtaatgaa  17520
acccgccacc cttgacctgc ctccaccacc cacgcccgct ccaccgaagg cagctccggt  17580
tgtgcagccc cctccggtgg cgaccgccgt gcgccgcgtc cccgcccgcc gccaggccca  17640
gaactggcag agcacgctgc acagtattgt gggcctggga gtgaaaagtc tgaagcgccg  17700
```

-continued

```
ccgatgctat tgagagagag gaaggaggac actaaaggga gagcttaact tgtatgtgcc  17760
ttaccgccag agaacgcgcg aagatggcca ccccctcgat gatgccgcag tgggcgtaca  17820
tgcacatcgc cgggcaggac gcctcggagt acctgagccc gggtctggtg cagtttgccc  17880
gcgccaccga cacgtacttc agcctgggca acaagtttag gaaccccacg gtggccccga  17940
cccacgatgt gaccacggac cggtcccagc gtctgacgct gcgctttgtg cccgtggatc  18000
gcgaggacac cagtactcgt acaaggcgcg cttcactctg gccgtgggcg acaaccgggt  18060
gctagacatg gccagcacgt actttgacat ccgcggcgtc ctggaccgcg gtcccagttt  18120
caaaccctac tcgggcacgg cttacaacag ccttgccccc aagggcgctc ccaatcccag  18180
tcagtgggtt gccaaagaaa atggtcaggg aactgataag acacatactt atggctcagc  18240
tgccatggga ggaagcaaca tcaccattga aggtttagta attggaactg atgaaaaagc  18300
tgaggatggc aaaaaagata tttttgcaaa taaactttat cagccagaac ctcaagtagg  18360
tgaagaaaac tggcaagagt ctgaagcctt ctatggaggc agagctctta agaaagacac  18420
aaaaatgaag ccctgctatg gctcatttgc aagacctacc aatgaaaaag gcggacaagc  18480
taaatttaag ccagtggaag aggggcagca acctaaagat tatgacatag atttggcttt  18540
ctttgacaca cctggaggca ccatcacagg aggcacagac gaagaatata aagcagacat  18600
tgtgttgtac actgaaaatg tcaaccttga aaccccagac acccacgtgg tatacaagcc  18660
aggaaaagag gatgacagtt cagaagtaaa tttgacacag cagtccatgc ccaacaggcc  18720
taactacatt ggcttcagag acaactttgt gggactcatg tactacaaca gtactggcaa  18780
catgggtgtg ctggctggtc aggcctctca attgaatgct gtggtcgact tgcaagacag  18840
aaacaccgag ctgtcttacc agctcttgct agattctctg ggtgacagaa ccagatactt  18900
cagcatgtgg aactctgcgg tggatagcta tgatccagat gtcaggatca ttgaaaatca  18960
tggtgtggaa gatgaacttc caaactattg cttcccattg aatggcactg gcaccaattc  19020
aacatatctt ggcgtaaagg tgaaaccaga tcaagatggt gatgttgaaa gcgagtggga  19080
taaagatgat accattgcaa ggcagaatca aatcgccaag ggcaacgtct ttgccatgga  19140
gatcaacctc caggccaacc tgtggaagag ttttctgtac tcgaacgtgg ccttgtacct  19200
gcccgactcc tacaagtaca cgccggccaa tgttacgctg cccgccaaca ccaacaccta  19260
cgagtacatg aacggccgcg tggtagcccc ctcgctggtg gacgcctaca tcaacatagg  19320
cgcccgatgg tcgctggacc ccatggacaa cgtcaacccc ttcaaccacc accgcaatgc  19380
gggcctgcgc taccgctcca tgcttctggg caacggccgc tacgtgccct tccacatcca  19440
agtgccccaa aagttctttg ccatcaagaa cctgctcctg ctcccgggct cctacaccta  19500
cgagtggaac ttccgcaagg atgtcaacat gatcctgcag agttccctcg gcaacgacct  19560
gcgcgtcgac ggcgcctccg tccgcttcga cagcgtcaac ctctacgcca ccttcttccc  19620
catggcgcac aacaccgcct ccaccctgga agccatgctg cgcaacgaca ccaacgacca  19680
gtccttcaac gactacctct cggccgccaa catgctctac cccatcccgg ccaaggccac  19740
caacgtgccc atctccatcc cctcgcgcaa ctgggccgct tttcgcggct ggagtttcac  19800
ccgtctgaaa accaaggaaa ctccctccct cggctcgggt tttgacccct actttgtcta  19860
ctcgggctcg atcccctacc ttgacggacc cttttacctt aaccacacct tcaagaaagt  19920
ctccatcatg ttcgactcct cggtcagctg gcccggcaac gaccggctgc tcacgccgaa  19980
cgagttcgag atcaagcgca gcgtcgacgg ggaaggctac aacgtggccc aatgcaacat  20040
gaccaaggac tggttcctcg tccagatgct ctcccactac aacatcggct accagggctt  20100
```

-continued

```
ccacgtgccc gagggctaca aggaccgcat gtactccttc ttccgcaact tccagcccat  20160
gagcaggcag gtggtcgatg agatcaacta caaggactac aaggccgtca ccctgccctt  20220
ccagcacaac aactcgggct tcaccggcta ccttgcaccc accatgcgcc aagggcagcc  20280
ctaccccgcc aacttcccct acccgctcat cggccagaca gccgtgccat ccgtcaccca  20340
gaaaagtctc ctctgcgaca gggtcatgtg gcgcatcccc ttctccagca acttcatgtc  20400
catgggcgcc ttcaccgacc tgggtcagaa catgttctac gccaactcgg cccacgcgct  20460
cgacatgacc ttcgaggtgg accccatgga tgagcccacc gtcctctatc ttctcttcga  20520
agtgttcgac gtggtcagag tgcaccagcc gcaccgcggc gtcatcgagg ccgtctacct  20580
gcgcacgccg ttctccgccg gaaacgccac cacctaagca tgagcggctc cagcgaaaga  20640
gagctcgcgt ccatcgtgcg cgacctgggc tgcgggccta ctttttgggc acccacgaca  20700
cagcgattcc cgggctttct tgccggcgac aagctggcct gcgccattgt caacacggcc  20760
ggccgcgaga ccggaggcgt gcactggctc gccttcggct ggaacccgcg ctcgcgcacc  20820
tgctacatgt tcgacccctt tgggttctcg gaccgccggc tcaagcagat ttacagcttc  20880
gagtacgagg ccatgctgcg ccgaagcgcc gtggcctctt cgcccgaccg ctgtctcagc  20940
ctcgaacagt ccacccagac cgtgcagggg cccgactccg ccgcctgcgg acttttctgt  21000
tgcatgttct tgcatgcctt cgtgcactgg cccgaccgac ccatggacgg gaaccccacc  21060
atgaacttgc tgacgggggt gcccaacggc atgctacaat cgccacaggt gctgcccacc  21120
ctcaggcgca accaggagga gctctatcgc ttcctcgcgc gccactcccc ttactttcgc  21180
tcccaccgcg ccgccatcga acacgccacc gcttttgaca aaatgaaaca actgcgtgta  21240
tctcaataaa cagcactttt attttacatg cactggagta tatgcaagtt atttaaaagt  21300
cgaaggggtt ctcgcgctca tcgttgtgcg ccgcgctggg gagggccacg ttgcggtact  21360
ggtacttggg ctgccacttg aactcgggga tcaccagttt gggcactggg gtctcgggga  21420
aggtctcgct ccacatacgc cggctcatct gcagggcgcc cagcatgtcc ggggcggata  21480
tcttgaaatc gcagttggga ccggtgctct gcgcgcgcga gttgcggtac acggggttgc  21540
agcactggaa caccatcaga ctggggtact ttacgctggc cagcacgctc ttgtcgctga  21600
tctgatcctt gtccagatcc tcggcgttgc tcacgccgaa tggggtcatc ttgcacagtt  21660
ggcgacccag gaatggcacg ctctgaggct tgtggttaca ctcgcagtgc acgggcatca  21720
gcatcatccc cgcgccgcgc tgcatattcg ggtagaggcc ttgacaaagg ccgtgatctg  21780
cttgaaagct tgttgggcct tggcccccctc gctgaaaaac aggccgcagc tcttcccgct  21840
gaactggtta ttcccgcacc cggcatcctg cacgcagcag cgcgcgtcat ggctggtcag  21900
ttgcaccacg cttcttcccc agcggttctg ggtcaccttg gctttgctgg gttgctcctt  21960
caacgcgcgc tgcccgttct cgctggtcac atccatctcc accacgtggt ccttgtggat  22020
catcaccgtt ccatgcagac acttgagctg gccttccacc tcggtgcagc cgtgatccca  22080
cagggcactg ccggtgcact cccagttctt gtgcgcgatc ccgctgtggc tgaagatgta  22140
accttgcaag aggcgaccca tgatggtgct aaagctcttc tgggtggtga aggttagttg  22200
cagaccgcgg gcctcctcgt tcatccaggt ctggcacatc ttttggaaga tctcggtctg  22260
ctcgggcatg agcttgtaag catcgcgcag gccgctgtcg acgcggtaac gttccatcag  22320
cacgttcatg gtatccatgc ccttttccca ggacgagacc agaggcagac tcagggggtt  22380
gcgcacgttc aggacaccgg gggtckcggg ctcgacgata cgttttccgt ccttgccttc  22440
```

-continued

```
cttcaacaga accggaggct ggctgaatcc cactcccaca atcacggcat cttcctgggg  22500
catctcttcg tcggggtcta ccttggtcac atgcttggtc tttctggctt gcttcttttt  22560
tggagggctg tccacgggga ccacgtcctc tcggaagacc cggagcccac ccgctgatac  22620
tttcggcgct tggtgggcag aggaggtggc ggcggcgagg ggctcctctc gtgctccggc  22680
ggatagcgcg ccgacccgtg gccccggggc ggagtggcct ctcgctccat gaaccggcgc  22740
acgtctgact gccgccggcc attgtttcct aggggaagat ggaggagcag ccgcgtaagc  22800
aggagcagga ggaggactta accacccacg agcaacccaa aatcgagcag gacctgggct  22860
tcgaagagcc ggctcgtcta gaaccccaca ggatgaacag gagcacgagc aagacgcagg  22920
ccaggaggag accgacgctg ggctcgagca tggctacctg ggaggagagg aggatgtgct  22980
gctgaaacac ctgcagcgcc agtccctcat cctccgggac gccctggccg accggagcga  23040
aacccccctc agcgtcgagg agctgtgtcg ggcctacgag ctcaacctct tctcgccgcg  23100
cgtgcccccc aaacgccagc ccaacggcac ctgcgagccc aacccgcgtc tcaacttcta  23160
tcccgtcttt gcggtccccg aggcccttgc cacctatcac atctttttca agaaccaaaa  23220
gatccccgtc tcctgccgcg ccaaccgcac ccgcgccgac gcgctcctcg ctctggggcc  23280
cggcgcgcgc atacctgata ttgcttccct ggaagagtgc ccaaaatctt cgaagggctc  23340
ggtcgggacg agacgcgcgc ggcgaaacgc tctgaaagaa acagcagagg aagagggtca  23400
cactagcgcc ctggtagagt tggaaggcga caacgccagg ctggccgtgc tcaagcgcag  23460
cgttgagctc acccacttcg cctaccccgc cgtcaacctc ccgcccaagg tcatgcgtcg  23520
catcatggat cagctaatca tgccccacat cgaggccctc gatgaaagtc aggagcagcg  23580
ccccgaggac acccggcccg tggtcagcga tgagcagctt gcgcgctggc ttggtacccg  23640
cgacccccag gccctggagc agcggcgcaa gctcatgctg gccgtggtcc tggtcaccct  23700
cgagctcgaa tgcatgcgac gctttttcag cgaccccgag acctgcgcaa ggtcgaggag  23760
acctgcacta cacttttagc acgtttcgtc aggcaggcat gcaagatctc caacgtggag  23820
ctgaccaact ggtctcctgc ctgggaatcc tgcacgagaa ccgcctgggg cagacagtgc  23880
tccactcgac cctgaagggc gaggcgcggc gggactatgt ccgcgactgc gtctttctct  23940
ttctctgcca cacatggcaa gctgccatgg gcgtgtggca gcagtgtctc gaggacgaga  24000
acctgaagga gctggacaag cttcttgcta gaaacctcaa aaagctgtgg acgggctttg  24060
acgagcgcac cgtcgcctcg gacctggccg agatcgtcct cccccgagcg cctgaggcag  24120
acgctgaaag gcgggctgcc cgacttcatg agccagagca tgttgcaaaa ctaccgcact  24180
ttcattctcg agcgatctgg gatgctgccc gccacctgca acgccttccc ctccgacttt  24240
gtcccgctga gctaccgcga gtgtcccccg ccgctgtgga gccactgcta cctcttgcag  24300
ctggccaact acatcgccta ccactcggat gttatcgagg acgtgagcgg cgaggggctg  24360
ctagagtgcc actgccgctg caacctgtgc tctccgcacc gctcctggtc tgcaaccccc  24420
agctcctgag cgagacccag gtcatcggta ccttcgagct gcaaggtccg caggagtcca  24480
ccgctccgct gaaactcacg ccggggttgt ggacttccgc gtacctgcgc aaatttgtac  24540
ccgaggacta ccacgcccat gagataaagt tcttcgagga ccaatcgcgc ccgcagcacg  24600
cggatctcac ggcctgcgtc atcacccagg gcgcgatcct cgcccaattg cacgccatcc  24660
aaaaatcccg ccaagagttt cttttgaaaa agggtagagg ggtctatctg gacccccaga  24720
cgggcgaagt gctcaacccg ggtctccccc agcatgccga agaagaacag gagccgctag  24780
tggaagagat ggaagaagaa tgggacagcc agcagaagaa gacgaatggg aagaagagac  24840
```

-continued

```
agaagaagaa gaattggaaa agtggaagaa gagcagcaca gacaccgtcg ccgcaccatc  24900
cgcgccgcag cccggcggtc acggatacaa ctcgcagtcc gccaagctcc tcgtagatgg  24960
atcgagtgaa ggtgacggta agcacgagcg gcagggctac gaatcatgga ggcccacaaa  25020
gcgggatcat cgcctgcttg caagactgcg gggggaacat cgtttcgccc gccgctatct  25080
gctcttccat cgcggggtga acatcccccg caacgtgttg cattactacc gtcaccttca  25140
cagctaagaa aaaatcagag taagaggagt cgccggagga ggcntgagga tcgcggcgaa  25200
cgagccattg accaccaggg agctgaggaa tcggatcttc cccactcttt atgccatttt  25260
tcagcagagt cgaggtcagc agcaagagct caaagtaaaa aaccggtctc tgcgctcgct  25320
cacccgcagt tgcttgtacc acaaaaacga agatcagctg cagcgcactc tcgaagacgc  25380
cgaggctctg ttccacaagt actgcgcgct cactcttaaa gactaaggcg cgcccacccg  25440
gaaaaaaggc gggaattacc tcatcgccac catgagcaag gagattccca cccccttacat  25500
gtggagctat cagccccaga tgggcctggc cgcgggcgcc tcccaggact actccacccg  25560
catgaactgg ctcagtgccg gcccctcgat gatctcacgg gtcaacgggg tccgtaacca  25620
tcgaaaccag atattgttgg agcaggcggc ggtcacctca acgcccaggc aaagctcaac  25680
ccgcgtaatt ggccctccac cctggtgtat caggaaatcc ccgggccgac taccgtacta  25740
cttccgcgtg acgcactggc cgaagtccgc atgactaact caggtgtcca gctggccggc  25800
ggcgcttccc ggtgcccgct ccgcccacaa tcgggtataa aaaccctggt gatacgaggc  25860
agaggcacac agctcaacga cgagttggtg agctcttcaa tcggtctgcg accggacgga  25920
gtgttccaac tagccggagc cgggagatcg tccttcactc ccaaccaggc tacctgacct  25980
tgcagagcag ctcttcggag cctcgctccg gaggcatcgg aaccctccag tttgtggagg  26040
agtttgtgcc ctcggtctac ttcaacccct tctcgggatc gccaggcctc tacccggacg  26100
agttcatacc gaacttcgac gcagtgagag aagcggtgga cggccacgac tgaatgtctt  26160
atggtgactc ggctgagctc gctcggttga ggcacctaga ccactgccgc cgcctgcgct  26220
gcttcgcccg ggagagctgc ggacttatct actttgagtt tcccgaggag caccccaacg  26280
gccctgcaca cggagtgcgg atcaccgtag agggcaccac cgagtctcac ctggttaggt  26340
tcttcaccca gcaacccttc ctggtcgagc gggaccgggg aggcaccacc tacaccgtct  26400
actgcatctg tccaaccccg aagttgcatg agaatttttg ttgtactctg tgtgctgagt  26460
ttaataaaag ctaaactcct acaatactct gggatcccgt gtcgtcgcac tcgcaacaag  26520
accttcaacc tcaccaacca gactgaggta aaattcaact gcagaccggg ggacaaatac  26580
atcctctggc tttttaaaaa cacttccttc gcagtctcca acgcctgcgc caacgacggt  26640
attgaaatac ccaacaacct taccagtgga ctaacttata ctaccagaaa gactaagcta  26700
gtactctaca atccttttgt agagggaacc taccactgcc agagcggacc ttgcttccac  26760
actttcactt tggtgaacgt taccgacagc agcacagccg ctacagaaac atctaacctt  26820
ctttttgata ctaacactcc taaaaccgga ggtgagctct gggttccctc tctaacagag  26880
gggggtaaac atattgaagc ggttgggtat ttgattttag ggtggtcct gggtgggtgc  26940
atagcggtgc tgtattacct tccttgctgg atcgaaatca aaatctttat ctgctgggtc  27000
agacattgtt gggaggaacc atgaaggggc tcttgctgat tatcctttcc ctggtggggg  27060
gtgtactgtc atgccacgaa cagccacgat gtaacatcac cacaggcaat gagaggagtg  27120
tgatatgcac agtagtcatc aaatgcgagc atacatgccc tctcaacatc acattcaaaa  27180
```

-continued

```
accgtaccat gggaaatgca tgggtgggcg actgggaacc aggagatgag cagaactaca  27240
cggtcactgt ccatggtagc aatggaaatc acacttttgg tttcaaattc atttttgaag  27300
tcatgtgtga tatcacactg catgtggcta gacttcatgg cttgtggccc cctaccaagg  27360
ataacatggt tgggttttct ttggcttttg tgatcatggc ctgtgcaatg tcaggtctgc  27420
tggtaggggc tttagtgtgg ttcctaaagc gcaagcctag gtatggaaat gaggagaagg  27480
aaaaattgct ataaatcttt tctcttcgca gaaccatgaa tacagtgatc cgtatcgtgc  27540
tgctctctct tcttgtaact tttagtcagg caggattcat accatcaatg ctacatggtg  27600
ggctaatata actttagtgg gacctcagat attccagatc acatggtatg atagcactgg  27660
attgcaattt tgtgatggaa gtacagttaa gaatccacag atcagacata gttgtaatga  27720
tcaaaactta actctgattc atgtgaacaa aacccatgaa agaacataca tgggctataa  27780
taagcagagt actcataaag aagactataa agtcacagtt ataccacctc ctcctgttac  27840
tgtaaagcca caaccagagc cagaatatgt gtatgttaat atgggagaga acaaaacctt  27900
agttgggcct ccaggaattc cagttagttg gtttaatcag gatggtttac aattttgcat  27960
tggggataaa gtttttcatc cagaattcaa ccacacctgt gacatgcaaa atcttacact  28020
gttgtttata aatcttacac atgatggagc ttatcttggt tataatcgcc agggaactga  28080
aagaacttgg tatgaggttg tagtgtcaga tggttttcca aaatcagaag agatgaaggt  28140
agaagaccat agtaaagaaa cagaacaaaa acagactggt caaaaacaaa gtgaccataa  28200
gcagggtggg caaaaagaaa caagtcaaaa gaaaactaat gacaaacaaa agccatcgcg  28260
caggaggcca tctaaactaa agccaaacac acctgacaca aaactaatta cagtcactag  28320
tgggtcaaac gtaactttag ttggtccaga tggaaaggtc acttggtatg atgatgattt  28380
aaaaagacca tgtgagcctg ggtataagtt agggtgtaag tgtgacaatc aaaacctaac  28440
cctaatcaat gtaactaaac tttatgaggg agtttactat ggtactaatg acagaggcaa  28500
cagcaaaaga tacagagtaa aagtaaacac tactaattct caaagtgtga aaattcagcc  28560
gtacaccagg cctactactc ctgatcagaa acacagattt gaattgcaaa ttgattctaa  28620
tcaagacaaa attccatcaa ctactgtggc aatcgtggtg ggagtgatcg cgggctttgt  28680
aactctaatc attattttca tatgctacat ctgctgccgc aagcgtccca ggtcatacaa  28740
tcatatggta gacccactac tcagcttctc ttactgaaac tcagtcactc tcatttcaga  28800
accatgaagg ctttcacagc ttgcgttctg attagcatag tcacacttag ttcagctgca  28860
atgattaatg ttaatgtcac tagaggtggt aaaattacat tgaatgggac ttatccacaa  28920
actacatgga caagatatca taaagatgga tggaaaaata tttgtgaatg gaatgttact  28980
gcatacaaat gcttcaataa tggaagcatt actattactg ccactgccaa cattacttct  29040
ggcacataca aagctgaaag ctataaaaat gaaattaaaa aattaaccta taaaaacaac  29100
aaaaccacat ttgaagattc tggaaattat gagcatcaaa aattatcttt ttatatgttg  29160
acaataattg aactgcctac aaccaaggca cccaccacag ttagtacaac tacacagtca  29220
actgttaaga ccactactca cactacacag ctagacacca cagtgcagaa taatactgtg  29280
ttggttaggt atttgttgag ggaggaaagt actactgaac agacagaggc tacctcaagt  29340
gcctttatca gcactgcaaa tttaacttcg cttgcttgga ctaatgaaac cggagtatca  29400
ttgatgcatg gccagcctta ctcaggtttg gatattcaaa ttacttttct ggttgtctgt  29460
gggatcttta ttcttgtggt tcttctgtac tttgtctgct gtaaagccag aaagaaatct  29520
aggaggccca tctacaggcc agtgattggg gaacctcagc cactccaagt ggatggaggc  29580
```

-continued

```
ttaaggaatc ttcttttctc ttttacagta tggtgatcag ccatgattcc tagttcttcc  29640
tatttaacat cctcttctgt ctcttcaaca tctgtgctgc ctttgcggca gtttcgcacg  29700
cctcgcccga ctgtctaggg cctttcccca cctactcctc tttgccctgc tcacctgcac  29760
ctgcgtctgc agcattgtct gcctggtcat caccttcctg cagctcatcg actggtgctg  29820
cgcgcgctac aattacttca tcatagtccc gaatacaggg acgagaacgt agccagaatt  29880
ttaaggctca tatgaccatg cagactctgc tcatactgct atcgctctta tcccatgccc  29940
tcgctactgc tgattactct aaatgcaaat tggcggacat atggaatttc ttagactgct  30000
atcaggagaa aattgatatg ccctcctatt acttggtgat tgtgggaata gttatggtct  30060
gctcctgcac tttctttgcc atcatgatct acccctgttt tgatcttgga tggaactctg  30120
ttgaggcatt cacatacaca ctagaaagca gttcactagc ctccacgcca ccacccacac  30180
cgcctccccg cagaaatcag tttcccatga ttcagtactt agaagagccc cctccccgac  30240
ccccttccac tgttagctac tttcacataa ccggcggcga tgactgacca ccacctggac  30300
ctcgagatgg acggccaggc ctccgagcag cgcatcctgc aactgcgcgt ccgtcagcag  30360
caggagcgtg ccgccaagga gctcctcgat gccatcaaca tccaccagtg caagaagggc  30420
atcttctgcc tggtcaaaca ggcaaagatc acctacgagc tcgtgtccaa cggcaaacag  30480
catcgcctca cctatgagat gccccagcag aagcagaagt tcacctgcat ggtgggcgtc  30540
aaccccatag tcatcaccca gcagtcgggc gagaccaacg gctgcatcca ctgctcctgc  30600
gaaagccccg agtgtatcta ctcccttctc aagacccttt gcggactccg cgacctcctc  30660
cccatgaact gatgttgatt aaaaaccaaa aaaaacaatc agccccttcc cctatcccaa  30720
attactcgca aaaataaatc attggaacta atcatttaat aaagatcact tacttgaaat  30780
ctgaaagtat gtctctggtg tagttgttca gcagcacctc ggtaccctcc tcccaactct  30840
ggtactccag tctccggcgg gcggcgaact ttctccacac cttgaaaggg atgtcaaatt  30900
cctggtccac aattttcatt gtcttccctc tcagatgtca aagaggctcc gggtggaaga  30960
tgacttcaac cccgtctacc cctatggcta cgcgcggaat cagaatatcc ccttcctcac  31020
tcccccccttt gtctcctccg atggattcaa aaacttcccc cctggggtcc tgtcactcaa  31080
actggctgac ccaatcacca tagccaatgg tgatgtctca ctcaaggtgg gagggggact  31140
tactttgcaa gaaggaagta tgactgtaga ccctaaggct cccttgcaac ttgcaaacaa  31200
taaaaaactt gagcttgttt atgttgatcc atttgaggtt agtgccaata aacttagttt  31260
aaaagtagga catggattaa aatattagat tgacaaaagt gctggagggt tgaaagattt  31320
aattggcaaa cttgtggttt taacagggaa aggaataggc actgaaaatt tgcaaaatac  31380
agatggtagc agcagaggaa ttggtataag tgtaagagca agagaagggt taacatttga  31440
caatgatgga tacttggtag catggaaccc aaagtatgac acgcgcacac tttggacaac  31500
accagacaca tctcctaatt gcaggattga taaggagaag gattcaaaac tcactttggt  31560
acttacaaag tgtggaagtc aaatattagc taatgtgtct ttgattgtgg tgtcaggaaa  31620
atatcaatac atagaccacg ctacaaatcc aactcttaaa tcatttaaaa taaaacttct  31680
ttttgataat aaaggtgtac ttctcccaag ttcaaacctt gattccacat attggaactt  31740
tagaagtgac aatttaactg tatctgaggc atataaaaat gcagttgaat ttatgcctaa  31800
tttggtagcc tacccaaaac ctaccactgg ctctaaaaaa tatgcaaggg atatagtcta  31860
tgggaacata tatcttggag gtttggcata tcagccagtt gtaattaagg ttacttttaa  31920
```

-continued tgaagaagca gatagtgctt actctataac atttgaattt gtatggaata aagaatatgc 31980
cagggttgaa tttgaaacca cttcctttac cttctcctat attgcccaac aataaaagac 32040
caataaacgt gttttttatt tcaaatttta tgtatcttta ttgattttta caccagcgcg 32100
agtagtcaat ctcccaccac cagcccattt cacagtgtac acggttctct cagcacggtg 32160
gccttaaata aggaaatgtt ctgattattg cgggaactgg acttggggtc tataatccac 32220
acagtttcct gacgagccaa acggggatcg gtgattgaaa tgaagccgtc ctctgaaaag 32280
tcatccaagc gggcctcaca gtccaggtca cagtctggtg gaacgagaag aacgcacaga 32340
ttcatactcg gaaaacagga tgggtctgtg cctctccatc agcgccctca gcagtctctg 32400
ccgccggggc tcggtgcggc tgctgcaaat gggatcggga tcacaagtct ctctaactat 32460
gatcccaaca gccttcagca tcagtctcct ggtgcgtcga gcacagcacc gcatcctgat 32520
ctctgccatg ttctcacagt aagtgcagca cataatcacc atgttattca gcagcccata 32580
attcagggtg ctccagccaa agctcatgtt ggggatgatg gaacccacgt gaccatcgta 32640
ccagatgcgg cagtatatca ggtgcctgcc cctcatgaac acactgccca tatacatgat 32700
ctctttgggc atgtttctgt ttacaatctg gcggtaccag gggaagcgct ggttgaacat 32760
gcacccgtaa atgactctcc tgaaccacac ggccagcagg gtgcctcccg cccgacactg 32820
cagggagcca ggggatgaac agtggcaatg caggatccag cgctcgtacc cgctcaccat 32880
ctgagctctt accaagtcca gggtagcggg gcacaggcac actgacatac atctttttaa 32940
aatttttatt tcctctgtgg tgaggatcat atcccagggg actggaaact cttggagcag 33000
ggtaaagcca gcagcacatg gtaatccacg gacagaactt acattatgat aatctgcatg 33060
atcacaatcg ggcaacaggg gatgttgatc agtcagtgaa gccctggttt catcatcaga 33120
tcgtggtaaa cgggccctgc gatatggatg atggcggagc gagctggatt gaatctcggt 33180
ttgcattgta gtggattctc ttgcgtacct tgtcgtactt ctgccagcag aaatgggccc 33240
ttgaacagca tatacccctc ctgcggccgt cctttcgctg ctgccgctca gtcatccaac 33300
tgaagtacat ccattctcga agattctgga gaagttcctc tgcatctgat gaaataaaaa 33360
acccgtccat gcgaattccc ctcatcacat cagccaggac tctgtaggcc atccccatcc 33420
agttaatgct gccttgtcta tcattcagag gggcggtggg caggattgga agaaccattt 33480
ttattccaaa cggtctcgaa ggacgataaa gtgcaagtca cgcaggtgac agcgttcccc 33540
tccgctgtgc tggtggaaac agacagccag gtcaaaaccc actctatttt caaggtgctc 33600
gaccgtggct tcgagcagtg gctctacgcg tacatccagc ataagaatca cattaaaggc 33660
tggccctcca tcgatttcat caatcatcag gttacattcc tgcaccatcc ccaggtaatt 33720
ctcatttttc cagccttgga ttatctctac aaattgttgg tgtaaatcca ctccgcacat 33780
gttgaaaagc tcccacagtg ccccctccac tttcataatc aggcagacct tcataataga 33840
aacagatcct gctgctccac cacctgcagc gtgttcaaaa caacaagatt caataaggtt 33900
ctgccctccg ccctgagctc gcgcctcaat gtcagctgca aaaagtcact taagtcctgg 33960
gccactacag ctgacaattc agagccaggg ctaagcgtgg gactggcaag cgtgagggaa 34020
aactttaatg ctccaaagct agcacccaaa aactgcatgc tggaataagc tctctttgtg 34080
tctccggtga tgccttccaa aatgtgagtg ataaagcgtg gtagtttttt ctttaatcat 34140
ttgcgtaata gaaaagtcct gtaaataagt cactaggacc ccagggacca caatgtggta 34200
gcttacaccg cgtcgctgaa agcatggtta gtagagatga gagtctgaaa aacagaaagc 34260
atgcgctaaa ctaaggtggc tattttcact gaaggaaaaa tcactctttc cagcagcagg 34320
gtacccactg ggtggccctt gcggacatac aaaaatcggt ccgtgtgatt aaaaagcagc 34380
acagtaagtt cctgtcttct tccggcaaaa atcacatcgg actgggttag tatgtccctg 34440
gcatggtagt cattcaaggc cataaatctg ccctgatatc cagtaggaac cagcacactc 34500
acttttaggt gaagcaatac caccccatgc ggaggaatgt ggaaagattc agggcaaaaa 34560
aaattatatc tattgctagc ccttcctgga cgggagcaat cctccaggac tatctatgaa 34620
agcatacaga gattcagcca tagctcagcc cgcttaccag tagacaaaga gcacagcagt 34680
acaagcgcca acagcagcga ctgactaccc actgacttag ctccctattt aaaggcacct 34740
tacactgacg taatgaccaa aggtctaaaa accccgccaa aaaaacacac acgccctggg 34800
tgtttttgcg aaaacacttc cgcgttctca cttcctcgta tcgatttcgt gacttgactt 34860
ccgggttccc acgttacgtc acttttgccc ttacatgtaa cttagtcgta gggcgccatc 34920
ttgcccacgt ccaaaatggc ttacatgtcc agttacgcct ccgcggcgac cgttagccgt 34980
gcgtcgtgac gtcatttgca tcaacgtttc tcggccaatc agcagtagcc ccgccctaaa 35040
tttaaaacct catttgcata ttaacttttg tttactttgt ggggtatatt attgatgatg 35100

<210> SEQ ID NO 27
<211> LENGTH: 34214
<212> TYPE: DNA
<213> ORGANISM: Human adenovirus type 40

<400> SEQUENCE: 27
catcatcaat aatatacctt aaaactggaa acgagccaat atgataatga gggaggaggg 60
actaggggtg gtgtaaggtg acgtagaggc gggcggggtg ggaaagggtg gaggcggatg 120
acgtgtgggg tcggaggacg ggcgcggtgc ggcggaagtg acggaaaatc tggtgtattg 180
ggcgggtttt tgtaactttt ggccattttg gcgcgaaaac tgagtaatga ggacgtggga 240
cgaactttgg acttttgtgt ttatggagga aaaactgctg attattactg aactttggcc 300
catgacgaac cggtttttct acgtggcagt gccacgagac ggctcaaagt cctaattttt 360
tattgtgtgc tcagcccgtt tgagggtatt taaacacagc cagaacatca agaggccact 420
cttgagtgcg agcgagtaga gttttctcct ccattgctgt tggcgctttt gacatagcca 480
ccaagatgag aatgctgccg gattttttta ccgggaactg ggatgacatg ttccaggggt 540
tgctggagac tgaatatgtg tttgatttcc ctgaaccttc tgaggcttct gaagaaatgt 600
cgcttcatga tctttttgat gtggaggtgg atggtttcga agaggacgcc aaccaggaag 660
cggttgatgg tatgtttccc gagaggttgc tgtccgaggc tgagagcgct gcagagagcg 720
gttcgggtga ttctggggtt ggcgaagagt tgttgccggt tgatctggat ttgaaatgct 780
atgaagacgg tttgcctcct agcgatcctg aaactgatga ggctacagag gcggaagaag 840
aggcggctat gccgacttat gtgaatgaaa atgaaaatga gctggtgctg gactgtccag 900
agaaccctgg gcgaggttgt cgggcttgtg atttccatcg gggcactagt ggcaatcctg 960
aagctatgtg tgctttgtgt tatatgcgtt taactggaca ctgtatctac agtaagtaaa 1020
aaagttttta tttgtttggt ggtgttggtt aatatgaaca agagttaacg actttttgtt 1080
attttaggtc caatttcaga tgcggaaggg gagtctgagt cggggtcgcc tgaggacact 1140
gattttcccc accctttaac cgccacgccg ccacatggaa ttgtgagaac catcccgtgc 1200
agagtttctt gtagacgacg cccagctgtt gagtgcatag aagatttact tgaggaagat 1260
ccaacagatg aacctttgaa cctgtcctta aagcgcccca agtgctcctg agatcatagt 1320

-continued

```
aataaagtta ttgaccctta ccctgtgttt atttcttggg cgtgtttgtg ggtatataag   1380
caggtagaat ggttttagtg ttagtttatt ctgatggagt tgtggagtga gttacaaagt   1440
tatcagaacc tccgacgctt gctggagttg gcttctgcca gaacttccag ctgttggaga   1500
atcctttttg gctcaacttt aactaatgta atctatagag ctaaggagga gtactcttcg   1560
cggtttgctg accttttgtc gcataaccct ggaatttttg cttctttgaa tttggggcat   1620
cactcatttt ttcaagaaat tgtgatcaga aatttagatt tttcttctcc tggccgtacg   1680
gtttctgggc ttgcttttat ttgttttata ttggatcaat ggagcgccca aactcatctg   1740
tcgcagggtt atactctgga ttacatggca atggctctgt ggagaacctt gctacggagg   1800
aagagggtct taggttgctt gccggcgcag cgtccgcacg gtttggatcc agtgcaggaa   1860
gaggaggagg aggaggagaa cctgagggcc ggcctggacc cttcaacgga attgtaactg   1920
agcctgatcc cgaagagggt actagcagtg ggcaaagggg gggcattaat gggcaaaggg   1980
ggacaaagag aaagatggaa aacgaggggg aggacttttt aaaggagtta accttgagtt   2040
taatgtctcg tcgccatcat gagtctgttt ggtgggctga tttggaagat gagtttaaaa   2100
acggtgaaat gaatttgtta tacaagtata catttgaaca gctgaagaca cattggctgg   2160
aggcttggga ggattttgag ttagctctga acacttttgc caaagtggct cttcgcccgg   2220
acactattta taccattaag aagactgtta atatacgtaa atgtgcctat gtgctgggga   2280
atggagctgt ggtgcggttt caaacatgtg accgtgtagc ctttaactgc gcaatgcaga   2340
gcttgggccc tgggcttatt ggcatgagtg gggtaacttt tatgaatgtg agatttgtag   2400
tggagggatt taatggcaca gtgtttgctt ctaccactca attaaccttg catggtgtgt   2460
tttttcaaaa ttgcagcggt atctgcgtgg attcctgggg tagggtgtct gccagagggt   2520
gtacgtttgt tgcatgttgg aaaggggtgg tggggcgaaa caaaagtcaa atgtctgtaa   2580
agaagtgtgt gtttgaacgt tgcattatgg ccatggtggt agaaggtcag gcgcggattc   2640
gccataatgc gggctctgat aatgtgtgtt ttttactgct aaagggaact gccagtgtaa   2700
agcataacat gatttgtggc ggtggtcact ctcagctgct aacctgtgca gatggaaact   2760
gtcaggctct gagagtgttt cacgtagtat ctcatccccg ccgcccctgg cctgtttttg   2820
agcacaacat gcttatgcgc tgtactgtgc atttgggagc tcgtcgtggc atgttttctc   2880
cataccagag taacttttgc cacactaaag ttttaatgga aactgatgct tttctcggg    2940
tatggtggaa cggggtattt gatttaacca tggagctatt taaagtggtg aggtatgatg   3000
agtcaaaggt tcgttgtcgc ccctgtgagt gtggagctaa tcatattagg ttatatccag   3060
caactctgaa cgtgaccgag cagctgcgta cggaccacca gatgatgtcg tgtctgcgta   3120
ctgactacga atccagcgat gaggattaag ggtaaggggc ggagcctatt acaggtataa   3180
aggttggggt agagtaaaaa aaagggaagt tacaaaatga gtggcttcac ggaaggaaac   3240
gctgtgagtt ttgagggtgg ggtgtttagc ccatatctga caacccgtct tccctcttgg   3300
gcaggagtgc gtcagaatgt ggtggggtcc aacgttgatg gtcgtcctgt cgcccctgcc   3360
aactcgacaa cccttaccta cgccactatt ggatcgtcgg tggataccgc tgcagctgct   3420
gccgcgtctg ctgctgcctc tactgctcgt ggcatggcag cagattttgg actgtacaat   3480
caactggccg cgtctcggtt aagagaagaa gatgccctgt ccgtggtgtt gacccgcttg   3540
gaggagctgt ctcagcagtt gcaagatatg tctgccaaaa tggctctgct taaccctccc   3600
gctaatactt cttaataaag acacaattgg ttggaaaagt caaaagtgtt tatttatttc   3660
ttttgcggta ggccctagac cacctgtcgc ggtcgtttaa aactttatgg atgttttcca   3720
```

-continued

```
agacccggta caggtgggct tggatgttca aatacatagg cattaggccg tccctgggat   3780
gcaggtagga ccactggagg gcgtcatgct ctggggtggt gttgtaaata atccaatcgt   3840
agcagggttt ttgagcatga aactggaaga tgtccttaag gaggaggcta atggccagag   3900
gtagcccctt ggtgaaggta ttaacaaatc gattaagttg ggagggatgc atgcgagggg   3960
aaatcagatg cattttggcc tgaattttta ggttggcaat gttgccaccg agatcacgtc   4020
tggggttcat gttgtgcaga accactagca cggtatagcc ggtgcacttg gggaatttgt   4080
catgcaactt ggaagggaag gcgtggaaaa acttggaaac ccctttgtgc cctcccaaat   4140
tttccatgca ctcatccata atgatggcga tggggccttg ggatgcagcc ttagcaaaaa   4200
tgttatcggg gtgggaaaca tcgtagtttt gctccagggt aagctcgtca taggccattt   4260
tgatgaagcg tggtaaaagg gtgcccgact ggggtataat ggtcccttct ggacctgggg   4320
cgtagttacc ctcgcagatt tgcatctccc aagccttaat ttctgagggg gggatcatgt   4380
ccacctgagg ggcaataaaa aaaacggttt cgggtggagg gttaataagc tgggtggaaa   4440
gcaagtttcg caaaagctgg gatttgccgc agccagtggg accgtaaatg accccaatga   4500
caggctgtag ttgatagttt aaggagatgc aactgccatc ttcccgcaaa agcggagtga   4560
cttcgttcat catgcttctg acatgctggt tttctttaac caagtcttgc aagagacgct   4620
caccgcccag ggaaagtagc tcttccaagc tgcggaaatg ctttagtggt tttaggccat   4680
cggccatggt catttttttca agggattgac gcagcaaata gagccgatcc cagagctcgg   4740
taatatggtc tatggcatct cgatccaaca aacttcttgg ttgcggggt tgggacggct   4800
ttggctgtac ggtaccagtc ggtgggcgtc cagtggagca agggtaatgt ctttccaggg   4860
tcgcagggtt cgcgttaggt tggtttcggt gacggtaaag ggcgcgctc cgggttgggc   4920
gcttgccagg gttctcttca ggctcatcct gctggtgtga aaacgcgcgt cttcgccctg   4980
aaagtcggcc aagtagcatt ttaacatgag atcatagttg agggtttcgg cagcgtgtcc   5040
tttggcgcga agcttgccct tggaaatttg ctgacagctg ggacagcgga ggcattttag   5100
ggcgtagagt ttgggagcca ggaagacgga ctctggtgaa taagcgtcgg cgccacactg   5160
tgcacacacg gtttcgcact ccactaacca ggcgagctca gggtgttttg ggtcaaaaac   5220
cagattgcct ccgtgttttt tgatgcgttt cttacctcgt gtttccatga ggcggtatcc   5280
ggcttcggtg acaaacaagc tgtctgtgtc tccgtaaact gatttgaggg tacgctgttc   5340
caacggtgtg cctctgtcct ctgcgtacaa gatctcggac cattctgaga caaaagcccg   5400
ggtccaggct aaaacaaagg aggcgatttg ggagggataa cggttgtttt ccaccagggg   5460
gtcgaccttt tctagggtgt gaaggcaaag gtcatcttct tctgcatcca taaaggtaat   5520
tggtttgtaa gtgtaggtca cgtggtcatt gggcttgtgc gtgggtgtat aaaaggggc   5580
gtgtccgggc tcttcatcac tttcttccgc atcgctgtgg acgacagcca gctgttcggg   5640
tgagtatgcg cgttgaaagg tgggcataac ttcagcactt agagtgtcag tttccacaaa   5700
cgaggtggat ttgatattta tctgccctgc ggcaatgctt ttgatggtgg ctgaatccat   5760
ttggtcagaa aatacaattt ttttgttatc aagtttggta gcaaaggatc catagagggc   5820
gttggagagc agtttggcaa tggaacgcag tgtttggttt ttttcgcggt cggcacgctc   5880
cttggcggtg atattaagat gaacgtactc ttttgccacg cagcgccact cgggaaagac   5940
agtggcgcgc tcgtcgggaa gcaaccgcac atgccagccc cggttgtgca gtgttataag   6000
gtccacactg gtaactacct cgccgcgcag ggctcattg gtccagcaaa ggcgccctcc   6060
```

-continued

```
tttgcgcgaa cagagtgggg gcaaaacatc tagtaggttt tcaggtgggg ggtcggcgtc   6120
gatggtaaaa atgccaggca gcagggtgcg attgaaataa tcaatggggg taccaacttg   6180
caaaagagcg tgttcccaat ctcggaccgc tagggcgcgc tcgtagggat tgagtgggaa   6240
gccccacggc atgggatggg taagtgcaga ggcgtacatg ccacagatgt cataaacgta   6300
aagtggttcg cgtagcaccc caatgtaagt tggataacag cgtcctccgc gaatgctagc   6360
ccgaacatag tcatacattt cgtgggaagg ggccagcaag ctgccgccta ggtccgaccg   6420
ctggggtttt actgtccggt acaagatttg acgaaagatg gcgtgggagt tggaggagat   6480
ggtgggccgc tgaaagacgt taaagctggc ttcgggtaga cctaccgcgt cgcggataaa   6540
ctgagcgtag gattcgcgca acttttgcac cagggcggcg gtaacaagca catccagggc   6600
acagtaatca agggtttcac gcaccaggtc gtaatgagga cattgctttt tttcccagag   6660
ttcgcggttc aggaggtact cctcgcgatc cttccagtaa tcttcggcag gaaagccacg   6720
ctcgtctgcg cggtaagaac ccagcatgta aaactcgttt acggccttgt atgggcagca   6780
tcctttttct accggaaggg tataggcttg tgcggctttt cgcagagacg tgtgtgtgag   6840
ggcaaaagtg tcgcgcacca taaccttgag gaattgatac ttaaaatcag agtcgtcgca   6900
ggcgccctgc tcccataggc gatagtcggt gcgttttttt gagcttggat taggaagggc   6960
aaaggtgata tcattaaaaa ggattttgcc ggctctaggc ataaagttgc gggtgatttt   7020
gaaaggcccg ggcacatcag aacggttgtt aataacctga gctgcaagta cgatttcatc   7080
gaagccgttg atgttatgcc ccacaatgta aagttctaaa aagcgggggc gtccctggag   7140
tttgggggcc ttttgtaact cttcataggt aaggtaatca ggagaaaaaa gacccatttc   7200
caagcaagcc cattctgcca gttggggatt ggcggctaga aaaccgcgcc atagctggag   7260
ggcaaaatgg gcttgcaagc ggttgcggta ctctcgaaac tttttgccca ccgccaattt   7320
ttcgggggtc accacgtaaa aggtacgttc gtcgtttccc caagtgtccc actgcaactc   7380
gcaggccagt cggcaggctt ccttaacaag ggcttcctcc cccgagagat gcataactag   7440
cataaagggg accagctgtt taccaaaggc tcccatccac gtgtaggttt cgacgtcgta   7500
ggtgacaaag aggcgttcga cgcgaggatg agagccgatc ggaaagaaat tgattttctg   7560
ccaccagccg gaggagtggg cgttgatatg atgaaagtag aagtctctcc ggcggaccgt   7620
gcattcgtgc tgatatttgt aaaagcgggc gcaatactcg cagcgttgca cgctctgcat   7680
ctcttgaatg aggtgtacct gtcgcccacg tacgagaaat cggagaggga agttgagaaa   7740
atcctcagtg tcttgccttt caccctcgtc gccctcttct gcacctgcac gctcttgctg   7800
tgggtggatg atggagggaa cgacaacgcc ccgcgagcca caggtccaga cctcaacgcg   7860
gggcaccttc agcttgagag caagagtgcg gatttgggaa ctgtccaggg agtccaggaa   7920
ggcctcgttc agatcagcgg gcacagatcg aaggttgact tgcaggagac gggtaagggc   7980
cgatgccagg cggcgatgaa acttgatttc cattggtgag ttggtagcag tgtcaatagc   8040
atacagaaga ccttgtccgc ggggagctac aatggtacca cgcaggcgag agttgggggt   8100
aaggcttaca ttgttcgctg cgggcgggcg tccggaggca gtggtggatg ggggttcgcc   8160
tggagaggcg gtagcggcac gtcggcgtgg agctcgggta gcggttggtg ctgcgcccgc   8220
agttgactgg cgtacgcgac gacgcggcgg ttgaggtcct gaatgtgtct ccgctgggag   8280
aaaaccaccg gccctcggac tcggaacctg aaagagagtt caacagaatc aatatcggca   8340
tcgttgaccg cggcttgtcg cagaatctcc tgcacgtcgc cagagttgtc ttggtaggca   8400
atctccgaca taaactggtc aatctcttcg tcctggagtt ctccgtgtcc tgcgcgctcc   8460
```

-continued

```
accgtggctg caaggtcatt agagatgcgc ctcatgagct gggagaaagc gttaagaccg   8520
ttttcgttcc acacgcggct gtagaccacg tcgccaacag tgtttcgggc gcgcatcacc   8580
acttgtgcaa tgttcagttc tacgtgtctt gcaaagacgg cgtagttgcg tagacgctgg   8640
aagaggtagt tgagcgtggt ggcaatgtgc tcgcaaacaa agaagtacat gacccagcgc   8700
cgaagcgtca tttcgttaat atctccgagg gcttccaagc ggtccattgc ctcgtagaag   8760
tcaaccgcga agttgaagaa ctgggagttg cgcgccgcaa acgtcaactc ctcttgcagg   8820
agccgaattg cctcggctac agtttcgcgc acctcttgtt cgaaggctgc cggcgtttcc   8880
tcgatttcca taaactcctc ttcctccaca gcgggaccct cggggctgac cggcgctggg   8940
acgggttgtc gtcgacgacg gcgccggacg ggcagccggt caatgaaacg ttgaatcatt   9000
tctccgcgac ggcgacgcat ggtttcggtg acggcgcgcc cgttttctcg ggggcgaagt   9060
tcaaagacgc cgccttgcat gcccgagccg gagaggggag gaagtaggtg gggcccctga   9120
ggcagcgaca gggcgctaac tgtgcatctt atcatctgtt gcataggtag agactgccaa   9180
gcctcattga gcgagtccag ttggacggga tcagagaatt tttcgaggaa agcttccagc   9240
caatcgcagt cgcaaggtaa gctaaggacg gtggcatgag ggattctaag ggaggcagca   9300
gaggaggtga tgctgctgat gaggaaattg aagtaggcgg tcttcaaacg gcggatggtg   9360
gcaaggagag tgacgtcttt tggtccggcc tgttgaattc gcaggcggtc tgccatgccc   9420
caagcttcgt tctgacatcg gcgcaggtcc ttgtaataat cttgcatgag actttctacg   9480
ggtatttcca attcccctcg gtcggccatg cgtgtggaac caaacccgcg caggggctgc   9540
agcagggcca agtcggcaac tacgcgttcg gcgagcacag cctgctgtat ctgagttaaa   9600
gtgttttgga aatcatccaa gtccacaaag cggtggtagg aaccggtgtt gatggtgtac   9660
gtgcagttgg ccatgacgga ccagttgact acttgcatcc cgggctgtgt aatctcggta   9720
tacctaaggc gcgagtaggc tctggattca aaaacgtagt cgttgcaggt gcgaaccaag   9780
tactggtagc caacaaggaa gtggggcggc ggctcgcggt aaaggggcca gcgaagtgtg   9840
gcgggcgtac cgggggccag gtcctccagc ataaggcgat ggtagtggta aacatatcga   9900
gagagccagg tgatgccggc ggcggtagtg gcggcgcggg cgtattcgcg aacgcggttc   9960
cagatgttac gcaacgggga gaagcgttcc atggcgggca cgctttgacc agtcagacgg  10020
gcgcaatctt gtacgctcta gatgaaaaaa cagagagcgg tcacggactt tcctccgtag  10080
cctggaggac agaccgccag ggtgcagtgg caaacaaccc ccggttcgag accggctgga  10140
tctgccactc ccgacgcgcc ggccgtgcgt ccacgacgga aaccccgccg agacctagcc  10200
gcggtccctg gatctccaga tacggagggg agtctttttg ttgtttttttg tagatgcatc  10260
cggtgttgcg acagatgcgt ccgacggcgc ctccaacaca gccgccgctc ccgcccccca  10320
ctagcgcccc tgcagccgtt gctctctccg gagccggcgg tggcaaccct gaggaggagg  10380
ccatcctgga cctggaagag ggcgagggc tggcccgctt gggggcgcca tcccccgagc  10440
gccatccccg cgtgcaactt aaaaaggact cacgccaggc gtacgtaccg cctcagaatt  10500
tattcaggga tcgcagcggg caggagcccg aagagatgag ggatcgcagg ttttacgcgg  10560
ggcaggagct gcgggccggt tttaaccgcc aacgggtgct acgcgccgaa gattttgaac  10620
ccgacgaaca tagcggaata agtccggcac gggcgcacgt gtcggcggcc gatttggtaa  10680
ccgcgtacga gcaaacggtg aacgaggagc gcaactttca gaaaagtttt aacaatcacg  10740
tgcgcaccct ggtggcgcgc gaggaggtgg ccattgggct gatgcatttg tgggacttta  10800
```

-continued

```
tggaggcgta cgtgcaaaat ccttcgagca agccgctgac ggcgcagctg tttttgattg  10860
tgcaacacag ccgggacaac gaggctttcc gcgaggccat gctgaatatt gcggagcctg  10920
agggtcgctg gcttttggac ctggttaata tccttcagag cattgtggta caggagcgca  10980
gtctaagcct ggccgacaag gtggcggcca ttaattacag catgcttagc ctcggcaagt  11040
tttacgcccg caagatttac aaaacccccct atgtgcccat agacaaggag gttaaaatag  11100
atagctttta catgcgcatg gcgctaaagg tgttaacgct gagtgacgat ctgggggtgt  11160
accgcaacga ccgtattcac aaagctgtga gcgccagccg ccgtcgcgag cttagcgacc  11220
gcgaactaat gcacagcctg cgtcgggctc taacgggcac cggcactgat gccgaaactg  11280
aatcttactt tgacatgggg gcggacctgc aatggcagcc cagcgcccgg gccctggagg  11340
cggctggtta tgttggcgcg gaagaagatg aggaggacta tgaggacgag ccctgatcag  11400
ccaggtggtg tttttgtaga tgctgcgttc gacggcggtg gcggacgggt cgcagcaggt  11460
gaatcccgct atgttggcgg ccctgcaaag ccaaccttcg ggcgtgacac cctcagacga  11520
ctgggcggcg gccatggatc gcatcctggc cctaaccacc cgcaatcccg aagccttcag  11580
gcagcagccc caggccaacc gcttttcggc cattttggaa gccgtggttc cttctcgcac  11640
taaccctacc cacgaaaagg tgttggcgat tgtaaacgct ctggtagaaa gcaaagccat  11700
ccgcaaggat gaggcgggac tgatatataa tgccttactg gagcgggtag cgcgctataa  11760
tagcaccaac gtgcaggcca acctagaccg actgacaacg gacgtgagag aggcggtggc  11820
gcagcgggaa cgctttatgc atgacgttaa cctaggatcc caagtggccc ttaatgcttt  11880
tctgagcaca ttgccagcta atgtgccgcg cgggcaggag gactatgtca gctttatcag  11940
cgcgcttcgc ctcctggtgg cggaggtgcc ccagagtgag gtgtaccagt ccgggccaga  12000
ctactttttc caaacttcac ggcagggttt gcaaactgta aacctaacac aggcgtttaa  12060
aaacttgcaa ggaatgtggg gcgtgcgagc cccccgtgggg gaccgagcca ccatctccag  12120
cttattgacg ccgaacactc ggttgttgct gttgttgata gcgccattta ccaatagcag  12180
caccattagc cgtgactcgt accttggtca tctaatcacg ctgtaccagg aggctattgg  12240
ccagacgcag gtggacgaac agaccttcca ggaaatcacc agcgtgagtc gggctcttgg  12300
tcagcaagac accagtagct tggaagccac gctgaacttt ttgctaacca accgccggca  12360
aaaaattcca tcgcaattta ctttaaattc tgaagaggaa cgtattttgc gctatgtgca  12420
gcagtccgtc agcttgtatt taatgcgcga gggggctact gcgtcgtcgg ctctggacat  12480
gacggcacgt aacatggaac cgtcgctata ctcgtccaac cggccttttta ttaaccgcct  12540
gatggactat ctgcaccgcg cggcggccat gaacagcgag tacttcacca atgccattct  12600
taacccgcac tggatgccac cgtccggttt ttacacgggc gagtttgacg tgcctgaggg  12660
cgacgacgga tttttgtggg atgacgtgtc cgaaagcatt ttcgaaccaa tgcgttcccg  12720
taaaaaggag ggcggagacg agctgccgct gtcgttagtg gaggcagctt ctcgaggcca  12780
aaccccccgtt cccagtctgc catcgctgac cagcagcagc agcggacggg tgtttcgacc  12840
ccgtttgccc ggggagttgg actacctcag cgatccccta ttgcgaccgg cccggaaaaa  12900
aaattttccc aacaacgggg tggaaagcct ggtagataag atgaatcgct ggaaaaccta  12960
cgcccaggag cagcgggaag agaggcagcc ccgcccactg accggcacct tcagtcgttg  13020
gcgccggcgg gaagaggacg cttacgactc ggccgatgat agtagcgtgt tggacttggg  13080
gggaaccggc gccgcttctg atccctttgc tcatctgcgg cctcagggtc aactgggtcg  13140
tttgtattaa aaaaataaaa taaaaagaaa tccacttacc agagccatag caacagcgtc  13200
```

-continued

```
cgtccctttg tctgtttttt ccctcttccc ggtagtcaaa atgagacgtg cggtgggagt  13260
gccgccggtg atggcgtacg ccgagggtcc tcctccttct tacgaaagcg tgatggaaac  13320
agcggatttg ccggcaacgc tgcaggcgct ccacgtccct ccccgttacc tggggcctac  13380
ggaagggcgg aacagcatac gttactcgga gctggcgcct ctatacgaca ccacccgggt  13440
ttacctggtg gacaacaagt cggcggacat tgcctccctg aactaccaga acgaccatag  13500
taactttcaa accacggtgg tacaaaataa tgactttacc ccgacagagg ccggtaccca  13560
gaccatcaat tttgacgatc gctccaggtg gggcggcgac ctgaaaacca ttttgcgcac  13620
caatatgccc aacatcaatg agtttatgtc taccaacaag tttcgggcgc gggtgatggt  13680
agaaaaagtg aaccggaaaa ccaacgctcc tcgttacgag tggttcgagt tcactttgcc  13740
agagggcaac tattcggaaa ctatgactat agaccttatg aataacgcga tcgtagacaa  13800
ctacttagca gtaggacgtc agaacggcgt gctggaaagc gacattgggg tgaagtttga  13860
cacgcgcaac ttccggttgg gttgggatcc cgtaaccaag ttggtgatgc ccggcgtgta  13920
caccaacgag gcctttcacc cagacattgt tttgctacct ggttgcggcg tggatttcac  13980
gcaaagtcgt ctgaacaact tgctaggaat acgcaagcga atgccctttc aaaaaggttt  14040
ccaaatcatg tatgaggatt tggagggcgg caacattcct gctctattag atgtggaaaa  14100
gtacgaagct agcataaaag aagcacagga gatccgtgga gccgacttca agcccaatcc  14160
tcaagacttg gaaatcgtgc ccgtggaaaa agacagcaag gaaagaagtt acaatctcct  14220
agagggagat aaaaataaca ctgcctaccg cagctggttt ttggcctaca actacggaga  14280
tgcagagaaa ggagtaaagt cttggacctt gttaacaacc acggatgtga cctgtgggtc  14340
gcagcaggtg tactggtccc ttcccgacat gatgcaagat ccagtaacgt ttcgaccgtc  14400
cacgcaagtc agcaactacc ctgtagtggg ggtggaatta ctgccagtac atgccaagag  14460
tttttacaac gagcaggccg tgtattctca gcttattcgc cagtccaccg cgcttacgca  14520
catcttcaat cgttttcctg agaatcagat actagtgcgt ccgcccgctc cgaccattac  14580
caccgtcagt gaaaacgttc ccgccctcac agatcacgga accctgccgc tgcgcagcag  14640
tatcagtgga gttcagcgcg tgaccatcac tgacgcccgc cgtcggacct gcccctacgt  14700
gcacaaagct ctgggcatag ttgctcccaa agtgctgtct agccgcacgt tttaacatgt  14760
ccattcttat ttcgcccgac aacaataccg gctggggact ttgctccgcc ggcatgtacg  14820
gcggcgccaa acggcgttct agccaacacc ctgttcgcgt gcgcggacat taccgcgccc  14880
cctgggggc ttacacccgc ggtgttatct caagacgtac caccgttgat gacgtcattg  14940
actccgtggt agccgatgcc caacgctaca cgcggcccgt tgccacgtcc accgtggatt  15000
ccgtgattga tagtgtggtg gccaacgcca ggcgttacgc gcaacgcaag agacgtttgc  15060
aacgtcgccg tcgtcggcct actgccgcca tgactgccgc tcgggcggta ctaaggcggg  15120
cacaaaggat aggacgtcgg gccatgcgcc gagcggctgc ttctgccagt gcaggtcggg  15180
cccgtcgtca ggccgcccgt caggccgcgg cggctattgc cagcatggct cagccccgcc  15240
gggggaatat ctactgggtg cgagatgcgt cgggcgtgcg ggtgccggtg cgaagccgtc  15300
cccctcggag ttagaagacg cgttcacaaa atggacgaag actgagtttc cctgtcgttg  15360
ccagccggtc cccgtcagca tgagcaagcg caagttcaaa gaagagctgc tggaggccct  15420
tgtgcctgaa atctatggcc ctgccgcgga cgtcaagccc gacattaagc ctcgcgtgct  15480
caagcgggtt aaaaagcgag aaaaaaaaga ggaaaaggag gaagcagggt tgctagacga  15540
```

-continued

```
cggtgttgag tttgtgcggt cctttgcccc ccggcggcgg gtgcagtggc ggggacgtaa  15600
agtccagcgc gtgcttagac ccggcactac tgtagtattt actcccggag agcggtccgt  15660
cacgcgggcc ttaaaacggg attacgatga ggtttacgct gacgaagaca ttcttgagca  15720
ggccgcccaa caggttgggg aattcgccta cggcaagcgc ggccgctacg gagagttggg  15780
actcttgctg gaccaaagca accccacgcc aagcctgaag cccgcaacgg cgcagcagat  15840
ccttcccgtg acagaaatca agcggggcgt caagagggaa aacaaagacg aattgcagcc  15900
caccatgcaa ctcatggtgc caaagcggca aaagcttgag gaggtgttgg agaacatgaa  15960
agtggatccc agcgttgagc cggaagttaa agtgcgcccc attaaagaaa tagggcccgg  16020
acttggcgtg cagacggtgg atatccaaat ccccgtgcgt gcgtcttcgt ccaccgttag  16080
cactgcggtg gaggccatgg aaacgcagcc tgagctgcca gaggccgtag cccgtgcggt  16140
tgcggccacg cgagagatgg gtttgcaaac ggatccgtgg tacgaattcg tggcccctac  16200
cagccgtcca cgctcccgga aatacacaac cgctaattcg attttaccgg agtatgcctt  16260
gcatccatcc atcacgccaa cgcccggtta ccgcggaaca accttcaaac ccagccgcac  16320
tcgctccacc cgccgtcgtc gctctgtccg ccgccgctca aggcgcacgg cccccatctc  16380
tgtgcgtcgc gtaacccgcc gtggacgcac gctgaccctt cccaacgcgc gttaccaccc  16440
tagcattctc gtttaatccg tgcgctgccg tttttcaga tggctttgac ttgccggttt  16500
cgcattcccg ttccgtccta ccgaggaaga tctcgccgta ggagaggcat ggcgggcagt  16560
ggccgccgac gcgctttgcg caggcgaata aaaggcggat tttgcccgc gttgattccc  16620
atcatcgccg ccgccatagg cgcaatccca ggcgtggcct ccgtggcctt gcaagcagct  16680
cgcaaacaat aaaagaaggc ttaacactga cttcctggtc ctgactattt tatgcagaca  16740
agacatggaa gacatcaatt ttgcgtcgct ggctccgcgg cacggctcgc ggccgtttat  16800
gggcacctgg aacgagatcg gcaccagcca gctcaacggg ggcgctttca gttggagcag  16860
cctgtggagt ggcattaaaa actttgggtc ctccattaag tcatttggta acaaggcctg  16920
gaacagtaac acaggtcaaa tgctccggga taagctaaag gaccaaaact ttcaacaaaa  16980
agtcgtggac gggctggctt ccggcattaa cggcgtggtg gatatagcca accaggcctt  17040
gcaaaaccaa atcaatcagc ggctggaaaa tagccgccag cctccggtgg ctctgcagca  17100
gcgcccgcct cccaaagtcg aggaggtaga agtggaggaa aaactaccgc ctttggaggt  17160
ggcacccccc ctgcctagta aaggcgaaaa gcggccgcga ccggatctgg aggaaaccct  17220
agttgtggaa tcccgcgagc ccccctcgta cgagcaggct ttgaaagagg gcgcttcacc  17280
ttatcccatg accaaaccta ttggttccat ggcccgacct gtatacggga aggaaagcaa  17340
acccgtgacc ttagaactac ctccacccgt gcccaccgtt ccgcccatgc cggctccgac  17400
gcttggcacc gccgtttctc gccccaccgc ccccactgtt gccgtggcta cccccgcccg  17460
ccgccctcgc ggggctaact ggcagagcac tcttaacagc attgtgggtc tgggagtaaa  17520
aagcctgaaa cgccgccggt gctattaaaa tggaaccaag ctaaatgcca ttattgtgta  17580
cgcctcctgt gttacgccag agagccgagt gacacgtcac cgccaagagc gccgcttgca  17640
agatggccac cccctcgatg atgccgcaat ggtcttacat gcacatcgcc gggcaggacg  17700
cctcggagta cctgagcccg ggcctggtgc agttcgcccg tgccaccgat acctacttca  17760
gcctggggaa caagttcaga aaccccaccg tggctcccac ccacgatgta accacagaca  17820
ggtcgcagcg actgacgctg cgcttcgtgc ccgtcgaccg cgaggaaacc gcctactctt  17880
acaaagtgcg ctttacgctg gccgtgggcg acaaccgggt tttggacatg gccagcacct  17940
```

-continued

```
actttgacat ccgcggcgtg ctggatcgtg gtcccagctt taaaccctat tcgggcactg  18000
catacaactc cctggccccc aaaggtgctc ccaatcctag ccagtggaca aaccaaaaca  18060
aaacaaactc ctttggacaa gctccctata taggacaaaa aatcaccaat cagggcgtgc  18120
aagtgggctc agactccaac aatcgcgatg tgtttgccga taaaacgtac caaccggagc  18180
ctcaagtggg gcagacgcaa tggaacatta atccaatgca aaacgctgcg ggaagaatac  18240
taaaacaaac cacgcccatg cagccatgtt atgggtcata cgctagacca acaaacgaaa  18300
aaggaggtca agccaagctg gtaaaaaatg acgacaatca gaccacaaca acaaacgtag  18360
gtttaaactt ttttaccact gccactgaaa ccgctaattt ttcaccaaag gtggttctgt  18420
acagcgaaga tgttaactta gaagcgcccg atacccacct tgtgtttaag ccagatgtca  18480
acggcacaag tgccgagctt ttactgggac agcaggccgc tcccaatcga cctaattaca  18540
ttggttttag ggacaacttc attggtttga tgtactacaa ttccactggc aacatgggag  18600
tgctggccgg gcaagcttct cagctcaacg cagtggtgga cttacaagat agaaacacgg  18660
agctgtctta ccagttaatg cttgacgctt taggggatcg gagtcgatac ttctccatgt  18720
ggaaccaggc agtggacagc tatgacccag acgtgagaat tattgaaaat catggcgtgg  18780
aagacgagct ccccaactat tgctttcctc ttaatgggca aggaatatct aacagttacc  18840
aaggcgtaaa gactgacaat ggaactaact ggtctcagaa taatacagac gtctcaagca  18900
acaacgaaat ttccattggc aatgtgtttg ccatggagat taatctggcg gctaacttgt  18960
ggagaagctt cttgtactca aatgtagccc tgtacttgcc tgactcttac aaaataaccc  19020
ccgataacat tactttaccc gacaacaaaa atacatatgc ctacatgaac ggtcgggttg  19080
ccgtccccag cgccctggat acatacgtga acattggggc gcggtggtct ccagacccca  19140
tggacaacgt taatcccttt aaccaccacc gcaatgctgg tctgcgctac cgttctatgc  19200
tcctgggtaa cggccgctac gtgccttttc acatccaagt gccccagaaa tttttcgcca  19260
ttaaaaatct cctgctcctg cccgggtcct acacctatga gtggaacttc cggaaggatg  19320
ttaacatgat tctccaaagc agtctcggta acgacctcag ggtcgatgga gccagcgtca  19380
ggtttgacag cattaacctg tatgccaact tttccccat ggctcacaac accgcttcca  19440
ccttggaagc aatgcttcgt aatgatacca acgatcagtc tttcaacgac tacctctgcg  19500
ctgcaaacat gctttacccc atacccgcca acgctactag cgtgcccatt tctattcctt  19560
cgcgaaattg ggctgctttt cgggggtgga gttttactag actaaaaact aaagaaaccc  19620
cctctttggg gtccgggttt gatccatatt tcacctactc tggctccgtc ccatacttgg  19680
atggcacctt ttacctgaac cacactttta aaaaggtgtc cgttatgttc gactcctctg  19740
tgagctggcc tggtaacgac cgactactta ctcccaacga gtttgaaatc aaacgaaccg  19800
tggatgggga aggatacaac gtggctcaat gtaacatgac caaggactgg ttcctcatac  19860
aaatgctcag tcactacaat attggctacc agggtttcca cgtaccagaa agctacaagg  19920
acaggatgta ctccttttc cgaaacttcc aacccatgag ccgccaggtg gtagacacta  19980
ccacctacac ggagtatcag aatgtaactc tccctttcca gcataataac tctggctttg  20040
taggatacat gggacctgcc atacgggagg gacaagctta ccccgccaac tatccatacc  20100
cccttattgg tcagacggcc gtaccaagcc tgactcagaa aaaatttctt tgcgatcgta  20160
ccatgtggcg cattcccttt tccagcaact ttatgtctat gggggccctg accgacctgg  20220
ggcaaaacat gctgtacgcc aactccgccc acgcgctcga catgactttt gaggtggacc  20280
```

-continued

```
ccatggatga gcccacactt ctctatgttc tgttcgaagt tttcgacgtt gtgcgcatcc  20340
accagccgca ccgcggcgtc atcgaggccg tctacctgcg tacgccgttc tcggccggta  20400
acgccaccac ataagaagcc agccaatggg ctccagcgag caggagttgg tcgccatcgt  20460
gcgcgaactg ggctgcggac cttactttct gggcacgttt gacaaacgct ttccgggttt  20520
tatggcaccg cataagctgg cgtgtgccat tgttaacacg gcgggccgcg aaaccggcgg  20580
cgtacactgg ctggccctgg cctggaaccc aaagaaccgt acctgctacc tcttcgaccc  20640
atttggcttt tcggacgagc gcctcaaaca gatttaccag tttgagtatg aaggtctcct  20700
aaagcgtagt gcgttggcct caaccccgga ccattgtatc accctaatta agtccaccca  20760
aactgttcaa ggaccgtttt cggcggcctg cggccttttc tgctgcatgt tttacatgc  20820
ttttgtaaac tggcccacca gtcccatgga gcgcaacccc accatggacc ttcttaccgg  20880
cgttccaaac agcatgcttc aaagccccca ggttgtaccc accctgcgtc acaaccagga  20940
gcggttgtac cgtttcctgg cgcaacgttc tccctacttt cagcgtcatt gcgagcgtat  21000
caaaaaagcc accgcgtttg accaaatgaa aaacaacatg taacggttca ataaaagctt  21060
ttattgattc aaaaaattca tgcatgcaga ctttttattt taaaatggtt ctttctcccc  21120
atcgccgtgg ctggcgggca aagctacgtt gcgatactgc aaacgagagg accacttaaa  21180
ttctggaatc agcatcttag gaagggggcc atcgacgttc tctccccaca gccgtcgtac  21240
aagttgcaaa gctcccaaaa ggtcaggtgc agaaattttg aaatcacagt tgggaccttg  21300
gccaccacgg gagttgcggt atacggggtt agcgcactgg taaaccagca cacagggata  21360
ctggatactg gcaagagcca ccttgtcggt tacttcttca gctctaagac tgtcaacatt  21420
gcttagagcg aaaggggtgg ctttacacat ttgccgaccc aattggggca caccggtggg  21480
cttgtacagg cagtcgcagc gcatcaccat taataggcgt tttagcccgt tttgcatttt  21540
tggatattcg gcttgcataa aagcttctat ctgcaaaaaa gccgtctgag cctttgttcc  21600
ttccgagaaa aacagaccgc aggacttggc agaaaacaca ttggtggcac agctcacgtc  21660
ttctacacaa caacgggcat cgtcattctt cagttgaacc acgctgcgcc cccaccggtt  21720
ttgtaccacc ttggctcgac tcgggtgctc ctttaacgcc cgctgagcgt tctcgctcgc  21780
tacatccatt tccaccaact gctctttttg aatcatttcc aggccatgat aacagcgtag  21840
cactccctct tgctcggtgc agccgtgaag ccaaatcgcg caaccagtgg gctcccattc  21900
attgtttttt accccggcgt acgactccac gtaggctctc aaaaaacgtc ccatcatttc  21960
cacaaatgtc ttgtggctgg tgaaggtgag agggaggccg cgatgctcct cgttaagcca  22020
cgtttggcaa attttgcgat aaacgttgct ttgttcgggt aggaacttga agccattctt  22080
ctcttcggcc tccacatgat acttttccat tagctttatc attaaatcca tgcctttctc  22140
ccaggcggaa accaagggct ctgcctgcgg attaagaacc actgatgtaa cagctttgga  22200
agtgctaggc tcttcttcct cgttgttttc ctctgacggg ggaggcacac ctttgggctc  22260
caagcgtctt acatatcgct tgccactggc cttttgaacg acctgcacgc cggggtgact  22320
gaacccggtg tacaccacct cttcttcttc ctcctcgctg tctggaacca cttcgggaga  22380
cggaggcaaa actggaacgc gatccggcac ttgaacattc ttgcgcaact tctttttggg  22440
aggaagtgac ggggcccgtt ctggactcgt ctcctgcaag tagggagtga tggtggggag  22500
ttcttgctga cggccggcca tgctttactc ctaggcgaga aaatatggag gaggatctta  22560
agctgcagcc agactccgaa accttaacca cccccaactc tgaggtcggc gccgtcgagc  22620
tagtgaaaca tgaggaggaa aatgagcaag tggagcaaga tccgggctat gtaacgcccc  22680
```

-continued

```
ccgaggacgg caaggaacca gtggccgcac tcagcgaacc caactatttg ggaggggagg  22740
acgacgtgct cctgaagcac atagcgcgac agagcaccat tgtacgagaa gccctcaagg  22800
aatgcacaca gactccgctg acggtggagg aattaagccg cgcgtatgaa gctaacctgt  22860
tttcgccgcg tgtaccgcca aaaaagcagc ctaacggcac ctgcgaaaca aacccgcgcc  22920
tcaattttta tcccgtcttt gcggtgcctg aagcactggc tacttatcac atctttttca  22980
agaaccaacg cattcccctc tcttgccgcg ccaaccgtac acgcggtgac ggccttttgc  23040
atctcaaagc tggagctcac atacctgaga tcgtttcttt agaagaagta cccaagattt  23100
ttgaaggtct tggcaaggac gaaaaacggg cggcaaatgc tctgcaaaaa aacgaaaccg  23160
agaatcagaa cgtgttggta gagctggagg gtgacaacgc gcgtttggcc gtactcaaac  23220
gcaccattga agtttcacac tttgcttatc ccgcgctaaa tcttcctccc aaagtaatgc  23280
gttctgttat ggatcaagtg cttattaagc gagcagagcc cattgatccc caacaacccg  23340
acctaaactc tgaggacgga caacccgtag tctcagacga cgagcttgct cgctggctag  23400
gtacccagga tccctcagag ctgcaagagc ggcgaaaaat gatgatggca gcagttttgg  23460
ttacagtgga attggaatgc ctgcagcgct tctttgctaa ccctcaaaca ctgcgcaaag  23520
tcgaggagtc cctgcactat gccttccgtc atggctacgt tcgtcaggcc tgcaagatct  23580
ccaacgtaga gctcagcaat ctgatctctt acatgggcat tctacacgaa aaccggctgg  23640
ggcagaacgt tcttcactgc accttgcaag gggaggcccg ccgagactac gtccgcgact  23700
gcatctatct tttccttatt ctcacctggc aaaccgctat gggagtctgg cagcagtgct  23760
tggaagagca aaacctccag gagcttaata aattgctagt acgagcccgt cgcgaactct  23820
ggacgtcttt tgacgagcgt acggttgccc gccagctggc aaacctcatt tttcccgagc  23880
ggcttatgca aacattgcaa aatggtttgc cagactttgt cagccaaagt atcttgcaaa  23940
actttcgctc ctttgtactc gagcgttccg gcatcttgcc ggctatgagt tgtgctttgc  24000
cctccgattt tgtcccccctc tgctaccgcg aatgcccccc accgttgtgg agtcactgct  24060
acctcctccg tctagccaac tatttggccc accactctga tcttatggaa gactctagcg  24120
gcgacggact gctagaatgt cactgccgtt gcaacctctg caccccctcat cgctcactgg  24180
tctgtaacac cgagcttctt agcgaaaccc aagtaatcgg tacctttgag attcaagggc  24240
cagagcaaca agaaggtgct tccagcctca aactcacgcc ggcgttgtgg acttccgcct  24300
acctacgcaa atttattccc gaagactatc acgcccacca aattaaattt tatgaagacc  24360
aatcacgacc tcccaaagtc cccttacag cctgtgttat cacccaaagc caaattctgg  24420
cccaattaca agctattcag caggcgcgtc aggaatttct tttaaaaaaa ggacacgggg  24480
tctatttgga cccccaaacc ggtgaagaac ttaatacccc gtcactctcc gccgccgctt  24540
cgtgccgttc gcagaaacat gccacccaag ggaaacaagc atcccatcgc gcaacggcaa  24600
tcccagcaga aactacaaaa gcagtgggac gaggaggaga cgtgggacga cagccaggca  24660
gaggaagttt cagacgagga ggcggaggag cagatggaga gctgggacag cctagacgag  24720
gaggacctag aggacgtgga ggaagaaacc atcgccagcg acaaggcacc atctttcaaa  24780
aaacccgttc ggagccaacc tccgaaaact atcccgcccc tgccaccgca accatgttca  24840
ctgaaagcca gccgtaggtg ggacaccgtc tccatcgccg gatcgccaac agccccagct  24900
ggtaagcagc ctaagcgcgc acgacgggga tactgctcct ggcgagccca taaaagcaat  24960
attgtcgcat gcctccagca ctgccggggc aatatctcat tcgcacggcg ttacttgctt  25020
```

-continued

```
tttcacgacg gggtggcggt tcctcgcaac gtcctctact attaccgtca tctctacagc  25080
ccctacgaaa cgtttggaga aaacacctcg agtgcgtaag acctcatccg ccattgccac  25140
ccgccaggat tcgcccgcca cgcaggagct cagaaaacgc atctttccga cgctgtatgc  25200
tattttccag cagagccgcg gtcaacagct ggaactcaaa gtaaaaaacc gatcactccg  25260
ttcgctcacc cgcagctgct tgtatcacag aagtgaagac caactgcagc gcacgctgga  25320
ggacgccgag gcactgttca ataaatattg ctcggtgtct cttaaggact aaacacccgc  25380
gctttttta ggcgccaaat tacgtcattg acattatgag caaagacatt cccacgcctt  25440
acatgtggag ctatcagccg caaatgggcc tggcagctgg agcttctcag gattactcca  25500
gtcgcatgaa ttggcttagt gccggccccc acatgattgg gcgggtaaat ggaattcgtg  25560
ccactcgaaa ccaaattctg ctagaacagg ccgccctaac ctctaccccg cgacgtcagc  25620
tgaacccacc ctcttggcct gccgcccagg tttatcagga aaaccccgcc ccgaccacag  25680
tccttctgcc acgcgacgcg gaagccgaag tccaaatgac taactccgga gcgcaattag  25740
cgggcggcgc cagacacgtc aggttcagag atcgaccctc gccctattcc tccggctcta  25800
taaaaaggct aatcattcga ggccgaggta tccagctcaa cgacgaggta gtgagctctt  25860
ccaccggtcc tagacctgac ggagtctttc agcttggagg cgccgggcgg tcttccttca  25920
ctcctcgcca ggcgtactta acgcttcaga gctcttcatc ccagcctcgc tccggcggca  25980
tcggaaccct ccagtttgtg gaggagtttg taccctccgt ttacttcaac cccttctcgg  26040
gcgctcctgg tctttaccca gacgacttca tcccgaacta cgacgcggtg agcgaatctg  26100
tggacggcta cgactgaaga ccgatagtac ggccgtgact gcgcggctgt aacatctgca  26160
tcggtgccgt aaccttcgct gctttactta aaaagcctgt gatttcattt accaccccag  26220
cacttggatt acatgaagat ctgtgttctt ttttgtgtgc taagtttaac aagtagccta  26280
aggacttcac ctacaaccgt tggttcctta cgtcagctac aagattccac caaaggtaca  26340
caccaaactc tttatttttc tgagtctacc acttctattg cacttaactg ttcttgtcgt  26400
aaccaactcg ttcagtggcg cgctaacaga caattttgca aactattctg ggacgctctt  26460
attgttcaag gaaacaacag cctttgtaac aactgtactg ctactacttt aactcttaca  26520
cctccttttg ttcccggtcc atacttgtgc attggcacag gaagagggcc tagctgcttt  26580
aatcgctgga ctttacaaaa agagaatcta accactacca ccctccttcc ccttactact  26640
tatacttttt cccaaaaaaa gaattacttt ttgcccatta ttgcactttt ggcctttgtc  26700
tgtgttatta ccgctaatta tattttaatt ttcaatcttg ataattttta ctaatcatgc  26760
tgctgttttt actttgcctt cttttctgct ctgcctatgc cgccgtgcca gaaaaaaccc  26820
ttaacaacct cgttcgggtg tacgccttag ttggtaccaa tctatccctt gattctatga  26880
aaactcctca gattgacgaa cttactagtc ttagctggat caaacaggaa gacaatccta  26940
acaaaaactt acaatcattt ttttttattg gtcaaaaact ctgtgaagtt accaaagaca  27000
aaatcactgt ttttaactat tatccgttgg aattttcctg cgctaacgta accttgtatt  27060
tgtataatct taaaactgac gattctggcc tctataatgg aaaggcccat accaaagagc  27120
ttgaacataa cacctatgtt aggctttatg ttattgacat tcctccgcct aagtgtgaca  27180
ttacttcacg ttacttaggc atacaggcta ctggggaaga ttattgttta attgaaatta  27240
attgcactaa ctccaaatac ccagctgtgg ttaaatttaa tggcaggcaa agcaacttct  27300
accattatgt tagcgaaaac ggaaacaaaa aacttccaaa tttttatgaa acacacatca  27360
ctgttaatgg tacccacaaa agctttcact ttaattaccc ttttaacgac ctttgtcaaa  27420
```

-continued

```
caaccagcgc tctacaatat aatgacaatg tccaggtagt cctcattctt ctcatagtag  27480
ttggcttaat aataatttcc gctagtttaa tattgcttta ttgccaccgc aaaaaaatca  27540
aggccaaagt tcaacatcaa ccagtgcata tttgtttaga aaaataaaaa tttttttctt  27600
ttcagtatgg taactcctct tctcctgctt gtctgtctgc caattatcta cgcctccacc  27660
accttcgccg cagtctccca ccttgatacg gattgtcttc ccgccttgct gacttatctc  27720
atcttcacct ctgtttgctg cactgccatc tgcagcattg ccactttttt tgtggccatt  27780
ttccaaactg cggactacct atacgttaga gtggcatact atcgtcatca tccccaatat  27840
aggaaccacg aggtggctac ccttctgtgc ctgtcatgaa agttcctctt ctctgtctta  27900
tcctccttca caaagtcctg gccaactgcc acctccaccg gcccaccgag ttcctgcgct  27960
gctactcaac agaaacctct tccttttggc tgtactccat tatttttatt ttgattttct  28020
ttgccacctt tttgggatta caaatttacg ggtgccttca cctgggctgg atgcatcctc  28080
ccaacaacct acccagattt cctggtttcc tattacagcc cccaccgccc ccaccggctc  28140
ctgtgcagcg cgctccatca gttattagct actttcatct taactctgaa gatgtctgac  28200
caactagaaa tcgacgggca gtgcactgag cagcttatcc ttgctcggcg aaaactcaaa  28260
caacaaaatc aggaactgtt caaccttcaa gccctacacc aatgcaaaaa gggtcttttt  28320
tgtctggtta aacaagctga actttgttat gatgtaaccc aacagggaca cgagctgtca  28380
tatactttaa acaagcaaag acagagcttt atgactatgg tgggggttaa gcccattaag  28440
gttactcagc aatccggccc agttgaggga agcattcttt gtcagtgtac caatcctgaa  28500
tgcatgtaca ctatggtaaa aaccctgtgt ggtctaaggg aacttctccc ctttaattaa  28560
agttattctg attaataaag cttaccttaa atttgatatc agttgtttgt caagtttttc  28620
cagcagcacc acctgccctt cctcccaact ttcgtacggg atgtgccaac gggcggcaaa  28680
ctttctccac gtcctaaagg gtatatcggt gttcaccttt ttaccctgac ccacaatctt  28740
catcttgcag atgaaaagaa ccagaattga agacgacttc aaccccgtct acccctatga  28800
cacctcctca actcccagca ttccctatgt agctccgccc ttcgtttctt ccgacgggtt  28860
acaggaaaac cccccgggag ttttagcact caagtacact gaccccatta ctaccaatgc  28920
taaacatgag cttactttaa aacttggcag caacataact ttacaaaatg ggttactttc  28980
ggccaccgtt cccactgttt ctcctcccct tacaaacagt aacaactcct tgggtttagc  29040
cacatccgct cctatagctg tgtcagctaa ctctcttaca ttggccaccg ccgcaccact  29100
gacagtaagc aacaaccagc ttagtattaa cactggcaga ggcttagtta taactaacaa  29160
tgccgtagca gttaatccta ccggagcgtt aggctttaac aacacaggag ctttacaatt  29220
aaacgctgcg ggaggaatga gagtggacgg cgccaactta attcttcatg tagcataccc  29280
ctttgaagca atcaaccaac taacactgcg attagaaaac gggttagaag taaccaacgg  29340
aggaaaactc aacgttaagt tgggatcagg cctccaattt gacaataacg gacgcattac  29400
cattagtaat cgcatccaga ctcgaggtgt aacatccctc actaccattt ggtctatctc  29460
gcctacgcct aactgctcca tctatgaaac ccaagatgca aatctatttc tttgtctaac  29520
taaaaacgga gctcacgtgt taggtactat aacaattaaa ggtcttaaag gagcactgcg  29580
ggaaatgaac gataacgctt tatctgtaaa acttcccttt gacaatcagg gaaatttact  29640
caactgtgcc ttggaatcat ccacctggcg ttaccaggaa accaacgcag tggcctctaa  29700
tgccttaaca tttatgccca acagtacagt gtatccccga aacaaaaccg ccgacccagg  29760
```

-continued

```
caacatgctc atccaaatct cgcctaacat caccttcagt gtcgtctaca acgagataaa  29820
cagtgggtat gcttttacgt ttaaatggtc agccgaaccg ggaaaacctt ttcacccacc  29880
caccgctgta ttttgctaca taactgaaca ataaaatcat tgcaggcgca atcttcgcat  29940
ttcttttttc cagatgaaac gagccagatt tgaagatgac ttcaaccccg tctaccctta  30000
cgaacactac aatccccttg acattccatt tattacaccc ccgtttgctt cctccaacgg  30060
cttgcaagaa aaacctccgg gagtcctcag cctgaaatac actgatccac ttacaaccaa  30120
aaacggggct ttaaccttaa aattgggcac gggactaaac attgataaaa atggagatct  30180
ttcttcagat gctagcgtgg aagttagcgc ccctatcact aaaaccaaca aaatcgtagg  30240
tttaaattac actaagcctc tcgctctgca aaataacgcg cttactcttt cttacaacgc  30300
gccctttaac gtagtaaata ataatttagc tctaaatatg tcacagcctg ttactattaa  30360
tgcaaacaac gaactttctc tcttaataga cgccccactt aatgctgaca cgggcactct  30420
tcgccttcga agtgatgcac ctcttggact agtagacaaa acactaaagg ttttgttttc  30480
tagccccctc tatctagata ataactttct tacactagcc attgaacgcc cgctagctct  30540
atccagtaac agagcagtgg cccttaagta ttcaccacct ttaaaaatag aaaacgaaaa  30600
cttaacccta agcacaggcg gaccttttac tgtaagcggg ggaaatttaa acctggcaac  30660
atcggcaccc ctctccgtgc aaaacaattc tctctcctta ggggttaacc cgcctttttct  30720
catcactgac tctggattag ctatggactt aggagacggt cttgcattag gtggctctaa  30780
gttaataatc aatcttggtc caggtttaca aatgtctaat ggagctatta ctttagcact  30840
agatgcagcg ctgcctttgc aatataaaaa caaccaactt caactcagaa ttggctccgc  30900
gtctgcttta attatgagcg gagtaacaca aacattaaac gtcaatgcca ataccagcaa  30960
aggtcttgct attgaaaata actcactagt tgttaagcta ggaaacggtc ttcgctttga  31020
tagctgggga agcatagctg tctcacctac taccactacc cctaccaccc tatggaccac  31080
cgcggacccg tctcctaacg ccacttttta tgaatcacta gacgccaaag tgtggctagt  31140
tttagtaaaa tgcaacggca tggttaacgg gaccatatcc attaaagctc aaaaaggcac  31200
tttacttaaa cccacagcta gctttatttc ctttgtcatg tatttttaca gcgacggaac  31260
gtggaggaaa aactatcccg tgtttgacaa cgaagggata ctagcaaaca gtgccacatg  31320
gggttatcga caaggacagt ctgccaacac taacgtttcc aatgctgtag aatttatgcc  31380
tagctctaaa aggtatccca atgaaaaagg ttctgaagtt cagaacatgg ctcttaccta  31440
cactttttg caaggtgacc ctaacatggc catatctttt cagagcattt ataatcatgc  31500
aatagaaggc tactcattaa aattcacctg gcgcgttcga aataatgaac gttttgacat  31560
cccctgttgc tcattttctt atgtaacaga acaataaaat attgttattt tgtattttca  31620
actttattga tacttttaca gaattctaac cgttaatctc cctcccccct tccactttac  31680
cttatacacc tccctttccc cctgtaccac cgcaaacaac tgcaatttag gatttacaca  31740
acgattcttc tgtgacaaaa tcaacacagg ttctttgctg gcaaagcgct gatccgtaat  31800
ggaaatgaaa ccttcagaaa catcgtccaa cagcacggtg gagtccaaag cagagctctg  31860
caaaaacaaa tacagtcaag ctctccacgg gttctcgcct ctgttgtagt ctgccaacgt  31920
aaacgggcag taccgctcca tcaagccccg cagtaatccc tgtctccggg gttccaccaa  31980
```

-continued

```
gctcctcatg agtgacctaa cggtgaagct tcccaacact ttcaccgcct tggccagcag  32040
ccgccgcgtc cgacgagcgc agcaccgcac agaaagctca tccaagtttt tacaataggt  32100
acagcccaac accaccatat tattcataat tccataacta aaaaaactcc acccaaacga  32160
catgcgctcc aacactatag ccgcgtgccc atcatacagc aggcgaatat atataaaatg  32220
cctacctctg acaaacacgc tccccataaa taacacttcc ttgggcatgc cacaatttac  32280
aatttctcga taccaaggga atcttaagtt atacagtgaa ccataaatca tcattttaaa  32340
ccaatttgct aacactacac cccccgcctt acattgaaga gacccaggtt taatacagtg  32400
acagtgtata gtccagcgtt caaaacctct tacaatttga ttaaaatcaa cattaatagt  32460
ggcacagcaa acacaaacac gcatgtaaat tttgcacaca tgcttttccc atttagacaa  32520
tatcatgtcc caccacattg gccactcctg caatactaca aaaggcgcac aagatggaat  32580
agacctcacc tcgctcacat aatgcatatt caaatgttca cactctaaaa gtccaggagt  32640
cctttccatt gtggcaatag gcacagaatc ctcagaggga ggtggaagac ggtgggtttg  32700
gtacgaactc agtctgcagc gaaaccatct gtcgcgttgc atcataaatt aaaagctcgc  32760
gcacagcttc gtacttctgt tttaagaaac gaacacgctg ccaacaaatg ttcgcaaatc  32820
gacggtttcg ttgtcgcgct ctttcagttt tcagggcaac gttcagccac tcctgcagtc  32880
cacttaacag ctcctcagcc cgtggagata tgctgacatt ataccttatt atgtccccat  32940
aaacgttcaa acagcaggtt aaagccaact ccaaccaaga aatacaaagg ccttgatccc  33000
gactcactgg aggtggaggg agagacggaa gaggcataat tattccagac ggttgtaaag  33060
cgagccaaag tgcaagtcac gaagatcaca cctctcccca ccgctgcgtt ggtgaaaaat  33120
tacagccaag tcaaaaaaga tgcgattttc caaattacca atcacggctt ccactaaggc  33180
tggcacacgc acttcaagaa acacaaacat agcaaaagca ttttcctcaa aatcttcaaa  33240
cattaagctg caatcttgaa taattcccaa ataattttcc gcttgccacc cgcgcaacac  33300
atccattaaa atttcttgta aactggcgcc atgtaattca aaaagtttgt taagagcacc  33360
ctctactgtc atacgcaggc acaccttcat ggttgaaaaa gatcaggttc ccgtgtcacc  33420
tgcagttcat ttaaaagatt aacattaggc tcaaaacccc gatcccgaat ctccatgcgt  33480
agcattagtt gtacaaagtc atccaaatca ttgcatataa gctctgtcag ttcgctatca  33540
ggaagcagct caggtgatgc tacacaacaa atcatctcta gcgtaggagc taaagacgtt  33600
aaggtaaagc cacaataagc agcttgaaga actggagtaa cacaatgcaa aatgtgcagc  33660
aaaaactccg acatgtttgt ctttaaaaaa tctaccacag aaatgtccat attatttaaa  33720
taaaacatca ggggctcagg aaccaccacc gaaataaaaa ccggtcgtaa caaatacatt  33780
gtgtcctgca acaaaaaaaa aatattaatg cccacacctg ggaaaacctg ttctaaaacc  33840
aaacaggtat aagtattaca aatgcctccc tttgccccccc aatccaaacc aaataagctg  33900
ccccgtctta ccgcgacaaa gcacacagaa caaaacacac tccgcagacg aacacaatat  33960
ttatacactc cctttgccgt caaaagtcca caaaaactcc aaaggtcaga aaaaccgcca  34020
catgaacact tccgcatact gtttcacata tcgtcacttc cgccgcaccg cgcccgtcct  34080
ccgaccccac acgtcatccg cctccaccct ttcccacccc gcccgcctct acgtcacctt  34140
acaccacccc tagtccctcc tccctcatta tcatattggc tcgtttccag ttttaaggta  34200
tattattgat gatg                                                    34214
```